US010927161B2

(12) United States Patent
Seidel, III et al.

(10) Patent No.: US 10,927,161 B2
(45) Date of Patent: Feb. 23, 2021

(54) METHODS FOR MODULATING AN IMMUNE RESPONSE

(71) Applicant: Cue Biopharma, Inc., Cambridge, MA (US)

(72) Inventors: Ronald D. Seidel, III, Cambridge, MA (US); Rodolfo J. Chaparro, Cambridge, MA (US)

(73) Assignee: Cue Biopharma, Inc., Cambridge, MA (US)

( * ) Notice: Subject to any disclaimer, the term of this patent is extended or adjusted under 35 U.S.C. 154(b) by 0 days.

(21) Appl. No.: 16/922,697

(22) Filed: Jul. 7, 2020

(65) Prior Publication Data

US 2020/0331982 A1 Oct. 22, 2020

Related U.S. Application Data

(63) Continuation of application No. 16/830,831, filed on Mar. 26, 2020, which is a continuation of application No. 16/489,586, filed as application No. PCT/US2018/022492 on Mar. 14, 2018, now abandoned.

(60) Provisional application No. 62/521,009, filed on Jun. 16, 2017, provisional application No. 62/471,832, filed on Mar. 15, 2017.

(51) Int. Cl.

| | |
|---|---|
| ***A61K 47/68*** | (2017.01) |
| ***A61P 37/06*** | (2006.01) |
| ***C07K 14/55*** | (2006.01) |
| ***C07K 14/74*** | (2006.01) |
| ***A61K 47/64*** | (2017.01) |
| ***A61K 9/00*** | (2006.01) |
| ***C07K 14/79*** | (2006.01) |
| ***C07K 16/28*** | (2006.01) |
| ***C12N 15/62*** | (2006.01) |

(52) U.S. Cl.
CPC ...... *C07K 14/70539* (2013.01); *A61K 9/0019* (2013.01); *A61K 47/644* (2017.08); *A61K 47/68* (2017.08); *A61P 37/06* (2018.01); *C07K 14/55* (2013.01); *C07K 14/79* (2013.01); *C07K 16/2818* (2013.01); *C07K 16/2827* (2013.01); *C12N 15/62* (2013.01)

(58) Field of Classification Search
CPC .. C07K 14/70539; C07K 14/55; A61K 47/68; A61K 47/644; A61P 37/06
USPC ...................................................... 424/185.1
See application file for complete search history.

(56) References Cited

U.S. PATENT DOCUMENTS

| | | | |
|---|---|---|---|
| 5,635,363 | A | 6/1997 | Altman et al. |
| 6,197,302 | B1 | 3/2001 | Hirsch et al. |
| 6,211,342 | B1 | 4/2001 | Hirsch et al. |
| 6,268,411 | B1 | 7/2001 | Schneck et al. |
| 6,696,304 | B1 | 2/2004 | Parker |
| 7,098,306 | B2 | 8/2006 | Economou et al. |
| 7,186,804 | B2 | 3/2007 | Gillies et al. |
| 7,432,351 | B1 | 10/2008 | Chen |
| 7,670,595 | B2 | 3/2010 | Gillies et al. |
| 8,992,937 | B2 | 3/2015 | Hansen et al. |
| 9,284,349 | B2 | 3/2016 | Tsunoda et al. |
| 9,359,424 | B2 | 6/2016 | Maoult et al. |
| 9,494,588 | B2 | 11/2016 | Springer et al. |
| 2002/0006664 | A1 | 1/2002 | Sabatini |
| 2002/0031520 | A1 | 3/2002 | Economou et al. |
| 2004/0038349 | A1 | 2/2004 | Hilbert et al. |
| 2004/0161817 | A1 | 8/2004 | Benton et al. |
| 2004/0209363 | A1 | 10/2004 | Watts et al. |
| 2005/0003431 | A1 | 1/2005 | Wucherpfennig et al. |
| 2005/0009012 | A1 | 1/2005 | Holzberg et al. |
| 2005/0100926 | A1 | 5/2005 | Hedley et al. |
| 2006/0034865 | A1 | 2/2006 | Hildebrand et al. |
| 2006/0269515 | A1 | 11/2006 | Deniz-Mize et al. |
| 2007/0036752 | A1 | 2/2007 | Gillies et al. |
| 2007/0148162 | A1 | 6/2007 | Bhardwaj et al. |
| 2007/0286843 | A1 | 12/2007 | Pfizenmaier et al. |
| 2008/0199485 | A1 | 8/2008 | Kundig et al. |
| 2008/0219947 | A1 | 9/2008 | Linette et al. |
| 2008/0269070 | A1 | 10/2008 | Ramseier et al. |
| 2010/0159594 | A1 | 6/2010 | Hansen et al. |
| 2011/0002956 | A1 | 1/2011 | Weiner et al. |
| 2011/0268737 | A1 | 11/2011 | Favier et al. |
| 2011/0318380 | A1 | 12/2011 | Brix et al. |
| 2012/0003220 | A1 | 1/2012 | Chen |
| 2012/0121577 | A1 | 5/2012 | Weidanz et al. |

(Continued)

FOREIGN PATENT DOCUMENTS

| | | |
|---|---|---|
| CN | 1791675 | 6/2006 |
| CN | 101418309 | 4/2009 |

(Continued)

OTHER PUBLICATIONS

Medina et al. (Pharmacotherapy 2016;36(3):317-334).*

(Continued)

*Primary Examiner* — Yan Xiao

(74) *Attorney, Agent, or Firm* — Bozicevic, Field & Francis LLP; Paula A. Borden

(57) ABSTRACT

The present disclosure provides methods of modulating an immune response in an individual. The present disclosure provides methods of treatment. The present disclosure provides methods comprising administering a multimeric polypeptide (synTac) and an immune checkpoint inhibitor to an individual. The present disclosure provides methods comprising administering a multimeric polypeptide (synTac) to an individual who is undergoing treatment with immune checkpoint inhibitor.

16 Claims, 100 Drawing Sheets

Specification includes a Sequence Listing.

(56) References Cited

U.S. PATENT DOCUMENTS

| | | | |
|---|---|---|---|
| 2012/0177595 | A1 | 7/2012 | Wong et al. |
| 2012/0264161 | A1 | 10/2012 | Scholler et al. |
| 2013/0017199 | A1 | 1/2013 | Langermann |
| 2013/0149305 | A1 | 6/2013 | Ostrand-Rosenberg |
| 2014/0046026 | A1 | 2/2014 | Garcia et al. |
| 2014/0162293 | A1 | 6/2014 | Springer et al. |
| 2014/0242077 | A1 | 8/2014 | Choi et al. |
| 2015/0071987 | A1 | 3/2015 | Selvaraj |
| 2015/0224186 | A1 | 8/2015 | Nakagawa |
| 2015/0232532 | A1 | 8/2015 | Ostrand-Rosenberg |
| 2015/0374788 | A1 | 12/2015 | Paulsen et al. |
| 2016/0011204 | A1 | 1/2016 | Almo et al. |
| 2016/0083477 | A1 | 3/2016 | Klein et al. |
| 2016/0090407 | A1 | 3/2016 | Hosse et al. |
| 2016/0114019 | A1 | 4/2016 | Li et al. |
| 2016/0152725 | A1 | 6/2016 | Cheung et al. |
| 2016/0304580 | A1 | 10/2016 | Ellmark et al. |
| 2016/0362465 | A1 | 12/2016 | Nishimura et al. |
| 2017/0044229 | A1 | 2/2017 | Garcia et al. |
| 2017/0058015 | A1 | 3/2017 | Seidel, III et al. |
| 2017/0334951 | A1 | 11/2017 | O'Reilly et al. |
| 2018/0064795 | A1 | 3/2018 | Sugiyama |
| 2018/0208626 | A1 | 7/2018 | Scheinberg et al. |

FOREIGN PATENT DOCUMENTS

| | | |
|---|---|---|
| CN | 101448951 | 6/2009 |
| JP | 2000515363 | 11/2000 |
| JP | 2004501364 | 1/2004 |
| JP | 2005506058 | 3/2005 |
| JP | 2007530021 | 11/2007 |
| JP | 2009537175 | 10/2009 |
| JP | 2010524506 | 7/2010 |
| JP | 2012516854 | 7/2012 |
| JP | 2015537043 | 12/2015 |
| WO | WO 1997/028191 | 8/1997 |
| WO | WO 2001/090747 | 11/2001 |
| WO | WO 2002/072631 | 9/2002 |
| WO | WO 2002/087613 | 11/2002 |
| WO | WO 2002/093129 | 11/2002 |
| WO | WO 2002/102299 | 12/2002 |
| WO | WO 2004/029197 | 4/2004 |
| WO | WO 2004/111190 | 12/2004 |
| WO | WO 2007/136778 | 11/2007 |
| WO | WO 2008/019888 | 2/2008 |
| WO | WO 2008/116468 | 10/2008 |
| WO | WO 2008/134461 | 11/2008 |
| WO | WO 2010/037395 | 4/2010 |
| WO | WO 2010/091122 | 8/2010 |
| WO | WO 2011/066342 | 6/2011 |
| WO | WO 2011/066389 | 6/2011 |
| WO | WO 2012/127464 | 9/2012 |
| WO | WO 2012/175508 | 12/2012 |
| WO | WO 2013/003761 | 1/2013 |
| WO | WO 2014/083004 | 6/2014 |
| WO | WO 2014/093118 | 6/2014 |
| WO | WO 2015/112541 | 7/2015 |
| WO | WO 2015/164815 | 10/2015 |
| WO | WO 2015/195531 | 12/2015 |
| WO | WO 2016/000619 | 1/2016 |
| WO | WO 2016/014428 | 1/2016 |
| WO | WO 2016/029043 | 2/2016 |
| WO | WO 2016/164937 | 10/2016 |
| WO | WO 2016/168771 | 10/2016 |
| WO | WO 2017/023779 | 2/2017 |
| WO | WO 2017/059819 | 4/2017 |
| WO | WO 2017/151818 | 9/2017 |
| WO | WO 2017/151940 | 9/2017 |
| WO | WO 2017/201131 | 11/2017 |
| WO | WO 2019/051126 | 3/2019 |

OTHER PUBLICATIONS

Genebank:NP_001009066.1; 2 pages (2003).

Lazar-Molnar, et al.; "Crystal structure of the complex between programmed death-1 (PD-1) and its ligand PD-L2"; PNAS; vol. 105, No. 30, pp. 10483-10488 (Jul. 29, 2008).

Medina, et al.; "PD-1 Pathway Inhibitors: Immuno-Onology Agents for Restoring Anititumor Immune Responses"; Pharmacotherapy; vol. 36, No. 3, pp. 317-334 (2016).

Trolle, et al.; "The length distribution of class I restricted T cell epitopes is determined by both peptide supply and MHC allele specific binding preference"; J Immunol; vol. 196, No. 4, pp. 1480-1487 (Feb. 15, 2016).

Wang, et al.; "Molcular Modeling and Functional Mapping of B7-H1 and B7-DC Uncouple Costimulatory Function from PD-1 Interaction"; J. Exp. Med.; vol. 197, No. 9, pp. 1083-1091 (May 5, 2003).

Quayle, et al.; "CUE-101, a Novel E7-pHLA-IL2-Fc Fusion Protein, Enhances Tumor Antigen-Specific T-Cell Activation for the Treatment of HPV16-Driven Malignancies"; Clin Cancer Res; vol. 26, No. 8, pp. 1953-1964 (Jan. 21, 2020).

Lin, et al.; "The PD-1/PD-L1 complex resembles the antigen-binding Fv domains of antibodies and T cell receptors"; PNAS; vol. 105, No. 8, pps. 3011-3016 (Feb. 26, 2008).

Buonaguro, et al.; "Translating Tumor Antigens into Cancer Vaccines"; Clinical and Vaccine Immunology; vol. 18, No. 1, pps. 23-24 (Jan. 2011).

Celis, et al.; "Identification of Potential CTL Epitopes of Tumor-Associated Antigen Mage-1 for Five Common HLA-A Alleles"; Molecular Immunology; vol. 31, No. 18, pps. 1423-1430 (1994).

De Charette, et al.; "Turning tumour cells into antigen presenting cells: The next step to improve cancer immunotherapy?"; European Journal of Cancer; vol. 68, pps. 134-147 (2016).

HLA Nomenclature; "HLA Alleles Numbers"; 2 pages (Mar. 17, 2015).

Karin, et al.; "Reversal of Experimental Autoimmune Encephalomyelitis by a Soluble Peptide Variant of a Myelin Basic Protein Epitope: T Cell Receptor Antagonism and Reduction of Interferon y and Tumor Necrosis Factor a Production"; J. Exp. Med.; vol. 180, pp. 2227-2237 (Dec. 1994).

Martin-Orozco, et al.; "Melanoma Cells Express ICOS Ligand to Promote the Activation and Expansion of T-Regulatory Cells"; Cancer Research; vol. 70, No. 23, pp. 9581-9590 (2010).

Motz, et al.; "Tumor Endothelium FasL Establishes a Selective Immune Barrier Promoting Tolerance in Tumors"; Nat. Med.; vol. 20, No. 6, pp. 607-615 (Jun. 2014).

Ochoa-Garay, et al.; "The Ability of Peptides to Induce Cytotoxic T Cells in Vitro Does Not Strongly Correlate with Their Affinity for the H-2$L^d$Molecule: Implications for Vaccine Design and Immunotherapy"; Molecular Immunology; vol. 34, No. 3, pp. 273-281 (1997).

Repana, et al.; "The Network of Cancer Genes (NCG): a comprehensive catalogue of known and candidate cancer genes from cancer sequencing screens"; Genome Biology; vol. 20, No. 1, 12 pages (2019).

Schumacher, et al.; "Neoantigens in cancer immunotherapy"; Science; vol. 348, No. 6230, pp. 69- 74 (Apr. 2, 2015).

White, et al.; "Soluble Class I MHC with $\beta^2$-MicroglobulinCovalently Linked Peptides: Specific Binding to a T Cell Hybridoma"; J Immunol; vol. 162, pp. 2671-2676 (1999).

* cited by examiner

FIG. 2A

IL2 – *Homo sapiens*

APTSSSTKKT QLQLEHLLLD LQMILNGINN YKNPKLTRML TFKFYMPKKA TELKHLQCLE

EELKPLEEVL NLAQSKNFHL RPRDLISNIN VIVLELKGSE TTFMCEYADE TATIVEFLNR

WITFCQSIIS TLT (SEQ ID NO:1)

APTSSSTKKT QLQLEHLLLD LQMILNGINN YKNPKLTRML TXKFYMPKKA TELKHLQCLE

EELKPLEEVL NLAQSKNFHL RPRDLISNIN VIVLELKGSE TTFMCEYADE TATIVEFLNR

WITFCQSIIS TLT (SEQ ID NO:2)

APTSSSTKKT QLQLEHLLLX LQMILNGINN YKNPKLTRML TFKFYMPKKA TELKHLQCLE

EELKPLEEVL NLAQSKNFHL RPRDLISNIN VIVLELKGSE TTFMCEYADE TATIVEFLNR

WITFCQSIIS TLT (SEQ ID NO:3)

APTSSSTKKT QLQLXHLLLD LQMILNGINN YKNPKLTRML TFKFYMPKKA TELKHLQCLE

EELKPLEEVL NLAQSKNFHL RPRDLISNIN VIVLELKGSE TTFMCEYADE TATIVEFLNR

WITFCQSIIS TLT (SEQ ID NO:4)

APTSSSTKKT QLQLEXLLLD LQMILNGINN YKNPKLTRML TFKFYMPKKA TELKHLQCLE

EELKPLEEVL NLAQSKNFHL RPRDLISNIN VIVLELKGSE TTFMCEYADE TATIVEFLNR

WITFCQSIIS TLT (SEQ ID NO:5)

APTSSSTKKT QLQLEHLLLD LQMILNGINN YKNPKLTRML TFKFXMPKKA TELKHLQCLE

EELKPLEEVL NLAQSKNFHL RPRDLISNIN VIVLELKGSE TTFMCEYADE TATIVEFLNR

WITFCQSIIS TLT (SEQ ID NO:6)

APTSSSTKKT QLQLEHLLLD LQMILNGINN YKNPKLTRML TFKFYMPKKA TELKHLQCLE

EELKPLEEVL NLAQSKNFHL RPRDLISNIN VIVLELKGSE TTFMCEYADE TATIVEFLNR

WITFCXSIIS TLT (SEQ ID NO:7)

APTSSSTKKT QLQLEXLLLD LQMILNGINN YKNPKLTRML TXKFYMPKKA TELKHLQCLE

EELKPLEEVL NLAQSKNFHL RPRDLISNIN VIVLELKGSE TTFMCEYADE TATIVEFLNR

WITFCQSIIS TLT (SEQ ID NO:8)

APTSSSTKKT QLQLEHLLLX LQMILNGINN YKNPKLTRML TXKFYMPKKA TELKHLQCLE

EELKPLEEVL NLAQSKNFHL RPRDLISNIN VIVLELKGSE TTFMCEYADE TATIVEFLNR

WITFCQSIIS TLT (SEQ ID NO:9)

APTSSSTKKT QLQLXHLLLX LQMILNGINN YKNPKLTRML TXKFYMPKKA TELKHLQCLE

EELKPLEEVL NLAQSKNFHL RPRDLISNIN VIVLELKGSE TTFMCEYADE TATIVEFLNR

WITFCQSIIS TLT (SEQ ID NO:10)

APTSSSTKKT QLQLEXLLLX LQMILNGINN YKNPKLTRML TXKFYMPKKA TELKHLQCLE

EELKPLEEVL NLAQSKNFHL RPRDLISNIN VIVLELKGSE TTFMCEYADE TATIVEFLNR

WITFCQSIIS TLT (SEQ ID NO:11)

APTSSSTKKT QLQLEHLLLX LQMILNGINN YKNPKLTRML TXKFYMPKKA TELKHLQCLE

EELKPLEEVL NLAQSKNFHL RPRDLISNIN VIVLELKGSE TTFMCEYADE TATIVEFLNR

WITFCXSIIS TLT (SEQ ID NO:12)

APTSSSTKKT QLQLEHLLLX LQMILNGINN YKNPKLTRML TXKFXMPKKA TELKHLQCLE

EELKPLEEVL NLAQSKNFHL RPRDLISNIN VIVLELKGSE TTFMCEYADE TATIVEFLNR

WITFCQSIIS TLT (SEQ ID NO:13)

APTSSSTKKT QLQLEXLLLX LQMILNGINN YKNPKLTRML TXKFXMPKKA TELKHLQCLE

EELKPLEEVL NLAQSKNFHL RPRDLISNIN VIVLELKGSE TTFMCEYADE TATIVEFLNR

WITFCQSIIS TLT (SEQ ID NO:14)

APTSSSTKKT QLQLEHLLLX LQMILNGINN YKNPKLTRML TXKFXMPKKA TELKHLQCLE

EELKPLEEVL NLAQSKNFHL RPRDLISNIN VIVLELKGSE TTFMCEYADE TATIVEFLNR

WITFCXSIIS TLT (SEQ ID NO:15)

APTSSSTKKT QLQLEXLLLX LQMILNGINN YKNPKLTRML TXKFXMPKKA TELKHLQCLE

EELKPLEEVL NLAQSKNFHL RPRDLISNIN VIVLELKGSE TTFMCEYADE TATIVEFLNR

WITFCXSIIS TLT (SEQ ID NO:16)

APTSSSTKKT QLQLEXLLLD LQMILNGINN YKNPKLTRML TXKFYMPKKA TELKHLQCLE

EELKPLEEVL NLAQSKNFHL RPRDLISNIN VIVLELKGSE TTFMCEYADE TATIVEFLNR

WITFCXSIIS TLT (SEQ ID NO: 17)

FIG. 3A
IL2R-alpha chain
*Homo sapiens*

```
  1 MDSYLLMWGL LTFIMVPGCQ AELCDDDPPE IPHATFKAMA YKEGTMLNCE CKRGFRRIKS
 61 GSLYMLCTGN SSHSSWDNQC QCTSSATRNT TKQVTPQPEE QKERKTTEMQ SPMQPVDQAS
121 LPGHCREPPP WENEATERIY HFVVGQMVYY QCVQGYRALH RGPAESVCKM THGKTRWTQP
181 QLICTGEMET SQFPGEEKPQ ASPEGRPESE TSCLVTTTDF QIQTEMAATM ETSIFTTEYQ
241 VAVAGCVFLL ISVLLLSGLT WQRRQRKSRR TI   (SEQ ID NO:18)
```

Mature = amino acids 22-272

FIG. 3B
IL2R-beta chain
*Homo sapiens*

```
  1 MAAPALSWRL PLLILLLPLA TSWASAAVNG TSQFTCFYNS RANISCVWSQ DGALQDTSCQ
 61 VHAWPDRRRW NQTCELLPVS QASWACNLIL GAPDSQKLTT VDIVTLRVLC REGVRWRVMA
121 IQDFKPFENL RLMAPISLQV VHVETHRCNI SWEISQASHY FERHLEFEAR TLSPGHTWEE
181 APLLTLKQKQ EWICLETLTP DTQYEFQVRV KPLQGEFTTW SPWSQPLAFR TKPAALGKDT
241 IPWLGHLLVG LSGAFGFIIL VYLLINCRNT GPWLKKVLKC NTPDPSKFFS QLSSEHGGDV
301 QKWLSSPFPS SSFSPGGLAP EISPLEVLER DKVTQLLLQQ DKVPEPASLS SNHSLTSCFT
361 NQGYFFFHLP DALEIEACQV YFTYDPYSEE DPDEGVAGAP TGSSPQPLQP LSGEDDAYCT
421 FPSRDDLLLF SPSLLGGPSP PSTAPGGSGA GEERMPPSLQ ERVPRDWDPQ PLGPPTPGVP
481 DLVDFQPPPE LVLREAGEEV PDAGPREGVS FPWSRPPGQG EFRALNARLP LNTDAYLSLQ
541 ELQGQDPTHL V (SEQ ID NO:19)
```

Mature = amino acids 27-551

FIG. 3C
IL2R-gamma chain
*Homo sapiens*

```
  1 MLKPSLPFTS LLFLQLPLLG VGLNTTILTP NGNEDTTADF FLTTMPTDSL SVSTLPLPEV
 61 QCFVFNVEYM NCTWNSSSEP QPTNLTLHYW YKNSDNDKVQ KCSHYLFSEE ITSGCQLQKK
121 EIHLYQTFVV QLQDPREPRR QATQMLKLQN LVIPWAPENL TLHKLSESQL ELNWNNRFLN
181 HCLEHLVQYR TDWDHSWTEQ SVDYRHKFSL PSVDGQKRYT FRVRSRFNPL CGSAQHWSEW
241 SHPIHWGSNT SKENPFLFAL EAVVISVGSM GLIISLLCVY FWLERTMPRI PTLKNLEDLV
301 TEYHGNFSAW SGVSKGLAES LQPDYSERLC LVSEIPPKGG ALGEGPGASP CNQHSPYWAP
361 PCYTLKPET (SEQ ID NO:20)
```

Mature = amino acids 23-369

Figure 4A
GenBank 3S7G_A
*Homo sapiens* IgG1 Fc (SEQ ID NO: 21)
227 aa

```
  1 dkthtcppcp apellggpsv flfppkpkdt lmisrtpevt cvvvdvshed pevkfnwyvd
 61 gvevhnaktk preeqynsty rvvsvltvlh qdwlngkeyk ckvsnkalpa piektiskak
121 gqprepqvyt lppsrdeltk nqvsltclvk gfypsdiave wesngqpenn ykttppvlds
181 dgsfflyskl tvdksrwqqg nvfscsvmhe alhnhytqks lslspgk
```

GenBank AAN76044
*Homo sapiens* IgG2 Fc (amino acids 99-325) (SEQ ID NO: 22)
227 aa

```
  1 stkgpsvfpl apcsrstses taalgclvkd yfpepvtvsw nsgaltsgvh tfpavlqssg
 61 lyslssvvtv pssnfgtqty tcnvdhkpsn tkvdktverk ccvecppcpa ppvagpsvfl
121 fppkpkdtlm isrtpevtcv vvdvshedpe vqfnwyvdgv evhnaktkpr eeqfnstfrv
181 vsvltvvhqd wlngkeykck vsnkglpapi ektisktkgq prepqvytlp psreemtknq
241 vsltclvkgf ypsdiavewe sngqpennyk ttppmldsdg sfflyskltv dksrwqqgnv
301 fscsvmheal hnhytqksls lspgk
```

GenBank AAW65947
*Homo sapiens* IgG3 Fc (amino acids 19-246) (SEQ ID NO: 23)
238 aa

```
  1 hkpsntkvdk rvelktplgd tthtcppcpa pellggpsvf lfppkpkdtl misrtpevtc
 61 vvvdvshedp evkfnwyvdg vevhnaktkp reeqynstyr vvsvltvlhq dwlngkeykc
121 kvsnkalpap iektiskakg qprepqvytl ppsrdeltkn qvsltclvkg fypsdiavew
181 esngqpenny kttppvldsd gsfflysklt vdksrwqqgn vfscsvmhea lhnhytqksl
241 slspgk
```

Figure 4B

GenBank AAA52770
*Homo sapiens* IgD Fc (amino acids 162-383) (SEQ ID NO: 24)
222 aa

```
  1 ptkapdvfpi isgcrhpkdn spvvlaclit gyhptsvtvt wymgtqsqpq rtfpeiqrrd
 61 syymtssqls tplqqwrqge ykcvvqhtas kskkeifrwp espkaqassv ptaqpqaegs
121 lakattapat trntgrggee kkkekekeeq eeretktpec pshtqplgvy lltpavqdlw
181 lrdkatftcf vvgsdlkdah ltwevagkvp tggveeglle rhsngsqsqh srltlprslw
241 nagtsvtctl nhpslppqrl malrepaaqa pvklslnlla ssdppeaasw llcevsgfsp
301 pnillmwled qrevntsgfa parpppqprs ttfwawsvlr vpappspqpa tytcvvshed
361 srtllnasrs levsyvtdhg pmk
```

GenBank 0308221A
*Homo sapiens* IgM Fc (SEQ ID NO: 25)
276 aa

```
  1 vtstltikzs dwlgesmftc rvdhrgltfq qnassmcvpd qdtairvfai ppsfasiflt
 61 kstkltclvt dlttybsvti swtreengav kthtnisesh pnatfsavge asicedbdws
121 gerftctvth tdlpsplkqt isrpkgvalh rpbvyllppa rzzlnlresa titclvtgfs
181 padvfvewmq rgeplspqky vtsapmpepq apgryfahsi ltvseeewnt ggtytcvvah
241 ealpnrvter tvdkstgkpt lynvslvmsd tagtcy
```

Figure 4C

GenBank P01876
*Homo sapiens* IgA Fc (amino acids 120-353) (SEQ ID NO: 26)
234 aa

```
  1 asptspkvfp lslcstqpdg nvviaclvqg ffpqeplsvt wsesgqgvta rnfppsqdas
 61 gdlyttssql tlpatqclag ksvtchvkhy tnpsqdvtvp cpvpstpptp spstpptpsp
121 scchprlslh rpaledlllg seanltctlt glrdasgvtf twtpssgksa vqgpperdlc
181 gcysvssvlp gcaepwnhgk tftctaaype sktpltatls ksgntfrpev hllpppseel
241 alnelvtltc largfspkdv lvrwlqgsqe lprekyltwa srqepsqgtt tfavtsilrv
301 aaedwkkgdt fscmvgheal plaftqktid rlagkpthvn vsvvmaevdg tcy
```

GenBank 1F6A_B
*Homo sapiens* IgE Fc (amino acids 6-222) (SEQ ID NO: 27)
212 aa

```
  1 adpcdsnprg vsaylsrpsp fdlfirkspt itclvvdlap skgtvnltws rasgkpvnhs
 61 trkeekqrng tltvtstlpv gtrdwieget yqcrvthphl pralmrsttk tsgpraapev
121 yafatpewpg srdkrtlacl iqnfmpedis vqwlhnevql pdarhsttqp rktkgsgffv
181 fsrlevtrae weqkdeficr avheaaspsq tvqravsvnp gk
```

GenBank P01861
*Homo sapiens* IgG4 Fc (amino acids 100-327) (SEQ ID NO: 28)
228 aa

```
  1 astkgpsvfp lapcsrstse staalgclvk dyfpepvtvs wnsgaltsgv htfpavlqss
 61 glyslssvvt vpssslgtkt ytcnvdhkps ntkvdkrves kygppcpscp apeflggpsv
121 flfppkpkdt lmisrtpevt cvvvdvsqed pevqfnwyvd gvevhnaktk preeqfnsty
181 rvvsvltvlh qdwlngkeyk ckvsnkglps siektiskak gqprepqvyt lppsqeemtk
241 nqvsltclvk gfypsdiave wesngqpenn ykttppvlds dgsfflysrl tvdksrwqeg
301 nvfscsvmhe alhnhytqks lslslgk
```

Figure 5A
*Homo sapiens*
GenBank NP_001229687
HLA-A
Amino acids 25-365 (SEQ ID NO: 29)

```
  1 mavmaprtll lllsgalalt qtwagshsmr yfftsvsrpg rgeprfiavg yvddtqfvrf
 61 dsdaasqkme prapwieqeg peywdqetrn mkahsqtdra nlgtlrgyyn qsedgshtiq
121 imygcdvgpd grflrgyrqd aydgkdyial nedlrswtaa dmaaqitkrk weavhaaeqr
181 rvylegrcvd glrrylengk etlqrtdppk thmthhpisd heatlrcwal gfypaeitlt
241 wqrdgedqtq dtelvetrpa gdgtfqkwaa vvvpsgeeqr ytchvqhegl pkpltlrwel
301 ssqptipivg iiaglvllga vitgavvaav mwrrkssdrk ggsytqaass dsaqgsdvsl
361 tackv
```

Figure 5B
*Homo sapiens*
GenBank NP_005505
HLA-B
Amino acids 25-362 (SEQ ID NO: 30)

```
  1 mlvmaprtvl lllsaalalt etwagshsmr yfytsvsrpg rgeprfisvg yvddtqfvrf
 61 dsdaaspree prapwieqeg peywdrntqi ykaqaqtdre slrnlrgyyn qseagshtlq
121 smygcdvgpd grllrghdqy aydgkdyial nedlrswtaa dtaaqitqrk weaareaeqr
181 raylegecve wlrrylengk dkleradppk thvthhpisd heatlrcwal gfypaeitlt
241 wqrdgedqtq dtelvetrpa gdrtfqkwaa vvvpsgeeqr ytchvqhegl pkpltlrwep
301 ssqstvpivg ivaglavlav vvigavvaav mcrrkssggk ggsysqaacs dsaqgsdvsl
361 ta
```

Figure 5C
*Homo sapiens*
GenBank NP_001229971
HLA-C
Amino acids 25-366 (SEQ ID NO: 31)

1 mrvmaprall lllsgglalt etwacshsmr yfdtavsrpg rgeprfisvg yvddtqfvrf
61 dsdaasprge prapwveqeg peywdretqn ykrqaqadrv slrnlrgyyn qsedgshtlq
121 rmygcdlgpd grllrgydqs aydgkdyial nedlrswtaa dtaaqitqrk leaaraaeql
181 raylegtcve wlrrylengk etlqraeppk thvthhplsd heatlrcwal gfypaeitlt
241 wqrdgedqtq dtelvetrpa gdgtfqkwaa vvvpsgqeqr ytchmqhegl qepltlswep
301 ssqptipimg ivaglavlvv lavlgavvta mmcrrkssgg kggscsqaac snsaqgsdes
361 litcka

FIG. 6

| | | |
|---|---|---|
| NP_004039.1 | MSRSVALAVLALLSLSGLEAIQRTPKIQVYSRHPAENGKSNFLNCYVSGFHPSDIEVDLL | 60 |
| NP_001009066.1 | MSRSVALAVLALLSLSGLEAIQRTPKIQVYSRHPAENGKSNFLNCYVSGFHPSDIEVDLL | 60 |
| NP_001046602.1 | MSRSVALAVLALLSLSGLEAIQRTPKIQVYSRHPENGKPNFLNCYVSGFHPSDIEVDLL | 60 |
| NP_776318.1 | MARFVALVLLGLLSLSGLDAIQREPKIQVYSRHPPEDGKPNYLNCYVYGFHPPQIEIDLL | 60 |
| NP_033865.2 | MARSVTLVFLVFLVLVSLTGLYAIQKTPQIQVYSRHPENGKPMILNCYVTQFHPPHIETQML | 60 |
| | *:*  *:  **  :*  *:*****  ****: **.:*   *  ***.: ***.. *** |  |
| NP_004039.1 | KNGERIEKVEHSDLSFSKDWSFYLLYYTEFTPTEKDEYACRVNHVTLSQPKIVKWDRDM | 119 |
| NP_001009066.1 | KNGERIEKVEHSDLSFSKDWSFYLLYYTEFTPTEKDEYACRVNHVTLSQPKIVKWDRDM | 119 |
| NP_001046602.1 | KNGERMGKVEHSDLSFSKDWSFYLLYYTEFTPNEKDEYACRVNHVTLSGPRTVKWDRDM | 119 |
| NP_776318.1 | KNGEKI-KSEQSDLSFSKDWSFYLLSHAEFTPNSKDQYSCRVKHVTLEQPRIVKWDRDL | 118 |
| NP_033865.2 | KNGKKIPKVVEMSDMSFSKDWSFVILAHTEFTPTETDTYACRVKHASMAEPKTVYWDRDM | 119 |
| | ****.:  *  ** **:********:::   ****: * ::*** :::::  * ::****  |  |

Number of IL-2 Repeats versus Mutations

FIG. 14A
One copy of IL-2
Mutation: F42A, D20K
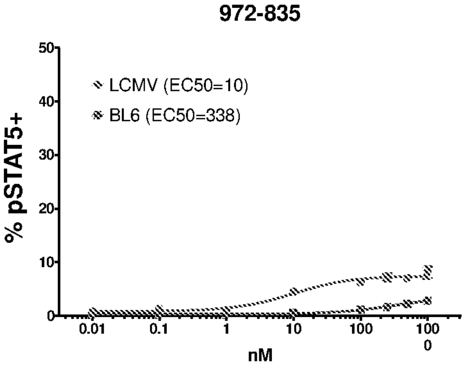
Mutation: F42A, D20K, Q126A
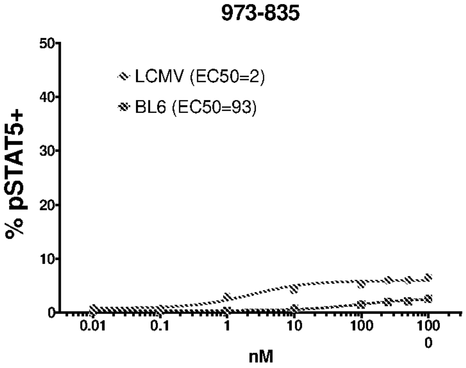
Mutation: F42A, D20K, E15A
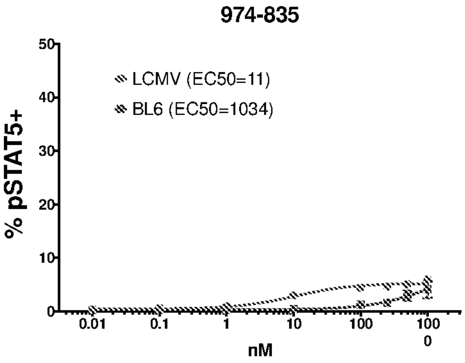
Mutation: F42A, D20K, H16A
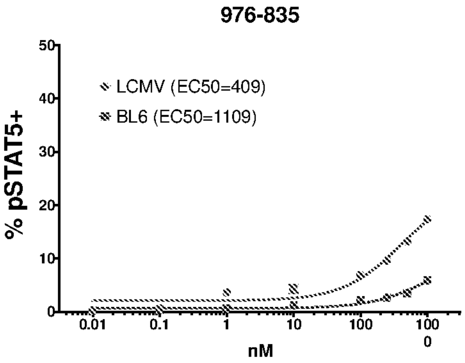

FIG. 14B
One copy of IL-2
Mutation: F42A, Y45A, D20K, H16A
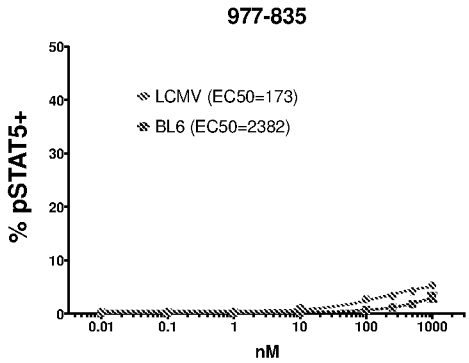
Mutation: F42A, Y45A, D20K
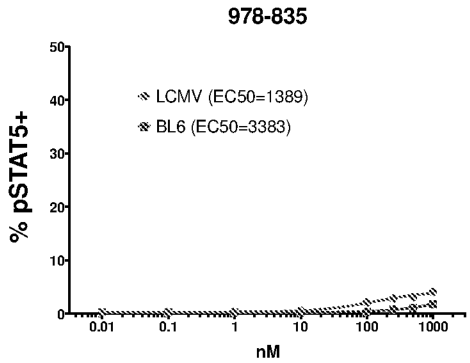
Mutation: F42A, Y45A, D20K, H16A, Q126A
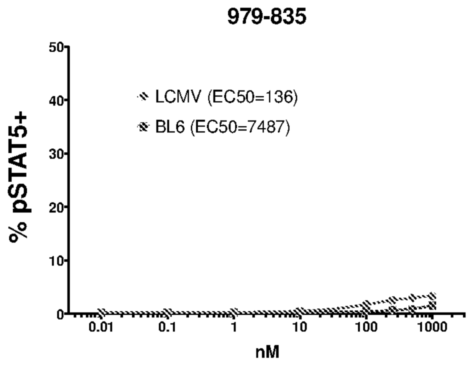
Mutation: F42A, Y45A, D20K, Q126A
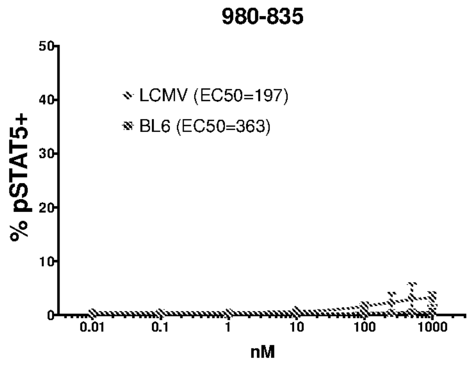

FIG. 14C
Two copies of IL-2
Mutation: F42A, D20K
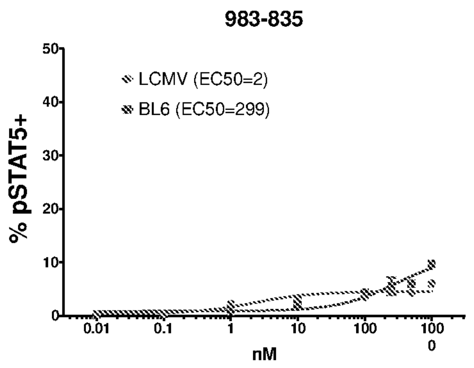
Mutation: F42A, D20K, Q126A
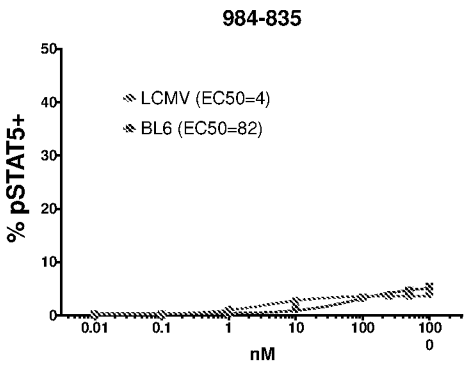
Mutation: F42A, D20K, H16A
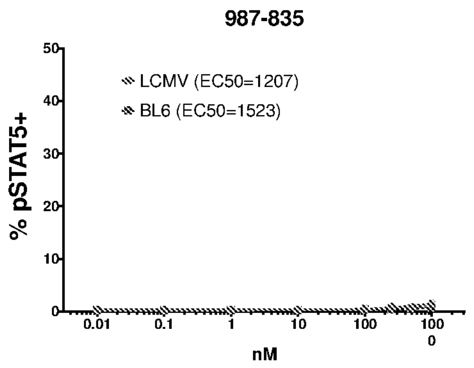

FIG. 14D
Two copies of IL-2
Mutation: F42A, Y45A, D20K, H16A
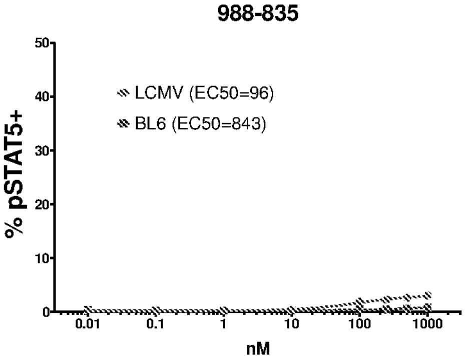
Mutation: F42A, Y45A, D20K
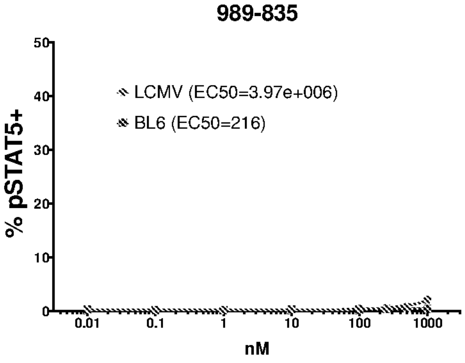
Mutation: F42A, Y45A, D20K, H16A, Q126A
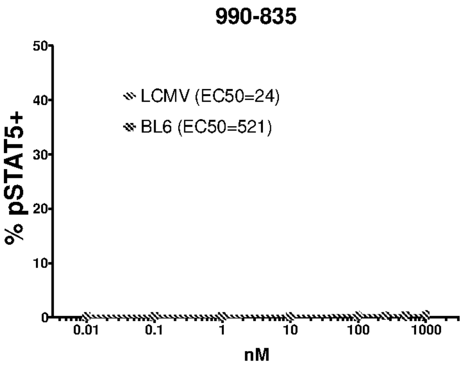
Mutation: F42A, Y45A, D20K, Q126A
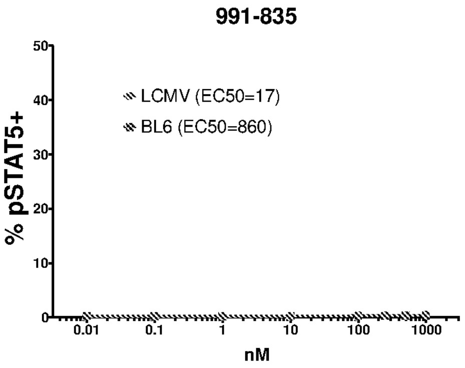

FIG. 14E
Three copies of IL-2
Mutation: F42A, D20K
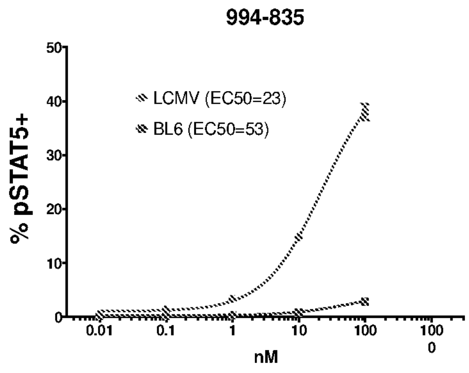
Mutation: F42A, D20K, E15A
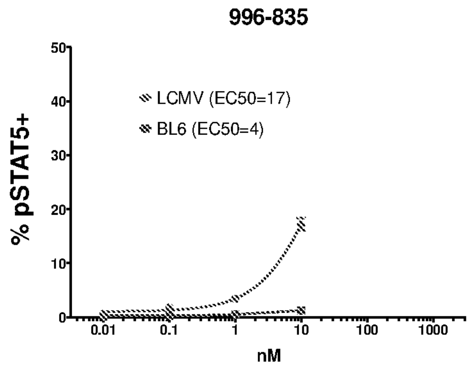
Mutation: F42A, D20K, H16A
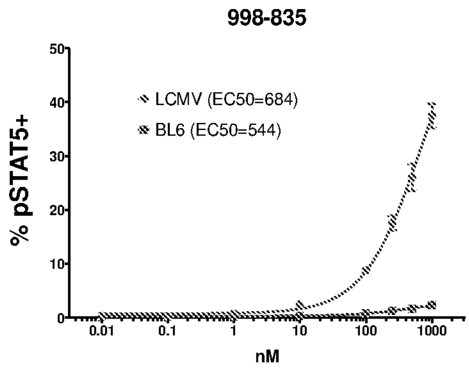

FIG. 14F
Three copies of IL-2
Mutation: F42A, Y45A, D20K, H16A
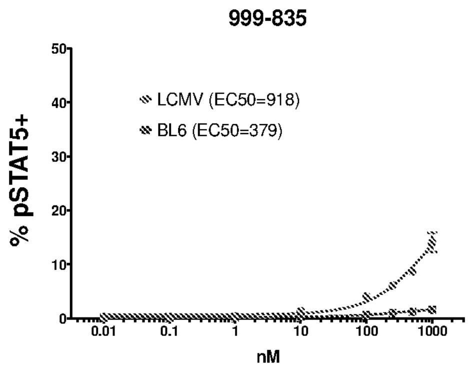
Mutation: F42A, Y45A, D20K
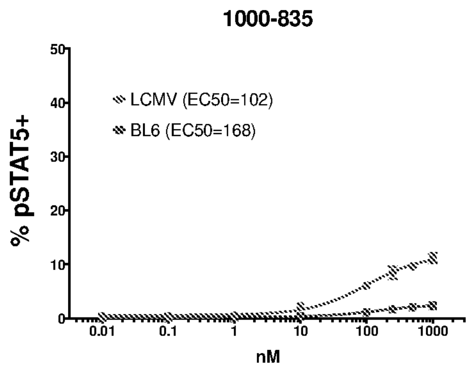
Mutation: F42A, Y45A, D20K, H16A, Q126A
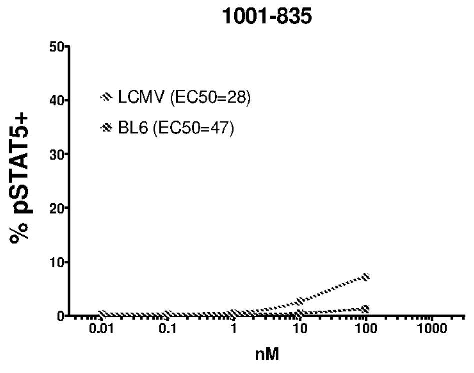
Mutation: F42A, Y45A, D20K, Q126A
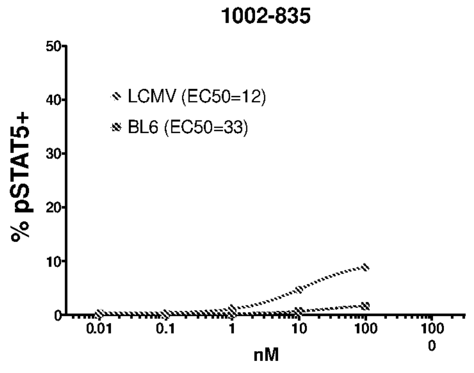

FIG. 21 (SEQ ID NO:32)
CUE101-N297A with leader peptide
*MYRMQLLSCIALSLALVTNS*APTSSSTKKTQLQLEALLLDLQMILNGINNYKNPKLTRML
TAKFYMPKKATELKHLQCLEEELKPLEEVLNLAQSKNFHLRPRDLISNINVIVLELKGSE
TTFMCEYADETATIVEFLNRWITFCQSIISTLTGGGGSGGGGSGGGGSGGGGSAPTSSST
KKTQLQLEALLLDLQMILNGINNYKNPKLTRMLTAKFYMPKKATELKHLQCLEEELKPLE
EVLNLAQSKNFHLRPRDLISNINVIVLELKGSETTFMCEYADETATIVEFLNRWITFCQS
IISTLTGGGGSGGGGSGGGGSGGGGSGSHSMRYFFTSVSRPGRGEPRFIAVGYVDDTQFV
RFDSDAASQRMEPRAPWIEQEGPEYWDGETRKVKAHSQTHRVDLGTLRGAYNQSEAGSHT
VQRMYGCDVGSDWRFLRGYHQYAYDGKDYIALKEDLRSWTAADMAAQTTKHKWEAAHVAE
QLRAYLEGTCVEWLRRYLENGKETLQRTDAPKTHMTHHAVSDHEATLRCWALSFYPAEIT
LTWQRDGEDQTQDTELVETRPCGDGTFQKWAAVVVPSGQEQRYTCHVQHEGLPKPLTLRW
EAAAGGDKTHTCPPCPAPELLGGPSVFLFPPKPKDTLMISRTPEVTCVVVDVSHEDPEVK
FNWYVDGVEVHNAKTKPREEQYASTYRVVSVLTVLHQDWLNGKEYKCKVSNKALPAPIEK
TISKAKGQPREPQVYTLPPSREEMTKNQVSLTCLVKGFYPSDIAVEWESNGQPENNYKTT
PPVLDSDGSFFLYSKLTVDKSRWQQGNVFSCSVMHEALHNHYTQKSLSLSPGK Human IL2 Leader sequence – italics
IL-2 (H16A/F42A) – bold (with H16 and F42 underlined)
(G4S)4 Linkers – single underlined
MHC H chain Y84A; A236C– double underlined (with Y84A and A236C in bold)
AAAGG linker – single underlined
Human IgG1 Fc; N297A – (bold and underlined, with N297A unbolded)

FIG. 22 (SEQ ID NO:33)
CUE101-N297A without leader peptide

APTSSSTKKTQLQLEALLLDLQMILNGINNYKNPKLTRML
TAKFYMPKKATELKHLQCLEEELKPLEEVLNLAQSKNFHLRPRDLISNINVIVLELKGSE
TTFMCEYADETATIVEFLNRWITFCQSIISTLTGGGGSGGGGSGGGGSGGGGSAPTSSST
KKTQLQLEALLLDLQMILNGINNYKNPKLTRMLTAKFYMPKKATELKHLQCLEEELKPLE
EVLNLAQSKNFHLRPRDLISNINVIVLELKGSETTFMCEYADETATIVEFLNRWITFCQS
IISTLTGGGGSGGGGSGGGGSGGGGSGSHSMRYFFTSVSRPGRGEPRFIAVGYVDDTQFV
RFDSDAASQRMEPRAPWIEQEGPEYWDGETRKVKAHSQTHRVDLGTLRGAYNQSEAGSHT
VQRMYGCDVGSDWRFLRGYHQYAYDGKDYIALKEDLRSWTAADMAAQTTKHKWEAAHVAE
QLRAYLEGTCVEWLRRYLENGKETLQRTDAPKTHMTHHAVSDHEATLRCWALSFYPAEIT
LTWQRDGEDQTQDTELVETRPCGDGTFQKWAAVVVPSGQEQRYTCHVQHEGLPKPLTLRW
EAAAGG DKTHTCPPCPAPELLGGPSVFLFPPKPKDTLMISRTPEVTCVVVDVSHEDPEVK
FNWYVDGVEVHNAKTKPREEQYASTYRVVSVLTVLHQDWLNGKEYKCKVSNKALPAPIEK
TISKAKGQPREPQVYTLPPSREEMTKNQVSLTCLVKGFYPSDIAVEWESNGQPENNYKTT
PPVLDSDGSFFLYSKLTVDKSRWQQGNVFSCSVMHEALHNHYTQKSLSLSPGK

IL-2 (H16A/F42A) – bold (with H16 and F42 underlined)
(G4S)4 Linkers – single underlined
MHC H chain Y84A; A236C– double underlined (with Y84A and A236C in bold)
AAAGG linker – single underlined
Human IgG1 Fc; N297A – (bold and underlined, with N297A unbolded)

FIG. 23A (SEQ ID NO:34)

CUE101-N297A

1360:

*ATGTACAGGATGCAACTCCTGTCTTGCATTGCACTAAGTCTTGCACTTGTCACAAACAGT*GCACCTACTTC
AAGTTCTACAAAGAAAACACAGCTACAACTGGAGGCATTACTGCTGGATTTACAGATGATTTTGAATG
GAATTAATAATTACAAGAATCCCAAACTCACCAGGATGCTCACAGCAAAGTTTTACATGCCCAAGAAG
GCCACAGAACTGAAACATCTTCAGTGTCTAGAAGAAGAACTCAAACCTCTGGAGGAAGTGCTAAATTT
AGCTCAAAGCAAAAACTTTCACTTAAGACCCAGGGACTTAATCAGCAATATCAACGTAATAGTTCTGGA
ACTAAAGGGATCTGAAACAACATTCATGTGTGAATATGCTGATGAGACAGCAACCATTGTAGAATTTC
TGAACAGATGGATTACCTTTTGTCAAAGCATCATCTCAACACTGACTGGAGGCGGAGGATCTGGTGGTG
GAGGTTCTGGTGGTGGGGGATCTGGAGGCGGAGGATCTGCACCTACTTCAAGTTCTACAAAGAAAACA
CAGCTACAACTGGAGGCATTACTGCTGGATTTACAGATGATTTTGAATGGAATTAATAATTACAAGAAT
CCCAAACTCACCAGGATGCTCACAGCAAAGTTTTACATGCCCAAGAAGGCCACAGAACTGAAACATCTT
CAGTGTCTAGAAGAAGAACTCAAACCTCTGGAGGAAGTGCTAAATTTAGCTCAAAGCAAAAACTTTCA
CTTAAGACCCAGGGACTTAATCAGCAATATCAACGTAATAGTTCTGGAACTAAAGGGATCTGAAACAA
CATTCATGTGTGAATATGCTGATGAGACAGCAACCATTGTAGAATTTCTGAACAGATGGATTACCTTTT
GTCAAAGCATCATCTCAACACTGACTGGAGGCGGAGGATCTGGTGGTGGAGGTTCTGGTGGTGGGGGA
TCTGGAGGCGGAGGATCTGGCTCTCACTCCATGAGGTATTTCTTCACATCCGTGTCCCGGCCCGGCCGCG
GGGAGCCCCGCTTCATCGCAGTGGGCTACGTGGACGACACGCAGTTCGTGCGGTTCGACAGCGACGCCG
CGAGCCAGAGGATGGAGCCGCGGGCGCCGTGGATAGAGCAGGAGGGTCCGGAGTATTGGGACGGGGA
GACACGGAAAGTGAAGGCCCACTCACAGACTCACCGAGTGGACCTGGGGACCCTGCGCGGCGCCTACA
ACCAGAGCGAGGCCGGTTCTCACACCGTCCAGAGGATGTATGGCTGCGACGTGGGGTCGGACTGGCGC
TTCCTCCGCGGGTACCACCAGTACGCCTACGACGGCAAGGATTACATCGCCCTGAAAGAGGACCTGCGCT
CTTGGACCGCGGCGGACATGGCAGCTCAGACCACCAAGCACAAGTGGGAGGCGGCCCATGTGGCGGAG
CAGTTGAGAGCCTACCTGGAGGGCACGTGCGTGGAGTGGCTCCGCAGATACCTGGAGAACGGGAAGGA
GACGCTGCAGCGCACGGACGCCCCCAAAACGCATATGACTCACCACGCTGTCTCTGACCATGAAGCCACC
CTGAGGTGCTGGGCCCTGAGCTTCTACCCTGCGGAGATCACACTGACCTGGCAGCGGGATGGGGAGGA
CCAGACCCAGGACACGGAGCTCGTGGAGACCAGGCCTTGCGGGGATGGAACCTTCCAGAAGTGGGCGG
CTGTGGTGGTGCCTTCTGGACAGGAGCAGAGATACACCTGCCATGTGCAGCATGAGGGTTTGCCCAAGC
CCCTCACCCTGAGATGGGAGGCAGCTGCGGGTGGCGACAAAACTCACACATGCCCACCGTGCCCAGCA
CCTGAACTCCTGGGGGGACCGTCAGTCTTCCTCTTCCCCCCAAAACCCAAGGACACCCTCATGATCTCCC
GGACCCCTGAGGTCACATGCGTGGTGGTGGACGTGAGCCACGAAGACCCTGAGGTCAAGTTCAACTG
GTACGTGGACGGCGTGGAGGTGCATAATGCCAAGACAAAGCCGCGGGAGGAGCAGTACGCAAGCAC
GTACCGTGTGGTCAGCGTCCTCACCGTCCTGCACCAGGACTGGCTGAATGGCAAGGAGTACAAGTGCA
AGGTCTCCAACAAAGCCCTCCCAGCCCCCATCGAGAAAACCATCTCCAAAGCCAAAGGGCAGCCCCGA
GAACCACAGGTGTACACCCTGCCCCCATCCCGGGAGGAGATGACCAAGAACCAGGTCAGCCTGACCTG
CCTGGTCAAAGGCTTCTATCCCAGCGACATCGCCGTGGAGTGGGAGAGCAATGGGCAGCCGGAGAAC
AACTACAAGACCACGCCTCCCGTGCTGGACTCCGACGGCTCCTTCTTCCTCTACAGCAAGCTCACCGTGG
ACAAGAGCAGATGGCAGCAGGGGAACGTCTTCTCATGCTCCGTGATGCACGAGGCTCTGCACAACCAC
TACACGCAGAAGTCCCTCTCCCTGTCTCCGGGTAAATAGTGA

FIG. 23B

Human IL2 Leader sequence – italics

Human IL2; H16A=GCA; F42A=GCA – bold (with GCA underlined)

(G4S)4 linker – single underlined

Human A0201; Y84A=GCC; A236C=TGC

AAAGG linker – single underlined

Human IgG1 Fc; N297A= *GCA*; AGG to AGA (still R) and AGC to TCC (still S) – (bold and underlined, with GCA italicized)

Stop codons (TAGTGA)

FIG. 24 (SEQ ID NO:35)

CUE101-LALA with leader peptide

*MYRMQLLSCIALSLALVTNS*APTSSSTKKTQLQLEALLLDLQMILNGINNYKNPKLTRML
TAKFYMPKKATELKHLQCLEEELKPLEEVLNLAQSKNFHLRPRDLISNINVIVLELKGSE
TTFMCEYADETATIVEFLNRWITFCQSIISTLTGGGGSGGGGSGGGGSGGGGSAPTSSST
KKTQLQLEALLLDLQMILNGINNYKNPKLTRMLTAKFYMPKKATELKHLQCLEEELKPLE
EVLNLAQSKNFHLRPRDLISNINVIVLELKGSETTFMCEYADETATIVEFLNRWITFCQS
IISTLTGGGGSGGGGSGGGGSGGGGSGSHSMRYFFTSVSRPGRGEPRFIAVGYVDDTQFV
RFDSDAASQRMEPRAPWIEQEGPEYWDGETRKVKAHSQTHRVDLGTLRGAYNQSEAGSHT
VQRMYGCDVGSDWRFLRGYHQYAYDGKDYIALKEDLRSWTAADMAAQTTKHKWEAAHVAE
QLRAYLEGTCVEWLRRYLENGKETLQRTDAPKTHMTHHAVSDHEATLRCWALSFYPAEIT
LTWQRDGEDQTQDTELVETRPCGDGTFQKWAAVVVPSGQEQRYTCHVQHEGLPKPLTLRW
EAAAGGDKTHTCPPCPAPEAAGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIEK
TISKAKGQPREPQVYTLPPSREEMTKNQVSLTCLVKGFYPSDIAVEWESNGQPENNYKTT
PPVLDSDGSFFLYSKLTVDKSRWQQGNVFSCSVMHEALHNHYTQKSLSLSPGK

Leader peptide – italics

IL-2 (H16A/F42A) – bold (with H16 and F42 underlined)

(G4S)4 Linkers – single underlined

MHC H chain Y84A; A236C– double underlined (with Y84A and A236C in bold)

AAAGG linker – single underlined

Human IgG1 Fc; L234A; L235A – (bold and underlined, with L234A and L235A unbolded)

FIG. 25 (SEQ ID NO:36)

CUE101-LALA without leader peptide

APTSSSTKKTQLQLEALLLDLQMILNGINNYKNPKLTRML
TAKFYMPKKATELKHLQCLEEELKPLEEVLNLAQSKNFHLRPRDLISNINVIVLELKGSE
TTFMCEYADETATIVEFLNRWITFCQSIISTLTGGGGSGGGGSGGGGSGGGGSAPTSSST
KKTQLQLEALLLDLQMILNGINNYKNPKLTRMLTAKFYMPKKATELKHLQCLEEELKPLE
EVLNLAQSKNFHLRPRDLISNINVIVLELKGSETTFMCEYADETATIVEFLNRWITFCQS
IISTLTGGGGSGGGGSGGGGSGGGGSGSHSMRYFFTSVSRPGRGEPRFIAVGYVDDTQFV
RFDSDAASQRMEPRAPWIEQEGPEYWDGETRKVKAHSQTHRVDLGTLRGAYNQSEAGSHT
VQRMYGCDVGSDWRFLRGYHQYAYDGKDYIALKEDLRSWTAADMAAQTTKHKWEAAHVAE
QLRAYLEGTCVEWLRRYLENGKETLQRTDAPKTHMTHHAVSDHEATLRCWALSFYPAEIT
LTWQRDGEDQTQDTELVETRPCGDGTFQKWAAVVVPSGQEQRYTCHVQHEGLPKPLTLRW
EAAAGGDKTHTCPPCPAPEAAGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIEK
TISKAKGQPREPQVYTLPPSREEMTKNQVSLTCLVKGFYPSDIAVEWESNGQPENNYKTT
PPVLDSDGSFFLYSKLTVDKSRWQQGNVFSCSVMHEALHNHYTQKSLSLSPGK

IL-2 (H16A/F42A) – bold (with H16 and F42 underlined)

(G4S)4 Linkers – single underlined

MHC H chain Y84A; A236C– double underlined (with Y84A and A236C in bold)

AAAGG linker – single underlined

Human IgG1 Fc; L234A; L235A – (bold and underlined, with L234A and L235A unbolded)

FIG. 26A (SEQ ID NO:37)

CUE101-LALA: nucleotide sequence encoding CUE101-LALA with leader peptide

*ATGTACAGGATGCAACTCCTGTCTTGCATTGCACTAAGTCTTGCACTTGTCACAAACAGT*GCACCTACTTC
AAGTTCTACAAAGAAAACACAGCTACAACTGGAGGCATTACTGCTGGATTTACAGATGATTTTGAATG
GAATTAATAATTACAAGAATCCCAAACTCACCAGGATGCTCACAGCAAAGTTTTACATGCCCAAGAAG
GCCACAGAACTGAAACATCTTCAGTGTCTAGAAGAAGAACTCAAACCTCTGGAGGAAGTGCTAAATTT
AGCTCAAAGCAAAAACTTTCACTTAAGACCCAGGGACTTAATCAGCAATATCAACGTAATAGTTCTGGA
ACTAAAGGGATCTGAAACAACATTCATGTGTGAATATGCTGATGAGACAGCAACCATTGTAGAATTTC
TGAACAGATGGATTACCTTTTGTCAAAGCATCATCTCAACACTGACTGGAGGCGGAGGATCTGGTGGTG
GAGGTTCTGGTGGTGGGGGATCTGGAGGCGGAGGATCTGCACCTACTTCAAGTTCTACAAAGAAAACA
CAGCTACAACTGGAGGCATTACTGCTGGATTTACAGATGATTTTGAATGGAATTAATAATTACAAGAAT
CCCAAACTCACCAGGATGCTCACAGCAAAGTTTTACATGCCCAAGAAGGCCACAGAACTGAAACATCTT
CAGTGTCTAGAAGAAGAACTCAAACCTCTGGAGGAAGTGCTAAATTTAGCTCAAAGCAAAAACTTTCA
CTTAAGACCCAGGGACTTAATCAGCAATATCAACGTAATAGTTCTGGAACTAAAGGGATCTGAAACAA
CATTCATGTGTGAATATGCTGATGAGACAGCAACCATTGTAGAATTTCTGAACAGATGGATTACCTTTT
GTCAAAGCATCATCTCAACACTGACTGGAGGCGGAGGATCTGGTGGTGGAGGTTCTGGTGGTGGGGGA
TCTGGAGGCGGAGGATCTGGCTCTCACTCCATGAGGTATTTCTTCACATCCGTGTCCCGGCCCGGCCGCG
GGGAGCCCCGCTTCATCGCAGTGGGCTACGTGGACGACACGCAGTTCGTGCGGTTCGACAGCGACGCCG
CGAGCCAGAGGATGGAGCCGCGGGCGCCGTGGATAGAGCAGGAGGGTCCGGAGTATTGGGACGGGGA
GACACGGAAAGTGAAGGCCCACTCACAGACTCACCGAGTGGACCTGGGGACCCTGCGCGGCGCCTACA
ACCAGAGCGAGGCCGGTTCTCACACCGTCCAGAGGATGTATGGCTGCGACGTGGGGTCGGACTGGCGC
TTCCTCCGCGGGTACCACCAGTACGCCTACGACGGCAAGGATTACATCGCCCTGAAAGAGGACCTGCGCT
CTTGGACCGCGGCGGACATGGCAGCTCAGACCACCAAGCACAAGTGGGAGGCGGCCCATGTGGCGGAG
CAGTTGAGAGCCTACCTGGAGGGCACGTGCGTGGAGTGGCTCCGCAGATACCTGGAGAACGGGAAGGA
GACGCTGCAGCGCACGGACGCCCCCAAAACGCATATGACTCACCACGCTGTCTCTGACCATGAAGCCACC
CTGAGGTGCTGGGCCCTGAGCTTCTACCCTGCGGAGATCACACTGACCTGGCAGCGGGATGGGGAGGA
CCAGACCCAGGACACGGAGCTCGTGGAGACCAGGCCTTGCGGGGATGGAACCTTCCAGAAGTGGGCGG
CTGTGGTGGTGCCTTCTGGACAGGAGCAGAGATACACCTGCCATGTGCAGCATGAGGGTTTGCCCAAGC
CCCTCACCCTGAGATGGGAGGCAGCTGCGGGTGGCGACAAAACTCACACATGCCCACCGTGCCCAGCA
CCTGAAGCCGCCGGGGGACCGTCAGTCTTCCTCTTCCCCCCAAAACCCAAGGACACCCTCATGATCTCCC
GGACCCCTGAGGTCACATGCGTGGTGGTGGACGTGAGCCACGAAGACCCTGAGGTCAAGTTCAACTG
GTACGTGGACGGCGTGGAGGTGCATAATGCCAAGACAAAGCCGCGGGAGGAGCAGTACAACAGCAC
GTACCGTGTGGTCAGCGTCCTCACCGTCCTGCACCAGGACTGGCTGAATGGCAAGGAGTACAAGTGCA
AGGTCTCCAACAAAGCCCTCCCAGCCCCCATCGAGAAAACCATCTCCAAAGCCAAAGGGCAGCCCCGA
GAACCACAGGTGTACACCCTGCCCCCATCCCGGGAGGAGATGACCAAGAACCAGGTCAGCCTGACCTG
CCTGGTCAAAGGCTTCTATCCCAGCGACATCGCCGTGGAGTGGGAGAGCAATGGGCAGCCGGAGAAC
AACTACAAGACCACGCCTCCCGTGCTGGACTCCGACGGCTCCTTCTTCCTCTACAGCAAGCTCACCGTGG
ACAAGAGCAGATGGCAGCAGGGGAACGTCTTCTCATGCTCCGTGATGCACGAGGCTCTGCACAACCAC
TACACGCAGAAGTCCCTCTCCCTGTCTCCGGGTAAATAGTGA

FIG. 26B

Human IL2 Leader sequence – italics
Human IL2; H16A=GCA; F42A=GCA – bold (with GCA underlined)
(G4S)4 linker – single underlined
Human A0201; Y84A=GCC; A236C=TGC – double underlined (with GCC and TGC in bold)
AAAGG linker – single underlined
Human IgG1 Fc; L234A, L235A = GCCGCC
N297= AAC; AGG to AGA (still R) and AGC to TCC (still S) – (bold and underlined, with GCCGCC italicized)
Stop codons (TAGTGA)

FIG. 27 (SEQ ID NO:38)

CUE101-TM with leader peptide

MYRMQLLSCIALSLALVTNSAPTSSSTKKTQLQLEALLLDLQMILNGINNYKNPKLTRML
TAKFYMPKKATELKHLQCLEEELKPLEEVLNLAQSKNFHLRPRDLISNINVIVLELKGSE
TTFMCEYADETATIVEFLNRWITFCQSIISTLTGGGGSGGGGSGGGGSGGGGSAPTSSST
KKTQLQLEALLLDLQMILNGINNYKNPKLTRMLTAKFYMPKKATELKHLQCLEEELKPLE
EVLNLAQSKNFHLRPRDLISNINVIVLELKGSETTFMCEYADETATIVEFLNRWITFCQS
IISTLTGGGGSGGGGSGGGGSGGGGSGSHSMRYFFTSVSRPGRGEPRFIAVGYVDDTQFV
RFDSDAASQRMEPRAPWIEQEGPEYWDGETRKVKAHSQTHRVDLGTLRGAYNQSEAGSHT
VQRMYGCDVGSDWRFLRGYHQYAYDGKDYIALKEDLRSWTAADMAAQTTKHKWEAAHVAE
QLRAYLEGTCVEWLRRYLENGKETLQRTDAPKTHMTHHAVSDHEATLRCWALSFYPAEIT
LTWQRDGEDQTQDTELVETRPCGDGTFQKWAAVVVPSGQEQRYTCHVQHEGLPKPLTLRW
EAAAGGDKTHTCPPCPAPEFEGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPASIEK
TISKAKGQPREPQVYTLPPSREEMTKNQVSLTCLVKGFYPSDIAVEWESNGQPENNYKTT
PPVLDSDGSFFLYSKLTVDKSRWQQGNVFSCSVMHEALHNHYTQKSLSLSPGK

Leader peptide – italics

IL-2 (H16A/F42A) – bold (with H16 and F42 underlined)

(G4S)4 Linkers – single underlined

MHC H chain Y84A; A236C– double underlined (with Y84A and A236C in bold)

AAAGG linker – single underlined

Human IgG1 Fc; L234F; L235E; P331S – (bold and underlined, with L234F, L235E, and P331S unbolded)

FIG. 28 (SEQ ID NO:39)

CUE101-TM without leader peptide

APTSSSTKKTQLQLEALLLDLQMILNGINNYKNPKLTRML
TAKFYMPKKATELKHLQCLEEELKPLEEVLNLAQSKNFHLRPRDLISNINVIVLELKGSE
TTFMCEYADETATIVEFLNRWITFCQSIISTLTGGGGSGGGGSGGGGSGGGGSAPTSSST
KKTQLQLEALLLDLQMILNGINNYKNPKLTRMLTAKFYMPKKATELKHLQCLEEELKPLE
EVLNLAQSKNFHLRPRDLISNINVIVLELKGSETTFMCEYADETATIVEFLNRWITFCQS
IISTLTGGGGSGGGGSGGGGSGGGGSGSHSMRYFFTSVSRPGRGEPRFIAVGYVDDTQFV
RFDSDAASQRMEPRAPWIEQEGPEYWDGETRKVKAHSQTHRVDLGTLRGAYNQSEAGSHT
VQRMYGCDVGSDWRFLRGYHQYAYDGKDYIALKEDLRSWTAADMAAQTTKHKWEAAHVAE
QLRAYLEGTCVEWLRRYLENGKETLQRTDAPKTHMTHHAVSDHEATLRCWALSFYPAEIT
LTWQRDGEDQTQDTELVETRPCGDGTFQKWAAVVVPSGQEQRYTCHVQHEGLPKPLTLRW
EAAAGG DKTHTCPPCPAPEFEGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPASIEK
TISKAKGQPREPQVYTLPPSREEMTKNQVSLTCLVKGFYPSDIAVEWESNGQPENNYKTT
PPVLDSDGSFFLYSKLTVDKSRWQQGNVFSCSVMHEALHNHYTQKSLSLSPGK

IL-2 (H16A/F42A) – bold (with H16 and F42 underlined)

(G4S)4 Linkers – single underlined

MHC H chain Y84A; A236C– double underlined (with Y84A and A236C in bold)

AAAGG linker – single underlined

Human IgG1 Fc; L234F; L235E; P331S – (bold and underlined, with L234F, L235E, and P331S unbolded)

FIG. 29A (SEQ ID NO:40)

CUE101-TM: nucleotide sequence encoding CUE101-TM with leader sequence

ATGTACAGGATGCAACTCCTGTCTTGCATTGCACTAAGTCTTGCACTTGTCACAAACAGTGCACCTACTTC
AAGTTCTACAAAGAAAACACAGCTACAACTGGAGGCATTACTGCTGGATTTACAGATGATTTTGAATG
GAATTAATAATTACAAGAATCCCAAACTCACCAGGATGCTCACAGCAAAGTTTTACATGCCCAAGAAG
GCCACAGAACTGAAACATCTTCAGTGTCTAGAAGAAGAACTCAAACCTCTGGAGGAAGTGCTAAATTT
AGCTCAAAGCAAAAACTTTCACTTAAGACCCAGGGACTTAATCAGCAATATCAACGTAATAGTTCTGGA
ACTAAAGGGATCTGAAACAACATTCATGTGTGAATATGCTGATGAGACAGCAACCATTGTAGAATTTC
TGAACAGATGGATTACCTTTTGTCAAAGCATCATCTCAACACTGACTGGAGGCGGAGGATCTGGTGGTG
GAGGTTCTGGTGGTGGGGGATCTGGAGGCGGAGGATCTGCACCTACTTCAAGTTCTACAAAGAAAACA
CAGCTACAACTGGAGGCATTACTGCTGGATTTACAGATGATTTTGAATGGAATTAATAATTACAAGAAT
CCCAAACTCACCAGGATGCTCACAGCAAAGTTTTACATGCCCAAGAAGGCCACAGAACTGAAACATCTT
CAGTGTCTAGAAGAAGAACTCAAACCTCTGGAGGAAGTGCTAAATTTAGCTCAAAGCAAAAACTTTCA
CTTAAGACCCAGGGACTTAATCAGCAATATCAACGTAATAGTTCTGGAACTAAAGGGATCTGAAACAA
CATTCATGTGTGAATATGCTGATGAGACAGCAACCATTGTAGAATTTCTGAACAGATGGATTACCTTTT
GTCAAAGCATCATCTCAACACTGACTGGAGGCGGAGGATCTGGTGGTGGAGGTTCTGGTGGTGGGGGA
TCTGGAGGCGGAGGATCTGGCTCTCACTCCATGAGGTATTTCTTCACATCCGTGTCCCGGCCCGGCCGCG
GGGAGCCCCGCTTCATCGCAGTGGGCTACGTGGACGACACGCAGTTCGTGCGGTTCGACAGCGACGCCG
CGAGCCAGAGGATGGAGCCGCGGGCGCCGTGGATAGAGCAGGAGGGTCCGGAGTATTGGGACGGGGA
GACACGGAAAGTGAAGGCCCACTCACAGACTCACCGAGTGGACCTGGGGACCCTGCGCGGCGCCTACA
ACCAGAGCGAGGCCGGTTCTCACACCGTCCAGAGGATGTATGGCTGCGACGTGGGGTCGGACTGGCGC
TTCCTCCGCGGGTACCACCAGTACGCCTACGACGGCAAGGATTACATCGCCCTGAAAGAGGACCTGCGCT
CTTGGACCGCGGCGGACATGGCAGCTCAGACCACCAAGCACAAGTGGGAGGCGGCCCATGTGGCGGAG
CAGTTGAGAGCCTACCTGGAGGGCACGTGCGTGGAGTGGCTCCGCAGATACCTGGAGAACGGGAAGGA
GACGCTGCAGCGCACGGACGCCCCCAAAACGCATATGACTCACCACGCTGTCTCTGACCATGAAGCCACC
CTGAGGTGCTGGGCCCTGAGCTTCTACCCTGCGGAGATCACACTGACCTGGCAGCGGGATGGGGAGGA
CCAGACCCAGGACACGGAGCTCGTGGAGACCAGGCCTTGCGGGGATGGAACCTTCCAGAAGTGGGCGG
CTGTGGTGGTGCCTTCTGGACAGGAGCAGAGATACACCTGCCATGTGCAGCATGAGGGTTTGCCCAAGC
CCCTCACCCTGAGATGGGAGGCAGCTGCGGGTGGCGACAAAACTCACACATGCCCACCGTGCCCAGCA
CCTGAATTCGAGGGGGGACCGTCAGTCTTCCTCTTCCCCCCAAAACCCAAGGACACCCTCATGATCTCCC
GGACCCCTGAGGTCACATGCGTGGTGGTGGACGTGAGCCACGAAGACCCTGAGGTCAAGTTCAACTG
GTACGTGGACGGCGTGGAGGTGCATAATGCCAAGACAAAGCCGCGGGAGGAGCAGTACAACAGCAC
GTACCGTGTGGTCAGCGTCCTCACCGTCCTGCACCAGGACTGGCTGAATGGCAAGGAGTACAAGTGCA
AGGTCTCCAACAAAGCCCTCCCAGCCAGCATCGAGAAAACCATCTCCAAAGCCAAAGGGCAGCCCCGA
GAACCACAGGTGTACACCCTGCCCCCATCCCGGGAGGAGATGACCAAGAACCAGGTCAGCCTGACCTG
CCTGGTCAAAGGCTTCTATCCCAGCGACATCGCCGTGGAGTGGGAGAGCAATGGGCAGCCGGAGAAC
AACTACAAGACCACGCCTCCCGTGCTGGACTCCGACGGCTCCTTCTTCCTCTACAGCAAGCTCACCGTGG
ACAAGAGCAGATGGCAGCAGGGGAACGTCTTCTCATGCTCCGTGATGCACGAGGCTCTGCACAACCAC
TACACGCAGAAGTCCCTCTCCCTGTCTCCGGGTAAATAGTGA

FIG. 29B

Human IL2 Leader sequence – italics
Human IL2; H16A=GCA; F42A=GCA – bold (with GCA underlined)
(G4S)4 linker – single underlined
Human A0201; Y84A=GCC; A236C=TGC – double underlined (with GCC and TGC in bold)
AAAGG linker – single underlined
Human IgG1 Fc; L234F=*TTC*; L235E=*GAG*; P331S=*AGC*
N297= *AAC*; AGG to AGA (still R) and AGC to TCC (still S) – (bold and underlined, with TTC, GAG, AAC, and AGC italicized)
Stop codons (TAGTGA)

FIG. 30 (SEQ ID NO:41)
1274:
*MSRSVALAVLALLSLSGLEA*YMLDLQPETTGGGGSGGGGSGGGGSIQRTPKIQVYSCHPA
ENGKSNFLNCYVSGFHPSDIEVDLLKNGERIEKVEHSDLSFSKDWSFYLLYYTEFTPTEK
DEYACRVNHVTLSQPKIVKWDRDM

Human β2M leader sequence -- italics
E7(11-20) – bold and underlined
(G4S)3 linker – single underlined
Human β2M; R12C– double underlined (R12C bolded)

FIG. 31 (SEQ ID NO:42)

1274 without leader peptide

YMLDLQPETTGGGGSGGGGSGGGGSIQYMLDLQPETTGGGGSGGGGSGGGGSIQRTPKIQVYSCH
PAENGKSNFLNCYVSGFHPSDIEVDLLKNGERIEKVEHSDLSFSKDWSFYLLYYTEFTPTEKDEY
ACRVNHVTLSQPKIVKWDRDMRTPKIQVYSCHPAENGKSNFLNCYVSGFHPSDIEVDLLKNGERI
EKVEHSDLSFSKDWSFYLLYYTEFTPTEKDEYACRVNHVTLSQPKIVKWDRDM

E7(11-20) – bold and underlined (YMLDLQPETT; SEQ ID NO:77)
(G4S)3 linker – single underlined (GGGGSGGGGSGGGGS (SEQ ID NO: 207)
Human β2M; R12C – double underlined

FIG. 32 (SEQ ID NO:43)
1274 nucleotide sequence encoding 1274 with leader peptide

*ATGTCTCGCTCCGTGGCCTTAGCTGTGCTCGCGCTACTCTCTCTTTCTGGCCTGGAGGCC*TACATGCTCGA
TTTGCAGCCCGAAACGACGGGTGGAGGTGGTTCTGGAGGAGGCGGTTCGGGCGGAGGTGGTAGTATC
CAGCGTACTCCAAAGATTCAGGTTTACTCATGCCATCCAGCAGAGAATGGAAAGTCAAATTTCCTGAATT
GCTATGTGTCTGGGTTTCATCCATCCGACATTGAAGTTGACTTACTGAAGAATGGAGAGAGAATTGAAAA
AGTGGAGCATTCAGACTTGTCTTTCAGCAAGGACTGGTCTTTCTATCTCTTGTATTATACTGAATTCACCCC
CACTGAAAAAGATGAGTATGCCTGCCGTGTGAACCACGTGACTTTGTCACAGCCCAAGATAGTTAAGTG
GGATCGAGACATGTAGTGA

Human β2M leader sequence -- italics
E7(11-20) – bold and underlined
(G4S)3 linker – single underlined
Human β2M; R12C=TGC -- double underlined (TGC in bold)
Stop codons TAGTGA

FIG. 33A (SEQ ID NO:44)

WT Human IgG1 Fc Sequence:

DKTHTCPPCPAPELLGGPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSREEMTKNQVSLTCLVKGFYPSDIAVEWESNGQPENNYKTTPPVLDSDGSFFLYSK
LTVDKSRWQQGNVFSCSVMHEALHNHYTQKSLSLSPGK

FIG. 33B (SEQ ID NO:45)

Human IgG1 Fc Mutant: L234F/L235E/P331S (Triple Mutant "TM")

DKTHTCPPCPAPEFEGGPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPASIEKTISKAKGQPREP
QVYTLPPSREEMTKNQVSLTCLVKGFYPSDIAVEWESNGQPENNYKTTPPVLDSDGSFFLYSK
LTVDKSRWQQGNVFSCSVMHEALHNHYTQKSLSLSPGK

FIG. 33C (SEQ ID NO:46)

Human IgG1 Fc Mutant: N297A

DKTHTCPPCPAPELLGGPSVFLFPPKPKDTLMISRTPEVTCVVVDVSHEDPEVKFNWYVDGVE
VHNAKTKPREEQYASTYRVVSVLTVLHQDWLNGKEYKCKVSNKALPAPIEKTISKAKGQPREP
QVYTLPPSREEMTKNQVSLTCLVKGFYPSDIAVEWESNGQPENNYKTTPPVLDSDGSFFLYSK
LTVDKSRWQQGNVFSCSVMHEALHNHYTQKSLSLSPGK

FIG. 33D (SEQ ID NO:47)

Human IgG1 Fc Mutant: L234A/L235A ("LALA")

DKTHTCPPCPAPEAAGGPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSREEMTKNQVSLTCLVKGFYPSDIAVEWESNGQPENNYKTTPPVLDSDGSFFLYSK
LTVDKSRWQQGNVFSCSVMHEALHNHYTQKSLSLSPGK

Residue numbered according to EU index (Kabat Numbering)

FIG. 34A (SEQ ID NO:48)

B2M R12C

IQRTPKIQVYSCHPAENGKSNFLNCYVSGFHPSDIEVDLLKNGERIEKVEHSDLSFSKDWSFYLL
YYTEFTPTEKDEYACRVNHVTLSQPKIVKWDRDM

FIG. 34B (SEQ ID NO:49)

IL-2 (H16A; F42A)

APTSSSTKKTQLQLEALLLDLQMILNGINNYKNPKLTRMLTAKFYMPKKATELKHLQCLEEELKP
LEEVLNLAQSKNFHLRPRDLISNINVIVLELKGSETTFMCEYADETATIVEFLNRWITFCQSIIS
TLT

FIG. 34C (SEQ ID NO:50)

Class I MHC-H chain A0201 (Y84A; A236C)

GSHSMRYFFTSVSRPGRGEPRFIAVGYVDDTQFVRFDSDAASQRMEPRAPWIEQEGPEYWDGETR
KVKAHSQTHRVDLGTLRGAYNQSEAGSHTVQRMYGCDVGSDWRFLRGYHQYAYDGKDYIALKEDL
RSWTAADMAAQTTKHKWEAAHVAEQLRAYLEGTCVEWLRRYLENGKETLQRTDAPKTHMTHHAVS
DHEATLRCWALSFYPAEITLTWQRDGEDQTQDTELVETRPCGDGTFQKWAAVVVPSGQEQRYTCH
VQHEGLPKPLTLRWE

FIG. 36A

4-1-BBL
*Homo sapiens*
GenBank NP_003802
Cytoplasmic domain = 1-25
Transmembrane domain = 26-48
Ectodomain = 49-254
TNF homology domain = 80-254, 81-254, or 80-246

```
  1 MEYASDASLD PEAPWPPAPR ARACRVLPWA LVAGLLLLLL LAAACAVFLA CPWAVSGARA
 61 SPGSAASPRL REGPELSPDD PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:99)
```

```
 81                                PAGLLDLRQG MFAQLVAQNV LLIDGPLSWY SDPGLAGVSL
121 TGGLSYXEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:100)
```

```
 81                                PAGLLDLRQG MFAQLVAQNV LLIDGPLSWY SDPGLAGVSL
121 TGGLSYAEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:101)
```

```
 81                                 PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWXLTQ GATVLGLFRV
241 TPEIPAGLPS PRSE (SEQ ID NO:102)
```

```
 81                                 PAGLLDLRQG XFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:103)
```

```
 81                                 PAGLLDLRQG MXAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO: 104)
```

FIG. 36G
Q94

```
 81                                PAGLLDLRQG MFAXLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:105)
```

FIG. 36H
L95

```
 81                                PAGLLDLRQG MFAQXVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:106)
```

FIG. 36I
V96

```
 81                                PAGLLDLRQG MFAQLXAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:107)
```

```
 81                                  PAGLLDLRQG MFAQLVAXNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:108)
```

```
 81                                  PAGLLDLRQG MFAQLVAQXV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:109)
```

```
 81                                  PAGLLDLRQG MFAQLVAQNX LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:110)
```

FIG. 36M
L101

```
 81                                PAGLLDLRQG MFAQLVAQNV XLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:111)
```

FIG. 36N
L102

```
 81                                PAGLLDLRQG MFAQLVAQNV LXIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:112)
```

FIG. 36O
I103

```
 81                                PAGLLDLRQG MFAQLVAQNV LLXDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:113)
```

FIG. 36P
D104

```
 81                             PAGLLDLRQG MFAQLVAQNV LLIXGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:114)
```

FIG. 36Q
G105

```
 81                             PAGLLDLRQG MFAQLVAQNV LLIDXPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:115)
```

FIG. 36R
P106

```
 81                             PAGLLDLRQG MFAQLVAQNV LLIDGXLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:116)
```

FIG. 36S
L107

```
 81                             PAGLLDLRQG MFAQLVAQNV LLIDGPXSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:117)
```

FIG. 36T
S108

```
 81                             PAGLLDLRQG MFAQLVAQNV LLIDGPLXWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:118)
```

FIG. 36U
W109

```
 81                             PAGLLDLRQG MFAQLVAQNV LLIDGPLSXY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:119)
```

FIG. 36V
Y110

```
 81                                PAGLLDLRQG MFAQLVAQNV LLIDGPLSWX SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:120)
```

FIG. 36W
S111

```
 81                                PAGLLDLRQG MFAQLVAQNV LLIDGPLSWY XDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:121)
```

FIG. 36X
D112

```
 81                                PAGLLDLRQG MFAQLVAQNV LLIDGPLSWY SXPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:122)
```

FIG. 36Y
P113

```
 81                       PAGLLDLRQG MFAQLVAQNV LLIDGPLSWY SDXGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:123)
```

FIG. 36Z
G114

```
 81                       PAGLLDLRQG MFAQLVAQNV LLIDGPLSWY SDPXLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:124)
```

FIG. 36AA
L115

```
 81                       PAGLLDLRQG MFAQLVAQNV LLIDGPLSWY SDPGXAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO::125)
```

FIG. 36BB
G117

```
 81                       PAGLLDLRQG MFAQLVAQNV LLIDGPLSWY SDPGLAXVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:126)
```

FIG. 36CC
V118

```
 81                       PAGLLDLRQG MFAQLVAQNV LLIDGPLSWY SDPGLAGXSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:127)
```

FIG. 36DD
S119

```
 81                       PAGLLDLRQG MFAQLVAQNV LLIDGPLSWY SDPGLAGVXL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:128)
```

FIG. 36EE
L120

```
 81                       PAGLLDLRQG MFAQLVAQNV LLIDGPLSWY SDPGLAGVSX
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO::129)
```

FIG. 36FF
T121

```
 81                       PAGLLDLRQG MFAQLVAQNV LLIDGPLSWY SDPGLAGVSL
121 XGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:130)
```

```
 81                                PAGLLDLRQG MFAQLVAQNV LLIDGPLSWY SDPGLAGVSL
121 TXGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:131)
```

```
 81                                PAGLLDLRQG MFAQLVAQNV LLIDGPLSWY SDPGLAGVSL
121 TGXLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:132)
```

```
 81                                PAGLLDLRQG MFAQLVAQNV LLIDGPLSWY SDPGLAGVSL
121 TGGXSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:133)
```

FIG. 36JJ
S125

```
 81                                PAGLLDLRQG MFAQLVAQNV LLIDGPLSWY SDPGLAGVSL
121 TGGLXYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:134)
```

FIG. 36KK
Y126

```
 81                                PAGLLDLRQG MFAQLVAQNV LLIDGPLSWY SDPGLAGVSL
121 TGGLSXKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:135)
```

FIG. 36LL
E128

```
 81                                PAGLLDLRQG MFAQLVAQNV LLIDGPLSWY SDPGLAGVSL
121 TGGLSYKXDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:136)
```

FIG. 36MM
D129

```
 81                                PAGLLDLRQG MFAQLVAQNV LLIDGPLSWY SDPGLAGVSL
121 TGGLSYKEXT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:137)
```

```
 81                                  PAGLLDLRQG MFAQLVAQNV LLIDGPLSWY SDPGLAGVSL
121 TGGLSYKEDX KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:138)
```

```
 81                                  PAGLLDLRQG MFAQLVAQNV LLIDGPLSWY SDPGLAGVSL
121 TGGLSYKEDT XELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:139)
```

```
 81                                  PAGLLDLRQG MFAQLVAQNV LLIDGPLSWY SDPGLAGVSL
121 TGGLSYKEDT KXLVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:140)
```

```
 81                                  PAGLLDLRQG MFAQLVAQNV LLIDGPLSWY SDPGLAGVSL
121 TGGLSYKEDT KELVVAKAGV YYVXFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:141)
```

```
 81                       PAGLLDLRQG MFAQLVAQNV LLIDGPLSWY SDPGLAGVSL
121 TGGLSYKEDT KELVVAKAGV YYVFXQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:142)
```

```
 81                       PAGLLDLRQG MFAQLVAQNV LLIDGPLSWY SDPGLAGVSL
121 TGGLSYKEDT KELVVAKAGV YYVFFXLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:143
```

```
 81                       PAGLLDLRQG MFAQLVAQNV LLIDGPLSWY SDPGLAGVSL
121 TGGLSYKEDT KELVVAKAGV YYVFFQXELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:144)
```

```
 81                       PAGLLDLRQG MFAQLVAQNV LLIDGPLSWY SDPGLAGVSL
121 TGGLSYKEDT KELVVAKAGV YYVFFQLXLR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:145)
```

```
 81                       PAGLLDLRQG MFAQLVAQNV LLIDGPLSWY SDPGLAGVSL
121 TGGLSYKEDT KELVVAKAGV YYVFFQLEXR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:146)
```

```
 81                       PAGLLDLRQG MFAQLVAQNV LLIDGPLSWY SDPGLAGVSL
121 TGGLSYKEDT KELVVAKAGV YYVFFQLELX RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:147)
```

```
 81                       PAGLLDLRQG MFAQLVAQNV LLIDGPLSWY SDPGLAGVSL
121 TGGLSYKEDT KELVVAKAGV YYVFFQLELR XVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:148)
```

```
 81                       PAGLLDLRQG MFAQLVAQNV LLIDGPLSWY SDPGLAGVSL
121 TGGLSYKEDT KELVVAKAGV YYVFFQLELR RXVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:149)
```

```
 81                                PAGLLDLRQG MFAQLVAQNV LLIDGPLSWY SDPGLAGVSL
121 TGGLSYKEDT KELVVAKAGV YYVFFQLELR RVXAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:150)
```

```
 81                                PAGLLDLRQG MFAQLVAQNV LLIDGPLSWY SDPGLAGVSL
121 TGGLSYKEDT KELVVAKAGV YYVFFQLELR RVVAXEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:151)
```

```
 81                                PAGLLDLRQG MFAQLVAQNV LLIDGPLSWY SDPGLAGVSL
121 TGGLSYKEDT KELVVAKAGV YYVFFQLELR RVVAGXGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:152)
```

FIG. 36CCC
G157

```
 81                        PAGLLDLRQG MFAQLVAQNV LLIDGPLSWY SDPGLAGVSL
121 TGGLSYKEDT KELVVAKAGV YYVFFQLELR RVVAGEXSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:153)
```

FIG. 36DDD
S158

```
 81                        PAGLLDLRQG MFAQLVAQNV LLIDGPLSWY SDPGLAGVSL
121 TGGLSYKEDT KELVVAKAGV YYVFFQLELR RVVAGEGXGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO: 154)
```

FIG. 36EEE
D184

```
 81                        PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVXLPPASS EARNSAFGFQ GRLLHLSAGQ RLGVHLHTEA RARHAWQLTQ GATVLGLFRV
241 TPEIPAGLPS PRSE (SEQ ID NO: 155)
```

```
 81                              PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDXPPASS EARNSAFGFQ GRLLHLSAGQ RLGVHLHTEA RARHAWQLTQ GATVLGLFRV
241 TPEIPAGLPS PRSE (SEQ ID NO:156)
```

```
 81                              PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLXPASS EARNSAFGFQ GRLLHLSAGQ RLGVHLHTEA RARHAWQLTQ GATVLGLFRV
241 TPEIPAGLPS PRSE (SEQ ID NO:157)
```

```
 81                              PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPXASS EARNSAFGFQ GRLLHLSAGQ RLGVHLHTEA RARHAWQLTQ GATVLGLFRV
241 TPEIPAGLPS PRSE (SEQ ID NO:158)
```

FIG. 36III
S189

```
 81                             PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPAXS EARNSAFGFQ GRLLHLSAGQ RLGVHLHTEA RARHAWQLTQ GATVLGLFRV
241 TPEIPAGLPS PRSE (SEQ ID NO:159)
```

FIG. 36JJJ
S190

```
 81                             PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASX EARNSAFGFQ GRLLHLSAGQ RLGVHLHTEA RARHAWQLTQ GATVLGLFRV
241 TPEIPAGLPS PRSE (SEQ ID NO:160)
```

FIG. 36KKK
E191

```
 81                             PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS XARNSAFGFQ GRLLHLSAGQ RLGVHLHTEA RARHAWQLTQ GATVLGLFRV
241 TPEIPAGLPS PRSE (SEQ ID NO:161)
```

FIG. 36LLL
R193

```
 81                             PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EAXNSAFGFQ GRLLHLSAGQ RLGVHLHTEA RARHAWQLTQ GATVLGLFRV
241 TPEIPAGLPS PRSE (SEQ ID NO:162)
```

FIG. 36MMM
N194

```
 81                                  PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARXSAFGFQ GRLLHLSAGQ RLGVHLHTEA RARHAWQLTQ GATVLGLFRV
241 TPEIPAGLPS PRSE (SEQ ID NO:163)
```

FIG. 36NNN
S195

```
 81                                  PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNXAFGFQ GRLLHLSAGQ RLGVHLHTEA RARHAWQLTQ GATVLGLFRV
241 TPEIPAGLPS PRSE (SEQ ID NO: 164)
```

FIG. 36OOO
F197

```
 81                                  PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAXGFQ GRLLHLSAGQ RLGVHLHTEA RARHAWQLTQ GATVLGLFRV
241 TPEIPAGLPS PRSE (SEQ ID NO:165)
```

FIG. 36PPP
Q210

```
 81                                  PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGX RLGVHLHTEA RARHAWQLTQ GATVLGLFRV
241 TPEIPAGLPS PRSE (SEQ ID NO:166)
```

FIG. 36QQQ
R211

```
 81                             PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ XLGVHLHTEA RARHAWQLTQ GATVLGLFRV
241 TPEIPAGLPS PRSE (SEQ ID NO:167)
```

FIG. 36RRR
L212

```
 81                             PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RXGVHLHTEA RARHAWQLTQ GATVLGLFRV
241 TPEIPAGLPS PRSE (SEQ ID NO:168)
```

FIG. 36SSS
G213

```
 81                             PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLXVHLHTEA RARHAWQLTQ GATVLGLFRV
241 TPEIPAGLPS PRSE (SEQ ID NO:169)
```

FIG. 36TTT
V214

```
 81                                PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGXHLHTEA RARHAWQLTQ GATVLGLFRV
241 TPEIPAGLPS PRSE (SEQ ID NO:170)
```

FIG. 36UUU
H215

```
 81                                PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVXLHTEA RARHAWQLTQ GATVLGLFRV
241 TPEIPAGLPS PRSE (SEQ ID NO:171)
```

FIG. 36VVV
L216

```
 81                                PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHXHTEA RARHAWQLTQ GATVLGLFRV
241 TPEIPAGLPS PRSE (SEQ ID NO:172)
```

FIG. 36WWW
H217

```
 81                             PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLXTEA RARHAWQLTQ GATVLGLFRV
241 TPEIPAGLPS PRSE (SEQ ID NO:173)
```

FIG. 36XXX
T218

```
 81                             PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHXEA RARHAWQLTQ GATVLGLFRV
241 TPEIPAGLPS PRSE (SEQ ID NO:174)
```

FIG. 36YYY
E219

```
 81                             PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTXA RARHAWQLTQ GATVLGLFRV
241 TPEIPAGLPS PRSE (SEQ ID NO:175)
```

```
 81                       PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA XARHAWQLTQ GATVLGLFRV
241 TPEIPAGLPS PRSE (SEQ ID NO:176)
```

FIG. 36AAAA

R223

```
 81                       PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RAXHAWQLTQ GATVLGLFRV
241 TPEIPAGLPS PRSE (SEQ ID NO:177)
```

FIG. 36BBBB

H224

```
 81                       PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARXAWQLTQ GATVLGLFRV
241 TPEIPAGLPS PRSE (SEQ ID NO:178)
```

FIG. 36CCCC
W226

```
 81                                 PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAXQLTQ GATVLGLFRV
241 TPEIPAGLPS PRSE (SEQ ID NO:179)
```

FIG. 36DDDD
L228

```
 81                                 PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQXTQ GATVLGLFRV
241 TPEIPAGLPS PRSE (SEQ ID NO:180)
```

FIG. 36EEEE
T229

```
 81                                 PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLXQ GATVLGLFRV
241 TPEIPAGLPS PRSE (SEQ ID NO:181)
```

FIG. 36FFFF
Q230

```
 81                                PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTX GATVLGLFRV
241 TPEIPAGLPS PRSE (SEQ ID NO:182)
```

FIG. 36GGGG
G231

```
 81                                PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ XATVLGLFRV
241 TPEIPAGLPS PRSE (SEQ ID NO:183)
```

FIG. 36HHHH
T233

```
 81                                PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GAXVLGLFRV
241 TPEIPAGLPS PRSE (SEQ ID NO:184)
```

FIG. 36IIII

V234

```
 81                        PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATXLGLFRV
241 TPEIPAGLPS PRSE (SEQ ID NO:185)
```

FIG. 37

*Homo sapiens*
4-1BB

```
  1 mgnscyniva tlllvlnfer trslqdpcsn cpagtfcdnn rnqicspcpp nsfssagggr
 61 tcdicrqckg vfrtrkecss tsnaecdctp gfhclgagcs mceqdckqgq eltkkgckdc
121 cfgtfndqkr gicrpwtncs ldgksvlvng tkerdvvcgp spadlspgas svtppapare
181 pghspqiisf flaltstall flffltlrf svvkrgrkkl lyifkqpfmr pvqttqeedg
241 cscrfpeeee ggcel (SEQ ID NO:186)
```

FIG. 47

| 4-1BBL variant | Expression level mg/L | Expression level mg/L | Fold over wild-type |
|---|---|---|---|
| M91A | 105.9 | 115.9 | 14 |
| F92A | 48.9 | 41.6 | 5.8 |
| Q94A | 13.8 | 23.1 | 2.3 |
| L95A | 81.8 | 63.3 | 9.2 |
| V96A | 16.2 | 24.4 | 2.6 |
| Q98A | 43.0 | 43.0 | 5.5 |
| N99A | 35.3 | 53.3 | 5.6 |
| V100A | 37.6 | 42.6 | 5.1 |
| L101A | 137.8 | 203.2 | 21.7 |
| L102A | 148.0 | 184.4 | 21.2 |
| I103A | 48.0 | 68.0 | 7.4 |
| D104A | 70.5 | 65.1 | 3.9 |
| G105A | 23.8 | 37.6 | 2.6 |
| P106A | 81.2 | 66.0 | 9.4 |
| L107A | 13.8 | 13.4 | 1.7 |
| S108A | 66.2 | 72.1 | 8.8 |
| W109A | 15.6 | 30.8 | 2.9 |
| Y110A | 107.0 | 110.1 | 13.8 |
| S111A | 104.0 | 109.0 | 13.6 |
| D112A | 28.0 | 32.1 | 3.8 |
| P113A | 60.1 | 60.4 | 7.7 |
| G114A | 94.8 | 81.7 | 3.9 |
| L115A | 23.0 | 26.4 | 3.1 |
| G117A | 4.4 | 12.5 | |
| V118A | 4.2 | 5.3 | |
| S119A | 4.6 | 5.6 | |
| L120A | 4.6 | 4.6 | |
| T121A | 4.9 | 6.3 | |
| G122A | 9.8 | 9.5 | |
| G123A | 2.5 | 10.4 | |
| L124A | 3.1 | 8.5 | |
| S125A | 8.9 | 8.3 | |
| Y126A | 2.3 | 0.6 | |
| E128A | 6.1 | 14.6 | |
| D129A | 2.2 | 0.0 | |

FIG. 47 (cont.)

| 4-1BBL variant | Expression level mg/L | Expression level mg/L | Fold over wild-type |
|---|---|---|---|
| T130A | 1.9 | 2.6 | |
| K131A | 7.0 | 15.3 | |
| E132A | 2.3 | 6.8 | |
| F144A | 1.5 | 0.0 | |
| F145A | 8.2 | 6.3 | |
| Q146A | 5.7 | 10.5 | |
| L147A | 10.3 | 16.8 | |
| E148A | 5.7 | 4.4 | |
| L149A | 9.9 | 12.9 | |
| R150A | 10.3 | 4.7 | |
| R151A | 1.8 | 0.0 | |
| V152A | 2.9 | 6.7 | |
| V153A | 3.7 | 7.9 | |
| G155A | 6.9 | 13.1 | |
| E156A | 4.3 | 4.0 | |
| G157A | 12.3 | 18.7 | |
| S158A | 6.7 | 6.3 | |
| D184A | 3.6 | 5.0 | |
| L185A | 2.2 | 0.0 | |
| P186A | 4.3 | 2.2 | |
| P187A | 2.9 | 0.0 | |
| S189A | 3.8 | 6.1 | |
| S190A | 2.4 | 3.1 | |
| E191A | 1.8 | 4.1 | |
| R193A | 6.6 | 7.5 | |
| N194A | 4.3 | 0.1 | |
| S195A | 3.2 | 1.6 | |
| F197A | 3.1 | 6.5 | |
| Q210A | 5.1 | 3.9 | |
| R211A | 1.6 | 3.5 | |
| L212A | 2.0 | 9.8 | |
| G213A | 5.0 | 2.9 | |
| V214A | 2.7 | 7.5 | |
| H215A | 3.3 | 2.4 | |
| L216A | 3.4 | 10.2 | |

FIG. 47 (cont.)

| 4-1BBL variant | Expression level mg/L | Expression level mg/L | Fold over wild-type |
|---|---|---|---|
| H217A | 8.6 | 3.2 | |
| T218A | 6.6 | 9.9 | |
| E219A | 2.8 | 5.2 | |
| R221A | 3.3 | 8.7 | |
| R223A | 6.2 | 9.7 | |
| H224A | 4.1 | 6.0 | |
| W226A | 1.9 | 0.0 | |
| L228A | 3.1 | 0.0 | |
| T229A | 6.0 | 7.8 | |
| Q230A | 2.7 | 4.7 | |
| G231A | 1.9 | 2.4 | |
| T233A | 1.8 | 0.0 | |
| V234A | 1.9 | 0.0 | |
| wt | 3.8 | 11.9 | |

FIG.50A
PD-L1
*Mus musculus*
NP_068693
Amino acids 19-290

```
  1 mrifagiift acchllraft itapkdlyvv eygsnvtmec rfpvereldl lalvvyweke
 61 deqviqfvag eedlkpqhsn frgraslpkd qllkgnaalq itdvklqdag vycciisygg
121 adykritlkv napyrkinqr isvdpatseh elicqaegyp eaeviwtnsd hqpvsgkrsv
181 ttsrtegmll nvtsslrvna tandvfyctf wrsqpgqnht aeliipelpa thppqnrthw
241 vllgsillfl ivvstvllfl rkqvrmldve kcgvedtssk nrndtqfeet
```

(SEQ ID NO:187)

FIG.50B
PD-L1
*Homo sapiens*
NP_054852
Amino acids 19-290

```
  1 mrifavfifm tywhllnaft vtvpkdlyvv eygsnmtiec kfpvekqldl aalivyweme
 61 dkniiqfvhg eedlkvqhss yrqrarllkd qlslgnaalq itdvklqdag vyrcmisygg
121 adykritvkv napynkinqr ilvvdpvtse heltcqaegy pkaeviwtss dhqvlsgktt
181 ttnskreekl fnvtstlrin tttneifyct frrldpeenh taelvipelp lahppnerth
241 lvilgaillc lgvaltfifr lrkgrmmdvk kcgiqdtnsk kqsdthleet
```

(SEQ ID NO:188)

FIG.51

CD80 (B7-1) Ectodomain

```
                                                  vihvtk evkevatlsc ghnvsveela
qtriywqkek kmvltmmsgd mniwpeyknr tifditnnls ivilalrpsd egtyecvvlk
yekdafkreh laevtlsvka dfptpsisdf eiptsnirri icstsggfpe phlswlenge
elnainttvs qdpetelyav sskldfnmtt nhsfmcliky ghlrvnqtfn wnttkqehfp
dn (SEQ ID NO:189)
```

FIG. 52
*Homo sapiens*
ICOS-L
GenBank NP_056074
Amino acids 19-302

```
  1 mrlgspgllf llfsslradt qekevramvg sdvelscacp egsrfdlndv yvywqtsesk
 61 tvvtyhipqn sslenvdsry rnralmspag mlrgdfslrl fnvtpqdeqk fhclvlsqsl
121 gfqevlsvev tlhvaanfsv pvvsaphsps qdeltftcts ingyprpnvy winktdnsll
181 dqalqndtvf lnmrglydvv svlriartps vnigccienv llqqnltvgs qtgndigerd
241 kitenpvstg eknaatwsil avlcllvvva vaigwvcrdr clqhsyagaw avspeteltg
301 hv
```

(SEQ ID NO:190)

FIG.53
*Homo sapiens*
GenBank NP_003317
OX4L

```
  1 mervqpleen vgnaarprfe rnklllvasv iqglglllcf tyiclhfsal qvshrypriq
 61 sikvqfteyk kekgfiltsq kedeimkvqn nsviincdgf ylislkgyfs qevnislhyq
121 kdeeplfqlk kvrsvnslmv asltykdkvy lnvttdntsl ddfhvnggel ilihqnpgef
181 cvl
```

(SEQ ID NO:191)

FIG. 54
*Homo sapiens*
GenBank NP_079515
PD-L2
Amino acids 20-273

```
  1 miflllmlsl elqlhqiaal ftvtvpkely iiehgsnvtl ecnfdtgshv nlgaitaslq
 61 kvendtsphr eratlleeql plgkasfhip qvqvrdegqy qciiiygvaw dykyltlkvk
121 asyrkinthi lkvpetdeve ltcqatgypl aevswpnvsv pantshsrtp eglyqvtsvl
181 rlkpppgrnf scvfwnthvr eltlasidlq sqmeprthpt wllhifipfc iiafifiatv
241 ialrkqlcqk lysskdttkr pvtttkrevn sai
```

(SEQ ID NO:192)

FIG. 55
*Homo sapiens*
GenBank NP_787058
CD86 (B7-2)
Amino acids 31-329

```
  1 mdpqctmgls nilfvmafll sgaaplkiqa yfnetadlpc qfansqnqsl selvvfwqdq
 61 enlvlnevyl gkekfdsvhs kymgrtsfds dswtlrlhnl qikdkglyqc iihhkkptgm
121 irihqmnsel svlanfsqpe ivpisniten vyinltcssi hgypepkkms vllrtknsti
181 eydgimqksq dnvtelydvs islsvsfpdv tsnmtifcil etdktrllss pfsieledpq
241 pppdhipwit avlptviicv mvfclilwkw kkkkrprnsy kcgtntmere eseqtkkrek
301 ihipersdea qrvfksskts scdksdtcf
```

(SEQ ID NO:193)

FIG. 56

Fas ligand (FasL)

*Homo sapiens*

GenBank NP_000630

Amino acids 1-281

```
  1 mqqpfnypyp qiywvdssas spwappgtvl pcptsvprrp gqrrpppppp ppplpppppp
 61 pplpplplpp lkkrgnhstg lcllvmffmv lvalvglglg mfqlfhlqke laelrestsq
121 mhtasslekq ighpspppek kelrkvahlt gksnsrsmpl ewedtygivl lsgvkykkgg
181 lvinetglyf vyskvyfrgq scnnlplshk vymrnskypq dlvmmegkmm syctttgqmwa
241 rssylgavfn ltsadhlyvn vselslvnfe esqtffglyk l
```

(SEQ ID NO:194)

SEQUENCE LISTING

```
<160> NUMBER OF SEQ ID NOS: 216

<210> SEQ ID NO 1
<211> LENGTH: 133
<212> TYPE: PRT
<213> ORGANISM: Homo sapiens

<400> SEQUENCE: 1

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95
```

```
Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130


<210> SEQ ID NO 2
<211> LENGTH: 133
<212> TYPE: PRT
<213> ORGANISM: Artificial Sequence
<220> FEATURE:
<223> OTHER INFORMATION: synthetic polypeptide
<220> FEATURE:
<221> NAME/KEY: MISC_FEATURE
<222> LOCATION: (42)..(42)
<223> OTHER INFORMATION: Xaa is any amino acid other than a
      phenylalanine

<400> SEQUENCE: 2

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Xaa Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130


<210> SEQ ID NO 3
<211> LENGTH: 133
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (20)..(20)
<223> OTHER INFORMATION: Xaa is any amino acid other than an aspartic
      acid

<400> SEQUENCE: 3

Ala Pro Thr Ser Ser Ser Thr Lys Lys Thr Gln Leu Gln Leu Glu His
1               5                   10                  15

Leu Leu Leu Xaa Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60
```

```
Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130


<210> SEQ ID NO 4
<211> LENGTH: 133
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (15)..(15)
<223> OTHER INFORMATION: Xaa is any amino acid other than a glutamic
      acid

<400> SEQUENCE: 4

Ala Pro Thr Ser Ser Ser Thr Lys Lys Thr Gln Leu Gln Leu Xaa His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130


<210> SEQ ID NO 5
<211> LENGTH: 133
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (16)..(16)
<223> OTHER INFORMATION: Xaa is any amino acid other than a histidine

<400> SEQUENCE: 5

Ala Pro Thr Ser Ser Ser Thr Lys Lys Thr Gln Leu Gln Leu Glu Xaa
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45
```

```
Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130


<210> SEQ ID NO 6
<211> LENGTH: 133
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (45)..(45)
<223> OTHER INFORMATION: Xaa is any amino acid other than a tyrosine

<400> SEQUENCE: 6

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Xaa Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130


<210> SEQ ID NO 7
<211> LENGTH: 133
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (126)..(126)
<223> OTHER INFORMATION: Xaa is any amino acid other than a glutamine

<400> SEQUENCE: 7

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30
```

```
Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Xaa Ser Ile
        115                 120                 125

Ile Ser Thr Leu Thr
    130


<210> SEQ ID NO 8
<211> LENGTH: 133
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (16)..(16)
<223> OTHER INFORMATION: Xaa is any amino acid other than a histidine
<220> FEATURE:
<221> NAME/KEY: MISC_FEATURE
<222> LOCATION: (42)..(42)
<223> OTHER INFORMATION: Xaa is any amino acid other than a
      phenylalanine

<400> SEQUENCE: 8

Ala Pro Thr Ser Ser Ser Thr Lys Lys Thr Gln Leu Gln Leu Glu Xaa
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Xaa Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130


<210> SEQ ID NO 9
<211> LENGTH: 133
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (20)..(20)
<223> OTHER INFORMATION: Xaa is any amino acid other than an aspartic
```

-continued

```
      acid
<220> FEATURE:
<221> NAME/KEY: MISC_FEATURE
<222> LOCATION: (42)..(42)
<223> OTHER INFORMATION: Xaa is any amino acid other than a
      phenylalanine

<400> SEQUENCE: 9

Ala Pro Thr Ser Ser Ser Thr Lys Lys Thr Gln Leu Gln Leu Glu His
1               5                   10                  15

Leu Leu Leu Xaa Leu Gln Met Ile Leu Asn Gly Ile Asn Asn Tyr Lys
            20                  25                  30

Asn Pro Lys Leu Thr Arg Met Leu Thr Xaa Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130


<210> SEQ ID NO 10
<211> LENGTH: 133
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (15)..(15)
<223> OTHER INFORMATION: Xaa is any amino acid other than a glutamic
      acid
<220> FEATURE:
<221> NAME/KEY: MISC_FEATURE
<222> LOCATION: (20)..(20)
<223> OTHER INFORMATION: Xaa is any amino acid other than an aspartic
      acid
<220> FEATURE:
<221> NAME/KEY: MISC_FEATURE
<222> LOCATION: (42)..(42)
<223> OTHER INFORMATION: Xaa is any amino acid other than a
      phenylalanine

<400> SEQUENCE: 10

Ala Pro Thr Ser Ser Ser Thr Lys Lys Thr Gln Leu Gln Leu Xaa His
1               5                   10                  15

Leu Leu Leu Xaa Leu Gln Met Ile Leu Asn Gly Ile Asn Asn Tyr Lys
            20                  25                  30

Asn Pro Lys Leu Thr Arg Met Leu Thr Xaa Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95
```

```
Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130


<210> SEQ ID NO 11
<211> LENGTH: 133
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (16)..(16)
<223> OTHER INFORMATION: Xaa is any amino acid other than a histidine
<220> FEATURE:
<221> NAME/KEY: MISC_FEATURE
<222> LOCATION: (20)..(20)
<223> OTHER INFORMATION: Xaa is any amino acid other than an aspartic
      acid
<220> FEATURE:
<221> NAME/KEY: MISC_FEATURE
<222> LOCATION: (42)..(42)
<223> OTHER INFORMATION: Xaa is any amino acid other than a
      phenylalanine

<400> SEQUENCE: 11

Ala Pro Thr Ser Ser Ser Thr Lys Lys Thr Gln Leu Gln Leu Glu Xaa
1               5                   10                  15

Leu Leu Leu Xaa Leu Gln Met Ile Leu Asn Gly Ile Asn Asn Tyr Lys
            20                  25                  30

Asn Pro Lys Leu Thr Arg Met Leu Thr Xaa Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130


<210> SEQ ID NO 12
<211> LENGTH: 133
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (20)..(20)
<223> OTHER INFORMATION: Xaa is any amino acid other than an aspartic
      acid
<220> FEATURE:
<221> NAME/KEY: MISC_FEATURE
<222> LOCATION: (42)..(42)
<223> OTHER INFORMATION: Xaa is any amino acid other than a
      phenylalanine
<220> FEATURE:
<221> NAME/KEY: MISC_FEATURE
```

```
<222> LOCATION: (126)..(126)
<223> OTHER INFORMATION: Xaa is any amino acid other than a glutamine

<400> SEQUENCE: 12

Ala Pro Thr Ser Ser Ser Thr Lys Lys Thr Gln Leu Gln Leu Glu His
1               5                   10                  15

Leu Leu Leu Xaa Leu Gln Met Ile Leu Asn Gly Ile Asn Asn Tyr Lys
            20                  25                  30

Asn Pro Lys Leu Thr Arg Met Leu Thr Xaa Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Xaa Ser Ile
        115                 120                 125

Ile Ser Thr Leu Thr
    130


<210> SEQ ID NO 13
<211> LENGTH: 133
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (20)..(20)
<223> OTHER INFORMATION: Xaa is any amino acid other than an aspartic
      acid
<220> FEATURE:
<221> NAME/KEY: MISC_FEATURE
<222> LOCATION: (42)..(42)
<223> OTHER INFORMATION: Xaa is any amino acid other than a
      phenylalanine
<220> FEATURE:
<221> NAME/KEY: MISC_FEATURE
<222> LOCATION: (45)..(45)
<223> OTHER INFORMATION: Xaa is any amino acid other than a tyrosine

<400> SEQUENCE: 13

Ala Pro Thr Ser Ser Ser Thr Lys Lys Thr Gln Leu Gln Leu Glu His
1               5                   10                  15

Leu Leu Leu Xaa Leu Gln Met Ile Leu Asn Gly Ile Asn Asn Tyr Lys
            20                  25                  30

Asn Pro Lys Leu Thr Arg Met Leu Thr Xaa Lys Phe Xaa Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125
```

```
Ile Ser Thr Leu Thr
    130


<210> SEQ ID NO 14
<211> LENGTH: 133
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (16)..(16)
<223> OTHER INFORMATION: Xaa is any amino acid other than a histidine
<220> FEATURE:
<221> NAME/KEY: MISC_FEATURE
<222> LOCATION: (20)..(20)
<223> OTHER INFORMATION: Xaa is any amino acid other than an aspartic
      acid
<220> FEATURE:
<221> NAME/KEY: MISC_FEATURE
<222> LOCATION: (42)..(42)
<223> OTHER INFORMATION: Xaa is any amino acid other than a
      phenylalanine
<220> FEATURE:
<221> NAME/KEY: MISC_FEATURE
<222> LOCATION: (45)..(45)
<223> OTHER INFORMATION: Xaa is any amino acid other than a tyrosine

<400> SEQUENCE: 14

Ala Pro Thr Ser Ser Ser Thr Lys Lys Thr Gln Leu Gln Leu Glu Xaa
1               5                   10                  15

Leu Leu Leu Xaa Leu Gln Met Ile Leu Asn Gly Ile Asn Asn Tyr Lys
            20                  25                  30

Asn Pro Lys Leu Thr Arg Met Leu Thr Xaa Lys Phe Xaa Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130


<210> SEQ ID NO 15
<211> LENGTH: 133
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (20)..(20)
<223> OTHER INFORMATION: Xaa is any amino acid other than an aspartic
      acid
<220> FEATURE:
<221> NAME/KEY: MISC_FEATURE
<222> LOCATION: (42)..(42)
<223> OTHER INFORMATION: Xaa is any amino acid other than a
      phenylalanine
<220> FEATURE:
<221> NAME/KEY: MISC_FEATURE
<222> LOCATION: (45)..(45)
```

```
<223> OTHER INFORMATION: Xaa is any amino acid other than a tyrosine
<220> FEATURE:
<221> NAME/KEY: MISC_FEATURE
<222> LOCATION: (126)..(126)
<223> OTHER INFORMATION: Xaa is any amino acid other than a glutamine

<400> SEQUENCE: 15

Ala Pro Thr Ser Ser Ser Thr Lys Lys Thr Gln Leu Gln Leu Glu His
1               5                   10                  15

Leu Leu Leu Xaa Leu Gln Met Ile Leu Asn Gly Ile Asn Asn Tyr Lys
            20                  25                  30

Asn Pro Lys Leu Thr Arg Met Leu Thr Xaa Lys Phe Xaa Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Xaa Ser Ile
        115                 120                 125

Ile Ser Thr Leu Thr
    130


<210> SEQ ID NO 16
<211> LENGTH: 133
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (16)..(16)
<223> OTHER INFORMATION: Xaa is any amino acid other than a histidine
<220> FEATURE:
<221> NAME/KEY: MISC_FEATURE
<222> LOCATION: (20)..(20)
<223> OTHER INFORMATION: Xaa is any amino acid other than an aspartic
      acid
<220> FEATURE:
<221> NAME/KEY: MISC_FEATURE
<222> LOCATION: (42)..(42)
<223> OTHER INFORMATION: Xaa is any amino acid other than a
      phenylalanine
<220> FEATURE:
<221> NAME/KEY: MISC_FEATURE
<222> LOCATION: (45)..(45)
<223> OTHER INFORMATION: Xaa is any amino acid other than a tyrosine
<220> FEATURE:
<221> NAME/KEY: MISC_FEATURE
<222> LOCATION: (126)..(126)
<223> OTHER INFORMATION: Xaa is any amino acid other than a glutamine

<400> SEQUENCE: 16

Ala Pro Thr Ser Ser Ser Thr Lys Lys Thr Gln Leu Gln Leu Glu Xaa
1               5                   10                  15

Leu Leu Leu Xaa Leu Gln Met Ile Leu Asn Gly Ile Asn Asn Tyr Lys
            20                  25                  30

Asn Pro Lys Leu Thr Arg Met Leu Thr Xaa Lys Phe Xaa Met Pro Lys
        35                  40                  45

Lys Ala Thr Glu Leu Lys His Leu Gln Cys Leu Glu Glu Glu Leu Lys
    50                  55                  60
```

```
Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Xaa Ser Ile
        115                 120                 125

Ile Ser Thr Leu Thr
    130


<210> SEQ ID NO 17
<211> LENGTH: 133
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (16)..(16)
<223> OTHER INFORMATION: Xaa is any amino acid other than a histidine
<220> FEATURE:
<221> NAME/KEY: MISC_FEATURE
<222> LOCATION: (42)..(42)
<223> OTHER INFORMATION: Xaa is any amino acid other than a
      phenylalanine
<220> FEATURE:
<221> NAME/KEY: MISC_FEATURE
<222> LOCATION: (126)..(126)
<223> OTHER INFORMATION: Xaa is any amino acid other than a glutamine

<400> SEQUENCE: 17

Ala Pro Thr Ser Ser Ser Thr Lys Lys Thr Gln Leu Gln Leu Glu Xaa
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Xaa Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Xaa Ser Ile
        115                 120                 125

Ile Ser Thr Leu Thr
    130


<210> SEQ ID NO 18
<211> LENGTH: 272
<212> TYPE: PRT
<213> ORGANISM: Homo sapiens

<400> SEQUENCE: 18

Met Asp Ser Tyr Leu Leu Met Trp Gly Leu Leu Thr Phe Ile Met Val
1               5                   10                  15

Pro Gly Cys Gln Ala Glu Leu Cys Asp Asp Asp Pro Pro Glu Ile Pro
            20                  25                  30
```

His Ala Thr Phe Lys Ala Met Ala Tyr Lys Glu Gly Thr Met Leu Asn
35 40 45

Cys Glu Cys Lys Arg Gly Phe Arg Arg Ile Lys Ser Gly Ser Leu Tyr
50 55 60

Met Leu Cys Thr Gly Asn Ser Ser His Ser Ser Trp Asp Asn Gln Cys
65 70 75 80

Gln Cys Thr Ser Ser Ala Thr Arg Asn Thr Thr Lys Gln Val Thr Pro
85 90 95

Gln Pro Glu Glu Gln Lys Glu Arg Lys Thr Thr Glu Met Gln Ser Pro
100 105 110

Met Gln Pro Val Asp Gln Ala Ser Leu Pro Gly His Cys Arg Glu Pro
115 120 125

Pro Pro Trp Glu Asn Glu Ala Thr Glu Arg Ile Tyr His Phe Val Val
130 135 140

Gly Gln Met Val Tyr Tyr Gln Cys Val Gln Gly Tyr Arg Ala Leu His
145 150 155 160

Arg Gly Pro Ala Glu Ser Val Cys Lys Met Thr His Gly Lys Thr Arg
165 170 175

Trp Thr Gln Pro Gln Leu Ile Cys Thr Gly Glu Met Glu Thr Ser Gln
180 185 190

Phe Pro Gly Glu Glu Lys Pro Gln Ala Ser Pro Glu Gly Arg Pro Glu
195 200 205

Ser Glu Thr Ser Cys Leu Val Thr Thr Thr Asp Phe Gln Ile Gln Thr
210 215 220

Glu Met Ala Ala Thr Met Glu Thr Ser Ile Phe Thr Thr Glu Tyr Gln
225 230 235 240

Val Ala Val Ala Gly Cys Val Phe Leu Leu Ile Ser Val Leu Leu Leu
245 250 255

Ser Gly Leu Thr Trp Gln Arg Arg Gln Arg Lys Ser Arg Arg Thr Ile
260 265 270

<210> SEQ ID NO 19
<211> LENGTH: 551
<212> TYPE: PRT
<213> ORGANISM: Homo sapiens

<400> SEQUENCE: 19

Met Ala Ala Pro Ala Leu Ser Trp Arg Leu Pro Leu Leu Ile Leu Leu
1 5 10 15

Leu Pro Leu Ala Thr Ser Trp Ala Ser Ala Ala Val Asn Gly Thr Ser
20 25 30

Gln Phe Thr Cys Phe Tyr Asn Ser Arg Ala Asn Ile Ser Cys Val Trp
35 40 45

Ser Gln Asp Gly Ala Leu Gln Asp Thr Ser Cys Gln Val His Ala Trp
50 55 60

Pro Asp Arg Arg Arg Trp Asn Gln Thr Cys Glu Leu Leu Pro Val Ser
65 70 75 80

Gln Ala Ser Trp Ala Cys Asn Leu Ile Leu Gly Ala Pro Asp Ser Gln
85 90 95

Lys Leu Thr Thr Val Asp Ile Val Thr Leu Arg Val Leu Cys Arg Glu
100 105 110

Gly Val Arg Trp Arg Val Met Ala Ile Gln Asp Phe Lys Pro Phe Glu
115 120 125

Asn Leu Arg Leu Met Ala Pro Ile Ser Leu Gln Val Val His Val Glu
130 135 140

-continued

```
Thr His Arg Cys Asn Ile Ser Trp Glu Ile Ser Gln Ala Ser His Tyr
145                 150                 155                 160

Phe Glu Arg His Leu Glu Phe Glu Ala Arg Thr Leu Ser Pro Gly His
                165                 170                 175

Thr Trp Glu Glu Ala Pro Leu Leu Thr Leu Lys Gln Lys Gln Glu Trp
            180                 185                 190

Ile Cys Leu Glu Thr Leu Thr Pro Asp Thr Gln Tyr Glu Phe Gln Val
        195                 200                 205

Arg Val Lys Pro Leu Gln Gly Glu Phe Thr Thr Trp Ser Pro Trp Ser
    210                 215                 220

Gln Pro Leu Ala Phe Arg Thr Lys Pro Ala Ala Leu Gly Lys Asp Thr
225                 230                 235                 240

Ile Pro Trp Leu Gly His Leu Leu Val Gly Leu Ser Gly Ala Phe Gly
                245                 250                 255

Phe Ile Ile Leu Val Tyr Leu Leu Ile Asn Cys Arg Asn Thr Gly Pro
            260                 265                 270

Trp Leu Lys Lys Val Leu Lys Cys Asn Thr Pro Asp Pro Ser Lys Phe
        275                 280                 285

Phe Ser Gln Leu Ser Ser Glu His Gly Gly Asp Val Gln Lys Trp Leu
    290                 295                 300

Ser Ser Pro Phe Pro Ser Ser Ser Phe Ser Pro Gly Gly Leu Ala Pro
305                 310                 315                 320

Glu Ile Ser Pro Leu Glu Val Leu Glu Arg Asp Lys Val Thr Gln Leu
                325                 330                 335

Leu Leu Gln Gln Asp Lys Val Pro Glu Pro Ala Ser Leu Ser Ser Asn
            340                 345                 350

His Ser Leu Thr Ser Cys Phe Thr Asn Gln Gly Tyr Phe Phe Phe His
        355                 360                 365

Leu Pro Asp Ala Leu Glu Ile Glu Ala Cys Gln Val Tyr Phe Thr Tyr
    370                 375                 380

Asp Pro Tyr Ser Glu Glu Asp Pro Asp Glu Gly Val Ala Gly Ala Pro
385                 390                 395                 400

Thr Gly Ser Ser Pro Gln Pro Leu Gln Pro Leu Ser Gly Glu Asp Asp
                405                 410                 415

Ala Tyr Cys Thr Phe Pro Ser Arg Asp Asp Leu Leu Leu Phe Ser Pro
            420                 425                 430

Ser Leu Leu Gly Gly Pro Ser Pro Pro Ser Thr Ala Pro Gly Gly Ser
        435                 440                 445

Gly Ala Gly Glu Glu Arg Met Pro Pro Ser Leu Gln Glu Arg Val Pro
    450                 455                 460

Arg Asp Trp Asp Pro Gln Pro Leu Gly Pro Pro Thr Pro Gly Val Pro
465                 470                 475                 480

Asp Leu Val Asp Phe Gln Pro Pro Pro Glu Leu Val Leu Arg Glu Ala
                485                 490                 495

Gly Glu Glu Val Pro Asp Ala Gly Pro Arg Glu Gly Val Ser Phe Pro
            500                 505                 510

Trp Ser Arg Pro Pro Gly Gln Gly Glu Phe Arg Ala Leu Asn Ala Arg
        515                 520                 525

Leu Pro Leu Asn Thr Asp Ala Tyr Leu Ser Leu Gln Glu Leu Gln Gly
    530                 535                 540

Gln Asp Pro Thr His Leu Val
545                 550
```

<210> SEQ ID NO 20
<211> LENGTH: 369
<212> TYPE: PRT
<213> ORGANISM: Homo sapiens

<400> SEQUENCE: 20

Met Leu Lys Pro Ser Leu Pro Phe Thr Ser Leu Leu Phe Leu Gln Leu
1 5 10 15

Pro Leu Leu Gly Val Gly Leu Asn Thr Thr Ile Leu Thr Pro Asn Gly
20 25 30

Asn Glu Asp Thr Thr Ala Asp Phe Phe Leu Thr Thr Met Pro Thr Asp
35 40 45

Ser Leu Ser Val Ser Thr Leu Pro Leu Pro Glu Val Gln Cys Phe Val
50 55 60

Phe Asn Val Glu Tyr Met Asn Cys Thr Trp Asn Ser Ser Ser Glu Pro
65 70 75 80

Gln Pro Thr Asn Leu Thr Leu His Tyr Trp Tyr Lys Asn Ser Asp Asn
85 90 95

Asp Lys Val Gln Lys Cys Ser His Tyr Leu Phe Ser Glu Glu Ile Thr
100 105 110

Ser Gly Cys Gln Leu Gln Lys Lys Glu Ile His Leu Tyr Gln Thr Phe
115 120 125

Val Val Gln Leu Gln Asp Pro Arg Glu Pro Arg Arg Gln Ala Thr Gln
130 135 140

Met Leu Lys Leu Gln Asn Leu Val Ile Pro Trp Ala Pro Glu Asn Leu
145 150 155 160

Thr Leu His Lys Leu Ser Glu Ser Gln Leu Glu Leu Asn Trp Asn Asn
165 170 175

Arg Phe Leu Asn His Cys Leu Glu His Leu Val Gln Tyr Arg Thr Asp
180 185 190

Trp Asp His Ser Trp Thr Glu Gln Ser Val Asp Tyr Arg His Lys Phe
195 200 205

Ser Leu Pro Ser Val Asp Gly Gln Lys Arg Tyr Thr Phe Arg Val Arg
210 215 220

Ser Arg Phe Asn Pro Leu Cys Gly Ser Ala Gln His Trp Ser Glu Trp
225 230 235 240

Ser His Pro Ile His Trp Gly Ser Asn Thr Ser Lys Glu Asn Pro Phe
245 250 255

Leu Phe Ala Leu Glu Ala Val Val Ile Ser Val Gly Ser Met Gly Leu
260 265 270

Ile Ile Ser Leu Leu Cys Val Tyr Phe Trp Leu Glu Arg Thr Met Pro
275 280 285

Arg Ile Pro Thr Leu Lys Asn Leu Glu Asp Leu Val Thr Glu Tyr His
290 295 300

Gly Asn Phe Ser Ala Trp Ser Gly Val Ser Lys Gly Leu Ala Glu Ser
305 310 315 320

Leu Gln Pro Asp Tyr Ser Glu Arg Leu Cys Leu Val Ser Glu Ile Pro
325 330 335

Pro Lys Gly Gly Ala Leu Gly Glu Gly Pro Gly Ala Ser Pro Cys Asn
340 345 350

Gln His Ser Pro Tyr Trp Ala Pro Pro Cys Tyr Thr Leu Lys Pro Glu
355 360 365

Thr

<210> SEQ ID NO 21
<211> LENGTH: 227
<212> TYPE: PRT
<213> ORGANISM: Homo sapiens

<400> SEQUENCE: 21

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

<210> SEQ ID NO 22
<211> LENGTH: 325
<212> TYPE: PRT
<213> ORGANISM: Homo sapiens

<400> SEQUENCE: 22

```
Ser Thr Lys Gly Pro Ser Val Phe Pro Leu Ala Pro Cys Ser Arg Ser
1               5                   10                  15

Thr Ser Glu Ser Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Asn Phe Gly Thr Gln Thr Tyr
65                  70                  75                  80

Thr Cys Asn Val Asp His Lys Pro Ser Asn Thr Lys Val Asp Lys Thr
                85                  90                  95
```

```
Val Glu Arg Lys Cys Cys Val Glu Cys Pro Pro Cys Pro Ala Pro Pro
            100                 105                 110

Val Ala Gly Pro Ser Val Phe Leu Phe Pro Pro Lys Pro Lys Asp Thr
        115                 120                 125

Leu Met Ile Ser Arg Thr Pro Glu Val Thr Cys Val Val Val Asp Val
    130                 135                 140

Ser His Glu Asp Pro Glu Val Gln Phe Asn Trp Tyr Val Asp Gly Val
145                 150                 155                 160

Glu Val His Asn Ala Lys Thr Lys Pro Arg Glu Glu Gln Phe Asn Ser
                165                 170                 175

Thr Phe Arg Val Val Ser Val Leu Thr Val Val His Gln Asp Trp Leu
            180                 185                 190

Asn Gly Lys Glu Tyr Lys Cys Lys Val Ser Asn Lys Gly Leu Pro Ala
        195                 200                 205

Pro Ile Glu Lys Thr Ile Ser Lys Thr Lys Gly Gln Pro Arg Glu Pro
    210                 215                 220

Gln Val Tyr Thr Leu Pro Pro Ser Arg Glu Glu Met Thr Lys Asn Gln
225                 230                 235                 240

Val Ser Leu Thr Cys Leu Val Lys Gly Phe Tyr Pro Ser Asp Ile Ala
                245                 250                 255

Val Glu Trp Glu Ser Asn Gly Gln Pro Glu Asn Asn Tyr Lys Thr Thr
            260                 265                 270

Pro Pro Met Leu Asp Ser Asp Gly Ser Phe Phe Leu Tyr Ser Lys Leu
        275                 280                 285

Thr Val Asp Lys Ser Arg Trp Gln Gln Gly Asn Val Phe Ser Cys Ser
    290                 295                 300

Val Met His Glu Ala Leu His Asn His Tyr Thr Gln Lys Ser Leu Ser
305                 310                 315                 320

Leu Ser Pro Gly Lys
                325


<210> SEQ ID NO 23
<211> LENGTH: 246
<212> TYPE: PRT
<213> ORGANISM: Homo sapiens

<400> SEQUENCE: 23

His Lys Pro Ser Asn Thr Lys Val Asp Lys Arg Val Glu Leu Lys Thr
1               5                   10                  15

Pro Leu Gly Asp Thr Thr His Thr Cys Pro Pro Cys Pro Ala Pro Glu
            20                  25                  30

Leu Leu Gly Gly Pro Ser Val Phe Leu Phe Pro Pro Lys Pro Lys Asp
        35                  40                  45

Thr Leu Met Ile Ser Arg Thr Pro Glu Val Thr Cys Val Val Val Asp
    50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
            100                 105                 110

Leu Asn Gly Lys Glu Tyr Lys Cys Lys Val Ser Asn Lys Ala Leu Pro
        115                 120                 125

Ala Pro Ile Glu Lys Thr Ile Ser Lys Ala Lys Gly Gln Pro Arg Glu
    130                 135                 140
```

```
Pro Gln Val Tyr Thr Leu Pro Pro Ser Arg Asp Glu Leu Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
    210                 215                 220

Ser Val Met His Glu Ala Leu His Asn His Tyr Thr Gln Lys Ser Leu
225                 230                 235                 240

Ser Leu Ser Pro Gly Lys
                245


<210> SEQ ID NO 24
<211> LENGTH: 383
<212> TYPE: PRT
<213> ORGANISM: Homo sapiens

<400> SEQUENCE: 24

Pro Thr Lys Ala Pro Asp Val Phe Pro Ile Ile Ser Gly Cys Arg His
1               5                   10                  15

Pro Lys Asp Asn Ser Pro Val Val Leu Ala Cys Leu Ile Thr Gly Tyr
            20                  25                  30

His Pro Thr Ser Val Thr Val Thr Trp Tyr Met Gly Thr Gln Ser Gln
        35                  40                  45

Pro Gln Arg Thr Phe Pro Glu Ile Gln Arg Arg Asp Ser Tyr Tyr Met
    50                  55                  60

Thr Ser Ser Gln Leu Ser Thr Pro Leu Gln Gln Trp Arg Gln Gly Glu
65                  70                  75                  80

Tyr Lys Cys Val Val Gln His Thr Ala Ser Lys Ser Lys Lys Glu Ile
                85                  90                  95

Phe Arg Trp Pro Glu Ser Pro Lys Ala Gln Ala Ser Ser Val Pro Thr
            100                 105                 110

Ala Gln Pro Gln Ala Glu Gly Ser Leu Ala Lys Ala Thr Thr Ala Pro
        115                 120                 125

Ala Thr Thr Arg Asn Thr Gly Arg Gly Gly Glu Glu Lys Lys Lys Glu
    130                 135                 140

Lys Glu Lys Glu Glu Gln Glu Glu Arg Glu Thr Lys Thr Pro Glu Cys
145                 150                 155                 160

Pro Ser His Thr Gln Pro Leu Gly Val Tyr Leu Leu Thr Pro Ala Val
                165                 170                 175

Gln Asp Leu Trp Leu Arg Asp Lys Ala Thr Phe Thr Cys Phe Val Val
            180                 185                 190

Gly Ser Asp Leu Lys Asp Ala His Leu Thr Trp Glu Val Ala Gly Lys
        195                 200                 205

Val Pro Thr Gly Gly Val Glu Glu Gly Leu Leu Glu Arg His Ser Asn
    210                 215                 220

Gly Ser Gln Ser Gln His Ser Arg Leu Thr Leu Pro Arg Ser Leu Trp
225                 230                 235                 240

Asn Ala Gly Thr Ser Val Thr Cys Thr Leu Asn His Pro Ser Leu Pro
                245                 250                 255

Pro Gln Arg Leu Met Ala Leu Arg Glu Pro Ala Ala Gln Ala Pro Val
```

```
            260                 265                 270

Lys Leu Ser Leu Asn Leu Leu Ala Ser Ser Asp Pro Pro Glu Ala Ala
        275                 280                 285

Ser Trp Leu Leu Cys Glu Val Ser Gly Phe Ser Pro Pro Asn Ile Leu
    290                 295                 300

Leu Met Trp Leu Glu Asp Gln Arg Glu Val Asn Thr Ser Gly Phe Ala
305                 310                 315                 320

Pro Ala Arg Pro Pro Pro Gln Pro Arg Ser Thr Thr Phe Trp Ala Trp
                325                 330                 335

Ser Val Leu Arg Val Pro Ala Pro Pro Ser Pro Gln Pro Ala Thr Tyr
            340                 345                 350

Thr Cys Val Val Ser His Glu Asp Ser Arg Thr Leu Leu Asn Ala Ser
        355                 360                 365

Arg Ser Leu Glu Val Ser Tyr Val Thr Asp His Gly Pro Met Lys
    370                 375                 380


<210> SEQ ID NO 25
<211> LENGTH: 276
<212> TYPE: PRT
<213> ORGANISM: Homo sapiens

<400> SEQUENCE: 25

Val Thr Ser Thr Leu Thr Ile Lys Glx Ser Asp Trp Leu Gly Glu Ser
1               5                   10                  15

Met Phe Thr Cys Arg Val Asp His Arg Gly Leu Thr Phe Gln Gln Asn
            20                  25                  30

Ala Ser Ser Met Cys Val Pro Asp Gln Asp Thr Ala Ile Arg Val Phe
        35                  40                  45

Ala Ile Pro Pro Ser Phe Ala Ser Ile Phe Leu Thr Lys Ser Thr Lys
    50                  55                  60

Leu Thr Cys Leu Val Thr Asp Leu Thr Thr Tyr Asx Ser Val Thr Ile
65                  70                  75                  80

Ser Trp Thr Arg Glu Glu Asn Gly Ala Val Lys Thr His Thr Asn Ile
                85                  90                  95

Ser Glu Ser His Pro Asn Ala Thr Phe Ser Ala Val Gly Glu Ala Ser
            100                 105                 110

Ile Cys Glu Asp Asx Asp Trp Ser Gly Glu Arg Phe Thr Cys Thr Val
        115                 120                 125

Thr His Thr Asp Leu Pro Ser Pro Leu Lys Gln Thr Ile Ser Arg Pro
    130                 135                 140

Lys Gly Val Ala Leu His Arg Pro Asx Val Tyr Leu Leu Pro Pro Ala
145                 150                 155                 160

Arg Glx Glx Leu Asn Leu Arg Glu Ser Ala Thr Ile Thr Cys Leu Val
                165                 170                 175

Thr Gly Phe Ser Pro Ala Asp Val Phe Val Glu Trp Met Gln Arg Gly
            180                 185                 190

Glu Pro Leu Ser Pro Gln Lys Tyr Val Thr Ser Ala Pro Met Pro Glu
        195                 200                 205

Pro Gln Ala Pro Gly Arg Tyr Phe Ala His Ser Ile Leu Thr Val Ser
    210                 215                 220

Glu Glu Glu Trp Asn Thr Gly Gly Thr Tyr Thr Cys Val Val Ala His
225                 230                 235                 240

Glu Ala Leu Pro Asn Arg Val Thr Glu Arg Thr Val Asp Lys Ser Thr
                245                 250                 255
```

```
Gly Lys Pro Thr Leu Tyr Asn Val Ser Leu Val Met Ser Asp Thr Ala
            260                 265                 270

Gly Thr Cys Tyr
        275


<210> SEQ ID NO 26
<211> LENGTH: 353
<212> TYPE: PRT
<213> ORGANISM: Homo sapiens

<400> SEQUENCE: 26

Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Ser Thr Pro Pro Thr Pro Ser Pro
            100                 105                 110

Ser Thr Pro Pro Thr Pro Ser Pro Ser Cys Cys His Pro Arg Leu Ser
        115                 120                 125

Leu His Arg Pro Ala Leu Glu Asp Leu Leu Leu Gly Ser Glu Ala Asn
    130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Glu
                165                 170                 175

Arg Asp Leu Cys Gly Cys Tyr Ser Val Ser Ser Val Leu Pro Gly Cys
            180                 185                 190

Ala Glu Pro Trp Asn His Gly Lys Thr Phe Thr Cys Thr Ala Ala Tyr
        195                 200                 205

Pro Glu Ser Lys Thr Pro Leu Thr Ala Thr Leu Ser Lys Ser Gly Asn
    210                 215                 220

Thr Phe Arg Pro Glu Val His Leu Leu Pro Pro Pro Ser Glu Glu Leu
225                 230                 235                 240

Ala Leu Asn Glu Leu Val Thr Leu Thr Cys Leu Ala Arg Gly Phe Ser
                245                 250                 255

Pro Lys Asp Val Leu Val Arg Trp Leu Gln Gly Ser Gln Glu Leu Pro
            260                 265                 270

Arg Glu Lys Tyr Leu Thr Trp Ala Ser Arg Gln Glu Pro Ser Gln Gly
        275                 280                 285

Thr Thr Thr Phe Ala Val Thr Ser Ile Leu Arg Val Ala Ala Glu Asp
    290                 295                 300

Trp Lys Lys Gly Asp Thr Phe Ser Cys Met Val Gly His Glu Ala Leu
305                 310                 315                 320

Pro Leu Ala Phe Thr Gln Lys Thr Ile Asp Arg Leu Ala Gly Lys Pro
                325                 330                 335

Thr His Val Asn Val Ser Val Val Met Ala Glu Val Asp Gly Thr Cys
            340                 345                 350
```

Tyr

<210> SEQ ID NO 27
<211> LENGTH: 222
<212> TYPE: PRT
<213> ORGANISM: Homo sapiens

<400> SEQUENCE: 27

Ala Asp Pro Cys Asp Ser Asn Pro Arg Gly Val Ser Ala Tyr Leu Ser
1 5 10 15

Arg Pro Ser Pro Phe Asp Leu Phe Ile Arg Lys Ser Pro Thr Ile Thr
20 25 30

Cys Leu Val Val Asp Leu Ala Pro Ser Lys Gly Thr Val Asn Leu Thr
35 40 45

Trp Ser Arg Ala Ser Gly Lys Pro Val Asn His Ser Thr Arg Lys Glu
50 55 60

Glu Lys Gln Arg Asn Gly Thr Leu Thr Val Thr Ser Thr Leu Pro Val
65 70 75 80

Gly Thr Arg Asp Trp Ile Glu Gly Glu Thr Tyr Gln Cys Arg Val Thr
85 90 95

His Pro His Leu Pro Arg Ala Leu Met Arg Ser Thr Thr Lys Thr Ser
100 105 110

Gly Pro Arg Ala Ala Pro Glu Val Tyr Ala Phe Ala Thr Pro Glu Trp
115 120 125

Pro Gly Ser Arg Asp Lys Arg Thr Leu Ala Cys Leu Ile Gln Asn Phe
130 135 140

Met Pro Glu Asp Ile Ser Val Gln Trp Leu His Asn Glu Val Gln Leu
145 150 155 160

Pro Asp Ala Arg His Ser Thr Thr Gln Pro Arg Lys Thr Lys Gly Ser
165 170 175

Gly Phe Phe Val Phe Ser Arg Leu Glu Val Thr Arg Ala Glu Trp Glu
180 185 190

Gln Lys Asp Glu Phe Ile Cys Arg Ala Val His Glu Ala Ala Ser Pro
195 200 205

Ser Gln Thr Val Gln Arg Ala Val Ser Val Asn Pro Gly Lys
210 215 220

<210> SEQ ID NO 28
<211> LENGTH: 327
<212> TYPE: PRT
<213> ORGANISM: Homo sapiens

<400> SEQUENCE: 28

Ala Ser Thr Lys Gly Pro Ser Val Phe Pro Leu Ala Pro Cys Ser Arg
1 5 10 15

Ser Thr Ser Glu Ser Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Lys Thr
65 70 75 80

Tyr Thr Cys Asn Val Asp His Lys Pro Ser Asn Thr Lys Val Asp Lys
85 90 95

Arg Val Glu Ser Lys Tyr Gly Pro Pro Cys Pro Ser Cys Pro Ala Pro
100 105 110

Glu Phe Leu Gly Gly Pro Ser Val Phe Leu Phe Pro Pro Lys Pro Lys
115 120 125

Asp Thr Leu Met Ile Ser Arg Thr Pro Glu Val Thr Cys Val Val Val
130 135 140

Asp Val Ser Gln Glu Asp Pro Glu Val Gln Phe Asn Trp Tyr Val Asp
145 150 155 160

Gly Val Glu Val His Asn Ala Lys Thr Lys Pro Arg Glu Glu Gln Phe
165 170 175

Asn Ser Thr Tyr Arg Val Val Ser Val Leu Thr Val Leu His Gln Asp
180 185 190

Trp Leu Asn Gly Lys Glu Tyr Lys Cys Lys Val Ser Asn Lys Gly Leu
195 200 205

Pro Ser Ser Ile Glu Lys Thr Ile Ser Lys Ala Lys Gly Gln Pro Arg
210 215 220

Glu Pro Gln Val Tyr Thr Leu Pro Pro Ser Gln Glu Glu Met Thr Lys
225 230 235 240

Asn Gln Val Ser Leu Thr Cys Leu Val Lys Gly Phe Tyr Pro Ser Asp
245 250 255

Ile Ala Val Glu Trp Glu Ser Asn Gly Gln Pro Glu Asn Asn Tyr Lys
260 265 270

Thr Thr Pro Pro Val Leu Asp Ser Asp Gly Ser Phe Phe Leu Tyr Ser
275 280 285

Arg Leu Thr Val Asp Lys Ser Arg Trp Gln Glu Gly Asn Val Phe Ser
290 295 300

Cys Ser Val Met His Glu Ala Leu His Asn His Tyr Thr Gln Lys Ser
305 310 315 320

Leu Ser Leu Ser Leu Gly Lys
325

<210> SEQ ID NO 29
<211> LENGTH: 365
<212> TYPE: PRT
<213> ORGANISM: Homo sapiens

<400> SEQUENCE: 29

Met Ala Val Met Ala Pro Arg Thr Leu Leu Leu Leu Leu Ser Gly Ala
1 5 10 15

Leu Ala Leu Thr Gln Thr Trp Ala Gly Ser His Ser Met Arg Tyr Phe
20 25 30

Phe Thr Ser Val Ser Arg Pro Gly Arg Gly Glu Pro Arg Phe Ile Ala
35 40 45

Val Gly Tyr Val Asp Asp Thr Gln Phe Val Arg Phe Asp Ser Asp Ala
50 55 60

Ala Ser Gln Lys Met Glu Pro Arg Ala Pro Trp Ile Glu Gln Glu Gly
65 70 75 80

Pro Glu Tyr Trp Asp Gln Glu Thr Arg Asn Met Lys Ala His Ser Gln
85 90 95

Thr Asp Arg Ala Asn Leu Gly Thr Leu Arg Gly Tyr Tyr Asn Gln Ser
100 105 110

Glu Asp Gly Ser His Thr Ile Gln Ile Met Tyr Gly Cys Asp Val Gly
115 120 125

Pro Asp Gly Arg Phe Leu Arg Gly Tyr Arg Gln Asp Ala Tyr Asp Gly
130 135 140

```
Lys Asp Tyr Ile Ala Leu Asn Glu Asp Leu Arg Ser Trp Thr Ala Ala
145                 150                 155                 160

Asp Met Ala Ala Gln Ile Thr Lys Arg Lys Trp Glu Ala Val His Ala
                165                 170                 175

Ala Glu Gln Arg Arg Val Tyr Leu Glu Gly Arg Cys Val Asp Gly Leu
            180                 185                 190

Arg Arg Tyr Leu Glu Asn Gly Lys Glu Thr Leu Gln Arg Thr Asp Pro
        195                 200                 205

Pro Lys Thr His Met Thr His His Pro Ile Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Leu Ser Ser Gln Pro
    290                 295                 300

Thr Ile Pro Ile Val Gly Ile Ile Ala Gly Leu Val Leu Leu Gly Ala
305                 310                 315                 320

Val Ile Thr Gly Ala Val Val Ala Ala Val Met Trp Arg Arg Lys Ser
                325                 330                 335

Ser Asp Arg Lys Gly Gly Ser Tyr Thr Gln Ala Ala Ser Ser Asp Ser
            340                 345                 350

Ala Gln Gly Ser Asp Val Ser Leu Thr Ala Cys Lys Val
        355                 360                 365


<210> SEQ ID NO 30
<211> LENGTH: 362
<212> TYPE: PRT
<213> ORGANISM: Homo sapiens

<400> SEQUENCE: 30

Met Leu Val Met Ala Pro Arg Thr Val Leu Leu Leu Leu Ser Ala Ala
1               5                   10                  15

Leu Ala Leu Thr Glu Thr Trp Ala Gly Ser His Ser Met Arg Tyr Phe
            20                  25                  30

Tyr Thr Ser Val Ser Arg Pro Gly Arg Gly Glu Pro Arg Phe Ile Ser
        35                  40                  45

Val Gly Tyr Val Asp Asp Thr Gln Phe Val Arg Phe Asp Ser Asp Ala
    50                  55                  60

Ala Ser Pro Arg Glu Glu Pro Arg Ala Pro Trp Ile Glu Gln Glu Gly
65                  70                  75                  80

Pro Glu Tyr Trp Asp Arg Asn Thr Gln Ile Tyr Lys Ala Gln Ala Gln
                85                  90                  95

Thr Asp Arg Glu Ser Leu Arg Asn Leu Arg Gly Tyr Tyr Asn Gln Ser
            100                 105                 110

Glu Ala Gly Ser His Thr Leu Gln Ser Met Tyr Gly Cys Asp Val Gly
        115                 120                 125

Pro Asp Gly Arg Leu Leu Arg Gly His Asp Gln Tyr Ala Tyr Asp Gly
    130                 135                 140

Lys Asp Tyr Ile Ala Leu Asn Glu Asp Leu Arg Ser Trp Thr Ala Ala
```

-continued

```
145                 150                 155                 160

Asp Thr Ala Ala Gln Ile Thr Gln Arg Lys Trp Glu Ala Ala Arg Glu
                165                 170                 175

Ala Glu Gln Arg Arg Ala Tyr Leu Glu Gly Glu Cys Val Glu Trp Leu
            180                 185                 190

Arg Arg Tyr Leu Glu Asn Gly Lys Asp Lys Leu Glu Arg Ala Asp Pro
        195                 200                 205

Pro Lys Thr His Val Thr His His Pro Ile Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Pro Ser Ser Gln Ser
    290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser Gly Gly Lys Gly Gly Ser Tyr Ser Gln Ala Ala Cys Ser Asp Ser
            340                 345                 350

Ala Gln Gly Ser Asp Val Ser Leu Thr Ala
        355                 360


<210> SEQ ID NO 31
<211> LENGTH: 366
<212> TYPE: PRT
<213> ORGANISM: Homo sapiens

<400> SEQUENCE: 31

Met Arg Val Met Ala Pro Arg Ala Leu Leu Leu Leu Leu Ser Gly Gly
1               5                   10                  15

Leu Ala Leu Thr Glu Thr Trp Ala Cys Ser His Ser Met Arg Tyr Phe
            20                  25                  30

Asp Thr Ala Val Ser Arg Pro Gly Arg Gly Glu Pro Arg Phe Ile Ser
        35                  40                  45

Val Gly Tyr Val Asp Asp Thr Gln Phe Val Arg Phe Asp Ser Asp Ala
    50                  55                  60

Ala Ser Pro Arg Gly Glu Pro Arg Ala Pro Trp Val Glu Gln Glu Gly
65                  70                  75                  80

Pro Glu Tyr Trp Asp Arg Glu Thr Gln Asn Tyr Lys Arg Gln Ala Gln
                85                  90                  95

Ala Asp Arg Val Ser Leu Arg Asn Leu Arg Gly Tyr Tyr Asn Gln Ser
            100                 105                 110

Glu Asp Gly Ser His Thr Leu Gln Arg Met Tyr Gly Cys Asp Leu Gly
        115                 120                 125

Pro Asp Gly Arg Leu Leu Arg Gly Tyr Asp Gln Ser Ala Tyr Asp Gly
    130                 135                 140

Lys Asp Tyr Ile Ala Leu Asn Glu Asp Leu Arg Ser Trp Thr Ala Ala
145                 150                 155                 160
```

Asp Thr Ala Ala Gln Ile Thr Gln Arg Lys Leu Glu Ala Ala Arg Ala
165 170 175

Ala Glu Gln Leu Arg Ala Tyr Leu Glu Gly Thr Cys Val Glu Trp Leu
180 185 190

Arg Arg Tyr Leu Glu Asn Gly Lys Glu Thr Leu Gln Arg Ala Glu Pro
195 200 205

Pro Lys Thr His Val Thr His His Pro Leu Ser Asp His Glu Ala Thr
210 215 220

Leu Arg Cys Trp Ala Leu Gly Phe Tyr Pro Ala Glu Ile Thr Leu Thr
225 230 235 240

Trp Gln Arg Asp Gly Glu Asp Gln Thr Gln Asp Thr Glu Leu Val Glu
245 250 255

Thr Arg Pro Ala Gly Asp Gly Thr Phe Gln Lys Trp Ala Ala Val Val
260 265 270

Val Pro Ser Gly Gln Glu Gln Arg Tyr Thr Cys His Met Gln His Glu
275 280 285

Gly Leu Gln Glu Pro Leu Thr Leu Ser Trp Glu Pro Ser Ser Gln Pro
290 295 300

Thr Ile Pro Ile Met Gly Ile Val Ala Gly Leu Ala Val Leu Val Val
305 310 315 320

Leu Ala Val Leu Gly Ala Val Val Thr Ala Met Met Cys Arg Arg Lys
325 330 335

Ser Ser Gly Gly Lys Gly Gly Ser Cys Ser Gln Ala Ala Cys Ser Asn
340 345 350

Ser Ala Gln Gly Ser Asp Glu Ser Leu Ile Thr Cys Lys Ala
355 360 365

<210> SEQ ID NO 32
<211> LENGTH: 833
<212> TYPE: PRT
<213> ORGANISM: Homo sapiens

<400> SEQUENCE: 32

Met Tyr Arg Met Gln Leu Leu Ser Cys Ile Ala Leu Ser Leu Ala Leu
1 5 10 15

Val Thr Asn Ser Ala Pro Thr Ser Ser Ser Thr Lys Lys Thr Gln Leu
20 25 30

Gln Leu Glu Ala Leu Leu Leu Asp Leu Gln Met Ile Leu Asn Gly Ile
35 40 45

Asn Asn Tyr Lys Asn Pro Lys Leu Thr Arg Met Leu Thr Ala Lys Phe
50 55 60

Tyr Met Pro Lys Lys Ala Thr Glu Leu Lys His Leu Gln Cys Leu Glu
65 70 75 80

Glu Glu Leu Lys Pro Leu Glu Glu Val Leu Asn Leu Ala Gln Ser Lys
85 90 95

Asn Phe His Leu Arg Pro Arg Asp Leu Ile Ser Asn Ile Asn Val Ile
100 105 110

Val Leu Glu Leu Lys Gly Ser Glu Thr Thr Phe Met Cys Glu Tyr Ala
115 120 125

Asp Glu Thr Ala Thr Ile Val Glu Phe Leu Asn Arg Trp Ile Thr Phe
130 135 140

Cys Gln Ser Ile Ile Ser Thr Leu Thr Gly Gly Gly Gly Ser Gly Gly
145 150 155 160

Gly Gly Ser Gly Gly Gly Gly Ser Gly Gly Gly Gly Ser Ala Pro Thr
165 170 175

```
Ser Ser Ser Thr Lys Lys Thr Gln Leu Gln Leu Glu Ala Leu Leu Leu
            180                 185                 190

Asp Leu Gln Met Ile Leu Asn Gly Ile Asn Asn Tyr Lys Asn Pro Lys
        195                 200                 205

Leu Thr Arg Met Leu Thr Ala Lys Phe Tyr Met Pro Lys Lys Ala Thr
    210                 215                 220

Glu Leu Lys His Leu Gln Cys Leu Glu Glu Glu Leu Lys Pro Leu Glu
225                 230                 235                 240

Glu Val Leu Asn Leu Ala Gln Ser Lys Asn Phe His Leu Arg Pro Arg
                245                 250                 255

Asp Leu Ile Ser Asn Ile Asn Val Ile Val Leu Glu Leu Lys Gly Ser
            260                 265                 270

Glu Thr Thr Phe Met Cys Glu Tyr Ala Asp Glu Thr Ala Thr Ile Val
        275                 280                 285

Glu Phe Leu Asn Arg Trp Ile Thr Phe Cys Gln Ser Ile Ile Ser Thr
    290                 295                 300

Leu Thr Gly Gly Gly Gly Ser Gly Gly Gly Gly Ser Gly Gly Gly Gly
305                 310                 315                 320

Ser Gly Gly Gly Gly Ser Gly Ser His Ser Met Arg Tyr Phe Phe Thr
                325                 330                 335

Ser Val Ser Arg Pro Gly Arg Gly Glu Pro Arg Phe Ile Ala Val Gly
            340                 345                 350

Tyr Val Asp Asp Thr Gln Phe Val Arg Phe Asp Ser Asp Ala Ala Ser
        355                 360                 365

Gln Arg Met Glu Pro Arg Ala Pro Trp Ile Glu Gln Glu Gly Pro Glu
    370                 375                 380

Tyr Trp Asp Gly Glu Thr Arg Lys Val Lys Ala His Ser Gln Thr His
385                 390                 395                 400

Arg Val Asp Leu Gly Thr Leu Arg Gly Ala Tyr Asn Gln Ser Glu Ala
                405                 410                 415

Gly Ser His Thr Val Gln Arg Met Tyr Gly Cys Asp Val Gly Ser Asp
            420                 425                 430

Trp Arg Phe Leu Arg Gly Tyr His Gln Tyr Ala Tyr Asp Gly Lys Asp
        435                 440                 445

Tyr Ile Ala Leu Lys Glu Asp Leu Arg Ser Trp Thr Ala Ala Asp Met
    450                 455                 460

Ala Ala Gln Thr Thr Lys His Lys Trp Glu Ala Ala His Val Ala Glu
465                 470                 475                 480

Gln Leu Arg Ala Tyr Leu Glu Gly Thr Cys Val Glu Trp Leu Arg Arg
                485                 490                 495

Tyr Leu Glu Asn Gly Lys Glu Thr Leu Gln Arg Thr Asp Ala Pro Lys
            500                 505                 510

Thr His Met Thr His His Ala Val Ser Asp His Glu Ala Thr Leu Arg
        515                 520                 525

Cys Trp Ala Leu Ser Phe Tyr Pro Ala Glu Ile Thr Leu Thr Trp Gln
    530                 535                 540

Arg Asp Gly Glu Asp Gln Thr Gln Asp Thr Glu Leu Val Glu Thr Arg
545                 550                 555                 560

Pro Cys Gly Asp Gly Thr Phe Gln Lys Trp Ala Ala Val Val Val Pro
                565                 570                 575

Ser Gly Gln Glu Gln Arg Tyr Thr Cys His Val Gln His Glu Gly Leu
            580                 585                 590
```

Pro Lys Pro Leu Thr Leu Arg Trp Glu Ala Ala Ala Gly Gly Asp Lys
        595                 600                 605

Thr His Thr Cys Pro Pro Cys Pro Ala Pro Glu Leu Leu Gly Gly Pro
    610                 615                 620

Ser Val Phe Leu Phe Pro Pro Lys Pro Lys Asp Thr Leu Met Ile Ser
625                 630                 635                 640

Arg Thr Pro Glu Val Thr Cys Val Val Val Asp Val Ser His Glu Asp
                645                 650                 655

Pro Glu Val Lys Phe Asn Trp Tyr Val Asp Gly Val Glu Val His Asn
            660                 665                 670

Ala Lys Thr Lys Pro Arg Glu Glu Gln Tyr Ala Ser Thr Tyr Arg Val
        675                 680                 685

Val Ser Val Leu Thr Val Leu His Gln Asp Trp Leu Asn Gly Lys Glu
    690                 695                 700

Tyr Lys Cys Lys Val Ser Asn Lys Ala Leu Pro Ala Pro Ile Glu Lys
705                 710                 715                 720

Thr Ile Ser Lys Ala Lys Gly Gln Pro Arg Glu Pro Gln Val Tyr Thr
                725                 730                 735

Leu Pro Pro Ser Arg Glu Glu Met Thr Lys Asn Gln Val Ser Leu Thr
            740                 745                 750

Cys Leu Val Lys Gly Phe Tyr Pro Ser Asp Ile Ala Val Glu Trp Glu
        755                 760                 765

Ser Asn Gly Gln Pro Glu Asn Asn Tyr Lys Thr Thr Pro Pro Val Leu
    770                 775                 780

Asp Ser Asp Gly Ser Phe Phe Leu Tyr Ser Lys Leu Thr Val Asp Lys
785                 790                 795                 800

Ser Arg Trp Gln Gln Gly Asn Val Phe Ser Cys Ser Val Met His Glu
                805                 810                 815

Ala Leu His Asn His Tyr Thr Gln Lys Ser Leu Ser Leu Ser Pro Gly
            820                 825                 830

Lys

<210> SEQ ID NO 33
<211> LENGTH: 813
<212> TYPE: PRT
<213> ORGANISM: homo sapiens

<400> SEQUENCE: 33

Ala Pro Thr Ser Ser Ser Thr Lys Lys Thr Gln Leu Gln Leu Glu Ala
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

```
Ile Ser Thr Leu Thr Gly Gly Gly Gly Ser Gly Gly Gly Gly Ser Gly
    130                 135                 140

Gly Gly Gly Ser Gly Gly Gly Gly Ser Ala Pro Thr Ser Ser Ser Thr
145                 150                 155                 160

Lys Lys Thr Gln Leu Gln Leu Glu Ala Leu Leu Leu Asp Leu Gln Met
                165                 170                 175

Ile Leu Asn Gly Ile Asn Asn Tyr Lys Asn Pro Lys Leu Thr Arg Met
            180                 185                 190

Leu Thr Ala Lys Phe Tyr Met Pro Lys Lys Ala Thr Glu Leu Lys His
        195                 200                 205

Leu Gln Cys Leu Glu Glu Glu Leu Lys Pro Leu Glu Glu Val Leu Asn
    210                 215                 220

Leu Ala Gln Ser Lys Asn Phe His Leu Arg Pro Arg Asp Leu Ile Ser
225                 230                 235                 240

Asn Ile Asn Val Ile Val Leu Glu Leu Lys Gly Ser Glu Thr Thr Phe
                245                 250                 255

Met Cys Glu Tyr Ala Asp Glu Thr Ala Thr Ile Val Glu Phe Leu Asn
            260                 265                 270

Arg Trp Ile Thr Phe Cys Gln Ser Ile Ile Ser Thr Leu Thr Gly Gly
        275                 280                 285

Gly Gly Ser Gly Gly Gly Gly Ser Gly Gly Gly Gly Ser Gly Gly Gly
    290                 295                 300

Gly Ser Gly Ser His Ser Met Arg Tyr Phe Phe Thr Ser Val Ser Arg
305                 310                 315                 320

Pro Gly Arg Gly Glu Pro Arg Phe Ile Ala Val Gly Tyr Val Asp Asp
                325                 330                 335

Thr Gln Phe Val Arg Phe Asp Ser Asp Ala Ala Ser Gln Arg Met Glu
            340                 345                 350

Pro Arg Ala Pro Trp Ile Glu Gln Glu Gly Pro Glu Tyr Trp Asp Gly
        355                 360                 365

Glu Thr Arg Lys Val Lys Ala His Ser Gln Thr His Arg Val Asp Leu
    370                 375                 380

Gly Thr Leu Arg Gly Ala Tyr Asn Gln Ser Glu Ala Gly Ser His Thr
385                 390                 395                 400

Val Gln Arg Met Tyr Gly Cys Asp Val Gly Ser Asp Trp Arg Phe Leu
                405                 410                 415

Arg Gly Tyr His Gln Tyr Ala Tyr Asp Gly Lys Asp Tyr Ile Ala Leu
            420                 425                 430

Lys Glu Asp Leu Arg Ser Trp Thr Ala Ala Asp Met Ala Ala Gln Thr
        435                 440                 445

Thr Lys His Lys Trp Glu Ala Ala His Val Ala Glu Gln Leu Arg Ala
    450                 455                 460

Tyr Leu Glu Gly Thr Cys Val Glu Trp Leu Arg Arg Tyr Leu Glu Asn
465                 470                 475                 480

Gly Lys Glu Thr Leu Gln Arg Thr Asp Ala Pro Lys Thr His Met Thr
                485                 490                 495

His His Ala Val Ser Asp His Glu Ala Thr Leu Arg Cys Trp Ala Leu
            500                 505                 510

Ser Phe Tyr Pro Ala Glu Ile Thr Leu Thr Trp Gln Arg Asp Gly Glu
        515                 520                 525

Asp Gln Thr Gln Asp Thr Glu Leu Val Glu Thr Arg Pro Cys Gly Asp
    530                 535                 540

Gly Thr Phe Gln Lys Trp Ala Ala Val Val Val Pro Ser Gly Gln Glu
```

```
545                 550                 555                 560

Gln Arg Tyr Thr Cys His Val Gln His Glu Gly Leu Pro Lys Pro Leu
                565                 570                 575

Thr Leu Arg Trp Glu Ala Ala Ala Gly Gly Asp Lys Thr His Thr Cys
            580                 585                 590

Pro Pro Cys Pro Ala Pro Glu Leu Leu Gly Gly Pro Ser Val Phe Leu
        595                 600                 605

Phe Pro Pro Lys Pro Lys Asp Thr Leu Met Ile Ser Arg Thr Pro Glu
    610                 615                 620

Val Thr Cys Val Val Val Asp Val Ser His Glu Asp Pro Glu Val Lys
625                 630                 635                 640

Phe Asn Trp Tyr Val Asp Gly Val Glu Val His Asn Ala Lys Thr Lys
                645                 650                 655

Pro Arg Glu Glu Gln Tyr Ala Ser Thr Tyr Arg Val Val Ser Val Leu
            660                 665                 670

Thr Val Leu His Gln Asp Trp Leu Asn Gly Lys Glu Tyr Lys Cys Lys
        675                 680                 685

Val Ser Asn Lys Ala Leu Pro Ala Pro Ile Glu Lys Thr Ile Ser Lys
    690                 695                 700

Ala Lys Gly Gln Pro Arg Glu Pro Gln Val Tyr Thr Leu Pro Pro Ser
705                 710                 715                 720

Arg Glu Glu Met Thr Lys Asn Gln Val Ser Leu Thr Cys Leu Val Lys
                725                 730                 735

Gly Phe Tyr Pro Ser Asp Ile Ala Val Glu Trp Glu Ser Asn Gly Gln
            740                 745                 750

Pro Glu Asn Asn Tyr Lys Thr Thr Pro Pro Val Leu Asp Ser Asp Gly
        755                 760                 765

Ser Phe Phe Leu Tyr Ser Lys Leu Thr Val Asp Lys Ser Arg Trp Gln
    770                 775                 780

Gln Gly Asn Val Phe Ser Cys Ser Val Met His Glu Ala Leu His Asn
785                 790                 795                 800

His Tyr Thr Gln Lys Ser Leu Ser Leu Ser Pro Gly Lys
                805                 810
```

<210> SEQ ID NO 34
<211> LENGTH: 2505
<212> TYPE: DNA
<213> ORGANISM: Artificial sequence
<220> FEATURE:
<223> OTHER INFORMATION: synthetic polynucleotide

<400> SEQUENCE: 34

```
atgtacagga tgcaactcct gtcttgcatt gcactaagtc ttgcacttgt cacaaacagt      60

gcacctactt caagttctac aaagaaaaca cagctacaac tggaggcatt actgctggat     120

ttacagatga ttttgaatgg aattaataat tacaagaatc ccaaactcac caggatgctc     180

acagcaaagt tttacatgcc caagaaggcc acagaactga aacatcttca gtgtctagaa     240

gaagaactca aacctctgga ggaagtgcta aatttagctc aaagcaaaaa ctttcactta     300

agacccaggg acttaatcag caatatcaac gtaatagttc tggaactaaa gggatctgaa     360

acaacattca tgtgtgaata tgctgatgag acagcaacca ttgtagaatt tctgaacaga     420

tggattacct tttgtcaaag catcatctca acactgactg gaggcggagg atctggtggt     480

ggaggttctg gtggtggggg atctggaggc ggaggatctg cacctacttc aagttctaca     540

aagaaaacac agctacaact ggaggcatta ctgctggatt tacagatgat tttgaatgga     600
```

```
attaataatt acaagaatcc caaactcacc aggatgctca cagcaaagtt ttacatgccc    660

aagaaggcca cagaactgaa acatcttcag tgtctagaag aagaactcaa acctctggag    720

gaagtgctaa atttagctca aagcaaaaac tttcacttaa gacccaggga cttaatcagc    780

aatatcaacg taatagttct ggaactaaag ggatctgaaa caacattcat gtgtgaatat    840

gctgatgaga cagcaaccat tgtagaattt ctgaacagat ggattacctt ttgtcaaagc    900

atcatctcaa cactgactgg aggcggagga tctggtggtg gaggttctgg tggtgggga    960

tctggaggcg gaggatctgg ctctcactcc atgaggtatt tcttcacatc cgtgtcccgg   1020

cccggccgcg gggagccccg cttcatcgca gtgggctacg tggacgacac gcagttcgtg   1080

cggttcgaca gcgacgccgc gagccagagg atggagccgc gggcgccgtg gatagagcag   1140

gagggtccgg agtattggga cggggagaca cggaaagtga aggcccactc acagactcac   1200

cgagtggacc tggggaccct gcgcggcgcc tacaaccaga gcgaggccgg ttctcacacc   1260

gtccagagga tgtatggctg cgacgtgggg tcggactggc gcttcctccg cgggtaccac   1320

cagtacgcct acgacggcaa ggattacatc gccctgaaag aggacctgcg ctcttggacc   1380

gcggcggaca tggcagctca gaccaccaag cacaagtggg aggcggccca tgtggcggag   1440

cagttgagag cctacctgga gggcacgtgc gtggagtggc tccgcagata cctggagaac   1500

gggaaggaga cgctgcagcg cacggacgcc cccaaaacgc atatgactca ccacgctgtc   1560

tctgaccatg aagccaccct gaggtgctgg gccctgagct tctaccctgc ggagatcaca   1620

ctgacctggc agcgggatgg ggaggaccag acccaggaca cggagctcgt ggagaccagg   1680

ccttgcgggg atggaacctt ccagaagtgg gcggctgtgg tggtgccttc tggacaggag   1740

cagagataca cctgccatgt gcagcatgag ggtttgccca agcccctcac cctgagatgg   1800

gaggcagctg cgggtggcga caaaactcac acatgcccac cgtgcccagc acctgaactc   1860

ctggggggac cgtcagtctt cctcttcccc ccaaaaccca aggacaccct catgatctcc   1920

cggacccctg aggtcacatg cgtggtggtg gacgtgagcc acgaagaccc tgaggtcaag   1980

ttcaactggt acgtggacgg cgtggaggtg cataatgcca agacaaagcc gcgggaggag   2040

cagtacgcaa gcacgtaccg tgtggtcagc gtcctcaccg tcctgcacca ggactggctg   2100

aatggcaagg agtacaagtg caaggtctcc aacaaagccc tcccagcccc catcgagaaa   2160

accatctcca aagccaaagg gcagccccga gaaccacagg tgtacaccct gcccccatcc   2220

cgggaggaga tgaccaagaa ccaggtcagc ctgacctgcc tggtcaaagg cttctatccc   2280

agcgacatcg ccgtggagtg ggagagcaat gggcagccgg agaacaacta caagaccacg   2340

cctcccgtgc tggactccga cggctccttc ttcctctaca gcaagctcac cgtggacaag   2400

agcagatggc agcaggggaa cgtcttctca tgctccgtga tgcacgaggc tctgcacaac   2460

cactacacgc agaagtccct ctccctgtct ccgggtaaat agtga                   2505
```

<210> SEQ ID NO 35
<211> LENGTH: 833
<212> TYPE: PRT
<213> ORGANISM: Homo sapiens

<400> SEQUENCE: 35

```
Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30
```

-continued

```
Gln Leu Glu Ala Leu Leu Leu Asp Leu Gln Met Ile Leu Asn Gly Ile
        35                  40                  45

Asn Asn Tyr Lys Asn Pro Lys Leu Thr Arg Met Leu Thr Ala Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr Gly Gly Gly Gly Ser Gly Gly
145                 150                 155                 160

Gly Gly Ser Gly Gly Gly Gly Ser Gly Gly Gly Gly Ser Ala Pro Thr
                165                 170                 175

Ser Ser Ser Thr Lys Lys Thr Gln Leu Gln Leu Glu Ala Leu Leu Leu
            180                 185                 190

Asp Leu Gln Met Ile Leu Asn Gly Ile Asn Asn Tyr Lys Asn Pro Lys
        195                 200                 205

Leu Thr Arg Met Leu Thr Ala Lys Phe Tyr Met Pro Lys Lys Ala Thr
    210                 215                 220

Glu Leu Lys His Leu Gln Cys Leu Glu Glu Glu Leu Lys Pro Leu Glu
225                 230                 235                 240

Glu Val Leu Asn Leu Ala Gln Ser Lys Asn Phe His Leu Arg Pro Arg
                245                 250                 255

Asp Leu Ile Ser Asn Ile Asn Val Ile Val Leu Glu Leu Lys Gly Ser
            260                 265                 270

Glu Thr Thr Phe Met Cys Glu Tyr Ala Asp Glu Thr Ala Thr Ile Val
        275                 280                 285

Glu Phe Leu Asn Arg Trp Ile Thr Phe Cys Gln Ser Ile Ile Ser Thr
    290                 295                 300

Leu Thr Gly Gly Gly Gly Ser Gly Gly Gly Gly Ser Gly Gly Gly Gly
305                 310                 315                 320

Ser Gly Gly Gly Gly Ser Gly Ser His Ser Met Arg Tyr Phe Phe Thr
                325                 330                 335

Ser Val Ser Arg Pro Gly Arg Gly Glu Pro Arg Phe Ile Ala Val Gly
            340                 345                 350

Tyr Val Asp Asp Thr Gln Phe Val Arg Phe Asp Ser Asp Ala Ala Ser
        355                 360                 365

Gln Arg Met Glu Pro Arg Ala Pro Trp Ile Glu Gln Glu Gly Pro Glu
    370                 375                 380

Tyr Trp Asp Gly Glu Thr Arg Lys Val Lys Ala His Ser Gln Thr His
385                 390                 395                 400

Arg Val Asp Leu Gly Thr Leu Arg Gly Ala Tyr Asn Gln Ser Glu Ala
                405                 410                 415

Gly Ser His Thr Val Gln Arg Met Tyr Gly Cys Asp Val Gly Ser Asp
            420                 425                 430

Trp Arg Phe Leu Arg Gly Tyr His Gln Tyr Ala Tyr Asp Gly Lys Asp
        435                 440                 445

Tyr Ile Ala Leu Lys Glu Asp Leu Arg Ser Trp Thr Ala Ala Asp Met
```

```
    450                 455                 460

Ala Ala Gln Thr Thr Lys His Lys Trp Glu Ala Ala His Val Ala Glu
465                 470                 475                 480

Gln Leu Arg Ala Tyr Leu Glu Gly Thr Cys Val Glu Trp Leu Arg Arg
                485                 490                 495

Tyr Leu Glu Asn Gly Lys Glu Thr Leu Gln Arg Thr Asp Ala Pro Lys
            500                 505                 510

Thr His Met Thr His His Ala Val Ser Asp His Glu Ala Thr Leu Arg
        515                 520                 525

Cys Trp Ala Leu Ser Phe Tyr Pro Ala Glu Ile Thr Leu Thr Trp Gln
    530                 535                 540

Arg Asp Gly Glu Asp Gln Thr Gln Asp Thr Glu Leu Val Glu Thr Arg
545                 550                 555                 560

Pro Cys Gly Asp Gly Thr Phe Gln Lys Trp Ala Ala Val Val Val Pro
                565                 570                 575

Ser Gly Gln Glu Gln Arg Tyr Thr Cys His Val Gln His Glu Gly Leu
            580                 585                 590

Pro Lys Pro Leu Thr Leu Arg Trp Glu Ala Ala Ala Gly Gly Asp Lys
        595                 600                 605

Thr His Thr Cys Pro Pro Cys Pro Ala Pro Glu Ala Ala Gly Gly Pro
    610                 615                 620

Ser Val Phe Leu Phe Pro Pro Lys Pro Lys Asp Thr Leu Met Ile Ser
625                 630                 635                 640

Arg Thr Pro Glu Val Thr Cys Val Val Val Asp Val Ser His Glu Asp
                645                 650                 655

Pro Glu Val Lys Phe Asn Trp Tyr Val Asp Gly Val Glu Val His Asn
            660                 665                 670

Ala Lys Thr Lys Pro Arg Glu Glu Gln Tyr Asn Ser Thr Tyr Arg Val
        675                 680                 685

Val Ser Val Leu Thr Val Leu His Gln Asp Trp Leu Asn Gly Lys Glu
    690                 695                 700

Tyr Lys Cys Lys Val Ser Asn Lys Ala Leu Pro Ala Pro Ile Glu Lys
705                 710                 715                 720

Thr Ile Ser Lys Ala Lys Gly Gln Pro Arg Glu Pro Gln Val Tyr Thr
                725                 730                 735

Leu Pro Pro Ser Arg Glu Glu Met Thr Lys Asn Gln Val Ser Leu Thr
            740                 745                 750

Cys Leu Val Lys Gly Phe Tyr Pro Ser Asp Ile Ala Val Glu Trp Glu
        755                 760                 765

Ser Asn Gly Gln Pro Glu Asn Asn Tyr Lys Thr Thr Pro Pro Val Leu
    770                 775                 780

Asp Ser Asp Gly Ser Phe Phe Leu Tyr Ser Lys Leu Thr Val Asp Lys
785                 790                 795                 800

Ser Arg Trp Gln Gln Gly Asn Val Phe Ser Cys Ser Val Met His Glu
                805                 810                 815

Ala Leu His Asn His Tyr Thr Gln Lys Ser Leu Ser Leu Ser Pro Gly
            820                 825                 830

Lys
```

<210> SEQ ID NO 36
<211> LENGTH: 813
<212> TYPE: PRT
<213> ORGANISM: Homo sapiens

<400> SEQUENCE: 36

Ala Pro Thr Ser Ser Ser Thr Lys Lys Thr Gln Leu Gln Leu Glu Ala
1 5 10 15

Leu Leu Leu Asp Leu Gln Met Ile Leu Asn Gly Ile Asn Asn Tyr Lys
20 25 30

Asn Pro Lys Leu Thr Arg Met Leu Thr Ala Lys Phe Tyr Met Pro Lys
35 40 45

Lys Ala Thr Glu Leu Lys His Leu Gln Cys Leu Glu Glu Glu Leu Lys
50 55 60

Pro Leu Glu Glu Val Leu Asn Leu Ala Gln Ser Lys Asn Phe His Leu
65 70 75 80

Arg Pro Arg Asp Leu Ile Ser Asn Ile Asn Val Ile Val Leu Glu Leu
85 90 95

Lys Gly Ser Glu Thr Thr Phe Met Cys Glu Tyr Ala Asp Glu Thr Ala
100 105 110

Thr Ile Val Glu Phe Leu Asn Arg Trp Ile Thr Phe Cys Gln Ser Ile
115 120 125

Ile Ser Thr Leu Thr Gly Gly Gly Gly Ser Gly Gly Gly Gly Ser Gly
130 135 140

Gly Gly Gly Ser Gly Gly Gly Gly Ser Ala Pro Thr Ser Ser Ser Thr
145 150 155 160

Lys Lys Thr Gln Leu Gln Leu Glu Ala Leu Leu Leu Asp Leu Gln Met
165 170 175

Ile Leu Asn Gly Ile Asn Asn Tyr Lys Asn Pro Lys Leu Thr Arg Met
180 185 190

Leu Thr Ala Lys Phe Tyr Met Pro Lys Lys Ala Thr Glu Leu Lys His
195 200 205

Leu Gln Cys Leu Glu Glu Glu Leu Lys Pro Leu Glu Glu Val Leu Asn
210 215 220

Leu Ala Gln Ser Lys Asn Phe His Leu Arg Pro Arg Asp Leu Ile Ser
225 230 235 240

Asn Ile Asn Val Ile Val Leu Glu Leu Lys Gly Ser Glu Thr Thr Phe
245 250 255

Met Cys Glu Tyr Ala Asp Glu Thr Ala Thr Ile Val Glu Phe Leu Asn
260 265 270

Arg Trp Ile Thr Phe Cys Gln Ser Ile Ile Ser Thr Leu Thr Gly Gly
275 280 285

Gly Gly Ser Gly Gly Gly Gly Ser Gly Gly Gly Gly Ser Gly Gly Gly
290 295 300

Gly Ser Gly Ser His Ser Met Arg Tyr Phe Phe Thr Ser Val Ser Arg
305 310 315 320

Pro Gly Arg Gly Glu Pro Arg Phe Ile Ala Val Gly Tyr Val Asp Asp
325 330 335

Thr Gln Phe Val Arg Phe Asp Ser Asp Ala Ala Ser Gln Arg Met Glu
340 345 350

Pro Arg Ala Pro Trp Ile Glu Gln Glu Gly Pro Glu Tyr Trp Asp Gly
355 360 365

Glu Thr Arg Lys Val Lys Ala His Ser Gln Thr His Arg Val Asp Leu
370 375 380

Gly Thr Leu Arg Gly Ala Tyr Asn Gln Ser Glu Ala Gly Ser His Thr
385 390 395 400

Val Gln Arg Met Tyr Gly Cys Asp Val Gly Ser Asp Trp Arg Phe Leu
405 410 415

```
Arg Gly Tyr His Gln Tyr Ala Tyr Asp Gly Lys Asp Tyr Ile Ala Leu
            420                 425                 430

Lys Glu Asp Leu Arg Ser Trp Thr Ala Ala Asp Met Ala Ala Gln Thr
        435                 440                 445

Thr Lys His Lys Trp Glu Ala Ala His Val Ala Glu Gln Leu Arg Ala
    450                 455                 460

Tyr Leu Glu Gly Thr Cys Val Glu Trp Leu Arg Arg Tyr Leu Glu Asn
465                 470                 475                 480

Gly Lys Glu Thr Leu Gln Arg Thr Asp Ala Pro Lys Thr His Met Thr
                485                 490                 495

His His Ala Val Ser Asp His Glu Ala Thr Leu Arg Cys Trp Ala Leu
            500                 505                 510

Ser Phe Tyr Pro Ala Glu Ile Thr Leu Thr Trp Gln Arg Asp Gly Glu
        515                 520                 525

Asp Gln Thr Gln Asp Thr Glu Leu Val Glu Thr Arg Pro Cys Gly Asp
    530                 535                 540

Gly Thr Phe Gln Lys Trp Ala Ala Val Val Val Pro Ser Gly Gln Glu
545                 550                 555                 560

Gln Arg Tyr Thr Cys His Val Gln His Glu Gly Leu Pro Lys Pro Leu
                565                 570                 575

Thr Leu Arg Trp Glu Ala Ala Ala Gly Gly Asp Lys Thr His Thr Cys
            580                 585                 590

Pro Pro Cys Pro Ala Pro Glu Ala Ala Gly Gly Pro Ser Val Phe Leu
        595                 600                 605

Phe Pro Pro Lys Pro Lys Asp Thr Leu Met Ile Ser Arg Thr Pro Glu
    610                 615                 620

Val Thr Cys Val Val Val Asp Val Ser His Glu Asp Pro Glu Val Lys
625                 630                 635                 640

Phe Asn Trp Tyr Val Asp Gly Val Glu Val His Asn Ala Lys Thr Lys
                645                 650                 655

Pro Arg Glu Glu Gln Tyr Asn Ser Thr Tyr Arg Val Val Ser Val Leu
            660                 665                 670

Thr Val Leu His Gln Asp Trp Leu Asn Gly Lys Glu Tyr Lys Cys Lys
        675                 680                 685

Val Ser Asn Lys Ala Leu Pro Ala Pro Ile Glu Lys Thr Ile Ser Lys
    690                 695                 700

Ala Lys Gly Gln Pro Arg Glu Pro Gln Val Tyr Thr Leu Pro Pro Ser
705                 710                 715                 720

Arg Glu Glu Met Thr Lys Asn Gln Val Ser Leu Thr Cys Leu Val Lys
                725                 730                 735

Gly Phe Tyr Pro Ser Asp Ile Ala Val Glu Trp Glu Ser Asn Gly Gln
            740                 745                 750

Pro Glu Asn Asn Tyr Lys Thr Thr Pro Pro Val Leu Asp Ser Asp Gly
        755                 760                 765

Ser Phe Phe Leu Tyr Ser Lys Leu Thr Val Asp Lys Ser Arg Trp Gln
    770                 775                 780

Gln Gly Asn Val Phe Ser Cys Ser Val Met His Glu Ala Leu His Asn
785                 790                 795                 800

His Tyr Thr Gln Lys Ser Leu Ser Leu Ser Pro Gly Lys
                805                 810
```

<210> SEQ ID NO 37
<211> LENGTH: 2505

<212> TYPE: DNA
<213> ORGANISM: Artificial sequence
<220> FEATURE:
<223> OTHER INFORMATION: synthetic polynucleotide

<400> SEQUENCE: 37
atgtacagga tgcaactcct gtcttgcatt gcactaagtc ttgcacttgt cacaaacagt 60
gcacctactt caagttctac aaagaaaaca cagctacaac tggaggcatt actgctggat 120
ttacagatga ttttgaatgg aattaataat tacaagaatc ccaaactcac caggatgctc 180
acagcaaagt tttacatgcc caagaaggcc acagaactga aacatcttca gtgtctagaa 240
gaagaactca aacctctgga ggaagtgcta aatttagctc aaagcaaaaa ctttcactta 300
agacccaggg acttaatcag caatatcaac gtaatagttc tggaactaaa gggatctgaa 360
acaacattca tgtgtgaata tgctgatgag acagcaacca ttgtagaatt tctgaacaga 420
tggattacct tttgtcaaag catcatctca acactgactg gaggcggagg atctggtggt 480
ggaggttctg gtggtggggg atctggaggc ggaggatctg cacctacttc aagttctaca 540
aagaaaacac agctacaact ggaggcatta ctgctggatt tacagatgat tttgaatgga 600
attaataatt acaagaatcc caaactcacc aggatgctca cagcaaagtt ttacatgccc 660
aagaaggcca cagaactgaa acatcttcag tgtctagaag aagaactcaa acctctggag 720
gaagtgctaa atttagctca aagcaaaaac tttcacttaa gacccaggga cttaatcagc 780
aatatcaacg taatagttct ggaactaaag ggatctgaaa caacattcat gtgtgaatat 840
gctgatgaga cagcaaccat tgtagaattt ctgaacagat ggattacctt ttgtcaaagc 900
atcatctcaa cactgactgg aggcggagga tctggtggtg gaggttctgg tggtggggga 960
tctggaggcg gaggatctgg ctctcactcc atgaggtatt tcttcacatc cgtgtcccgg 1020
cccggccgcg gggagccccg cttcatcgca gtgggctacg tggacgacac gcagttcgtg 1080
cggttcgaca gcgacgccgc gagccagagg atggagccgc gggcgccgtg gatagagcag 1140
gagggtccgg agtattggga cggggagaca cggaaagtga aggcccactc acagactcac 1200
cgagtggacc tggggaccct gcgcggcgcc tacaaccaga gcgaggccgg ttctcacacc 1260
gtccagagga tgtatggctg cgacgtgggg tcggactggc gcttcctccg cgggtaccac 1320
cagtacgcct acgacggcaa ggattacatc gccctgaaag aggacctgcg ctcttggacc 1380
gcggcggaca tggcagctca gaccaccaag cacaagtggg aggcggccca tgtggcggag 1440
cagttgagag cctacctgga gggcacgtgc gtggagtggc tccgcagata cctggagaac 1500
gggaaggaga cgctgcagcg cacggacgcc cccaaaacgc atatgactca ccacgctgtc 1560
tctgaccatg aagccaccct gaggtgctgg gccctgagct tctaccctgc ggagatcaca 1620
ctgacctggc agcgggatgg ggaggaccag acccaggaca cggagctcgt ggagaccagg 1680
ccttgcgggg atggaacctt ccagaagtgg gcggctgtgg tggtgccttc tggacaggag 1740
cagagataca cctgccatgt gcagcatgag ggtttgccca agcccctcac cctgagatgg 1800
gaggcagctg cgggtggcga caaaactcac acatgcccac cgtgcccagc acctgaagcc 1860
gccgggggac cgtcagtctt cctcttcccc ccaaaaccca aggacaccct catgatctcc 1920
cggacccctg aggtcacatg cgtggtggtg gacgtgagcc acgaagaccc tgaggtcaag 1980
ttcaactggt acgtggacgg cgtggaggtg cataatgcca agacaaagcc gcgggaggag 2040
cagtacaaca gcacgtaccg tgtggtcagc gtcctcaccg tcctgcacca ggactggctg 2100
aatggcaagg agtacaagtg caaggtctcc aacaaagccc tcccagcccc catcgagaaa 2160

```
accatctcca aagccaaagg gcagccccga gaaccacagg tgtacaccct gcccccatcc   2220

cgggaggaga tgaccaagaa ccaggtcagc ctgacctgcc tggtcaaagg cttctatccc   2280

agcgacatcg ccgtggagtg ggagagcaat gggcagccgg agaacaacta caagaccacg   2340

cctcccgtgc tggactccga cggctccttc ttcctctaca gcaagctcac cgtggacaag   2400

agcagatggc agcaggggaa cgtcttctca tgctccgtga tgcacgaggc tctgcacaac   2460

cactacacgc agaagtccct ctccctgtct ccgggtaaat agtga                   2505


<210> SEQ ID NO 38
<211> LENGTH: 833
<212> TYPE: PRT
<213> ORGANISM: Homo sapiens

<400> SEQUENCE: 38

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu Ala Leu Leu Leu Asp Leu Gln Met Ile Leu Asn Gly Ile
        35                  40                  45

Asn Asn Tyr Lys Asn Pro Lys Leu Thr Arg Met Leu Thr Ala Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr Gly Gly Gly Gly Ser Gly Gly
145                 150                 155                 160

Gly Gly Ser Gly Gly Gly Gly Ser Gly Gly Gly Gly Ser Ala Pro Thr
                165                 170                 175

Ser Ser Ser Thr Lys Lys Thr Gln Leu Gln Leu Glu Ala Leu Leu Leu
            180                 185                 190

Asp Leu Gln Met Ile Leu Asn Gly Ile Asn Asn Tyr Lys Asn Pro Lys
        195                 200                 205

Leu Thr Arg Met Leu Thr Ala Lys Phe Tyr Met Pro Lys Lys Ala Thr
    210                 215                 220

Glu Leu Lys His Leu Gln Cys Leu Glu Glu Glu Leu Lys Pro Leu Glu
225                 230                 235                 240

Glu Val Leu Asn Leu Ala Gln Ser Lys Asn Phe His Leu Arg Pro Arg
                245                 250                 255

Asp Leu Ile Ser Asn Ile Asn Val Ile Val Leu Glu Leu Lys Gly Ser
            260                 265                 270

Glu Thr Thr Phe Met Cys Glu Tyr Ala Asp Glu Thr Ala Thr Ile Val
        275                 280                 285

Glu Phe Leu Asn Arg Trp Ile Thr Phe Cys Gln Ser Ile Ile Ser Thr
    290                 295                 300

Leu Thr Gly Gly Gly Gly Ser Gly Gly Gly Gly Ser Gly Gly Gly Gly
305                 310                 315                 320
```

```
Ser Gly Gly Gly Gly Ser Gly Ser His Ser Met Arg Tyr Phe Phe Thr
                325                 330                 335

Ser Val Ser Arg Pro Gly Arg Gly Glu Pro Arg Phe Ile Ala Val Gly
            340                 345                 350

Tyr Val Asp Asp Thr Gln Phe Val Arg Phe Asp Ser Asp Ala Ala Ser
        355                 360                 365

Gln Arg Met Glu Pro Arg Ala Pro Trp Ile Glu Gln Glu Gly Pro Glu
    370                 375                 380

Tyr Trp Asp Gly Glu Thr Arg Lys Val Lys Ala His Ser Gln Thr His
385                 390                 395                 400

Arg Val Asp Leu Gly Thr Leu Arg Gly Ala Tyr Asn Gln Ser Glu Ala
                405                 410                 415

Gly Ser His Thr Val Gln Arg Met Tyr Gly Cys Asp Val Gly Ser Asp
            420                 425                 430

Trp Arg Phe Leu Arg Gly Tyr His Gln Tyr Ala Tyr Asp Gly Lys Asp
        435                 440                 445

Tyr Ile Ala Leu Lys Glu Asp Leu Arg Ser Trp Thr Ala Ala Asp Met
    450                 455                 460

Ala Ala Gln Thr Thr Lys His Lys Trp Glu Ala Ala His Val Ala Glu
465                 470                 475                 480

Gln Leu Arg Ala Tyr Leu Glu Gly Thr Cys Val Glu Trp Leu Arg Arg
                485                 490                 495

Tyr Leu Glu Asn Gly Lys Glu Thr Leu Gln Arg Thr Asp Ala Pro Lys
            500                 505                 510

Thr His Met Thr His His Ala Val Ser Asp His Glu Ala Thr Leu Arg
        515                 520                 525

Cys Trp Ala Leu Ser Phe Tyr Pro Ala Glu Ile Thr Leu Thr Trp Gln
    530                 535                 540

Arg Asp Gly Glu Asp Gln Thr Gln Asp Thr Glu Leu Val Glu Thr Arg
545                 550                 555                 560

Pro Cys Gly Asp Gly Thr Phe Gln Lys Trp Ala Ala Val Val Val Pro
                565                 570                 575

Ser Gly Gln Glu Gln Arg Tyr Thr Cys His Val Gln His Glu Gly Leu
            580                 585                 590

Pro Lys Pro Leu Thr Leu Arg Trp Glu Ala Ala Ala Gly Gly Asp Lys
        595                 600                 605

Thr His Thr Cys Pro Pro Cys Pro Ala Pro Glu Phe Glu Gly Gly Pro
    610                 615                 620

Ser Val Phe Leu Phe Pro Pro Lys Pro Lys Asp Thr Leu Met Ile Ser
625                 630                 635                 640

Arg Thr Pro Glu Val Thr Cys Val Val Val Asp Val Ser His Glu Asp
                645                 650                 655

Pro Glu Val Lys Phe Asn Trp Tyr Val Asp Gly Val Glu Val His Asn
            660                 665                 670

Ala Lys Thr Lys Pro Arg Glu Glu Gln Tyr Asn Ser Thr Tyr Arg Val
        675                 680                 685

Val Ser Val Leu Thr Val Leu His Gln Asp Trp Leu Asn Gly Lys Glu
    690                 695                 700

Tyr Lys Cys Lys Val Ser Asn Lys Ala Leu Pro Ala Ser Ile Glu Lys
705                 710                 715                 720

Thr Ile Ser Lys Ala Lys Gly Gln Pro Arg Glu Pro Gln Val Tyr Thr
                725                 730                 735
```

```
Leu Pro Pro Ser Arg Glu Glu Met Thr Lys Asn Gln Val Ser Leu Thr
            740                 745                 750

Cys Leu Val Lys Gly Phe Tyr Pro Ser Asp Ile Ala Val Glu Trp Glu
        755                 760                 765

Ser Asn Gly Gln Pro Glu Asn Asn Tyr Lys Thr Thr Pro Pro Val Leu
    770                 775                 780

Asp Ser Asp Gly Ser Phe Phe Leu Tyr Ser Lys Leu Thr Val Asp Lys
785                 790                 795                 800

Ser Arg Trp Gln Gln Gly Asn Val Phe Ser Cys Ser Val Met His Glu
                805                 810                 815

Ala Leu His Asn His Tyr Thr Gln Lys Ser Leu Ser Leu Ser Pro Gly
            820                 825                 830

Lys


<210> SEQ ID NO 39
<211> LENGTH: 813
<212> TYPE: PRT
<213> ORGANISM: Homo sapiens

<400> SEQUENCE: 39

Ala Pro Thr Ser Ser Ser Thr Lys Lys Thr Gln Leu Gln Leu Glu Ala
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Gly Ser Gly Gly Gly Gly Ser Gly
    130                 135                 140

Gly Gly Gly Ser Gly Gly Gly Gly Ser Ala Pro Thr Ser Ser Ser Thr
145                 150                 155                 160

Lys Lys Thr Gln Leu Gln Leu Glu Ala Leu Leu Leu Asp Leu Gln Met
                165                 170                 175

Ile Leu Asn Gly Ile Asn Asn Tyr Lys Asn Pro Lys Leu Thr Arg Met
            180                 185                 190

Leu Thr Ala Lys Phe Tyr Met Pro Lys Lys Ala Thr Glu Leu Lys His
        195                 200                 205

Leu Gln Cys Leu Glu Glu Glu Leu Lys Pro Leu Glu Glu Val Leu Asn
    210                 215                 220

Leu Ala Gln Ser Lys Asn Phe His Leu Arg Pro Arg Asp Leu Ile Ser
225                 230                 235                 240

Asn Ile Asn Val Ile Val Leu Glu Leu Lys Gly Ser Glu Thr Thr Phe
                245                 250                 255

Met Cys Glu Tyr Ala Asp Glu Thr Ala Thr Ile Val Glu Phe Leu Asn
            260                 265                 270
```

-continued

```
Arg Trp Ile Thr Phe Cys Gln Ser Ile Ile Ser Thr Leu Thr Gly Gly
        275                 280                 285

Gly Gly Ser Gly Gly Gly Gly Ser Gly Gly Gly Gly Ser Gly Gly Gly
    290                 295                 300

Gly Ser Gly Ser His Ser Met Arg Tyr Phe Phe Thr Ser Val Ser Arg
305                 310                 315                 320

Pro Gly Arg Gly Glu Pro Arg Phe Ile Ala Val Gly Tyr Val Asp Asp
                325                 330                 335

Thr Gln Phe Val Arg Phe Asp Ser Asp Ala Ala Ser Gln Arg Met Glu
            340                 345                 350

Pro Arg Ala Pro Trp Ile Glu Gln Glu Gly Pro Glu Tyr Trp Asp Gly
        355                 360                 365

Glu Thr Arg Lys Val Lys Ala His Ser Gln Thr His Arg Val Asp Leu
    370                 375                 380

Gly Thr Leu Arg Gly Ala Tyr Asn Gln Ser Glu Ala Gly Ser His Thr
385                 390                 395                 400

Val Gln Arg Met Tyr Gly Cys Asp Val Gly Ser Asp Trp Arg Phe Leu
                405                 410                 415

Arg Gly Tyr His Gln Tyr Ala Tyr Asp Gly Lys Asp Tyr Ile Ala Leu
            420                 425                 430

Lys Glu Asp Leu Arg Ser Trp Thr Ala Ala Asp Met Ala Ala Gln Thr
        435                 440                 445

Thr Lys His Lys Trp Glu Ala Ala His Val Ala Glu Gln Leu Arg Ala
    450                 455                 460

Tyr Leu Glu Gly Thr Cys Val Glu Trp Leu Arg Arg Tyr Leu Glu Asn
465                 470                 475                 480

Gly Lys Glu Thr Leu Gln Arg Thr Asp Ala Pro Lys Thr His Met Thr
                485                 490                 495

His His Ala Val Ser Asp His Glu Ala Thr Leu Arg Cys Trp Ala Leu
            500                 505                 510

Ser Phe Tyr Pro Ala Glu Ile Thr Leu Thr Trp Gln Arg Asp Gly Glu
        515                 520                 525

Asp Gln Thr Gln Asp Thr Glu Leu Val Glu Thr Arg Pro Cys Gly Asp
    530                 535                 540

Gly Thr Phe Gln Lys Trp Ala Ala Val Val Val Pro Ser Gly Gln Glu
545                 550                 555                 560

Gln Arg Tyr Thr Cys His Val Gln His Glu Gly Leu Pro Lys Pro Leu
                565                 570                 575

Thr Leu Arg Trp Glu Ala Ala Ala Gly Gly Asp Lys Thr His Thr Cys
            580                 585                 590

Pro Pro Cys Pro Ala Pro Glu Phe Glu Gly Gly Pro Ser Val Phe Leu
        595                 600                 605

Phe Pro Pro Lys Pro Lys Asp Thr Leu Met Ile Ser Arg Thr Pro Glu
    610                 615                 620

Val Thr Cys Val Val Val Asp Val Ser His Glu Asp Pro Glu Val Lys
625                 630                 635                 640

Phe Asn Trp Tyr Val Asp Gly Val Glu Val His Asn Ala Lys Thr Lys
                645                 650                 655

Pro Arg Glu Glu Gln Tyr Asn Ser Thr Tyr Arg Val Val Ser Val Leu
            660                 665                 670

Thr Val Leu His Gln Asp Trp Leu Asn Gly Lys Glu Tyr Lys Cys Lys
        675                 680                 685

Val Ser Asn Lys Ala Leu Pro Ala Ser Ile Glu Lys Thr Ile Ser Lys
```

```
    690                 695                 700

Ala Lys Gly Gln Pro Arg Glu Pro Gln Val Tyr Thr Leu Pro Pro Ser
705                 710                 715                 720

Arg Glu Glu Met Thr Lys Asn Gln Val Ser Leu Thr Cys Leu Val Lys
                725                 730                 735

Gly Phe Tyr Pro Ser Asp Ile Ala Val Glu Trp Glu Ser Asn Gly Gln
            740                 745                 750

Pro Glu Asn Asn Tyr Lys Thr Thr Pro Pro Val Leu Asp Ser Asp Gly
        755                 760                 765

Ser Phe Phe Leu Tyr Ser Lys Leu Thr Val Asp Lys Ser Arg Trp Gln
    770                 775                 780

Gln Gly Asn Val Phe Ser Cys Ser Val Met His Glu Ala Leu His Asn
785                 790                 795                 800

His Tyr Thr Gln Lys Ser Leu Ser Leu Ser Pro Gly Lys
                805                 810


<210> SEQ ID NO 40
<211> LENGTH: 2505
<212> TYPE: DNA
<213> ORGANISM: Artificial sequence
<220> FEATURE:
<223> OTHER INFORMATION: synthetic polynucleotide

<400> SEQUENCE: 40

atgtacagga tgcaactcct gtcttgcatt gcactaagtc ttgcacttgt cacaaacagt     60

gcacctactt caagttctac aaagaaaaca cagctacaac tggaggcatt actgctggat    120

ttacagatga ttttgaatgg aattaataat tacaagaatc ccaaactcac caggatgctc    180

acagcaaagt tttacatgcc caagaaggcc acagaactga aacatcttca gtgtctagaa    240

gaagaactca aacctctgga ggaagtgcta aatttagctc aaagcaaaaa ctttcactta    300

agacccaggg acttaatcag caatatcaac gtaatagttc tggaactaaa gggatctgaa    360

acaacattca tgtgtgaata tgctgatgag acagcaacca ttgtagaatt tctgaacaga    420

tggattacct tttgtcaaag catcatctca acactgactg gaggcggagg atctggtggt    480

ggaggttctg gtggtggggg atctggaggc ggaggatctg cacctacttc aagttctaca    540

aagaaaacac agctacaact ggaggcatta ctgctggatt tacagatgat tttgaatgga    600

attaataatt acaagaatcc caaactcacc aggatgctca cagcaaagtt ttacatgccc    660

aagaaggcca cagaactgaa acatcttcag tgtctagaag aagaactcaa acctctggag    720

gaagtgctaa atttagctca aagcaaaaac tttcacttaa gacccaggga cttaatcagc    780

aatatcaacg taatagttct ggaactaaag ggatctgaaa caacattcat gtgtgaatat    840

gctgatgaga cagcaaccat tgtagaattt ctgaacagat ggattacctt ttgtcaaagc    900

atcatctcaa cactgactgg aggcggagga tctggtggtg gaggttctgg tggtgggga     960

tctggaggcg gaggatctgg ctctcactcc atgaggtatt tcttcacatc cgtgtcccgg   1020

cccggccgcg gggagccccg cttcatcgca gtgggctacg tggacgacac gcagttcgtg   1080

cggttcgaca gcgacgccgc gagccagagg atggagccgc gggcgccgtg gatagagcag   1140

gagggtccgg agtattggga cggggagaca cggaaagtga aggcccactc acagactcac   1200

cgagtggacc tggggaccct gcgcggcgcc tacaaccaga gcgaggccgg ttctcacacc   1260

gtccagagga tgtatggctg cgacgtgggg tcggactggc gcttcctccg cgggtaccac   1320

cagtacgcct acgacggcaa ggattacatc gccctgaaag aggacctgcg ctcttggacc   1380
```

gcggcggaca tggcagctca gaccaccaag cacaagtggg aggcggccca tgtggcggag 1440
cagttgagag cctacctgga gggcacgtgc gtggagtggc tccgcagata cctggagaac 1500
gggaaggaga cgctgcagcg cacggacgcc cccaaaacgc atatgactca ccacgctgtc 1560
tctgaccatg aagccaccct gaggtgctgg gccctgagct tctaccctgc ggagatcaca 1620
ctgacctggc agcgggatgg ggaggaccag acccaggaca cggagctcgt ggagaccagg 1680
ccttgcgggg atggaacctt ccagaagtgg gcggctgtgg tggtgccttc tggacaggag 1740
cagagataca cctgccatgt gcagcatgag ggtttgccca agcccctcac cctgagatgg 1800
gaggcagctg cgggtggcga caaaactcac acatgcccac cgtgcccagc acctgaattc 1860 gagggggac cgtcagtctt cctcttcccc ccaaaaccca aggacaccct catgatctcc 1920
cggacccctg aggtcacatg cgtggtggtg gacgtgagcc acgaagaccc tgaggtcaag 1980
ttcaactggt acgtggacgg cgtggaggtg cataatgcca agacaaagcc gcgggaggag 2040
cagtacaaca gcacgtaccg tgtggtcagc gtcctcaccg tcctgcacca ggactggctg 2100
aatggcaagg agtacaagtg caaggtctcc aacaaagccc tcccagccag catcgagaaa 2160
accatctcca aagccaaagg gcagccccga gaaccacagg tgtacaccct gcccccatcc 2220
cgggaggaga tgaccaagaa ccaggtcagc ctgacctgcc tggtcaaagg cttctatccc 2280
agcgacatcg ccgtggagtg ggagagcaat gggcagccgg agaacaacta caagaccacg 2340
cctcccgtgc tggactccga cggctccttc ttcctctaca gcaagctcac cgtggacaag 2400
agcagatggc agcaggggaa cgtcttctca tgctccgtga tgcacgaggc tctgcacaac 2460
cactacacgc agaagtccct ctccctgtct ccgggtaaat agtga 2505

<210> SEQ ID NO 41
<211> LENGTH: 144
<212> TYPE: PRT
<213> ORGANISM: Artificial sequence
<220> FEATURE:
<223> OTHER INFORMATION: synthetic polypeptide

<400> SEQUENCE: 41

Met Ser Arg Ser Val Ala Leu Ala Val Leu Ala Leu Leu Ser Leu Ser
1 5 10 15

Gly Leu Glu Ala Tyr Met Leu Asp Leu Gln Pro Glu Thr Thr Gly Gly
20 25 30

Gly Gly Ser Gly Gly Gly Gly Ser Gly Gly Gly Gly Ser Ile Gln Arg
35 40 45

Thr Pro Lys Ile Gln Val Tyr Ser Cys His Pro Ala Glu Asn Gly Lys
50 55 60

Ser Asn Phe Leu Asn Cys Tyr Val Ser Gly Phe His Pro Ser Asp Ile
65 70 75 80

Glu Val Asp Leu Leu Lys Asn Gly Glu Arg Ile Glu Lys Val Glu His
85 90 95

Ser Asp Leu Ser Phe Ser Lys Asp Trp Ser Phe Tyr Leu Leu Tyr Tyr
100 105 110

Thr Glu Phe Thr Pro Thr Glu Lys Asp Glu Tyr Ala Cys Arg Val Asn
115 120 125

His Val Thr Leu Ser Gln Pro Lys Ile Val Lys Trp Asp Arg Asp Met
130 135 140

<210> SEQ ID NO 42
<211> LENGTH: 248
<212> TYPE: PRT

<213> ORGANISM: Artificial sequence
<220> FEATURE:
<223> OTHER INFORMATION: synthetic polypeptide

<400> SEQUENCE: 42

```
Tyr Met Leu Asp Leu Gln Pro Glu Thr Thr Gly Gly Gly Gly Ser Gly
1               5                   10                  15

Gly Gly Gly Ser Gly Gly Gly Gly Ser Ile Gln Tyr Met Leu Asp Leu
            20                  25                  30

Gln Pro Glu Thr Thr Gly Gly Gly Gly Ser Gly Gly Gly Gly Ser Gly
        35                  40                  45

Gly Gly Gly Ser Ile Gln Arg Thr Pro Lys Ile Gln Val Tyr Ser Cys
    50                  55                  60

His Pro Ala Glu Asn Gly Lys Ser Asn Phe Leu Asn Cys Tyr Val Ser
65                  70                  75                  80

Gly Phe His Pro Ser Asp Ile Glu Val Asp Leu Leu Lys Asn Gly Glu
                85                  90                  95

Arg Ile Glu Lys Val Glu His Ser Asp Leu Ser Phe Ser Lys Asp Trp
            100                 105                 110

Ser Phe Tyr Leu Leu Tyr Tyr Thr Glu Phe Thr Pro Thr Glu Lys Asp
        115                 120                 125

Glu Tyr Ala Cys Arg Val Asn His Val Thr Leu Ser Gln Pro Lys Ile
    130                 135                 140

Val Lys Trp Asp Arg Asp Met Arg Thr Pro Lys Ile Gln Val Tyr Ser
145                 150                 155                 160

Cys His Pro Ala Glu Asn Gly Lys Ser Asn Phe Leu Asn Cys Tyr Val
                165                 170                 175

Ser Gly Phe His Pro Ser Asp Ile Glu Val Asp Leu Leu Lys Asn Gly
            180                 185                 190

Glu Arg Ile Glu Lys Val Glu His Ser Asp Leu Ser Phe Ser Lys Asp
        195                 200                 205

Trp Ser Phe Tyr Leu Leu Tyr Tyr Thr Glu Phe Thr Pro Thr Glu Lys
    210                 215                 220

Asp Glu Tyr Ala Cys Arg Val Asn His Val Thr Leu Ser Gln Pro Lys
225                 230                 235                 240

Ile Val Lys Trp Asp Arg Asp Met
                245
```

<210> SEQ ID NO 43
<211> LENGTH: 438
<212> TYPE: DNA
<213> ORGANISM: Artificial sequence
<220> FEATURE:
<223> OTHER INFORMATION: synthetic polynucleotide

<400> SEQUENCE: 43

```
atgtctcgct ccgtggcctt agctgtgctc gcgctactct ctctttctgg cctggaggcc      60

tacatgctcg atttgcagcc cgaaacgacg ggtggaggtg gttctggagg aggcggttcg     120

ggcggaggtg gtagtatcca gcgtactcca aagattcagg tttactcatg ccatccagca     180

gagaatggaa agtcaaattt cctgaattgc tatgtgtctg ggtttcatcc atccgacatt     240

gaagttgact tactgaagaa tggagagaga attgaaaaag tggagcattc agacttgtct     300

ttcagcaagg actggtcttt ctatctcttg tattatactg aattcacccc cactgaaaaa     360

gatgagtatg cctgccgtgt gaaccacgtg actttgtcac agcccaagat agttaagtgg     420

gatcgagaca tgtagtga                                                   438
```

<210> SEQ ID NO 44
<211> LENGTH: 227
<212> TYPE: PRT
<213> ORGANISM: Homo sapiens

<400> SEQUENCE: 44

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

<210> SEQ ID NO 45
<211> LENGTH: 227
<212> TYPE: PRT
<213> ORGANISM: Homo sapiens

<400> SEQUENCE: 45

```
Asp Lys Thr His Thr Cys Pro Pro Cys Pro Ala Pro Glu Phe Glu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95
```

```
Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 46
<211> LENGTH: 227
<212> TYPE: PRT
<213> ORGANISM: Homo sapiens

<400> SEQUENCE: 46

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Ala Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
```

225

<210> SEQ ID NO 47
<211> LENGTH: 227
<212> TYPE: PRT
<213> ORGANISM: Homo sapiens

<400> SEQUENCE: 47

Asp Lys Thr His Thr Cys Pro Pro Cys Pro Ala Pro Glu Ala Ala Gly
1 5 10 15

Gly Pro Ser Val Phe Leu Phe Pro Pro Lys Pro Lys Asp Thr Leu Met
20 25 30

Ile Ser Arg Thr Pro Glu Val Thr Cys Val Val Val Asp Val Ser His
35 40 45

Glu Asp Pro Glu Val Lys Phe Asn Trp Tyr Val Asp Gly Val Glu Val
50 55 60

His Asn Ala Lys Thr Lys Pro Arg Glu Glu Gln Tyr Asn Ser Thr Tyr
65 70 75 80

Arg Val Val Ser Val Leu Thr Val Leu His Gln Asp Trp Leu Asn Gly
85 90 95

Lys Glu Tyr Lys Cys Lys Val Ser Asn Lys Ala Leu Pro Ala Pro Ile
100 105 110

Glu Lys Thr Ile Ser Lys Ala Lys Gly Gln Pro Arg Glu Pro Gln Val
115 120 125

Tyr Thr Leu Pro Pro Ser Arg Glu Glu Met Thr Lys Asn Gln Val Ser
130 135 140

Leu Thr Cys Leu Val Lys Gly Phe Tyr Pro Ser Asp Ile Ala Val Glu
145 150 155 160

Trp Glu Ser Asn Gly Gln Pro Glu Asn Asn Tyr Lys Thr Thr Pro Pro
165 170 175

Val Leu Asp Ser Asp Gly Ser Phe Phe Leu Tyr Ser Lys Leu Thr Val
180 185 190

Asp Lys Ser Arg Trp Gln Gln Gly Asn Val Phe Ser Cys Ser Val Met
195 200 205

His Glu Ala Leu His Asn His Tyr Thr Gln Lys Ser Leu Ser Leu Ser
210 215 220

Pro Gly Lys
225

<210> SEQ ID NO 48
<211> LENGTH: 99
<212> TYPE: PRT
<213> ORGANISM: Artificial sequence
<220> FEATURE:
<223> OTHER INFORMATION: synthetic polypeptide

<400> SEQUENCE: 48

Ile Gln Arg Thr Pro Lys Ile Gln Val Tyr Ser Cys His Pro Ala Glu
1 5 10 15

Asn Gly Lys Ser Asn Phe Leu Asn Cys Tyr Val Ser Gly Phe His Pro
20 25 30

Ser Asp Ile Glu Val Asp Leu Leu Lys Asn Gly Glu Arg Ile Glu Lys
35 40 45

Val Glu His Ser Asp Leu Ser Phe Ser Lys Asp Trp Ser Phe Tyr Leu
50 55 60

Leu Tyr Tyr Thr Glu Phe Thr Pro Thr Glu Lys Asp Glu Tyr Ala Cys
65 70 75 80

```
Arg Val Asn His Val Thr Leu Ser Gln Pro Lys Ile Val Lys Trp Asp
                85                  90                  95

Arg Asp Met


<210> SEQ ID NO 49
<211> LENGTH: 133
<212> TYPE: PRT
<213> ORGANISM: Homo sapiens

<400> SEQUENCE: 49

Ala Pro Thr Ser Ser Ser Thr Lys Lys Thr Gln Leu Gln Leu Glu Ala
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130


<210> SEQ ID NO 50
<211> LENGTH: 275
<212> TYPE: PRT
<213> ORGANISM: Homo sapiens

<400> SEQUENCE: 50

Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gly Glu Thr
    50                  55                  60

Arg Lys Val Lys Ala His Ser Gln Thr His Arg Val Asp Leu Gly Thr
65                  70                  75                  80

Leu Arg Gly Ala Tyr Asn Gln Ser Glu Ala Gly Ser His Thr Val Gln
                85                  90                  95

Arg Met Tyr Gly Cys Asp Val Gly Ser Asp Trp Arg Phe Leu Arg Gly
            100                 105                 110

Tyr His Gln Tyr Ala Tyr Asp Gly Lys Asp Tyr Ile Ala Leu Lys Glu
        115                 120                 125

Asp Leu Arg Ser Trp Thr Ala Ala Asp Met Ala Ala Gln Thr Thr Lys
    130                 135                 140

His Lys Trp Glu Ala Ala His Val Ala Glu Gln Leu Arg Ala Tyr Leu
145                 150                 155                 160
```

```
Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Cys Gly Asp Gly Thr
225                 230                 235                 240

Phe Gln Lys Trp Ala Ala Val Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu
        275


<210> SEQ ID NO 51
<211> LENGTH: 447
<212> TYPE: PRT
<213> ORGANISM: Artificial sequence
<220> FEATURE:
<223> OTHER INFORMATION: synthetic polypeptide

<400> SEQUENCE: 51

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240
```

```
Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445


<210> SEQ ID NO 52
<211> LENGTH: 218
<212> TYPE: PRT
<213> ORGANISM: Artificial sequence
<220> FEATURE:
<223> OTHER INFORMATION: synthetic polypeptide

<400> SEQUENCE: 52

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160
```

```
Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 53
<211> LENGTH: 440
<212> TYPE: PRT
<213> ORGANISM: Homo sapiens

<400> SEQUENCE: 53

```
Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320
```

```
Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440


<210> SEQ ID NO 54
<211> LENGTH: 214
<212> TYPE: PRT
<213> ORGANISM: Artificial sequence
<220> FEATURE:
<223> OTHER INFORMATION: synthetic polypeptide

<400> SEQUENCE: 54

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 55
```

<211> LENGTH: 448
<212> TYPE: PRT
<213> ORGANISM: Homo sapiens

<400> SEQUENCE: 55

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Thr Met His Trp Val Arg Gln Ala Pro Gly Lys Gly Leu Glu Trp Val
35 40 45

Thr Phe Ile Ser Tyr Asp Gly Asn Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Ile Tyr Tyr Cys
85 90 95

Ala Arg Thr Gly Trp Leu Gly Pro Phe Asp Tyr Trp Gly Gln Gly Thr
100 105 110

Leu Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Arg Val Glu Pro Lys Ser Cys Asp Lys Thr
210 215 220

His Thr Cys Pro Pro Cys Pro Ala Pro Glu Leu Leu Gly Gly Pro Ser
225 230 235 240

Val Phe Leu Phe Pro Pro Lys Pro Lys Asp Thr Leu Met Ile Ser Arg
245 250 255

Thr Pro Glu Val Thr Cys Val Val Val Asp Val Ser His Glu Asp Pro
260 265 270

Glu Val Lys Phe Asn Trp Tyr Val Asp Gly Val Glu Val His Asn Ala
275 280 285

Lys Thr Lys Pro Arg Glu Glu Gln Tyr Asn Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Ala Leu Pro Ala Pro Ile Glu Lys Thr
325 330 335

Ile Ser Lys Ala Lys Gly Gln Pro Arg Glu Pro Gln Val Tyr Thr Leu
340 345 350

Pro Pro Ser Arg Asp Glu Leu Thr Lys Asn Gln Val Ser Leu Thr Cys
355 360 365

Leu Val Lys Gly Phe Tyr Pro Ser Asp Ile Ala Val Glu Trp Glu Ser
370 375 380

Asn Gly Gln Pro Glu Asn Asn Tyr Lys Thr Thr Pro Pro Val Leu Asp

```
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 56
<211> LENGTH: 215
<212> TYPE: PRT
<213> ORGANISM: Homo sapiens

<400> SEQUENCE: 56

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 57
<211> LENGTH: 448
<212> TYPE: PRT
<213> ORGANISM: Homo sapiens

<400> SEQUENCE: 57

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
```

-continued

```
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 58
<211> LENGTH: 214
<212> TYPE: PRT
<213> ORGANISM: Artificial sequence
<220> FEATURE:
<223> OTHER INFORMATION: synthetic polypeptide

<400> SEQUENCE: 58

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 59
<211> LENGTH: 276
<212> TYPE: PRT
<213> ORGANISM: Homo sapiens

<400> SEQUENCE: 59

```
Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gly Glu Thr
    50                  55                  60

Arg Lys Val Lys Ala His Ser Gln Thr His Arg Val Asp Leu Gly Thr
65                  70                  75                  80

Leu Arg Gly Tyr Tyr Asn Gln Ser Glu Ala Gly Ser His Thr Val Gln
                85                  90                  95

Arg Met Tyr Gly Cys Asp Val Gly Ser Asp Trp Arg Phe Leu Arg Gly
            100                 105                 110

Tyr His Gln Tyr Ala Tyr Asp Gly Lys Asp Tyr Ile Ala Leu Lys Glu
        115                 120                 125
```

```
Asp Leu Arg Ser Trp Thr Ala Ala Asp Met Ala Ala Gln Thr Thr Lys
    130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu Pro
        275


<210> SEQ ID NO 60
<211> LENGTH: 274
<212> TYPE: PRT
<213> ORGANISM: Mus musculus

<400> SEQUENCE: 60

Gly Pro His Ser Leu Arg Tyr Phe Val Thr Ala Val Ser Arg Pro Gly
1               5                   10                  15

Leu Gly Glu Pro Arg Phe Ile Ala Val Gly Tyr Val Asp Asp Thr Gln
            20                  25                  30

Phe Val Arg Phe Asp Ser Asp Ala Asp Asn Pro Arg Phe Glu Pro Arg
        35                  40                  45

Ala Pro Trp Met Glu Gln Glu Gly Pro Glu Tyr Trp Glu Glu Gln Thr
    50                  55                  60

Gln Arg Ala Lys Ser Asp Glu Gln Trp Phe Arg Val Ser Leu Arg Thr
65                  70                  75                  80

Ala Gln Arg Tyr Tyr Asn Gln Ser Lys Gly Gly Ser His Thr Phe Gln
                85                  90                  95

Arg Met Phe Gly Cys Asp Val Gly Ser Asp Trp Arg Leu Leu Arg Gly
            100                 105                 110

Tyr Gln Gln Phe Ala Tyr Asp Gly Arg Asp Tyr Ile Ala Leu Asn Glu
        115                 120                 125

Asp Leu Lys Thr Trp Thr Ala Ala Asp Thr Ala Ala Leu Ile Thr Arg
    130                 135                 140

Arg Lys Trp Glu Gln Ala Gly Asp Ala Glu Tyr Tyr Arg Ala Tyr Leu
145                 150                 155                 160

Glu Gly Glu Cys Val Glu Trp Leu Arg Arg Tyr Leu Glu Leu Gly Asn
                165                 170                 175

Glu Thr Leu Leu Arg Thr Asp Ser Pro Lys Ala His Val Thr Tyr His
            180                 185                 190

Pro Arg Ser Gln Val Asp Val Thr Leu Arg Cys Trp Ala Leu Gly Phe
        195                 200                 205

Tyr Pro Ala Asp Ile Thr Leu Thr Trp Gln Leu Asn Gly Glu Asp Leu
    210                 215                 220
```

Thr Gln Asp Met Glu Leu Val Glu Thr Arg Pro Ala Gly Asp Gly Thr
225 230 235 240

Phe Gln Lys Trp Ala Ala Val Val Val Pro Leu Gly Lys Glu Gln Asn
245 250 255

Tyr Thr Cys His Val His His Lys Gly Leu Pro Glu Pro Leu Thr Leu
260 265 270

Arg Trp

<210> SEQ ID NO 61
<211> LENGTH: 99
<212> TYPE: PRT
<213> ORGANISM: Artificial sequence
<220> FEATURE:
<223> OTHER INFORMATION: synthetic polypeptide

<400> SEQUENCE: 61

Ile Gln Arg Thr Pro Lys Ile Gln Val Tyr Ser Arg His Pro Ala Glu
1 5 10 15

Asn Gly Lys Ser Asn Phe Leu Asn Cys Tyr Val Ser Gly Phe His Pro
20 25 30

Ser Asp Ile Glu Val Asp Leu Leu Lys Asn Gly Glu Arg Ile Glu Lys
35 40 45

Val Glu His Ser Asp Leu Ser Phe Ser Lys Asp Trp Ser Phe Tyr Leu
50 55 60

Leu Tyr Tyr Thr Glu Phe Thr Pro Thr Glu Lys Asp Glu Tyr Ala Cys
65 70 75 80

Arg Val Asn His Val Thr Leu Ser Gln Pro Lys Ile Val Lys Trp Asp
85 90 95

Arg Asp Met

<210> SEQ ID NO 62
<211> LENGTH: 276
<212> TYPE: PRT
<213> ORGANISM: Homo sapiens

<400> SEQUENCE: 62

Gly Ser His Ser Met Arg Tyr Phe Phe Thr Ser Val Ser Arg Pro Gly
1 5 10 15

Arg Gly Glu Pro Arg Phe Ile Ala Val Gly Tyr Val Asp Asp Thr Gln
20 25 30

Phe Val Arg Phe Asp Ser Asp Ala Ala Ser Gln Arg Met Glu Pro Arg
35 40 45

Ala Pro Trp Ile Glu Gln Glu Gly Pro Glu Tyr Trp Asp Gly Glu Thr
50 55 60

Arg Lys Val Lys Ala His Ser Gln Thr His Arg Val Asp Leu Gly Thr
65 70 75 80

Leu Arg Gly Tyr Tyr Asn Gln Ser Glu Ala Gly Ser His Thr Val Gln
85 90 95

Arg Met Tyr Gly Cys Asp Val Gly Ser Asp Trp Arg Phe Leu Arg Gly
100 105 110

Tyr His Gln Tyr Ala Tyr Asp Gly Lys Asp Tyr Ile Ala Leu Lys Glu
115 120 125

Asp Leu Arg Ser Trp Thr Ala Ala Asp Met Ala Ala Gln Thr Thr Lys
130 135 140

His Lys Trp Glu Ala Ala His Val Ala Glu Gln Leu Arg Ala Tyr Leu
145 150 155 160

```
Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Cys Gly Asp Gly Thr
225                 230                 235                 240

Phe Gln Lys Trp Ala Ala Val Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu Pro
        275


<210> SEQ ID NO 63
<211> LENGTH: 5
<212> TYPE: PRT
<213> ORGANISM: Artificial sequence
<220> FEATURE:
<223> OTHER INFORMATION: synthetic polypeptide

<400> SEQUENCE: 63

Gly Ser Gly Gly Ser
1               5


<210> SEQ ID NO 64
<211> LENGTH: 4
<212> TYPE: PRT
<213> ORGANISM: Artificial sequence
<220> FEATURE:
<223> OTHER INFORMATION: synthetic polypeptide

<400> SEQUENCE: 64

Gly Gly Gly Ser
1


<210> SEQ ID NO 65
<211> LENGTH: 4
<212> TYPE: PRT
<213> ORGANISM: Artificial sequence
<220> FEATURE:
<223> OTHER INFORMATION: synthetic polypeptide

<400> SEQUENCE: 65

Gly Gly Ser Gly
1


<210> SEQ ID NO 66
<211> LENGTH: 5
<212> TYPE: PRT
<213> ORGANISM: Artificial sequence
<220> FEATURE:
<223> OTHER INFORMATION: synthetic polypeptide

<400> SEQUENCE: 66

Gly Gly Ser Gly Gly
1               5


<210> SEQ ID NO 67
```

<211> LENGTH: 5
<212> TYPE: PRT
<213> ORGANISM: Artificial sequence
<220> FEATURE:
<223> OTHER INFORMATION: synthetic polypeptide

<400> SEQUENCE: 67

Gly Ser Gly Ser Gly
1               5

<210> SEQ ID NO 68
<211> LENGTH: 5
<212> TYPE: PRT
<213> ORGANISM: Artificial sequence
<220> FEATURE:
<223> OTHER INFORMATION: synthetic polypeptide

<400> SEQUENCE: 68

Gly Ser Gly Gly Gly
1               5

<210> SEQ ID NO 69
<211> LENGTH: 5
<212> TYPE: PRT
<213> ORGANISM: Artificial sequence
<220> FEATURE:
<223> OTHER INFORMATION: synthetic polypeptide

<400> SEQUENCE: 69

Gly Gly Gly Ser Gly
1               5

<210> SEQ ID NO 70
<211> LENGTH: 5
<212> TYPE: PRT
<213> ORGANISM: Artificial sequence
<220> FEATURE:
<223> OTHER INFORMATION: synthetic polypeptide

<400> SEQUENCE: 70

Gly Ser Ser Ser Gly
1               5

<210> SEQ ID NO 71
<211> LENGTH: 5
<212> TYPE: PRT
<213> ORGANISM: Artificial sequence
<220> FEATURE:
<223> OTHER INFORMATION: synthetic polypeptide

<400> SEQUENCE: 71

Gly Ser Ser Ser Ser
1               5

<210> SEQ ID NO 72
<211> LENGTH: 5
<212> TYPE: PRT
<213> ORGANISM: Artificial sequence
<220> FEATURE:
<223> OTHER INFORMATION: synthetic polypeptide

<400> SEQUENCE: 72

Gly Gly Gly Gly Ser
1               5

<210> SEQ ID NO 73
<211> LENGTH: 5

<212> TYPE: PRT
<213> ORGANISM: Artificial sequence
<220> FEATURE:
<223> OTHER INFORMATION: synthetic polypeptide

<400> SEQUENCE: 73

Ala Ala Ala Gly Gly
1               5

<210> SEQ ID NO 74
<211> LENGTH: 15
<212> TYPE: PRT
<213> ORGANISM: Artificial sequence
<220> FEATURE:
<223> OTHER INFORMATION: synthetic polypeptide

<400> SEQUENCE: 74

Gly Cys Gly Ala Ser Gly Gly Gly Gly Ser Gly Gly Gly Gly Ser
1               5                   10                  15

<210> SEQ ID NO 75
<211> LENGTH: 9
<212> TYPE: PRT
<213> ORGANISM: Artificial sequence
<220> FEATURE:
<223> OTHER INFORMATION: synthetic polypeptide

<400> SEQUENCE: 75

Leu Leu Met Gly Thr Leu Gly Ile Val
1               5

<210> SEQ ID NO 76
<211> LENGTH: 8
<212> TYPE: PRT
<213> ORGANISM: Artificial sequence
<220> FEATURE:
<223> OTHER INFORMATION: synthetic polypeptide

<400> SEQUENCE: 76

Thr Leu Gly Ile Val Cys Pro Ile
1               5

<210> SEQ ID NO 77
<211> LENGTH: 10
<212> TYPE: PRT
<213> ORGANISM: Artificial sequence
<220> FEATURE:
<223> OTHER INFORMATION: synthetic polypeptide

<400> SEQUENCE: 77

Tyr Met Leu Asp Leu Gln Pro Glu Thr Thr
1               5                   10

<210> SEQ ID NO 78
<211> LENGTH: 9
<212> TYPE: PRT
<213> ORGANISM: Artificial sequence
<220> FEATURE:
<223> OTHER INFORMATION: synthetic polypeptide

<400> SEQUENCE: 78

Tyr Met Leu Asp Leu Gln Pro Glu Thr
1               5

<210> SEQ ID NO 79
<211> LENGTH: 9
<212> TYPE: PRT

```
<213> ORGANISM: Artificial sequence
<220> FEATURE:
<223> OTHER INFORMATION: synthetic polypeptide

<400> SEQUENCE: 79

Tyr Pro Tyr Asp Val Pro Asp Tyr Ala
1               5


<210> SEQ ID NO 80
<211> LENGTH: 8
<212> TYPE: PRT
<213> ORGANISM: Artificial sequence
<220> FEATURE:
<223> OTHER INFORMATION: synthetic polypeptide

<400> SEQUENCE: 80

Asp Tyr Lys Asp Asp Asp Asp Lys
1               5


<210> SEQ ID NO 81
<211> LENGTH: 10
<212> TYPE: PRT
<213> ORGANISM: Artificial sequence
<220> FEATURE:
<223> OTHER INFORMATION: synthetic polypeptide

<400> SEQUENCE: 81

Glu Gln Lys Leu Ile Ser Glu Glu Asp Leu
1               5                   10


<210> SEQ ID NO 82
<211> LENGTH: 5
<212> TYPE: PRT
<213> ORGANISM: Artificial sequence
<220> FEATURE:
<223> OTHER INFORMATION: synthetic polypeptide

<400> SEQUENCE: 82

His His His His His
1               5


<210> SEQ ID NO 83
<211> LENGTH: 6
<212> TYPE: PRT
<213> ORGANISM: Artificial sequence
<220> FEATURE:
<223> OTHER INFORMATION: synthetic polypeptide

<400> SEQUENCE: 83

His His His His His His
1               5


<210> SEQ ID NO 84
<211> LENGTH: 8
<212> TYPE: PRT
<213> ORGANISM: Artificial sequence
<220> FEATURE:
<223> OTHER INFORMATION: synthetic polypeptide

<400> SEQUENCE: 84

Trp Ser His Pro Gln Phe Glu Lys
1               5


<210> SEQ ID NO 85
<211> LENGTH: 5
<212> TYPE: PRT
<213> ORGANISM: Artificial sequence
```

<220> FEATURE:
<223> OTHER INFORMATION: synthetic polypeptide

<400> SEQUENCE: 85

Arg Tyr Ile Arg Ser
1 5

<210> SEQ ID NO 86
<211> LENGTH: 4
<212> TYPE: PRT
<213> ORGANISM: Artificial sequence
<220> FEATURE:
<223> OTHER INFORMATION: synthetic polypeptide

<400> SEQUENCE: 86

Phe His His Thr
1

<210> SEQ ID NO 87
<211> LENGTH: 17
<212> TYPE: PRT
<213> ORGANISM: Artificial sequence
<220> FEATURE:
<223> OTHER INFORMATION: synthetic polypeptide

<400> SEQUENCE: 87

Trp Glu Ala Ala Ala Arg Glu Ala Cys Cys Arg Glu Cys Cys Ala Arg
1 5 10 15

Ala

<210> SEQ ID NO 88
<211> LENGTH: 8
<212> TYPE: PRT
<213> ORGANISM: Artificial sequence
<220> FEATURE:
<223> OTHER INFORMATION: synthetic polypeptide

<400> SEQUENCE: 88

Leu Glu Val Leu Phe Gln Gly Pro
1 5

<210> SEQ ID NO 89
<211> LENGTH: 4
<212> TYPE: PRT
<213> ORGANISM: Artificial sequence
<220> FEATURE:
<223> OTHER INFORMATION: synthetic polypeptide

<400> SEQUENCE: 89

Leu Val Pro Arg
1

<210> SEQ ID NO 90
<211> LENGTH: 7
<212> TYPE: PRT
<213> ORGANISM: Artificial sequence
<220> FEATURE:
<223> OTHER INFORMATION: synthetic polypeptide

<400> SEQUENCE: 90

Glu Asn Leu Tyr Thr Gln Ser
1 5

<210> SEQ ID NO 91
<211> LENGTH: 22
<212> TYPE: PRT

<213> ORGANISM: Artificial sequence
<220> FEATURE:
<223> OTHER INFORMATION: synthetic polypeptide

<400> SEQUENCE: 91

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 92
<211> LENGTH: 21
<212> TYPE: PRT
<213> ORGANISM: Artificial sequence
<220> FEATURE:
<223> OTHER INFORMATION: synthetic polypeptide

<400> SEQUENCE: 92

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 93
<211> LENGTH: 23
<212> TYPE: PRT
<213> ORGANISM: Artificial sequence
<220> FEATURE:
<223> OTHER INFORMATION: synthetic polypeptide

<400> SEQUENCE: 93

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 94
<211> LENGTH: 25
<212> TYPE: PRT
<213> ORGANISM: Artificial sequence
<220> FEATURE:
<223> OTHER INFORMATION: synthetic polypeptide

<400> SEQUENCE: 94

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 95
<211> LENGTH: 119
<212> TYPE: PRT
<213> ORGANISM: Homo sapiens

<400> SEQUENCE: 95

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

```
Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met
        115


<210> SEQ ID NO 96
<211> LENGTH: 119
<212> TYPE: PRT
<213> ORGANISM: Macaca mulatta

<400> SEQUENCE: 96

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Pro Glu Asn Gly Lys Pro Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Lys Met Gly Lys Val Glu His Ser Asp Leu Ser Phe Ser Lys Asp Trp
65                  70                  75                  80

Ser Phe Tyr Leu Leu Tyr Tyr Thr Glu Phe Thr Pro Asn Glu Lys Asp
                85                  90                  95

Glu Tyr Ala Cys Arg Val Asn His Val Thr Leu Ser Gly Pro Arg Thr
            100                 105                 110

Val Lys Trp Asp Arg Asp Met
        115


<210> SEQ ID NO 97
<211> LENGTH: 118
<212> TYPE: PRT
<213> ORGANISM: Bos taurus

<400> SEQUENCE: 97

Met Ala Arg Phe Val Ala Leu Val Leu Leu Gly Leu Leu Ser Leu Ser
1               5                   10                  15

Gly Leu Asp Ala Ile Gln Arg Pro Pro Lys Ile Gln Val Tyr Ser Arg
            20                  25                  30

His Pro Pro Glu Asp Gly Lys Pro Asn Tyr Leu Asn Cys Tyr Val Tyr
        35                  40                  45

Gly Phe His Pro Pro Gln Ile Glu Ile Asp Leu Leu Lys Asn Gly Glu
    50                  55                  60

Lys Ile Lys Ser Glu Gln Ser Asp Leu Ser Phe Ser Lys Asp Trp Ser
65                  70                  75                  80

Phe Tyr Leu Leu Ser His Ala Glu Phe Thr Pro Asn Ser Lys Asp Gln
                85                  90                  95

Tyr Ser Cys Arg Val Lys His Val Thr Leu Glu Gln Pro Arg Ile Val
            100                 105                 110

Lys Trp Asp Arg Asp Leu
        115


<210> SEQ ID NO 98
```

<211> LENGTH: 119
<212> TYPE: PRT
<213> ORGANISM: Mus musculus

<400> SEQUENCE: 98

Met Ala Arg Ser Val Thr Leu Val Phe Leu Val Leu Val Ser Leu Thr
1               5                   10                  15

Gly Leu Tyr Ala Ile Gln Lys Thr Pro Gln Ile Gln Val Tyr Ser Arg
            20                  25                  30

His Pro Pro Glu Asn Gly Lys Pro Asn Ile Leu Asn Cys Tyr Val Thr
        35                  40                  45

Gln Phe His Pro Pro His Ile Glu Ile Gln Met Leu Lys Asn Gly Lys
    50                  55                  60

Lys Ile Pro Lys Val Glu Met Ser Asp Met Ser Phe Ser Lys Asp Trp
65                  70                  75                  80

Ser Phe Tyr Ile Leu Ala His Thr Glu Phe Thr Pro Thr Glu Thr Asp
                85                  90                  95

Thr Tyr Ala Cys Arg Val Lys His Ala Ser Met Ala Glu Pro Lys Thr
            100                 105                 110

Val Tyr Trp Asp Arg Asp Met
        115

<210> SEQ ID NO 99
<211> LENGTH: 254
<212> TYPE: PRT
<213> ORGANISM: Homo sapiens

<400> SEQUENCE: 99

Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
            20                  25                  30

Ala Gly Leu Leu Leu Leu Leu Leu Leu Ala Ala Ala Cys Ala Val Phe
        35                  40                  45

Leu Ala Cys Pro Trp Ala Val Ser Gly Ala Arg Ala Ser Pro Gly Ser
    50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
                85                  90                  95

Ala Gln Asn Val Leu Leu Ile Asp Gly Pro Leu Ser Trp Tyr Ser Asp
            100                 105                 110

Pro Gly Leu Ala Gly Val Ser Leu Thr Gly Gly Leu Ser Tyr Lys Glu
        115                 120                 125

Asp Thr Lys Glu Leu Val Val Ala Lys Ala Gly Val Tyr Tyr Val Phe
    130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
            180                 185                 190

Arg Asn Ser Ala Phe Gly Phe Gln Gly Arg Leu Leu His Leu Ser Ala
        195                 200                 205

Gly Gln Arg Leu Gly Val His Leu His Thr Glu Ala Arg Ala Arg His
    210                 215                 220

```
Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250


<210> SEQ ID NO 100
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (47)..(47)
<223> OTHER INFORMATION: Xaa is any amino acid other than a lysine

<400> SEQUENCE: 100

Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Xaa Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 101
<211> LENGTH: 174
<212> TYPE: PRT
<213> ORGANISM: Artificial sequence
<220> FEATURE:
<223> OTHER INFORMATION: Synthetic sequence

<400> SEQUENCE: 101

Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Ala Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80
```

```
Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170
```

<210> SEQ ID NO 102
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (147)..(147)
<223> OTHER INFORMATION: Xaa is any amino acid other than a glutamine

<400> SEQUENCE: 102

```
Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Xaa Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170
```

<210> SEQ ID NO 103
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (11)..(11)
<223> OTHER INFORMATION: Xaa is any amino acid other than a methionine

<400> SEQUENCE: 103

```
Pro Ala Gly Leu Leu Asp Leu Arg Gln Gly Xaa Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 104
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (12)..(12)
<223> OTHER INFORMATION: Xaa is any amino acid other than a
      phenylalanine

<400> SEQUENCE: 104

Pro Ala Gly Leu Leu Asp Leu Arg Gln Gly Met Xaa Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
```

165 170

<210> SEQ ID NO 105
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (14)..(14)
<223> OTHER INFORMATION: Xaa is any amino acid other than a glutamine

<400> SEQUENCE: 105

Pro Ala Gly Leu Leu Asp Leu Arg Gln Gly Met Phe Ala Xaa Leu Val
1 5 10 15

Ala Gln Asn Val Leu Leu Ile Asp Gly Pro Leu Ser Trp Tyr Ser Asp
20 25 30

Pro Gly Leu Ala Gly Val Ser Leu Thr Gly Gly Leu Ser Tyr Lys Glu
35 40 45

Asp Thr Lys Glu Leu Val Val Ala Lys Ala Gly Val Tyr Tyr Val Phe
50 55 60

Phe Gln Leu Glu Leu Arg Arg Val Val Ala Gly Glu Gly Ser Gly Ser
65 70 75 80

Val Ser Leu Ala Leu His Leu Gln Pro Leu Arg Ser Ala Ala Gly Ala
85 90 95

Ala Ala Leu Ala Leu Thr Val Asp Leu Pro Pro Ala Ser Ser Glu Ala
100 105 110

Arg Asn Ser Ala Phe Gly Phe Gln Gly Arg Leu Leu His Leu Ser Ala
115 120 125

Gly Gln Arg Leu Gly Val His Leu His Thr Glu Ala Arg Ala Arg His
130 135 140

Ala Trp Gln Leu Thr Gln Gly Ala Thr Val Leu Gly Leu Phe Arg Val
145 150 155 160

Thr Pro Glu Ile Pro Ala Gly Leu Pro Ser Pro Arg Ser Glu
165 170

<210> SEQ ID NO 106
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (15)..(15)
<223> OTHER INFORMATION: Xaa is any amino acid other than a leucine

<400> SEQUENCE: 106

Pro Ala Gly Leu Leu Asp Leu Arg Gln Gly Met Phe Ala Gln Xaa Val
1 5 10 15

Ala Gln Asn Val Leu Leu Ile Asp Gly Pro Leu Ser Trp Tyr Ser Asp
20 25 30

Pro Gly Leu Ala Gly Val Ser Leu Thr Gly Gly Leu Ser Tyr Lys Glu
35 40 45

Asp Thr Lys Glu Leu Val Val Ala Lys Ala Gly Val Tyr Tyr Val Phe
50 55 60

Phe Gln Leu Glu Leu Arg Arg Val Val Ala Gly Glu Gly Ser Gly Ser
65 70 75 80

Val Ser Leu Ala Leu His Leu Gln Pro Leu Arg Ser Ala Ala Gly Ala

```
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 107
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (16)..(16)
<223> OTHER INFORMATION: Xaa is any amino acid other than a valine

<400> SEQUENCE: 107

Pro Ala Gly Leu Leu Asp Leu Arg Gln Gly Met Phe Ala Gln Leu Xaa
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 108
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (18)..(18)
<223> OTHER INFORMATION: Xaa is any amino acid other than a glutamine

<400> SEQUENCE: 108

Pro Ala Gly Leu Leu Asp Leu Arg Gln Gly Met Phe Ala Gln Leu Val
```

-continued

```
1               5                   10                  15

Ala Xaa Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 109
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (19)..(19)
<223> OTHER INFORMATION: Xaa is any amino acid other than a asparagine

<400> SEQUENCE: 109

Pro Ala Gly Leu Leu Asp Leu Arg Gln Gly Met Phe Ala Gln Leu Val
1               5                   10                  15

Ala Gln Xaa Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170
```

<210> SEQ ID NO 110
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (20)..(20)
<223> OTHER INFORMATION: Xaa is any amino acid other than a valine

<400> SEQUENCE: 110

```
Pro Ala Gly Leu Leu Asp Leu Arg Gln Gly Met Phe Ala Gln Leu Val
1               5                   10                  15

Ala Gln Asn Xaa Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170
```

<210> SEQ ID NO 111
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (21)..(21)
<223> OTHER INFORMATION: Xaa is any amino acid other than a leucine

<400> SEQUENCE: 111

```
Pro Ala Gly Leu Leu Asp Leu Arg Gln Gly Met Phe Ala Gln Leu Val
1               5                   10                  15

Ala Gln Asn Val Xaa Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95
```

```
Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 112
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (22)..(22)
<223> OTHER INFORMATION: Xaa is any amino acid other than a leucine

<400> SEQUENCE: 112

Pro Ala Gly Leu Leu Asp Leu Arg Gln Gly Met Phe Ala Gln Leu Val
1               5                   10                  15

Ala Gln Asn Val Leu Xaa Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 113
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (23)..(23)
<223> OTHER INFORMATION: Xaa is any amino acid other than a isoleucine

<400> SEQUENCE: 113

Pro Ala Gly Leu Leu Asp Leu Arg Gln Gly Met Phe Ala Gln Leu Val
1               5                   10                  15
```

-continued

```
Ala Gln Asn Val Leu Leu Xaa Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170
```

<210> SEQ ID NO 114
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (24)..(24)
<223> OTHER INFORMATION: Xaa is any amino acid other than a aspartic
acid

<400> SEQUENCE: 114

```
Pro Ala Gly Leu Leu Asp Leu Arg Gln Gly Met Phe Ala Gln Leu Val
1               5                   10                  15

Ala Gln Asn Val Leu Leu Ile Xaa Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170
```

```
<210> SEQ ID NO 115
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (25)..(25)
<223> OTHER INFORMATION: Xaa is any amino acid other than a glycine

<400> SEQUENCE: 115

Pro Ala Gly Leu Leu Asp Leu Arg Gln Gly Met Phe Ala Gln Leu Val
1               5                   10                  15

Ala Gln Asn Val Leu Leu Ile Asp Xaa Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 116
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (26)..(26)
<223> OTHER INFORMATION: Xaa is any amino acid other than a proline

<400> SEQUENCE: 116

Pro Ala Gly Leu Leu Asp Leu Arg Gln Gly Met Phe Ala Gln Leu Val
1               5                   10                  15

Ala Gln Asn Val Leu Leu Ile Asp Gly Xaa Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
```

```
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 117
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (27)..(27)
<223> OTHER INFORMATION: Xaa is any amino acid other than a leucine

<400> SEQUENCE: 117

Pro Ala Gly Leu Leu Asp Leu Arg Gln Gly Met Phe Ala Gln Leu Val
1               5                   10                  15

Ala Gln Asn Val Leu Leu Ile Asp Gly Pro Xaa Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 118
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (28)..(28)
<223> OTHER INFORMATION: Xaa is any amino acid other than a serine

<400> SEQUENCE: 118

Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Xaa Trp Tyr Ser Asp
```

```
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 119
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (29)..(29)
<223> OTHER INFORMATION: Xaa is any amino acid other than a Tryptophan

<400> SEQUENCE: 119

Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Xaa Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 120
<211> LENGTH: 174
```

<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (30)..(30)
<223> OTHER INFORMATION: Xaa is any amino acid other than a tyrosine

<400> SEQUENCE: 120

```
Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Xaa Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170
```

<210> SEQ ID NO 121
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (31)..(31)
<223> OTHER INFORMATION: Xaa is any amino acid other than a Serine

<400> SEQUENCE: 121

```
Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Xaa Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110
```

```
Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 122
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (32)..(32)
<223> OTHER INFORMATION: Xaa is any amino acid other than a Aspartic
      acid

<400> SEQUENCE: 122

Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Xaa
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 123
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (33)..(33)
<223> OTHER INFORMATION: Xaa is any amino acid other than a Proline

<400> SEQUENCE: 123

Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30
```

```
Xaa Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170
```

<210> SEQ ID NO 124
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (34)..(34)
<223> OTHER INFORMATION: Xaa is any amino acid other than a glycine

<400> SEQUENCE: 124

```
Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Xaa Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170
```

<210> SEQ ID NO 125
<211> LENGTH: 174
<212> TYPE: PRT

<213> ORGANISM: Artificial sequence
<220> FEATURE:
<223> OTHER INFORMATION: Synthetic sequence
<220> FEATURE:
<221> NAME/KEY: misc_feature
<222> LOCATION: (35)..(35)
<223> OTHER INFORMATION: Xaa is any amino acid other than a Leucine

<400> SEQUENCE: 125

Pro Ala Gly Leu Leu Asp Leu Arg Gln Gly Met Phe Ala Gln Leu Val
1 5 10 15

Ala Gln Asn Val Leu Leu Ile Asp Gly Pro Leu Ser Trp Tyr Ser Asp
20 25 30

Pro Gly Xaa Ala Gly Val Ser Leu Thr Gly Gly Leu Ser Tyr Lys Glu
35 40 45

Asp Thr Lys Glu Leu Val Val Ala Lys Ala Gly Val Tyr Tyr Val Phe
50 55 60

Phe Gln Leu Glu Leu Arg Arg Val Val Ala Gly Glu Gly Ser Gly Ser
65 70 75 80

Val Ser Leu Ala Leu His Leu Gln Pro Leu Arg Ser Ala Ala Gly Ala
85 90 95

Ala Ala Leu Ala Leu Thr Val Asp Leu Pro Pro Ala Ser Ser Glu Ala
100 105 110

Arg Asn Ser Ala Phe Gly Phe Gln Gly Arg Leu Leu His Leu Ser Ala
115 120 125

Gly Gln Arg Leu Gly Val His Leu His Thr Glu Ala Arg Ala Arg His
130 135 140

Ala Trp Gln Leu Thr Gln Gly Ala Thr Val Leu Gly Leu Phe Arg Val
145 150 155 160

Thr Pro Glu Ile Pro Ala Gly Leu Pro Ser Pro Arg Ser Glu
165 170

<210> SEQ ID NO 126
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (37)..(37)
<223> OTHER INFORMATION: Xaa is any amino acid other than a Glycine

<400> SEQUENCE: 126

Pro Ala Gly Leu Leu Asp Leu Arg Gln Gly Met Phe Ala Gln Leu Val
1 5 10 15

Ala Gln Asn Val Leu Leu Ile Asp Gly Pro Leu Ser Trp Tyr Ser Asp
20 25 30

Pro Gly Leu Ala Xaa Val Ser Leu Thr Gly Gly Leu Ser Tyr Lys Glu
35 40 45

Asp Thr Lys Glu Leu Val Val Ala Lys Ala Gly Val Tyr Tyr Val Phe
50 55 60

Phe Gln Leu Glu Leu Arg Arg Val Val Ala Gly Glu Gly Ser Gly Ser
65 70 75 80

Val Ser Leu Ala Leu His Leu Gln Pro Leu Arg Ser Ala Ala Gly Ala
85 90 95

Ala Ala Leu Ala Leu Thr Val Asp Leu Pro Pro Ala Ser Ser Glu Ala
100 105 110

Arg Asn Ser Ala Phe Gly Phe Gln Gly Arg Leu Leu His Leu Ser Ala

```
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 127
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (38)..(38)
<223> OTHER INFORMATION: Xaa is any amino acid other than a Valine

<400> SEQUENCE: 127

Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Xaa Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 128
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (39)..(39)
<223> OTHER INFORMATION: Xaa is any amino acid other than a Serine

<400> SEQUENCE: 128

Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Xaa Leu Thr Gly Gly Leu Ser Tyr Lys Glu
```

```
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 129
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (40)..(40)
<223> OTHER INFORMATION: Xaa is any amino acid other than a Leucine

<400> SEQUENCE: 129

Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Xaa Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 130
<211> LENGTH: 174
<212> TYPE: PRT
<213> ORGANISM: Artificial sequence
<220> FEATURE:
```

-continued

```
<223> OTHER INFORMATION: Synthetic sequence
<220> FEATURE:
<221> NAME/KEY: misc_feature
<222> LOCATION: (41)..(41)
<223> OTHER INFORMATION: Xaa is any amino acid other than a Threonine

<400> SEQUENCE: 130

Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Xaa Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 131
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (42)..(42)
<223> OTHER INFORMATION: Xaa is any amino acid other than a Glycine

<400> SEQUENCE: 131

Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Xaa Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125
```

```
Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 132
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (43)..(43)
<223> OTHER INFORMATION: Xaa is any amino acid other than a Glycine

<400> SEQUENCE: 132

Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Xaa Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 133
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (44)..(44)
<223> OTHER INFORMATION: Xaa is any amino acid other than a Leucine

<400> SEQUENCE: 133

Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Xaa Ser Tyr Lys Glu
        35                  40                  45
```

```
Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170
```

<210> SEQ ID NO 134
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (45)..(45)
<223> OTHER INFORMATION: Xaa is any amino acid other than a Serine

<400> SEQUENCE: 134

```
Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Xaa Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170
```

<210> SEQ ID NO 135
<211> LENGTH: 174
<212> TYPE: PRT
<213> ORGANISM: Artificial sequence
<220> FEATURE:
<223> OTHER INFORMATION: Synthetic sequence
<220> FEATURE:

<221> NAME/KEY: misc_feature
<222> LOCATION: (46)..(46)
<223> OTHER INFORMATION: Xaa is any amino acid other than a Tyrosine

<400> SEQUENCE: 135

```
Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Xaa Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170
```

<210> SEQ ID NO 136
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (48)..(48)
<223> OTHER INFORMATION: Xaa is any amino acid other than a Glutamic
      Acid

<400> SEQUENCE: 136

```
Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Xaa
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
```

```
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 137
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (49)..(49)
<223> OTHER INFORMATION: Xaa is any amino acid other than a Aspartic
      acid

<400> SEQUENCE: 137

Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Xaa Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 138
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (50)..(50)
<223> OTHER INFORMATION: Xaa is any amino acid other than a Threonine

<400> SEQUENCE: 138

Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45
```

```
Asp Xaa Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 139
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (51)..(51)
<223> OTHER INFORMATION: Xaa is any amino acid other than a Lysine

<400> SEQUENCE: 139

Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Xaa Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 140
<211> LENGTH: 174
<212> TYPE: PRT
<213> ORGANISM: Artificial sequence
<220> FEATURE:
<223> OTHER INFORMATION: Synthetic sequence
<220> FEATURE:
```

<221> NAME/KEY: misc_feature
<222> LOCATION: (52)..(52)
<223> OTHER INFORMATION: Xaa is any amino acid other than a Glutamic acid

<400> SEQUENCE: 140

```
Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Xaa Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170
```

<210> SEQ ID NO 141
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (64)..(64)
<223> OTHER INFORMATION: Xaa is any amino acid other than a Phenylalanine

<400> SEQUENCE: 141

```
Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Xaa
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125
```

```
Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 142
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (65)..(65)
<223> OTHER INFORMATION: Xaa is any amino acid other than a
      Phenylalanine

<400> SEQUENCE: 142

Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Xaa Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 143
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (66)..(66)
<223> OTHER INFORMATION: Xaa is any amino acid other than a Glutamine

<400> SEQUENCE: 143

Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45
```

```
Asp Thr Lys Glu Leu Val Val Ala Lys Ala Gly Val Tyr Tyr Val Phe
    50                  55                  60

Phe Xaa Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170
```

<210> SEQ ID NO 144
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (67)..(67)
<223> OTHER INFORMATION: Xaa is any amino acid other than a Leucine

<400> SEQUENCE: 144

```
Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Xaa Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170
```

<210> SEQ ID NO 145
<211> LENGTH: 174
<212> TYPE: PRT
<213> ORGANISM: Artificial sequence
<220> FEATURE:
<223> OTHER INFORMATION: Synthetic sequence

```
<220> FEATURE:
<221> NAME/KEY: misc_feature
<222> LOCATION: (68)..(68)
<223> OTHER INFORMATION: Xaa is any amino acid other than a Glutamic
      acid

<400> SEQUENCE: 145

Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Xaa Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 146
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (69)..(69)
<223> OTHER INFORMATION: Xaa is any amino acid other than a Leucine

<400> SEQUENCE: 146

Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Xaa Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125
```

```
Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 147
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (70)..(70)
<223> OTHER INFORMATION: Xaa is any amino acid other than a Arginine

<400> SEQUENCE: 147

Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Xaa Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 148
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (71)..(71)
<223> OTHER INFORMATION: Xaa is any amino acid other than a Arginine

<400> SEQUENCE: 148

Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45
```

```
Asp Thr Lys Glu Leu Val Val Ala Lys Ala Gly Val Tyr Tyr Val Phe
    50                  55                  60

Phe Gln Leu Glu Leu Arg Xaa Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 149
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (72)..(72)
<223> OTHER INFORMATION: Xaa is any amino acid other than a Valine

<400> SEQUENCE: 149

Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Xaa Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 150
<211> LENGTH: 174
<212> TYPE: PRT
<213> ORGANISM: Artificial sequence
<220> FEATURE:
<223> OTHER INFORMATION: Synthetic sequence
<220> FEATURE:
```

<221> NAME/KEY: misc_feature
<222> LOCATION: (73)..(73)
<223> OTHER INFORMATION: Xaa is any amino acid other than a Valine

<400> SEQUENCE: 150

```
Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Xaa Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170
```

<210> SEQ ID NO 151
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (75)..(75)
<223> OTHER INFORMATION: Xaa is any amino acid other than a Glycine

<400> SEQUENCE: 151

```
Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Xaa Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140
```

```
Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 152
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (76)..(76)
<223> OTHER INFORMATION: Xaa is any amino acid other than a Glutamic
      acid

<400> SEQUENCE: 152

Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Xaa Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 153
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (77)..(77)
<223> OTHER INFORMATION: Xaa is any amino acid other than a Glycine

<400> SEQUENCE: 153

Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
```

```
    50                  55                  60

Phe Gln Leu Glu Leu Arg Arg Val Val Ala Gly Glu Xaa Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 154
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (78)..(78)
<223> OTHER INFORMATION: Xaa is any amino acid other than a Serine

<400> SEQUENCE: 154

Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Xaa Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 155
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
```

<222> LOCATION: (104)..(104)
<223> OTHER INFORMATION: Xaa is any amino acid other than a Aspartic
      acid

<400> SEQUENCE: 155

```
Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Xaa Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170
```

<210> SEQ ID NO 156
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (105)..(105)
<223> OTHER INFORMATION: Xaa is any amino acid other than a Leucine

<400> SEQUENCE: 156

```
Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Xaa Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140
```

```
Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170
```

<210> SEQ ID NO 157
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (106)..(106)
<223> OTHER INFORMATION: Xaa is any amino acid other than a Proline

<400> SEQUENCE: 157

```
Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Xaa Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170
```

<210> SEQ ID NO 158
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (107)..(107)
<223> OTHER INFORMATION: Xaa is any amino acid other than a Proline

<400> SEQUENCE: 158

```
Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60
```

Phe Gln Leu Glu Leu Arg Arg Val Val Ala Gly Glu Gly Ser Gly Ser
65 70 75 80

Val Ser Leu Ala Leu His Leu Gln Pro Leu Arg Ser Ala Ala Gly Ala
85 90 95

Ala Ala Leu Ala Leu Thr Val Asp Leu Pro Xaa Ala Ser Ser Glu Ala
100 105 110

Arg Asn Ser Ala Phe Gly Phe Gln Gly Arg Leu Leu His Leu Ser Ala
115 120 125

Gly Gln Arg Leu Gly Val His Leu His Thr Glu Ala Arg Ala Arg His
130 135 140

Ala Trp Gln Leu Thr Gln Gly Ala Thr Val Leu Gly Leu Phe Arg Val
145 150 155 160

Thr Pro Glu Ile Pro Ala Gly Leu Pro Ser Pro Arg Ser Glu
165 170

<210> SEQ ID NO 159
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (109)..(109)
<223> OTHER INFORMATION: Xaa is any amino acid other than a Serine

<400> SEQUENCE: 159

Pro Ala Gly Leu Leu Asp Leu Arg Gln Gly Met Phe Ala Gln Leu Val
1 5 10 15

Ala Gln Asn Val Leu Leu Ile Asp Gly Pro Leu Ser Trp Tyr Ser Asp
20 25 30

Pro Gly Leu Ala Gly Val Ser Leu Thr Gly Gly Leu Ser Tyr Lys Glu
35 40 45

Asp Thr Lys Glu Leu Val Val Ala Lys Ala Gly Val Tyr Tyr Val Phe
50 55 60

Phe Gln Leu Glu Leu Arg Arg Val Val Ala Gly Glu Gly Ser Gly Ser
65 70 75 80

Val Ser Leu Ala Leu His Leu Gln Pro Leu Arg Ser Ala Ala Gly Ala
85 90 95

Ala Ala Leu Ala Leu Thr Val Asp Leu Pro Pro Ala Xaa Ser Glu Ala
100 105 110

Arg Asn Ser Ala Phe Gly Phe Gln Gly Arg Leu Leu His Leu Ser Ala
115 120 125

Gly Gln Arg Leu Gly Val His Leu His Thr Glu Ala Arg Ala Arg His
130 135 140

Ala Trp Gln Leu Thr Gln Gly Ala Thr Val Leu Gly Leu Phe Arg Val
145 150 155 160

Thr Pro Glu Ile Pro Ala Gly Leu Pro Ser Pro Arg Ser Glu
165 170

<210> SEQ ID NO 160
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (110)..(110)

<223> OTHER INFORMATION: Xaa is any amino acid other than a Serine

<400> SEQUENCE: 160

```
Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Xaa Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170
```

<210> SEQ ID NO 161
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (111)..(111)
<223> OTHER INFORMATION: Xaa is any amino acid other than a Glutamic acid

<400> SEQUENCE: 161

```
Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Xaa Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140
```

```
Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 162
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (113)..(113)
<223> OTHER INFORMATION: Xaa is any amino acid other than a Arginine

<400> SEQUENCE: 162

Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Xaa Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 163
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (114)..(114)
<223> OTHER INFORMATION: Xaa is any amino acid other than a Asparagine

<400> SEQUENCE: 163

Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60
```

Phe Gln Leu Glu Leu Arg Arg Val Val Ala Gly Glu Gly Ser Gly Ser
65 70 75 80

Val Ser Leu Ala Leu His Leu Gln Pro Leu Arg Ser Ala Ala Gly Ala
85 90 95

Ala Ala Leu Ala Leu Thr Val Asp Leu Pro Pro Ala Ser Ser Glu Ala
100 105 110

Arg Xaa Ser Ala Phe Gly Phe Gln Gly Arg Leu Leu His Leu Ser Ala
115 120 125

Gly Gln Arg Leu Gly Val His Leu His Thr Glu Ala Arg Ala Arg His
130 135 140

Ala Trp Gln Leu Thr Gln Gly Ala Thr Val Leu Gly Leu Phe Arg Val
145 150 155 160

Thr Pro Glu Ile Pro Ala Gly Leu Pro Ser Pro Arg Ser Glu
165 170

<210> SEQ ID NO 164
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (115)..(115)
<223> OTHER INFORMATION: Xaa is any amino acid other than a Serine

<400> SEQUENCE: 164

Pro Ala Gly Leu Leu Asp Leu Arg Gln Gly Met Phe Ala Gln Leu Val
1 5 10 15

Ala Gln Asn Val Leu Leu Ile Asp Gly Pro Leu Ser Trp Tyr Ser Asp
20 25 30

Pro Gly Leu Ala Gly Val Ser Leu Thr Gly Gly Leu Ser Tyr Lys Glu
35 40 45

Asp Thr Lys Glu Leu Val Val Ala Lys Ala Gly Val Tyr Tyr Val Phe
50 55 60

Phe Gln Leu Glu Leu Arg Arg Val Val Ala Gly Glu Gly Ser Gly Ser
65 70 75 80

Val Ser Leu Ala Leu His Leu Gln Pro Leu Arg Ser Ala Ala Gly Ala
85 90 95

Ala Ala Leu Ala Leu Thr Val Asp Leu Pro Pro Ala Ser Ser Glu Ala
100 105 110

Arg Asn Xaa Ala Phe Gly Phe Gln Gly Arg Leu Leu His Leu Ser Ala
115 120 125

Gly Gln Arg Leu Gly Val His Leu His Thr Glu Ala Arg Ala Arg His
130 135 140

Ala Trp Gln Leu Thr Gln Gly Ala Thr Val Leu Gly Leu Phe Arg Val
145 150 155 160

Thr Pro Glu Ile Pro Ala Gly Leu Pro Ser Pro Arg Ser Glu
165 170

<210> SEQ ID NO 165
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (117)..(117)
<223> OTHER INFORMATION: Xaa is any amino acid other than a Phenylalanine

<400> SEQUENCE: 165

Pro Ala Gly Leu Leu Asp Leu Arg Gln Gly Met Phe Ala Gln Leu Val
1 5 10 15

Ala Gln Asn Val Leu Leu Ile Asp Gly Pro Leu Ser Trp Tyr Ser Asp
20 25 30

Pro Gly Leu Ala Gly Val Ser Leu Thr Gly Gly Leu Ser Tyr Lys Glu
35 40 45

Asp Thr Lys Glu Leu Val Val Ala Lys Ala Gly Val Tyr Tyr Val Phe
50 55 60

Phe Gln Leu Glu Leu Arg Arg Val Val Ala Gly Glu Gly Ser Gly Ser
65 70 75 80

Val Ser Leu Ala Leu His Leu Gln Pro Leu Arg Ser Ala Ala Gly Ala
85 90 95

Ala Ala Leu Ala Leu Thr Val Asp Leu Pro Pro Ala Ser Ser Glu Ala
100 105 110

Arg Asn Ser Ala Xaa Gly Phe Gln Gly Arg Leu Leu His Leu Ser Ala
115 120 125

Gly Gln Arg Leu Gly Val His Leu His Thr Glu Ala Arg Ala Arg His
130 135 140

Ala Trp Gln Leu Thr Gln Gly Ala Thr Val Leu Gly Leu Phe Arg Val
145 150 155 160

Thr Pro Glu Ile Pro Ala Gly Leu Pro Ser Pro Arg Ser Glu
165 170

<210> SEQ ID NO 166
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (130)..(130)
<223> OTHER INFORMATION: Xaa is any amino acid other than a Glutamine

<400> SEQUENCE: 166

Pro Ala Gly Leu Leu Asp Leu Arg Gln Gly Met Phe Ala Gln Leu Val
1 5 10 15

Ala Gln Asn Val Leu Leu Ile Asp Gly Pro Leu Ser Trp Tyr Ser Asp
20 25 30

Pro Gly Leu Ala Gly Val Ser Leu Thr Gly Gly Leu Ser Tyr Lys Glu
35 40 45

Asp Thr Lys Glu Leu Val Val Ala Lys Ala Gly Val Tyr Tyr Val Phe
50 55 60

Phe Gln Leu Glu Leu Arg Arg Val Val Ala Gly Glu Gly Ser Gly Ser
65 70 75 80

Val Ser Leu Ala Leu His Leu Gln Pro Leu Arg Ser Ala Ala Gly Ala
85 90 95

Ala Ala Leu Ala Leu Thr Val Asp Leu Pro Pro Ala Ser Ser Glu Ala
100 105 110

Arg Asn Ser Ala Phe Gly Phe Gln Gly Arg Leu Leu His Leu Ser Ala
115 120 125

Gly Xaa Arg Leu Gly Val His Leu His Thr Glu Ala Arg Ala Arg His
130 135 140

Ala Trp Gln Leu Thr Gln Gly Ala Thr Val Leu Gly Leu Phe Arg Val

```
145                 150                 155                 160

Thr Pro Glu Ile Pro Ala Gly Leu Pro Ser Pro Arg Ser Glu
                165                 170


<210> SEQ ID NO 167
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (131)..(131)
<223> OTHER INFORMATION: Xaa is any amino acid other than a Asparagine

<400> SEQUENCE: 167

Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Xaa Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 168
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (132)..(132)
<223> OTHER INFORMATION: Xaa is any amino acid other than a Leucine

<400> SEQUENCE: 168

Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
```

```
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Xaa Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 169
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (133)..(133)
<223> OTHER INFORMATION: Xaa is any amino acid other than a Glycine

<400> SEQUENCE: 169

Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Xaa Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 170
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (134)..(134)
<223> OTHER INFORMATION: Xaa is any amino acid other than a Valine
```

<400> SEQUENCE: 170

Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Xaa His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170

<210> SEQ ID NO 171
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (135)..(135)
<223> OTHER INFORMATION: Xaa is any amino acid other than a Histidine

<400> SEQUENCE: 171

Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val Xaa Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
165 170

<210> SEQ ID NO 172
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (136)..(136)
<223> OTHER INFORMATION: Xaa is any amino acid other than a Leucine

<400> SEQUENCE: 172

Pro Ala Gly Leu Leu Asp Leu Arg Gln Gly Met Phe Ala Gln Leu Val
1 5 10 15

Ala Gln Asn Val Leu Leu Ile Asp Gly Pro Leu Ser Trp Tyr Ser Asp
20 25 30

Pro Gly Leu Ala Gly Val Ser Leu Thr Gly Gly Leu Ser Tyr Lys Glu
35 40 45

Asp Thr Lys Glu Leu Val Val Ala Lys Ala Gly Val Tyr Tyr Val Phe
50 55 60

Phe Gln Leu Glu Leu Arg Arg Val Val Ala Gly Glu Gly Ser Gly Ser
65 70 75 80

Val Ser Leu Ala Leu His Leu Gln Pro Leu Arg Ser Ala Ala Gly Ala
85 90 95

Ala Ala Leu Ala Leu Thr Val Asp Leu Pro Pro Ala Ser Ser Glu Ala
100 105 110

Arg Asn Ser Ala Phe Gly Phe Gln Gly Arg Leu Leu His Leu Ser Ala
115 120 125

Gly Gln Arg Leu Gly Val His Xaa His Thr Glu Ala Arg Ala Arg His
130 135 140

Ala Trp Gln Leu Thr Gln Gly Ala Thr Val Leu Gly Leu Phe Arg Val
145 150 155 160

Thr Pro Glu Ile Pro Ala Gly Leu Pro Ser Pro Arg Ser Glu
165 170

<210> SEQ ID NO 173
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (137)..(137)
<223> OTHER INFORMATION: Xaa is any amino acid other than a Histidine

<400> SEQUENCE: 173

Pro Ala Gly Leu Leu Asp Leu Arg Gln Gly Met Phe Ala Gln Leu Val
1 5 10 15

Ala Gln Asn Val Leu Leu Ile Asp Gly Pro Leu Ser Trp Tyr Ser Asp
20 25 30

Pro Gly Leu Ala Gly Val Ser Leu Thr Gly Gly Leu Ser Tyr Lys Glu
35 40 45

Asp Thr Lys Glu Leu Val Val Ala Lys Ala Gly Val Tyr Tyr Val Phe
50 55 60

Phe Gln Leu Glu Leu Arg Arg Val Val Ala Gly Glu Gly Ser Gly Ser
65 70 75 80

Val Ser Leu Ala Leu His Leu Gln Pro Leu Arg Ser Ala Ala Gly Ala
85 90 95

Ala Ala Leu Ala Leu Thr Val Asp Leu Pro Pro Ala Ser Ser Glu Ala
100 105 110

Arg Asn Ser Ala Phe Gly Phe Gln Gly Arg Leu Leu His Leu Ser Ala
115 120 125

Gly Gln Arg Leu Gly Val His Leu Xaa Thr Glu Ala Arg Ala Arg His
130 135 140

Ala Trp Gln Leu Thr Gln Gly Ala Thr Val Leu Gly Leu Phe Arg Val
145 150 155 160

Thr Pro Glu Ile Pro Ala Gly Leu Pro Ser Pro Arg Ser Glu
165 170

<210> SEQ ID NO 174
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (138)..(138)
<223> OTHER INFORMATION: Xaa is any amino acid other than a Threonine

<400> SEQUENCE: 174

Pro Ala Gly Leu Leu Asp Leu Arg Gln Gly Met Phe Ala Gln Leu Val
1 5 10 15

Ala Gln Asn Val Leu Leu Ile Asp Gly Pro Leu Ser Trp Tyr Ser Asp
20 25 30

Pro Gly Leu Ala Gly Val Ser Leu Thr Gly Gly Leu Ser Tyr Lys Glu
35 40 45

Asp Thr Lys Glu Leu Val Val Ala Lys Ala Gly Val Tyr Tyr Val Phe
50 55 60

Phe Gln Leu Glu Leu Arg Arg Val Val Ala Gly Glu Gly Ser Gly Ser
65 70 75 80

Val Ser Leu Ala Leu His Leu Gln Pro Leu Arg Ser Ala Ala Gly Ala
85 90 95

Ala Ala Leu Ala Leu Thr Val Asp Leu Pro Pro Ala Ser Ser Glu Ala
100 105 110

Arg Asn Ser Ala Phe Gly Phe Gln Gly Arg Leu Leu His Leu Ser Ala
115 120 125

Gly Gln Arg Leu Gly Val His Leu His Xaa Glu Ala Arg Ala Arg His
130 135 140

Ala Trp Gln Leu Thr Gln Gly Ala Thr Val Leu Gly Leu Phe Arg Val
145 150 155 160

Thr Pro Glu Ile Pro Ala Gly Leu Pro Ser Pro Arg Ser Glu
165 170

<210> SEQ ID NO 175
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (139)..(139)
<223> OTHER INFORMATION: Xaa is any amino acid other than a Glutamic
acid

<400> SEQUENCE: 175

```
Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Xaa Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 176
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (141)..(141)
<223> OTHER INFORMATION: Xaa is any amino acid other than Arginine

<400> SEQUENCE: 176

Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Xaa Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
```

165 170

<210> SEQ ID NO 177
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (143)..(143)
<223> OTHER INFORMATION: Xaa is any amino acid other than a Arginine

<400> SEQUENCE: 177

Pro Ala Gly Leu Leu Asp Leu Arg Gln Gly Met Phe Ala Gln Leu Val
1 5 10 15

Ala Gln Asn Val Leu Leu Ile Asp Gly Pro Leu Ser Trp Tyr Ser Asp
20 25 30

Pro Gly Leu Ala Gly Val Ser Leu Thr Gly Gly Leu Ser Tyr Lys Glu
35 40 45

Asp Thr Lys Glu Leu Val Val Ala Lys Ala Gly Val Tyr Tyr Val Phe
50 55 60

Phe Gln Leu Glu Leu Arg Arg Val Val Ala Gly Glu Gly Ser Gly Ser
65 70 75 80

Val Ser Leu Ala Leu His Leu Gln Pro Leu Arg Ser Ala Ala Gly Ala
85 90 95

Ala Ala Leu Ala Leu Thr Val Asp Leu Pro Pro Ala Ser Ser Glu Ala
100 105 110

Arg Asn Ser Ala Phe Gly Phe Gln Gly Arg Leu Leu His Leu Ser Ala
115 120 125

Gly Gln Arg Leu Gly Val His Leu His Thr Glu Ala Arg Ala Xaa His
130 135 140

Ala Trp Gln Leu Thr Gln Gly Ala Thr Val Leu Gly Leu Phe Arg Val
145 150 155 160

Thr Pro Glu Ile Pro Ala Gly Leu Pro Ser Pro Arg Ser Glu
165 170

<210> SEQ ID NO 178
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (144)..(144)
<223> OTHER INFORMATION: Xaa is any amino acid other than a Histidine

<400> SEQUENCE: 178

Pro Ala Gly Leu Leu Asp Leu Arg Gln Gly Met Phe Ala Gln Leu Val
1 5 10 15

Ala Gln Asn Val Leu Leu Ile Asp Gly Pro Leu Ser Trp Tyr Ser Asp
20 25 30

Pro Gly Leu Ala Gly Val Ser Leu Thr Gly Gly Leu Ser Tyr Lys Glu
35 40 45

Asp Thr Lys Glu Leu Val Val Ala Lys Ala Gly Val Tyr Tyr Val Phe
50 55 60

Phe Gln Leu Glu Leu Arg Arg Val Val Ala Gly Glu Gly Ser Gly Ser
65 70 75 80

Val Ser Leu Ala Leu His Leu Gln Pro Leu Arg Ser Ala Ala Gly Ala

-continued

```
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg Xaa
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 179
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (146)..(146)
<223> OTHER INFORMATION: Xaa is any amino acid other than a Tryptophan

<400> SEQUENCE: 179

Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Xaa Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 180
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (148)..(148)
<223> OTHER INFORMATION: Xaa is any amino acid other than a Leucine

<400> SEQUENCE: 180

Pro Ala Gly Leu Leu Asp Leu Arg Gln Gly Met Phe Ala Gln Leu Val
```

```
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Xaa Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170
```

```
<210> SEQ ID NO 181
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (149)..(149)
<223> OTHER INFORMATION: Xaa is any amino acid other than a Threonine

<400> SEQUENCE: 181

Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Xaa Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170
```

<210> SEQ ID NO 182
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (150)..(150)
<223> OTHER INFORMATION: Xaa is any amino acid other than a Glutamine

<400> SEQUENCE: 182

```
Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Xaa Gly Ala Thr Val Leu Gly Leu Phe Arg Val
145                 150                 155                 160

Thr Pro Glu Ile Pro Ala Gly Leu Pro Ser Pro Arg Ser Glu
                165                 170
```

<210> SEQ ID NO 183
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (151)..(151)
<223> OTHER INFORMATION: Xaa is any amino acid other than a Glycine

<400> SEQUENCE: 183

```
Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95
```

```
Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Xaa Ala Thr Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 184
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (153)..(153)
<223> OTHER INFORMATION: Xaa is any amino acid other than a Threonine

<400> SEQUENCE: 184

Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Xaa Val Leu Gly Leu Phe Arg Val
145                 150                 155                 160

Thr Pro Glu Ile Pro Ala Gly Leu Pro Ser Pro Arg Ser Glu
                165                 170


<210> SEQ ID NO 185
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (154)..(154)
<223> OTHER INFORMATION: Xaa is any amino acid other than a Valine

<400> SEQUENCE: 185

Pro Ala Gly Leu Leu Asp Leu Arg Gln Gly Met Phe Ala Gln Leu Val
1               5                   10                  15
```

-continued

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Lys Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Xaa Leu Gly Leu Phe Arg Val
145                 150                 155                 160

Thr Pro Glu Ile Pro Ala Gly Leu Pro Ser Pro Arg Ser Glu
                165                 170

<210> SEQ ID NO 186
<211> LENGTH: 255
<212> TYPE: PRT
<213> ORGANISM: Homo sapiens

<400> SEQUENCE: 186

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225 230 235 240

Cys Ser Cys Arg Phe Pro Glu Glu Glu Glu Gly Gly Cys Glu Leu
245 250 255

<210> SEQ ID NO 187
<211> LENGTH: 290
<212> TYPE: PRT
<213> ORGANISM: Mus musculus

<400> SEQUENCE: 187

Met Arg Ile Phe Ala Gly Ile Ile Phe Thr Ala Cys Cys His Leu Leu
1 5 10 15

Arg Ala Phe Thr Ile Thr Ala Pro Lys Asp Leu Tyr Val Val Glu Tyr
20 25 30

Gly Ser Asn Val Thr Met Glu Cys Arg Phe Pro Val Glu Arg Glu Leu
35 40 45

Asp Leu Leu Ala Leu Val Val Tyr Trp Glu Lys Glu Asp Glu Gln Val
50 55 60

Ile Gln Phe Val Ala Gly Glu Glu Asp Leu Lys Pro Gln His Ser Asn
65 70 75 80

Phe Arg Gly Arg Ala Ser Leu Pro Lys Asp Gln Leu Leu Lys Gly Asn
85 90 95

Ala Ala Leu Gln Ile Thr Asp Val Lys Leu Gln Asp Ala Gly Val Tyr
100 105 110

Cys Cys Ile Ile Ser Tyr Gly Gly Ala Asp Tyr Lys Arg Ile Thr Leu
115 120 125

Lys Val Asn Ala Pro Tyr Arg Lys Ile Asn Gln Arg Ile Ser Val Asp
130 135 140

Pro Ala Thr Ser Glu His Glu Leu Ile Cys Gln Ala Glu Gly Tyr Pro
145 150 155 160

Glu Ala Glu Val Ile Trp Thr Asn Ser Asp His Gln Pro Val Ser Gly
165 170 175

Lys Arg Ser Val Thr Thr Ser Arg Thr Glu Gly Met Leu Leu Asn Val
180 185 190

Thr Ser Ser Leu Arg Val Asn Ala Thr Ala Asn Asp Val Phe Tyr Cys
195 200 205

Thr Phe Trp Arg Ser Gln Pro Gly Gln Asn His Thr Ala Glu Leu Ile
210 215 220

Ile Pro Glu Leu Pro Ala Thr His Pro Pro Gln Asn Arg Thr His Trp
225 230 235 240

Val Leu Leu Gly Ser Ile Leu Leu Phe Leu Ile Val Val Ser Thr Val
245 250 255

Leu Leu Phe Leu Arg Lys Gln Val Arg Met Leu Asp Val Glu Lys Cys
260 265 270

Gly Val Glu Asp Thr Ser Ser Lys Asn Arg Asn Asp Thr Gln Phe Glu
275 280 285

Glu Thr
290

<210> SEQ ID NO 188
<211> LENGTH: 290
<212> TYPE: PRT
<213> ORGANISM: Homo sapiens

<400> SEQUENCE: 188

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290
```

<210> SEQ ID NO 189
<211> LENGTH: 208
<212> TYPE: PRT
<213> ORGANISM: Artificial sequence
<220> FEATURE:
<223> OTHER INFORMATION: Synthetic sequence

<400> SEQUENCE: 189

```
Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60
```

Leu Ser Ile Val Ile Leu Ala Leu Arg Pro Ser Asp Glu Gly Thr Tyr
65 70 75 80

Glu Cys Val Val Leu Lys Tyr Glu Lys Asp Ala Phe Lys Arg Glu His
85 90 95

Leu Ala Glu Val Thr Leu Ser Val Lys Ala Asp Phe Pro Thr Pro Ser
100 105 110

Ile Ser Asp Phe Glu Ile Pro Thr Ser Asn Ile Arg Arg Ile Ile Cys
115 120 125

Ser Thr Ser Gly Gly Phe Pro Glu Pro His Leu Ser Trp Leu Glu Asn
130 135 140

Gly Glu Glu Leu Asn Ala Ile Asn Thr Thr Val Ser Gln Asp Pro Glu
145 150 155 160

Thr Glu Leu Tyr Ala Val Ser Ser Lys Leu Asp Phe Asn Met Thr Thr
165 170 175

Asn His Ser Phe Met Cys Leu Ile Lys Tyr Gly His Leu Arg Val Asn
180 185 190

Gln Thr Phe Asn Trp Asn Thr Thr Lys Gln Glu His Phe Pro Asp Asn
195 200 205

<210> SEQ ID NO 190
<211> LENGTH: 302
<212> TYPE: PRT
<213> ORGANISM: Homo sapiens

<400> SEQUENCE: 190

Met Arg Leu Gly Ser Pro Gly Leu Leu Phe Leu Leu Phe Ser Ser Leu
1 5 10 15

Arg Ala Asp Thr Gln Glu Lys Glu Val Arg Ala Met Val Gly Ser Asp
20 25 30

Val Glu Leu Ser Cys Ala Cys Pro Glu Gly Ser Arg Phe Asp Leu Asn
35 40 45

Asp Val Tyr Val Tyr Trp Gln Thr Ser Glu Ser Lys Thr Val Val Thr
50 55 60

Tyr His Ile Pro Gln Asn Ser Ser Leu Glu Asn Val Asp Ser Arg Tyr
65 70 75 80

Arg Asn Arg Ala Leu Met Ser Pro Ala Gly Met Leu Arg Gly Asp Phe
85 90 95

Ser Leu Arg Leu Phe Asn Val Thr Pro Gln Asp Glu Gln Lys Phe His
100 105 110

Cys Leu Val Leu Ser Gln Ser Leu Gly Phe Gln Glu Val Leu Ser Val
115 120 125

Glu Val Thr Leu His Val Ala Ala Asn Phe Ser Val Pro Val Val Ser
130 135 140

Ala Pro His Ser Pro Ser Gln Asp Glu Leu Thr Phe Thr Cys Thr Ser
145 150 155 160

Ile Asn Gly Tyr Pro Arg Pro Asn Val Tyr Trp Ile Asn Lys Thr Asp
165 170 175

Asn Ser Leu Leu Asp Gln Ala Leu Gln Asn Asp Thr Val Phe Leu Asn
180 185 190

Met Arg Gly Leu Tyr Asp Val Val Ser Val Leu Arg Ile Ala Arg Thr
195 200 205

Pro Ser Val Asn Ile Gly Cys Cys Ile Glu Asn Val Leu Leu Gln Gln
210 215 220

Asn Leu Thr Val Gly Ser Gln Thr Gly Asn Asp Ile Gly Glu Arg Asp 225 230 235 240

Lys Ile Thr Glu Asn Pro Val Ser Thr Gly Glu Lys Asn Ala Ala Thr
245 250 255

Trp Ser Ile Leu Ala Val Leu Cys Leu Leu Val Val Val Ala Val Ala
260 265 270

Ile Gly Trp Val Cys Arg Asp Arg Cys Leu Gln His Ser Tyr Ala Gly
275 280 285

Ala Trp Ala Val Ser Pro Glu Thr Glu Leu Thr Gly His Val
290 295 300

<210> SEQ ID NO 191
<211> LENGTH: 183
<212> TYPE: PRT
<213> ORGANISM: Homo sapiens

<400> SEQUENCE: 191

Met Glu Arg Val Gln Pro Leu Glu Glu Asn Val Gly Asn Ala Ala Arg
1 5 10 15

Pro Arg Phe Glu Arg Asn Lys Leu Leu Leu Val Ala Ser Val Ile Gln
20 25 30

Gly Leu Gly Leu Leu Leu Cys Phe Thr Tyr Ile Cys Leu His Phe Ser
35 40 45

Ala Leu Gln Val Ser His Arg Tyr Pro Arg Ile Gln Ser Ile Lys Val
50 55 60

Gln Phe Thr Glu Tyr Lys Lys Glu Lys Gly Phe Ile Leu Thr Ser Gln
65 70 75 80

Lys Glu Asp Glu Ile Met Lys Val Gln Asn Asn Ser Val Ile Ile Asn
85 90 95

Cys Asp Gly Phe Tyr Leu Ile Ser Leu Lys Gly Tyr Phe Ser Gln Glu
100 105 110

Val Asn Ile Ser Leu His Tyr Gln Lys Asp Glu Glu Pro Leu Phe Gln
115 120 125

Leu Lys Lys Val Arg Ser Val Asn Ser Leu Met Val Ala Ser Leu Thr
130 135 140

Tyr Lys Asp Lys Val Tyr Leu Asn Val Thr Thr Asp Asn Thr Ser Leu
145 150 155 160

Asp Asp Phe His Val Asn Gly Gly Glu Leu Ile Leu Ile His Gln Asn
165 170 175

Pro Gly Glu Phe Cys Val Leu
180

<210> SEQ ID NO 192
<211> LENGTH: 273
<212> TYPE: PRT
<213> ORGANISM: Homo sapiens

<400> SEQUENCE: 192

Met Ile Phe Leu Leu Leu Met Leu Ser Leu Glu Leu Gln Leu His Gln
1 5 10 15

Ile Ala Ala Leu Phe Thr Val Thr Val Pro Lys Glu Leu Tyr Ile Ile
20 25 30

Glu His Gly Ser Asn Val Thr Leu Glu Cys Asn Phe Asp Thr Gly Ser
35 40 45

His Val Asn Leu Gly Ala Ile Thr Ala Ser Leu Gln Lys Val Glu Asn
50 55 60

Asp Thr Ser Pro His Arg Glu Arg Ala Thr Leu Leu Glu Glu Gln Leu

```
65                  70                  75                  80

Pro Leu Gly Lys Ala Ser Phe His Ile Pro Gln Val Gln Val Arg Asp
                85                  90                  95

Glu Gly Gln Tyr Gln Cys Ile Ile Ile Tyr Gly Val Ala Trp Asp Tyr
            100                 105                 110

Lys Tyr Leu Thr Leu Lys Val Lys Ala Ser Tyr Arg Lys Ile Asn Thr
        115                 120                 125

His Ile Leu Lys Val Pro Glu Thr Asp Glu Val Glu Leu Thr Cys Gln
    130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Pro Gly Arg Asn Phe Ser Cys
            180                 185                 190

Val Phe Trp Asn Thr His Val Arg Glu Leu Thr Leu Ala Ser Ile Asp
        195                 200                 205

Leu Gln Ser Gln Met Glu Pro Arg Thr His Pro Thr Trp Leu Leu His
    210                 215                 220

Ile Phe Ile Pro Phe Cys Ile Ile Ala Phe Ile Phe Ile Ala Thr Val
225                 230                 235                 240

Ile Ala Leu Arg Lys Gln Leu Cys Gln Lys Leu Tyr Ser Ser Lys Asp
                245                 250                 255

Thr Thr Lys Arg Pro Val Thr Thr Thr Lys Arg Glu Val Asn Ser Ala
            260                 265                 270

Ile


<210> SEQ ID NO 193
<211> LENGTH: 329
<212> TYPE: PRT
<213> ORGANISM: Homo sapiens

<400> SEQUENCE: 193

Met Asp Pro Gln Cys Thr Met Gly Leu Ser Asn Ile Leu Phe Val Met
1               5                   10                  15

Ala Phe Leu Leu Ser Gly Ala Ala Pro Leu Lys Ile Gln Ala Tyr Phe
            20                  25                  30

Asn Glu Thr Ala Asp Leu Pro Cys Gln Phe Ala Asn Ser Gln Asn Gln
        35                  40                  45

Ser Leu Ser Glu Leu Val Val Phe Trp Gln Asp Gln Glu Asn Leu Val
    50                  55                  60

Leu Asn Glu Val Tyr Leu Gly Lys Glu Lys Phe Asp Ser Val His Ser
65                  70                  75                  80

Lys Tyr Met Gly Arg Thr Ser Phe Asp Ser Asp Ser Trp Thr Leu Arg
                85                  90                  95

Leu His Asn Leu Gln Ile Lys Asp Lys Gly Leu Tyr Gln Cys Ile Ile
            100                 105                 110

His His Lys Lys Pro Thr Gly Met Ile Arg Ile His Gln Met Asn Ser
        115                 120                 125

Glu Leu Ser Val Leu Ala Asn Phe Ser Gln Pro Glu Ile Val Pro Ile
    130                 135                 140

Ser Asn Ile Thr Glu Asn Val Tyr Ile Asn Leu Thr Cys Ser Ser Ile
145                 150                 155                 160

His Gly Tyr Pro Glu Pro Lys Lys Met Ser Val Leu Leu Arg Thr Lys
```

```
                165                 170                 175

Asn Ser Thr Ile Glu Tyr Asp Gly Ile Met Gln Lys Ser Gln Asp Asn
            180                 185                 190

Val Thr Glu Leu Tyr Asp Val Ser Ile Ser Leu Ser Val Ser Phe Pro
        195                 200                 205

Asp Val Thr Ser Asn Met Thr Ile Phe Cys Ile Leu Glu Thr Asp Lys
    210                 215                 220

Thr Arg Leu Leu Ser Ser Pro Phe Ser Ile Glu Leu Glu Asp Pro Gln
225                 230                 235                 240

Pro Pro Pro Asp His Ile Pro Trp Ile Thr Ala Val Leu Pro Thr Val
                245                 250                 255

Ile Ile Cys Val Met Val Phe Cys Leu Ile Leu Trp Lys Trp Lys Lys
            260                 265                 270

Lys Lys Arg Pro Arg Asn Ser Tyr Lys Cys Gly Thr Asn Thr Met Glu
        275                 280                 285

Arg Glu Glu Ser Glu Gln Thr Lys Lys Arg Glu Lys Ile His Ile Pro
    290                 295                 300

Glu Arg Ser Asp Glu Ala Gln Arg Val Phe Lys Ser Ser Lys Thr Ser
305                 310                 315                 320

Ser Cys Asp Lys Ser Asp Thr Cys Phe
                325


<210> SEQ ID NO 194
<211> LENGTH: 281
<212> TYPE: PRT
<213> ORGANISM: Homo sapiens

<400> SEQUENCE: 194

Met Gln Gln Pro Phe Asn Tyr Pro Tyr Pro Gln Ile Tyr Trp Val Asp
1               5                   10                  15

Ser Ser Ala Ser Ser Pro Trp Ala Pro Pro Gly Thr Val Leu Pro Cys
            20                  25                  30

Pro Thr Ser Val Pro Arg Arg Pro Gly Gln Arg Arg Pro Pro Pro Pro
        35                  40                  45

Pro Pro Pro Pro Pro Leu Pro Pro Pro Pro Pro Pro Pro Pro Leu Pro
    50                  55                  60

Pro Leu Pro Leu Pro Pro Leu Lys Lys Arg Gly Asn His Ser Thr Gly
65                  70                  75                  80

Leu Cys Leu Leu Val Met Phe Phe Met Val Leu Val Ala Leu Val Gly
                85                  90                  95

Leu Gly Leu Gly Met Phe Gln Leu Phe His Leu Gln Lys Glu Leu Ala
            100                 105                 110

Glu Leu Arg Glu Ser Thr Ser Gln Met His Thr Ala Ser Ser Leu Glu
        115                 120                 125

Lys Gln Ile Gly His Pro Ser Pro Pro Pro Glu Lys Lys Glu Leu Arg
    130                 135                 140

Lys Val Ala His Leu Thr Gly Lys Ser Asn Ser Arg Ser Met Pro Leu
145                 150                 155                 160

Glu Trp Glu Asp Thr Tyr Gly Ile Val Leu Leu Ser Gly Val Lys Tyr
                165                 170                 175

Lys Lys Gly Gly Leu Val Ile Asn Glu Thr Gly Leu Tyr Phe Val Tyr
            180                 185                 190

Ser Lys Val Tyr Phe Arg Gly Gln Ser Cys Asn Asn Leu Pro Leu Ser
        195                 200                 205
```

His Lys Val Tyr Met Arg Asn Ser Lys Tyr Pro Gln Asp Leu Val Met
    210                 215                 220

Met Glu Gly Lys Met Met Ser Tyr Cys Thr Thr Gly Gln Met Trp Ala
225                 230                 235                 240

Arg Ser Ser Tyr Leu Gly Ala Val Phe Asn Leu Thr Ser Ala Asp His
                245                 250                 255

Leu Tyr Val Asn Val Ser Glu Leu Ser Leu Val Asn Phe Glu Glu Ser
            260                 265                 270

Gln Thr Phe Phe Gly Leu Tyr Lys Leu
        275                 280

<210> SEQ ID NO 195
<211> LENGTH: 119
<212> TYPE: PRT
<213> ORGANISM: Pan troglodytes

<400> SEQUENCE: 195

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met
        115

<210> SEQ ID NO 196
<211> LENGTH: 276
<212> TYPE: PRT
<213> ORGANISM: Artificial Sequence
<220> FEATURE:
<223> OTHER INFORMATION: Synthetic Sequence

<400> SEQUENCE: 196

Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gly Glu Thr
    50                  55                  60

Arg Lys Val Lys Ala His Ser Gln Thr His Arg Val Asp Leu Gly Thr
65                  70                  75                  80

Leu Arg Gly Cys Tyr Asn Gln Ser Glu Ala Gly Ser His Thr Val Gln
                85                  90                  95

Arg Met Tyr Gly Cys Asp Val Gly Ser Asp Trp Arg Phe Leu Arg Gly
            100                 105                 110

Tyr His Gln Tyr Ala Tyr Asp Gly Lys Asp Tyr Ile Ala Leu Lys Glu

```
        115                 120                 125

Asp Leu Arg Ser Trp Thr Ala Ala Asp Met Cys Ala Gln Thr Thr Lys
    130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu Pro
        275


<210> SEQ ID NO 197
<211> LENGTH: 275
<212> TYPE: PRT
<213> ORGANISM: Artificial Sequence
<220> FEATURE:
<223> OTHER INFORMATION: Synthetic Sequence

<400> SEQUENCE: 197

Gly Ser His Ser Met Arg Tyr Phe Tyr Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gln Glu Thr
    50                  55                  60

Arg Asn Val Lys Ala Gln Ser Gln Thr Asp Arg Val Asp Leu Gly Thr
65                  70                  75                  80

Leu Arg Gly Tyr Tyr Asn Gln Ser Glu Asp Gly Ser His Thr Ile Gln
                85                  90                  95

Ile Met Tyr Gly Cys Asp Val Gly Pro Asp Gly Arg Phe Leu Arg Gly
            100                 105                 110

Tyr Arg Gln Asp Ala Tyr Asp Gly Lys Asp Tyr Ile Ala Leu Asn Glu
        115                 120                 125

Asp Leu Arg Ser Trp Thr Ala Ala Asp Met Ala Ala Gln Ile Thr Lys
    130                 135                 140

Arg Lys Trp Glu Ala Ala His Ala Ala Glu Gln Gln Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Pro Pro Lys Thr His Met Thr His His
            180                 185                 190

Pro Ile Ser Asp His Glu Ala Thr Leu Arg Cys Trp Ala Leu Gly Phe
```

```
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu
        275


<210> SEQ ID NO 198
<211> LENGTH: 275
<212> TYPE: PRT
<213> ORGANISM: Artificial Sequence
<220> FEATURE:
<223> OTHER INFORMATION: Synthetic Sequence

<400> SEQUENCE: 198

Gly Ser His Ser Met Arg Tyr Phe Tyr Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gln Glu Thr
    50                  55                  60

Arg Asn Val Lys Ala Gln Ser Gln Thr Asp Arg Val Asp Leu Gly Thr
65                  70                  75                  80

Leu Arg Gly Ala Tyr Asn Gln Ser Glu Asp Gly Ser His Thr Ile Gln
                85                  90                  95

Ile Met Tyr Gly Cys Asp Val Gly Pro Asp Gly Arg Phe Leu Arg Gly
            100                 105                 110

Tyr Arg Gln Asp Ala Tyr Asp Gly Lys Asp Tyr Ile Ala Leu Asn Glu
        115                 120                 125

Asp Leu Arg Ser Trp Thr Ala Ala Asp Met Ala Ala Gln Ile Thr Lys
    130                 135                 140

Arg Lys Trp Glu Ala Ala His Ala Ala Glu Gln Gln Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Pro Pro Lys Thr His Met Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Cys Gly Asp Gly Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu
```

275

<210> SEQ ID NO 199
<211> LENGTH: 276
<212> TYPE: PRT
<213> ORGANISM: Artificial Sequence
<220> FEATURE:
<223> OTHER INFORMATION: Synthetic Sequence

<400> SEQUENCE: 199

Gly Ser His Ser Met Arg Tyr Phe Tyr Thr Ser Val Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Ser Asp Ala Ala Ser Pro Arg Glu Glu Pro Arg
        35                  40                  45

Ala Pro Trp Ile Glu Gln Glu Gly Pro Glu Tyr Trp Asp Arg Asn Thr
    50                  55                  60

Gln Ile Tyr Lys Ala Gln Ala Gln Thr Asp Arg Glu Ser Leu Arg Asn
65                  70                  75                  80

Leu Arg Gly Tyr Tyr Asn Gln Ser Glu Ala Gly Ser His Thr Leu Gln
                85                  90                  95

Ser Met Tyr Gly Cys Asp Val Gly Pro Asp Gly Arg Leu Leu Arg Gly
            100                 105                 110

His Asp Gln Tyr Ala Tyr Asp Gly Lys Asp Tyr Ile Ala Leu Asn Glu
        115                 120                 125

Asp Leu Arg Ser Trp Thr Ala Ala Asp Thr Ala Ala Gln Ile Thr Gln
    130                 135                 140

Arg Lys Trp Glu Ala Ala Arg Glu Ala Glu Gln Arg Arg Ala Tyr Leu
145                 150                 155                 160

Glu Gly Glu Cys Val Glu Trp Leu Arg Arg Tyr Leu Glu Asn Gly Lys
                165                 170                 175

Asp Lys Leu Glu Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro
        275

<210> SEQ ID NO 200
<211> LENGTH: 276
<212> TYPE: PRT
<213> ORGANISM: Artificial Sequence
<220> FEATURE:
<223> OTHER INFORMATION: Synthetic Sequence

<400> SEQUENCE: 200

Gly Ser His Ser Met Arg Tyr Phe Tyr Thr Ser Val Ser Arg Pro Gly
1               5                   10                  15

```
Arg Gly Glu Pro Arg Phe Ile Ser Val Gly Tyr Val Asp Asp Thr Gln
            20                  25                  30

Phe Val Arg Phe Asp Ser Asp Ala Ala Ser Pro Arg Glu Glu Pro Arg
        35                  40                  45

Ala Pro Trp Ile Glu Gln Glu Gly Pro Glu Tyr Trp Asp Arg Asn Thr
    50                  55                  60

Gln Ile Tyr Lys Ala Gln Ala Gln Thr Asp Arg Glu Ser Leu Arg Asn
65                  70                  75                  80

Leu Arg Gly Ala Tyr Asn Gln Ser Glu Ala Gly Ser His Thr Leu Gln
                85                  90                  95

Ser Met Tyr Gly Cys Asp Val Gly Pro Asp Gly Arg Leu Leu Arg Gly
            100                 105                 110

His Asp Gln Tyr Ala Tyr Asp Gly Lys Asp Tyr Ile Ala Leu Asn Glu
        115                 120                 125

Asp Leu Arg Ser Trp Thr Ala Ala Asp Thr Ala Ala Gln Ile Thr Gln
    130                 135                 140

Arg Lys Trp Glu Ala Ala Arg Glu Ala Glu Gln Arg Arg Ala Tyr Leu
145                 150                 155                 160

Glu Gly Glu Cys Val Glu Trp Leu Arg Arg Tyr Leu Glu Asn Gly Lys
                165                 170                 175

Asp Lys Leu Glu Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Cys Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro
        275
```

<210> SEQ ID NO 201
<211> LENGTH: 276
<212> TYPE: PRT
<213> ORGANISM: Artificial Sequence
<220> FEATURE:
<223> OTHER INFORMATION: Synthetic Sequence

<400> SEQUENCE: 201

```
Gly Ser His Ser Met Arg Tyr Phe Tyr Thr Ser Val Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Ser Asp Ala Ala Ser Pro Arg Glu Glu Pro Arg
        35                  40                  45

Ala Pro Trp Ile Glu Gln Glu Gly Pro Glu Tyr Trp Asp Arg Asn Thr
    50                  55                  60

Gln Ile Tyr Lys Ala Gln Ala Gln Thr Asp Arg Glu Ser Leu Arg Asn
65                  70                  75                  80

Leu Arg Gly Cys Tyr Asn Gln Ser Glu Ala Gly Ser His Thr Leu Gln
                85                  90                  95
```

```
Ser Met Tyr Gly Cys Asp Val Gly Pro Asp Gly Arg Leu Leu Arg Gly
            100                 105                 110

His Asp Gln Tyr Ala Tyr Asp Gly Lys Asp Tyr Ile Ala Leu Asn Glu
        115                 120                 125

Asp Leu Arg Ser Trp Thr Ala Ala Asp Thr Cys Ala Gln Ile Thr Gln
    130                 135                 140

Arg Lys Trp Glu Ala Ala Arg Glu Ala Glu Gln Arg Arg Ala Tyr Leu
145                 150                 155                 160

Glu Gly Glu Cys Val Glu Trp Leu Arg Arg Tyr Leu Glu Asn Gly Lys
                165                 170                 175

Asp Lys Leu Glu Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro
        275


<210> SEQ ID NO 202
<211> LENGTH: 276
<212> TYPE: PRT
<213> ORGANISM: Artificial Sequence
<220> FEATURE:
<223> OTHER INFORMATION: Synthetic Sequence

<400> SEQUENCE: 202

Cys Ser His Ser Met Arg Tyr Phe Asp Thr Ala Val Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Ser Asp Ala Ala Ser Pro Arg Gly Glu Pro Arg
        35                  40                  45

Ala Pro Trp Val Glu Gln Glu Gly Pro Glu Tyr Trp Asp Arg Glu Thr
    50                  55                  60

Gln Asn Tyr Lys Arg Gln Ala Gln Ala Asp Arg Val Ser Leu Arg Asn
65                  70                  75                  80

Leu Arg Gly Tyr Tyr Asn Gln Ser Glu Asp Gly Ser His Thr Leu Gln
                85                  90                  95

Arg Met Tyr Gly Cys Asp Leu Gly Pro Asp Gly Arg Leu Leu Arg Gly
            100                 105                 110

Tyr Asp Gln Ser Ala Tyr Asp Gly Lys Asp Tyr Ile Ala Leu Asn Glu
        115                 120                 125

Asp Leu Arg Ser Trp Thr Ala Ala Asp Thr Ala Ala Gln Ile Thr Gln
    130                 135                 140

Arg Lys Leu Glu Ala Ala Arg Ala Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175
```

```
Glu Thr Leu Gln Arg Ala Glu Pro Pro Lys Thr His Val Thr His His
            180                 185                 190

Pro Leu Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Gln Glu Gln Arg
                245                 250                 255

Tyr Thr Cys His Met Gln His Glu Gly Leu Gln Glu Pro Leu Thr Leu
            260                 265                 270

Ser Trp Glu Pro
        275
```

<210> SEQ ID NO 203
<211> LENGTH: 276
<212> TYPE: PRT
<213> ORGANISM: Artificial Sequence
<220> FEATURE:
<223> OTHER INFORMATION: Synthetic Sequence

<400> SEQUENCE: 203

```
Cys Ser His Ser Met Arg Tyr Phe Asp Thr Ala Val Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Ser Asp Ala Ala Ser Pro Arg Gly Glu Pro Arg
        35                  40                  45

Ala Pro Trp Val Glu Gln Glu Gly Pro Glu Tyr Trp Asp Arg Glu Thr
    50                  55                  60

Gln Asn Tyr Lys Arg Gln Ala Gln Ala Asp Arg Val Ser Leu Arg Asn
65                  70                  75                  80

Leu Arg Gly Ala Tyr Asn Gln Ser Glu Asp Gly Ser His Thr Leu Gln
                85                  90                  95

Arg Met Tyr Gly Cys Asp Leu Gly Pro Asp Gly Arg Leu Leu Arg Gly
            100                 105                 110

Tyr Asp Gln Ser Ala Tyr Asp Gly Lys Asp Tyr Ile Ala Leu Asn Glu
        115                 120                 125

Asp Leu Arg Ser Trp Thr Ala Ala Asp Thr Ala Ala Gln Ile Thr Gln
    130                 135                 140

Arg Lys Leu Glu Ala Ala Arg Ala Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Ala Glu Pro Pro Lys Thr His Val Thr His His
            180                 185                 190

Pro Leu Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Cys Gly Asp Gly Thr
225                 230                 235                 240

Phe Gln Lys Trp Ala Ala Val Val Val Pro Ser Gly Gln Glu Gln Arg
                245                 250                 255
```

-continued

```
Tyr Thr Cys His Met Gln His Glu Gly Leu Gln Glu Pro Leu Thr Leu
            260                 265                 270

Ser Trp Glu Pro
        275
```

<210> SEQ ID NO 204
<211> LENGTH: 276
<212> TYPE: PRT
<213> ORGANISM: Artificial Sequence
<220> FEATURE:
<223> OTHER INFORMATION: Synthetic Sequence

<400> SEQUENCE: 204

```
Cys Ser His Ser Met Arg Tyr Phe Asp Thr Ala Val Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Ser Asp Ala Ala Ser Pro Arg Gly Glu Pro Arg
        35                  40                  45

Ala Pro Trp Val Glu Gln Glu Gly Pro Glu Tyr Trp Asp Arg Glu Thr
    50                  55                  60

Gln Asn Tyr Lys Arg Gln Ala Gln Ala Asp Arg Val Ser Leu Arg Asn
65                  70                  75                  80

Leu Arg Gly Cys Tyr Asn Gln Ser Glu Asp Gly Ser His Thr Leu Gln
                85                  90                  95

Arg Met Tyr Gly Cys Asp Leu Gly Pro Asp Gly Arg Leu Leu Arg Gly
            100                 105                 110

Tyr Asp Gln Ser Ala Tyr Asp Gly Lys Asp Tyr Ile Ala Leu Asn Glu
        115                 120                 125

Asp Leu Arg Ser Trp Thr Ala Ala Asp Thr Cys Ala Gln Ile Thr Gln
    130                 135                 140

Arg Lys Leu Glu Ala Ala Arg Ala Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Ala Glu Pro Pro Lys Thr His Val Thr His His
            180                 185                 190

Pro Leu Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Gln Glu Gln Arg
                245                 250                 255

Tyr Thr Cys His Met Gln His Glu Gly Leu Gln Glu Pro Leu Thr Leu
            260                 265                 270

Ser Trp Glu Pro
        275
```

<210> SEQ ID NO 205
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 205

Gly Gly Gly Gly Ser
1 5

<210> SEQ ID NO 206
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 206

Gly Gly Gly Gly Ser Gly Gly Gly Gly Ser
1 5 10

<210> SEQ ID NO 207
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 207

Gly Gly Gly Gly Ser Gly Gly Gly Gly Ser Gly Gly Gly Gly Ser
1 5 10 15

<210> SEQ ID NO 208
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 208

Gly Gly Gly Gly Ser Gly Gly Gly Gly Ser Gly Gly Gly Gly Ser Gly
1 5 10 15

Gly Gly Gly Ser
20

<210> SEQ ID NO 209
<211> LENGTH: 25
<212> TYPE: PRT
<213> ORGANISM: Artificial Sequence
<220> FEATURE:
<223> OTHER INFORMATION: Synthetic Sequence

<400> SEQUENCE: 209

Gly Gly Gly Gly Ser Gly Gly Gly Gly Ser Gly Gly Gly Gly Ser Gly
1 5 10 15

Gly Gly Gly Ser Gly Gly Gly Gly Ser
20 25

<210> SEQ ID NO 210
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 210

Gly Ser Gly Gly Ser
1 5

<210> SEQ ID NO 211
<211> LENGTH: 4
<212> TYPE: PRT

<213> ORGANISM: Artificial Sequence
<220> FEATURE:
<223> OTHER INFORMATION: Synthetic Sequence

<400> SEQUENCE: 211

Gly Gly Gly Ser
1

<210> SEQ ID NO 212
<211> LENGTH: 5
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_Feature
<222> LOCATION: (4)..(4)
<223> OTHER INFORMATION: Xaa is any amino acid other than proline

<400> SEQUENCE: 212

Val Pro Gly Xaa Gly
1 5

<210> SEQ ID NO 213
<211> LENGTH: 174
<212> TYPE: PRT
<213> ORGANISM: Artificial Sequence
<220> FEATURE:
<223> OTHER INFORMATION: Synthetic Sequence

<400> SEQUENCE: 213

Pro Ala Gly Leu Leu Asp Leu Arg Gln Gly Met Phe Ala Gln Leu Val
1 5 10 15

Ala Gln Asn Val Leu Leu Ile Asp Gly Pro Leu Ser Trp Tyr Ser Asp
20 25 30

Pro Gly Leu Ala Gly Val Ser Leu Thr Gly Gly Leu Ser Tyr Lys Glu
35 40 45

Asp Thr Lys Glu Leu Val Val Ala Lys Ala Gly Val Tyr Tyr Val Phe
50 55 60

Phe Gln Leu Glu Leu Arg Arg Val Val Ala Gly Glu Gly Ser Gly Ser
65 70 75 80

Val Ser Leu Ala Leu His Leu Gln Pro Leu Arg Ser Ala Ala Gly Ala
85 90 95

Ala Ala Leu Ala Leu Thr Val Asp Leu Pro Pro Ala Ser Ser Glu Ala
100 105 110

Arg Asn Ser Ala Phe Gly Phe Gln Gly Arg Leu Leu His Leu Ser Ala
115 120 125

Gly Gln Arg Leu Gly Val His Leu His Thr Glu Ala Arg Ala Arg His
130 135 140

Ala Trp Gln Leu Thr Gln Gly Ala Thr Val Leu Gly Leu Phe Arg Val
145 150 155 160

Thr Pro Glu Ile Pro Ala Gly Leu Pro Ser Pro Arg Ser Glu
165 170

<210> SEQ ID NO 214
<211> LENGTH: 175
<212> TYPE: PRT
<213> ORGANISM: Artificial Sequence
<220> FEATURE:
<223> OTHER INFORMATION: Synthetic Sequence

<400> SEQUENCE: 214

```
Asp Pro Ala Gly Leu Leu Asp Leu Arg Gln Gly Met Phe Ala Gln Leu
1               5                   10                  15

Val Ala Gln Asn Val Leu Leu Ile Asp Gly Pro Leu Ser Trp Tyr Ser
            20                  25                  30

Asp Pro Gly Leu Ala Gly Val Ser Leu Thr Gly Gly Leu Ser Tyr Lys
        35                  40                  45

Glu Asp Thr Lys Glu Leu Val Val Ala Lys Ala Gly Val Tyr Tyr Val
    50                  55                  60

Phe Phe Gln Leu Glu Leu Arg Arg Val Val Ala Gly Glu Gly Ser Gly
65                  70                  75                  80

Ser Val Ser Leu Ala Leu His Leu Gln Pro Leu Arg Ser Ala Ala Gly
                85                  90                  95

Ala Ala Ala Leu Ala Leu Thr Val Asp Leu Pro Pro Ala Ser Ser Glu
            100                 105                 110

Ala Arg Asn Ser Ala Phe Gly Phe Gln Gly Arg Leu Leu His Leu Ser
        115                 120                 125

Ala Gly Gln Arg Leu Gly Val His Leu His Thr Glu Ala Arg Ala Arg
    130                 135                 140

His Ala Trp Gln Leu Thr Gln Gly Ala Thr Val Leu Gly Leu Phe Arg
145                 150                 155                 160

Val Thr Pro Glu Ile Pro Ala Gly Leu Pro Ser Pro Arg Ser Glu
                165                 170                 175


<210> SEQ ID NO 215
<211> LENGTH: 167
<212> TYPE: PRT
<213> ORGANISM: Artificial Sequence
<220> FEATURE:
<223> OTHER INFORMATION: Synthetic Sequence

<400> SEQUENCE: 215

Asp Pro Ala Gly Leu Leu Asp Leu Arg Gln Gly Met Phe Ala Gln Leu
1               5                   10                  15

Val Ala Gln Asn Val Leu Leu Ile Asp Gly Pro Leu Ser Trp Tyr Ser
            20                  25                  30

Asp Pro Gly Leu Ala Gly Val Ser Leu Thr Gly Gly Leu Ser Tyr Lys
        35                  40                  45

Glu Asp Thr Lys Glu Leu Val Val Ala Lys Ala Gly Val Tyr Tyr Val
    50                  55                  60

Phe Phe Gln Leu Glu Leu Arg Arg Val Val Ala Gly Glu Gly Ser Gly
65                  70                  75                  80

Ser Val Ser Leu Ala Leu His Leu Gln Pro Leu Arg Ser Ala Ala Gly
                85                  90                  95

Ala Ala Ala Leu Ala Leu Thr Val Asp Leu Pro Pro Ala Ser Ser Glu
            100                 105                 110

Ala Arg Asn Ser Ala Phe Gly Phe Gln Gly Arg Leu Leu His Leu Ser
        115                 120                 125

Ala Gly Gln Arg Leu Gly Val His Leu His Thr Glu Ala Arg Ala Arg
    130                 135                 140

His Ala Trp Gln Leu Thr Gln Gly Ala Thr Val Leu Gly Leu Phe Arg
145                 150                 155                 160

Val Thr Pro Glu Ile Pro Ala
                165


<210> SEQ ID NO 216
<211> LENGTH: 127
```

```
<212> TYPE: PRT
<213> ORGANISM: Artificial Sequence
<220> FEATURE:
<223> OTHER INFORMATION: Synthetic Sequence

<400> SEQUENCE: 216

Gln Val Gln Leu Gln Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
            20                  25                  30

Cys Met Ala Trp Phe Arg Gln Ala Pro Gly Lys Glu Arg Glu Arg Val
        35                  40                  45

Ala Lys Leu Leu Thr Thr Ser Gly Ser Thr Tyr Leu Ala Asp Ser Val
    50                  55                  60

Lys Gly Arg Phe Thr Ile Ser Gln Asn Asn Ala Lys Ser Thr Val Tyr
65                  70                  75                  80

Leu Gln Met Asn Ser Leu Lys Pro Glu Asp Thr Ala Met Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Gln Val Thr Val Ser
        115                 120                 125
```

METHODS FOR MODULATING AN IMMUNE RESPONSE

CROSS-REFERENCE

This application is a continuation of U.S. patent application Ser. No. 16/830,831, filed Mar. 26, 2020, which is a continuation of U.S. patent application Ser. No. 16/489,586, filed Aug. 28, 2019, which is a national stage filing under 35 U.S.C. § 371 of PCT/US2018/022492, filed Mar. 14, 2018, which claims the benefit of U.S. Provisional Patent Application No. 62/471,832, filed Mar. 15, 2017, and of U.S. Provisional Patent Application No. 62/521,009, filed Jun. 16, 2017, which applications are incorporated herein by reference in their entirety.

INTRODUCTION

An adaptive immune response involves the engagement of the T cell receptor (TCR), present on the surface of a T cell, with a small peptide antigen non-covalently presented on the surface of an antigen presenting cell (APC) by a major histocompatibility complex (MHC; also referred to in humans as a human leukocyte antigen (HLA) complex). This engagement represents the immune system's targeting mechanism and is a requisite molecular interaction for T cell modulation (activation or inhibition) and effector function. Following epitope-specific cell targeting, the targeted T cells are activated through engagement of costimulatory proteins found on the APC with counterpart costimulatory proteins the T cells. Both signals—epitope/TCR binding and engagement of APC costimulatory proteins with T cell costimulatory proteins—are required to drive T cell specificity and activation or inhibition. The TCR is specific for a given epitope; however, the costimulatory protein not epitope specific and instead is generally expressed on all T cells or on large T cell subsets.

SUMMARY

The present disclosure provides methods of modulating an immune response in an individual. The present disclosure provides methods of treatment. The present disclosure provides methods comprising administering a multimeric polypeptide (synTac) and an immune checkpoint inhibitor to an individual. The present disclosure provides methods comprising administering a multimeric polypeptide (synTac) to an individual who is undergoing treatment with immune checkpoint inhibitor.

BRIEF DESCRIPTION OF THE DRAWINGS

FIG. 2A-2Q provide an amino acid sequence of wild-type human IL-2 (FIG. 2A); and amino acid sequences of variant IL-2 polypeptides (FIG. 2B-2Q).

FIG. 3A-3C provide amino acid sequences of IL-2 receptor alpha chain (FIG. 3A), beta chain (FIG. 3B), and gamma chain (FIG. 3C).

FIG. 4A-4C provide amino acid sequences of immunoglobulin Fc polypeptides.

FIG. 5A-5C provide amino acid sequences of human leukocyte antigen (HLA) Class I heavy chain polypeptides. Signal sequences are underlined.

FIG. 6 provides a multiple amino acid sequence alignment of beta-2 microglobulin (β2M) precursors (i.e., including the leader sequence) from *Homo sapiens* (NP_004039.1; SEQ ID NO:95), *Pan troglodytes* (NP_001009066.1; SEQ ID NO:195), *Macaca mulatta* (NP_001040602.1; SEQ ID NO:96), *Bos taurus* (NP_776318.1; SEQ ID NO:97) and *Mus musculus* (NP_033865.2; SEQ ID NO:98). Amino acids 1-20 are a signal peptide.

FIG. 7A depicts unpurified yields; FIG. 7B depicts purified product.

FIG. 14A-14F depict the percent phospho-signal transducer and activator of transcription 5 (pSTAT5)-positive cells following stimulation of $CD8^+$ antigen-specific (LCMV) or non-specific (BL6) cells with IL-2/synTacs of the present disclosure at various IL-2/synTac concentrations.

FIG. 21 provides an amino acid sequence of a heavy chain of an IL-2/synTac of the present disclosure, with a leader peptide, where the IL-2/synTac heavy chain comprises an IgG1 Fc with an N297A substitution.

FIG. 22 provides an amino acid sequence of a heavy chain of an IL-2/synTac of the present disclosure, without a leader peptide, where the IL-2/synTac heavy chain comprises an IgG1 Fc with an N297A substitution.

FIG. 23A-23B provide a nucleotide sequence (FIG. 23A) encoding the IL-2/synTac heavy chain depicted in FIG. 21; and a key (FIG. 23B) to the sequence.

FIG. 24 provides an amino acid sequence of a heavy chain of an IL-2/synTac, with a leader peptide, where the IL-2/synTac heavy chain comprises an IgG1 Fc with L234A and L235A substitutions.

FIG. 25 provides an amino acid sequence of a heavy chain of an IL-2/synTac, without a leader peptide, where the IL-2/synTac heavy chain comprises an IgG1 Fc with L234A and L235A substitutions.

FIG. 26A-26B provide a nucleotide sequence (FIG. 26A) encoding the IL-2/synTac heavy chain depicted in FIG. 24; and a key (FIG. 26B) to the sequence.

FIG. 27 provides an amino acid sequence of a heavy chain of an IL-2/synTac, with a leader peptide, where the IL-2/synTac heavy chain comprises an IgG1 Fc with L234F, L235E, and P331S substitutions.

FIG. 28 provides an amino acid sequence of a heavy chain of an IL-2/synTac, without a leader peptide, where the IL-2/synTac heavy chain comprises an IgG1 Fc with L234F, L235E, and P331S substitutions.

FIG. 29A-29B provide a nucleotide sequence (FIG. 29A) encoding the IL-2/synTac heavy chain depicted in FIG. 27; and a key (FIG. 29B) to the sequence.

FIG. 30 provides an amino acid sequence of a light chain of an IL-2/synTac, with a leader peptide, where the IL-2/synTac light chain comprises a human papilloma virus (HPV) E7 epitope.

FIG. 31 provides an amino acid sequence of a light chain of an IL-2/synTac, without a leader peptide, where the IL-2/synTac light chain comprises an HPV E7 epitope.

FIG. 32 provides a nucleotide sequence encoding the IL-2/synTac light chain depicted in FIG. 30.

FIG. 33A-33D provide amino acid sequences of a wild-type human IgG1 Fc (FIG. 33A), an IgG1 Fc with L234F, L235E, and P331S substitutions (FIG. 33B), an IgG1 Fc with an N297A substitution (FIG. 33C), and an IgG1 Fc with L234A and L235A substitutions (FIG. 33D).

FIG. 34A-34C provide amino acid sequence of a β2-microglobulin (R12C) polypeptide (FIG. 34A), a variant IL-2 (H16A; F42A) polypeptide (FIG. 34B), and a Class I MHC-H chain A0201 (Y84A; A236C) (FIG. 34C).

FIG. 36A-36IIII provide an amino acid sequence of a 4-1BBL (FIG. 36A) and examples of variant 4-1BBL polypeptides (FIG. 36B-36IIII).

FIG. 37 provides an amino acid sequence of 4-1BB.

FIG. 47 depicts expression levels of various synTac polypeptides produced in CHO cells.

FIG. 50A-50B provide amino acid sequences of PD-L1 polypeptides.

FIG. 51 provides an amino acid sequence of a CD80 polypeptide.

FIG. 52 provides an amino acid sequence of an ICOS-L polypeptide.

FIG. 53 provides an amino acid sequence of an OX40L polypeptide.

FIG. 54 provides an amino acid sequence of a PD-L2 polypeptide.

FIG. 55 provides an amino acid sequence of a CD86 (B7-2) polypeptide.

FIG. 56 provides an amino acid sequence of a Fas ligand (FAS-L) polypeptide.

DEFINITIONS

Figure 1A:
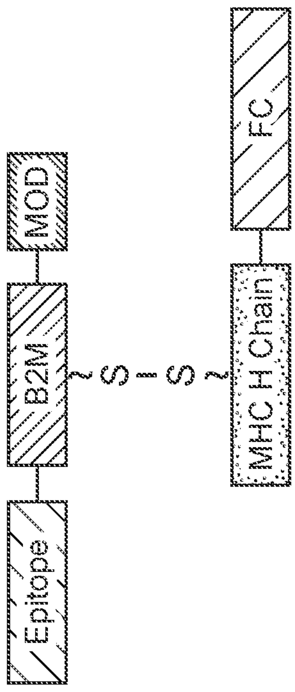
FIG. 1A-1D schematically depict various embodiments of a T-cell modulatory multimeric polypeptide. In these embodiments, disulfide bonds are formed between MHC (e.g., HLA) polypeptides present in separate polypeptides.
Figure 1B:
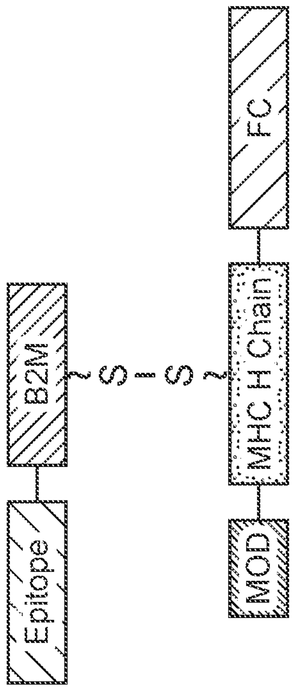
Figure 1C:
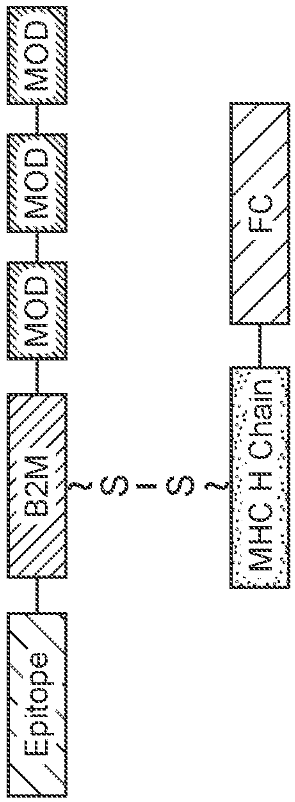
Figure 1D:
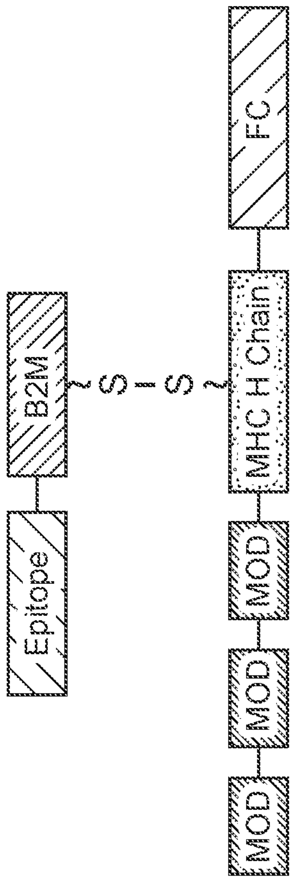

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence identity can be determined in a number of different ways. To determine sequence identity, sequences can be aligned using various convenient methods and computer programs (e.g., BLAST, T-COFFEE, MUSCLE, MAFFT, etc.), available over the world wide web at sites including ncbi.nlm.nili.gov/BLAST, ebi.ac.uk/Tools/msa/tcoffee/, ebi.ac.uk/Tools/msa/muscle/, mafft.cbrc.jp/alignment/software/. See, e.g., Altschul et al. (1990), J. Mol. Bioi. 215:403-10.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamate and aspartate; and a group of amino acids having sulfur containing side chains consists of cysteine and methionine. Exemplary conservative amino acid substitution groups are: valine-leucine-isoleucine, phenylalanine-tyrosine, lysine-arginine, alanine-valine-glycine, and asparagine-glutamine.

"Binding" as used herein (e.g. with reference to binding of a T-cell modulatory multimeric polypeptide to a polypeptide (e.g., a T-cell receptor) on a T cell) refers to a non-covalent interaction between. Binding interactions are generally characterized by a dissociation constant ($K_D$) of less than $10^{-6}$ M, less than $10^{-7}$ M, less than $10^{-8}$M, less than $10^{-9}$ M, less than $10^{-10}$ M, less than $10^{-11}$ M, less than $10^{-12}$ M, less than $10^{-13}$ M, less than $10^{-14}$ M, or less than $10^{-15}$ M. "Affinity" refers to the strength of binding, increased binding affinity being correlated with a lower $K_D$.

The term "immunological synapse" or "immune synapse" as used herein generally refers to the natural interface between two interacting immune cells of an adaptive immune response including, e.g., the interface between an antigen-presenting cell (APC) or target cell and an effector cell, e.g., a lymphocyte, an effector T cell, a natural killer cell, and the like. An immunological synapse between an APC and a T cell is generally initiated by the interaction of a T cell antigen receptor and major histocompatibility complex molecules, e.g., as described in Bromley et al., Annu Rev Immunol. 2001; 19:375-96; the disclosure of which is incorporated herein by reference in its entirety.

"T cell" includes all types of immune cells expressing CD3, including T-helper cells ($CD4^+$ cells), cytotoxic T-cells ($CD8^+$ cells), T-regulatory cells (Treg), and NK-T cells.

"Co-stimulatory polypeptide," (also referred to herein as an "immunomodulatory polypeptide") as the term is used herein, includes a polypeptide on an antigen presenting cell (APC) (e.g., a dendritic cell, a B cell, and the like) that specifically binds a cognate co-stimulatory polypeptide (also referred to herein as a "cognate co-immunomodulatory polypeptide") on a T cell, thereby providing a signal which, in addition to the primary signal provided by, for instance, binding of a TCR/CD3 complex with a major histocompatibility complex (MHC) polypeptide loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, Fas ligand (FasL), inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, LIGHT, NKG2C, B7-H3, and a ligand that specifically binds to CD83.

A "modulatory domain" ("MOD") of a T-cell modulatory multimeric polypeptide comprises a co-stimulatory polypeptide, e.g., an IL-2 polypeptide, such as a variant IL-2 polypeptide.

"Heterologous," as used herein, means a nucleotide or polypeptide that is not found in the native nucleic acid or protein, respectively.

"Recombinant," as used herein, means that a particular nucleic acid (DNA or RNA) is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments or from a series of synthetic oligonucleotides, to provide a synthetic nucleic acid which is capable of being expressed from a recombinant transcriptional unit contained in a cell or in a cell-free transcription and translation system.

The terms "recombinant expression vector," or "DNA construct" are used interchangeably herein to refer to a DNA molecule comprising a vector and one insert. Recombinant expression vectors are usually generated for the purpose of expressing and/or propagating the insert(s), or for the construction of other recombinant nucleotide sequences. The insert(s) may or may not be operably linked to a promoter sequence and may or may not be operably linked to DNA regulatory sequences.

The terms "antibodies" and "immunoglobulin" include antibodies or immunoglobulins of any isotype, fragments of antibodies that retain specific binding to antigen, including, but not limited to, Fab, Fv, scFv, and Fd fragments, chimeric antibodies, humanized antibodies, single-chain antibodies (scAb), single domain antibodies (dAb), single domain heavy chain antibodies, a single domain light chain antibodies, bi-specific antibodies, multi-specific antibodies, and fusion proteins comprising an antigen-binding (also referred to herein as antigen binding) portion of an antibody and a non-antibody protein. Also encompassed by the term are Fab', Fv, $F(ab')_2$, and or other antibody fragments that retain specific binding to antigen, and monoclonal antibodies. As used herein, a monoclonal antibody is an antibody produced by a group of identical cells, all of which were produced from a single cell by repetitive cellular replication. That is, the clone of cells only produces a single antibody species. While a monoclonal antibody can be produced using hybridoma production technology, other production methods known to those skilled in the art can also be used (e.g., antibodies derived from antibody phage display libraries). An antibody can be monovalent or bivalent. An antibody can be an Ig monomer, which is a "Y-shaped" molecule that consists of four polypeptide chains: two heavy chains and two light chains connected by disulfide bonds.

The term "humanized antibody" as used herein refers to an antibody comprising portions of antibodies of different origin, wherein at least one portion comprises amino acid sequences of human origin. For example, a humanized antibody can comprise portions derived from an immunoglobulin of nonhuman origin with the requisite specificity, such as a mouse, and from immunoglobulin sequences of human origin (e.g., chimeric immunoglobulin), joined together chemically by conventional techniques (e.g., synthetic) or prepared as a contiguous polypeptide using genetic engineering techniques (e.g., DNA encoding the protein portions of the chimeric antibody can be expressed to produce a contiguous polypeptide chain). Another example of a humanized antibody is an antibody containing one or more antibody chains comprising a CDR derived from an antibody of nonhuman origin and a framework region derived from a light and/or heavy chain of human origin (e.g., CDR-grafted antibodies with or without framework changes). Chimeric or CDR-grafted single chain antibodies are also encompassed by the term humanized immunoglobulin. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Padlan, E. A. et al., European Patent Application No. 0,519,596 A1. See also, Ladner et al., U.S. Pat. No. 4,946,778; Huston, U.S. Pat. No. 5,476,786; and Bird, R. E. et al., Science, 242: 423-426 (1988)), regarding single chain antibodies.

For example, humanized antibodies can be produced using synthetic and/or recombinant nucleic acids to prepare genes (e.g., cDNA) encoding the desired humanized chain. For example, nucleic acid (e.g., DNA) sequences coding for humanized variable regions can be constructed using PCR mutagenesis methods to alter DNA sequences encoding a human or humanized chain, such as a DNA template from a previously humanized variable region (see e.g., Kamman, M., et al., Nucl. Acids Res., 17: 5404 (1989)); Sato, K., et al., Cancer Research, 53: 851-856 (1993); Daugherty, B. L. et al., Nucleic Acids Res., 19(9): 2471-2476 (1991); and Lewis, A. P. and J. S. Crowe, Gene, 101: 297-302 (1991)). Using these or other suitable methods, variants can also be readily produced. For example, cloned variable regions can be mutagenized, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993)).

"Antibody fragments" comprise a portion of an intact antibody, for example, the antigen binding or variable region of the intact antibody. Examples of antibody fragments include Fab, Fab', $F(ab')_2$, and Fv fragments; diabodies; linear antibodies (Zapata et al., Protein Eng. 8(10): 1057-1062 (1995)); domain antibodies (dAb; Holt et al. (2003) Trends Biotechnol. 21:484); single-chain antibody molecules; and multi-specific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an $F(ab')_2$ fragment that has two antigen combining sites and is still capable of cross-linking antigen.

"Fv" is the minimum antibody fragment that contains a complete antigen-recognition and -binding site. This region consists of a dimer of one heavy- and one light-chain variable domain in tight, non-covalent association. It is in this configuration that the three CDRS of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The "Fab" fragment also contains the constant domain of the light chain and the first constant domain ($CH_1$) of the heavy chain. Fab fragments differ from Fab' fragments by the addition of a few residues at the carboxyl terminus of the heavy chain $CH_1$ domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG, and IgM, and several of these classes can be further divided into subclasses (isotypes), e.g., IgG1, IgG2, IgG3, IgG4, IgA, and IgA2. The subclasses can be further divided into types, e.g., IgG2a and IgG2b.

"Single-chain Fv" or "sFv" or "scFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains, which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al. (1993) *Proc. Natl. Acad. Sci. USA* 90:6444-6448.

As used herein, the term "affinity" refers to the equilibrium constant for the reversible binding of two agents (e.g., an antibody and an antigen) and is expressed as a dissociation constant ($K_D$). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1,000-fold greater, or more, than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femtomolar (fM) or more. As used herein, the term "avidity" refers to the resistance of a complex of two or more agents to dissociation after dilution. The terms "immunoreactive" and "preferentially binds" are used interchangeably herein with respect to antibodies and/or antigen-binding fragments.

The term "binding" refers to a direct association between two molecules, due to, for example, covalent, electrostatic, hydrophobic, and ionic and/or hydrogen-bond interactions, including interactions such as salt bridges and water bridges. "Specific binding" refers to binding with an affinity of at least about $10^{-7}$ M or greater, e.g., $5\times10^{-7}$ M, $10^{-8}$ M, $5\times10^{-8}$ M, and greater. "Non-specific binding" refers to binding with an affinity of less than about $10^{-7}$ M, e.g., binding with an affinity of $10^{-6}$ M, $10^{-5}$ M, $10^{-4}$ M, etc.

As used herein, the term "CDR" or "complementarity determining region" is intended to mean the non-contiguous antigen combining sites found within the variable region of both heavy and light chain polypeptides. CDRs have been described by Kabat et al., J. Biol. Chem. 252:6609-6616 (1977); Kabat et al., U.S. Dept. of Health and Human Services, "Sequences of proteins of immunological interest" (1991) (also referred to herein as Kabat 1991); by Chothia et al., J. Mol. Biol. 196:901-917 (1987) (also referred to herein as Chothia 1987); and MacCallum et al., J. Mol. Biol. 262:732-745 (1996), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues, which encompass the CDRs, as defined by each of the above cited references are set forth in the table below as a comparison. The CDRs listed in Table 2 were defined in accordance with Kabat 1991.

Table: CDR Definitions

| | Kabat[1] | Chothia[2] | MacCallum[3] |
|---|---|---|---|
| $V_H$ CDR-1 | 31-35 | 26-32 | 30-35 |
| $V_H$ CDR-2 | 50-65 | 53-55 | 47-58 |
| $V_H$ CDR-3 | 95-102 | 96-101 | 93-101 |
| $V_L$ CDR-1 | 24-34 | 26-32 | 30-36 |
| $V_L$ CDR-2 | 50-56 | 50-52 | 46-55 |
| $V_L$ CDR-3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra As used herein, the terms "CDR-L1", "CDR-L2", and "CDR-L3" refer, respectively, to the first, second, and third CDRs in a light chain variable region. As used herein, the terms "CDR-H1", "CDR-H2", and "CDR-H3" refer, respectively, to the first, second, and third CDRs in a heavy chain variable region. As used herein, the terms "CDR-1", "CDR-2", and "CDR-3" refer, respectively, to the first, second and third CDRs of either chain's variable region.

As used herein, the term "framework" when used in reference to an antibody variable region is intended to mean all amino acid residues outside the CDR regions within the variable region of an antibody. A variable region framework is generally a discontinuous amino acid sequence between about 100-120 amino acids in length but is intended to reference only those amino acids outside of the CDRs. As used herein, the term "framework region" is intended to mean each domain of the framework that is separated by the CDRs.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease or symptom in a mammal, and includes: (a) preventing the disease or symptom from occurring in a subject which may be predisposed to acquiring the disease or symptom but has not yet been diagnosed as having it; (b) inhibiting the disease or symptom, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

The terms "individual," "subject," "host," and "patient," are used interchangeably herein and refer to any mammalian subject for whom diagnosis, treatment, or therapy is desired. Mammals include, e.g., humans, non-human primates, rodents (e.g., rats; mice), lagomorphs (e.g., rabbits), ungulates (e.g., cows, sheep, pigs, horses, goats, and the like), etc.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a variant IL-2 polypeptide" includes a plurality of such polypeptides and reference to "the Class I HLA heavy chain polypeptide" includes reference to one or more Class I HLA heavy chain polypeptides and equivalents thereof known to those skilled in the art, and so forth. It is further noted that the claims may be drafted to exclude any optional element. As such, this statement is intended to serve as antecedent basis for use of such exclusive terminology as “solely,” “only” and the like in connection with the recitation of claim elements, or use of a “negative” limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides treatment methods comprising administering to an individual in need thereof a T-cell modulatory multimeric polypeptide (a “synTac” multimeric polypeptide) and at least one additional therapeutic agent. In some cases, the at least one additional therapeutic agent is an immune checkpoint inhibitor. In some cases, the immune checkpoint inhibitor is an antibody specific for the immune checkpoint. The present disclosure provides methods comprising administering a multimeric polypeptide (synTac) and an immune checkpoint inhibitor to an individual. The present disclosure provides methods comprising administering a multimeric polypeptide (synTac) to an individual who is undergoing treatment with immune checkpoint inhibitor.

A “T-cell modulatory multimeric polypeptide” is also referred herein to as a “synTac polypeptide” or a “synTac multimeric polypeptide” or simply “synTac.” A synTac polypeptide comprises a modulatory domain. In some cases, the modulatory domain comprises a wild-type amino acid sequence, e.g., an amino acid sequence found in a naturally-occurring modulatory polypeptide. In some cases, the modulatory domain is a variant modulatory domain, where the variant modulatory domain exhibits reduced binding affinity to an immunomodulatory polypeptide, compared to the affinity of a wild-type modulatory domain for the immunomodulatory polypeptide. A synTac polypeptide can modulate the activity of a target T-cell. A synTac polypeptide comprising a variant modulatory domain provides for enhanced target cell specificity.

In some cases, a treatment method of the present disclosure comprises administering to an individual in need thereof a synTac and an immune checkpoint inhibitor. In some cases, the synTac and the immune checkpoint inhibitor provide synergistic effects, compared to the effect(s) of the synTac when administered alone (in monotherapy) or the immune checkpoint inhibitor alone (in monotherapy).

The combination of a synTac and an immune checkpoint inhibitor is in some cases more effective than the additive effects of the synTac administered as monotherapy or the immune checkpoint inhibitor administered as monotherapy. For example, in some cases, a synergistic effect of a synTac and an immune checkpoint inhibitor permits the use of lower dosages of the synTac or the immune checkpoint inhibitor and/or less frequent administration of the synTac or the immune checkpoint inhibitor to an individual in need thereof. The ability to utilize lower dosages of therapeutic agents (a synTac or an immune checkpoint inhibitor) and/or to administer such agents less frequently can reduce toxicity or other adverse side effects that may be associated with the administration of the therapeutic agent in monotherapy, without reducing the efficacy of the therapeutic agent in a treatment. In addition, a synergistic effect of a synTac and an immune checkpoint inhibitor can result in enhanced clinical benefit, compared to the clinical benefit obtained with synTac monotherapy or immune checkpoint inhibitor monotherapy. Examples of clinical benefit include, e.g., reduced tumor mass in an individual; reduced number of cancer cells in an individual; increased survival time of the individual; increased remission time; and the like. Finally, a synergistic effect of a synTac and an immune checkpoint inhibitor can be reduced adverse or unwanted side effects associated with synTac monotherapy or immune checkpoint inhibitor monotherapy.

Immune Checkpoint Inhibitors

Exemplary immune checkpoint inhibitors include inhibitors that target immune checkpoint polypeptide such as CD27, CD28, CD40, CD122, CD96, CD73, CD47, OX40, GITR, CSF1R, JAK, PI3K delta, PI3K gamma, TAM, arginase, CD137 (also known as 4-1BB), ICOS, A2AR, B7-H3, B7-H4, BTLA, CTLA-4, LAG3, TIM3, VISTA, CD96, TIGIT, CD122, PD-1, PD-L1 and PD-L2. In some cases, the immune checkpoint polypeptide is a stimulatory checkpoint molecule selected from CD27, CD28, CD40, ICOS, OX40, GITR, CD122 and CD137. In some cases, the immune checkpoint polypeptide is an inhibitory checkpoint molecule selected from A2AR, B7-H3, B7-H4, BTLA, CTLA-4, IDO, KIR, LAG3, PD-1, TIM3, CD96, TIGIT and VISTA.

In some cases, the immune checkpoint inhibitor is an antibody specific for an immune checkpoint. In some cases, the anti-immune checkpoint antibody is a monoclonal antibody. In some cases, the anti-immune checkpoint antibody is humanized, or de-immunized such that the antibody does not substantially elicit an immune response in a human. In some cases, the anti-immune checkpoint antibody is a humanized monoclonal antibody. In some cases, the anti-immune checkpoint antibody is a de-immunized monoclonal antibody. In some cases, the anti-immune checkpoint antibody is a fully human monoclonal antibody. In some cases, the anti-immune checkpoint antibody inhibits binding of the immune checkpoint polypeptide to a ligand for the immune checkpoint polypeptide. In some cases, the anti-immune checkpoint antibody inhibits binding of the immune checkpoint polypeptide to a receptor for the immune checkpoint polypeptide.

Antibodies, e.g., monoclonal antibodies, that are specific for immune checkpoints and that function as immune checkpoint inhibitors, are known in the art. See, e.g., Wurz et al. (2016) *Ther. Adv. Med. Oncol.* 8:4; and Naidoo et al. (2015) *Ann. Oncol.* 26:2375.

Suitable anti-immune checkpoint antibodies include, but are not limited to, nivolumab (Bristol-Myers Squibb), pembrolizumab (Merck), pidilizumab (Curetech), AMP-224 (GlaxoSmithKline/Amplimmune), MPDL3280A (Roche), MDX-1105 (Medarex, Inc./Bristol Myer Squibb), MEDI- 4736 (Medimmune/AstraZeneca), arelumab (Merck Serono), ipilimumab (YERVOY, (Bristol-Myers Squibb), tremelimumab (Pfizer), pidilizumab (CureTech, Ltd.), IMP321 (Immutep S.A.), MGA271 (Macrogenics), BMS-986016 (Bristol-Meyers Squibb), lirilumab (Bristol-Myers Squibb), urelumab (Bristol-Meyers Squibb), PF-05082566 (Pfizer), IPH2101 (Innate Pharma/Bristol-Myers Squibb), MEDI-6469 (MedImmune/AZ), CP-870,893 (Genentech), Mogamulizumab (Kyowa Hakko Kirin), Varlilumab (CellDex Therapeutics), Avelumab (EMD Serono), Galiximab (Biogen Idec), AMP-514 (Amplimmune/AZ), AUNP 12 (Aurigene and Pierre Fabre), Indoximod (NewLink Genetics), NLG-919 (NewLink Genetics), INCB024360 (Incyte); KNO35; and combinations thereof.

Suitable anti-LAG3 antibodies include, e.g., BMS-986016 and LAG525. Suitable anti-GITR antibodies include, e.g., TRX518, MK-4166, INCAGN01876, and MK-1248. Suitable anti-OX40 antibodies include, e.g., MEDI0562, INCAGN01949, GSK2831781, GSK-3174998, MOXR-0916, PF-04518600, and LAG525. Suitable anti-VISTA antibodies are provided in, e.g., WO 2015/097536.

A suitable dosage of an anti-immune checkpoint antibody is from about 1 mg/kg to about 2400 mg/kg per day, such as from about 1 mg/kg to about 1200 mg/kg per day, including from about 50 mg/kg to about 1200 mg/kg per day. Other representative dosages of such agents include about 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 250 mg/kg, 300 mg/kg, 400 mg/kg, 500 mg/kg, 600 mg/kg, 700 mg/kg, 800 mg/kg, 900 mg/kg, 1000 mg/kg, 1100 mg/kg, 1200 mg/kg, 1300 mg/kg, 1400 mg/kg, 1500 mg/kg, 1600 mg/kg, 1700 mg/kg, 1800 mg/kg, 1900 mg/kg, 2000 mg/kg, 2100 mg/kg, 2200 mg/kg, and 2300 mg/kg per day. The effective dose of the antibody may be administered as two, three, four, five, six or more sub-doses, administered separately at appropriate intervals throughout the day.

Anti-PD-1 Antibodies

In some cases, an immune checkpoint inhibitor is an anti-PD-1 antibody.

Suitable anti-PD-1 antibodies include, e.g., nivolumab, pembrolizumab (also known as MK-3475), pidilizumab, SHR-1210, PDR001, and AMP-224. In some cases, the anti-PD-1 monoclonal antibody is nivolumab, pembrolizumab or PDR001. Suitable anti-PD1 antibodies are described in U.S. Patent Publication No. 2017/0044259. For pidilizumab, see, e.g., Rosenblatt et al. (2011) *J. Immunother.* 34:409-18.

In some cases, the anti-PD1 antibody is pembrolizumab. The amino acid sequence of the heavy chain of pembrolizumab is:

(SEQ ID NO: 51)
QVQLVQSGVEVKKPGASVKVSCKASGYTFTNYYMYWVRQAPGQG
LEWMGGINPSNGGTNFNEKFKNRVTLTTDSSTTTAYMELKSLQF
DDTAVYYCARRDYRFDMGFDYWGQGTTVTVSSASTKGPSVFPLA
PCSRSTSESTAALGCLVKDYFPEPVTVSWNSGALTSGVHTFPAV
LQSSGLYSLSSVVTVPSSSLGTKTYTCNVDHKPSNTKVDKRVES
KYGPPCPPCPAPEFLGGPSVFLFPPKPKDTLMISRTPEVTCVVV
DVSQEDPEVQFNWYVDGVEVHNAKTKPREEQFNSTYRVVSVLTV

-continued
LHQDWLNGKEYKCKVSNKGLPSSIEKTISKAKGQPREPQVYTLP
PSQEEMTKNQVSLTCLVKGFYPSDIAVEWESNGQPENNYKTTPP
VLDSDGSFFLYSRLTVDKSRWQEGNVFSCSVMHEALHNHYTQKS
LSLSLGK.

The amino acid sequence of the heavy chain variable (VH) region is underlined.

The amino acid sequence of the light chain of pembrolizumab is:

(SEQ ID NO: 52)
EIVLTQSPATLSLSPGERATLSCRASKGVSTSGYSYLHWYQQKP
GQAPRLLIYLASYLESGVPARFSGSGSGTDFTLTISSLEPEDFA
VYYCQHSRDLPLTFGGGTKVEIKRTVAAPSVFIFPPSDEQLKSG
TASVVCLLNNFYPREAKVQWKVDNALQSGNSQESVTEQDSKDST
YSLSSTLTLSKADYEKHKVYACEVTHQGLSSPVTKSFNRGEC.

The amino acid sequence of the light chain variable (VL) region is underlined.

In some cases, the anti-PD-1 antibody comprises the VH and VL regions of pembrolizumab. In some cases, the anti-PD-1 antibody comprises heavy and light chain CDRs of pembrolizumab.

In some cases, the anti-PD-1 antibody is nivolumab (also known as MDX-1106 or BMS-936558; see, e.g., Topalian et al. (2012) *N. Eng. J. Med.* 366:2443-2454; and U.S. Pat. No. 8,008,449). The amino acid sequence of the heavy chain of nivolumab is:

(SEQ ID NO: 53)
QVQLVESGGGVVQPGRSLRLDCKASGITFSNSGMHWVRQAPGK
GLEWVAVIWYDGSKRYYADSVKGRFTISRDNSKNTLFLQMNSL
RAEDTAVYYCATNDDYWGQGTLVTVSSASTKGPSVFPLAPCSR
STSESTAALGCLVKDYFPEPVTVSWNSGALTSGVHTFPAVLQS
SGLYSLSSVVTVPSSSLGTKTYTCNVDHKPSNTKVDKRVESKY
GPPCPPCPAPEFLGGPSVFLFPPKPKDTLMISRTPEVTCVVVD
VSQEDPEVQFNWYVDGVEVHNAKTKPREEQFNSTYRVVSVLTV
LHQDWLNGKEYKCKVSNKGLPSSIEKTISKAKGQPREPQVYTL
PPSQEEMTKNQVSLTCLVKGFYPSDIAVEWESNGQPENNYKTT
PPVLDSDGSFFLYSRLTVDKSRWQEGNVFSCSVMHEALHNHYT
QKSLSLSLGK.

The amino acid sequence of the light chain of nivolumab is:

(SEQ ID NO: 54)
EIVLTQSPATLSLSPGERATLSCRASQSVSSYLAWYQQKPGQA
PRLLIYDASNRATGIPARFSGSGSGTDFTLTISSLEPEDFAVY
YCQQSSNWPRTFGQGTKVEIKRTVAAPSVFIFPPSDEQLKSGT
ASVVCLLNNFYPREAKVQWKVDNALQSGNSQESVTEQDSKDST
YSLSSTLTLSKADYEKHKVYACEVTHQGLSSPVTKSFNRGEC.

In some cases, the anti-PD-1 antibody comprises heavy and light chain CDRs of nivolumab.

Anti-CTLA4 Antibodies

In some cases, the anti-CTLA-4 antibody is ipilimumab or tremelimumab. For tremelimumab, see, e.g., Ribas et al. (2013) *J. Clin. Oncol.* 31:616-22.

In some cases, the anti-CTLA-4 antibody is ipilimumab. The amino acid sequence of the heavy chain of ipilimumab is:

(SEQ ID NO: 55)
QVQLVESGGGVVQPGRSLRLSCAASGFTFSSYTMHWVRQAPGK
GLEWVTFISYDGNNKYYADSVKGRFTISRDNSKNTLYLQMNSL
RAEDTAIYYCARTGWLGPFDYWGQGTLVTVSSASTKGPSVFPL
APSSKSTSGGTAALGCLVKDYFPEPVTVSWNSGALTSGVHTFP
AVLQSSGLYSLSSVVTVPSSSLGTQTYICNVNHKPSNTKVDKR
VEPKSCDKTHTCPPCPAPELLGGPSVFLFPPKPKDTLMISRTP
EVTCVVVDVSHEDPEVKFNWYVDGVEVHNAKTKPREEQYNSTY
RVVSVLTVLHQDWLNGKEYKCKVSNKALPAPIEKTISKAKGQP
REPQVYTLPPSRDELTKNQVSLTCLVKGFYPSDIAVEWESNGQ
PENNYKTTPPVLDSDGSFFLYSKLTVDKSRWQQGNVFSCSVMH
EALHNHYTQKSLSLSPGK.

The amino acid sequence of the VH region is underlined.

The amino acid sequence of the light chain of ipilimumab is:

(SEQ ID NO: 56)
EIVLTQSPGTLSLSPGERATLSCRASQSVGSSYLAWYQQKPGQ
APRLLIYGAFSRATGIPDRFSGSGSGTDFTLTISRLEPEDFAV
YYCQQYGSSPWTFGQGTKVEIKRTVAAPSVFIFPPSDEQLKSG
TASVVCLLNNFYPREAKVQWKVDNALQSGNSQESVTEQDSKDS
TYSLSSTLTLSKADYEKHKVYACEVTHQGLSSPVTKSFNRGEC.

The amino acid sequence of the VL region is underlined.

In some cases, the anti-CTLA4 antibody comprises the VH and VL regions of ipilimumab. In some cases, the anti-CTLA4 antibody comprises heavy and light chain CDRs of ipilimumab.

Anti-PD-L1 Antibodies

In some cases, the immune checkpoint inhibitor is an anti-PD-L1 monoclonal antibody. In some cases, the anti-PD-L1 monoclonal antibody is BMS-935559, MEDI4736, MPDL3280A (also known as RG7446), KN035, or MSB0010718C. In some embodiments, the anti-PD-L1 monoclonal antibody is MPDL3280A (atezolizumab) or MEDI4736 (durvalumab). For durvalumab, see, e.g., WO 2011/066389. For atezolizumab, see, e.g., U.S. Pat. No. 8,217,149.

In some cases, the anti-PD-L1 antibody is atezolizumab. The amino acid sequence of the heavy chain of atezolizumab is:

(SEQ ID NO: 57)
EVQLVESGGGLVQPGGSLRLSCAASGFTFSDSWIHWVRQAPGKG
LEWVAWISPYGGSTYYADSVKGRFTISADTSKNTAYLQMNSLRA
EDTAVYYCARRHWPGGFDYWGQGTLVTVSSASTKGPSVFPLAPS

-continued

SKSTSGGTAALGCLVKDYFPEPVTVSWNSGALTSGVHTFPAVLQ
SSGLYSLSSVVTVPSSSLGTQTYICNVNHKPSNTKVDKKVEPKS
CDKTHTCPPCPAPELLGGPSVFLFPPKPKDTLMISRTPEVTCVV
VDVSHEDPEVKFNWYVDGVEVHNAKTKPREEQYASTYRVVSVLT
VLHQDWLNGKEYKCKVSNKALPAPIEKTISKAKGQPREPQVYTL
PPSREEMTKNQVSLTCLVKGFYPSDIAVEWESNGQPENNYKTTP
PVLDSDGSFFLYSKLTVDKSRWQQGNVFSCSVMHEALHNHYTQK
SLSLSPGK.

The amino acid sequence of the light chain of atezolizumab is:

(SEQ ID NO: 58)
DIQMTQSPSSLSASVGDRVTITCRASQDVSTAVAWYQQKPGKAP
KLLIYSASFLYSGVPSRFSGSGSGTDFTLTISSLQPEDFATYYC
QQYLYHPATFGQGTKVEIKRTVAAPSVFIFPPSDEQLKSGTASV
VCLLNNFYPREAKVQWKVDNALQSGNSQESVTEQDSKDSTYSLS
STLTLSKADYEKHKVYACEVTHQGLSSPVTKSFNRGEC.

In some cases, the anti-PD-L1 antibody comprises heavy and light chain CDRs of atezolizumab.

In some cases, the anti-PDL1 antibody is KN035, a fully humanized anti-PD-L1 single domain antibody fused to a human IgG1 Fc polypeptide. Zhang et al. (2017) *Cell Discov.* 3:17004; and WO 2017/020801. The single-domain antibody portion of KN035 can comprise the amino acid sequence:

(SEQ ID NO: 216)
QVQLQESGGGLVQPGGSLRLSCAASGKMSSRRCMAWFRQAPGKE
RERVAKLLTTSGSTYLADSVKGRFTISQNNAKSTVYLQMNSLKP
EDTAMYYCAADSFEDPTCTLVTSSGAFQYWGQGTQVTVS,
where the underlined amino acids are CDR1, CDR2, and CDR3.

T-Cell Modulatory Multimeric Polypeptides (Syntacs)

Multimeric (e.g., heterodimeric, heterotrimeric) polypeptides suitable for use in a method of the present disclosure are described below. The multimeric polypeptides are T cell modulatory polypeptides, and are also referred to herein as "T-cell modulatory multimeric polypeptides," or "synTac" (for "immunological synapse for T cell activation").

A T-cell modulatory multimeric polypeptide comprises: a) a first polypeptide comprising, in order from N-terminus to C-terminus: i) an epitope; ii) a first major histocompatibility complex (MHC) polypeptide; and b) a second polypeptide comprising, in order from N-terminus to C-terminus: i) a second MHC polypeptide; and ii) optionally an immunoglobulin (Ig) Fc polypeptide or a non-Ig scaffold, where the multimeric polypeptide comprises one or more immunomodulatory ("MOD") domains, wherein the one or more immunomodulatory domain is: A) at the C-terminus of the first polypeptide; B) at the N-terminus of the second polypeptide; C) at the C-terminus of the second polypeptide; or D) at the C-terminus of the first polypeptide and at the N-terminus of the second polypeptide. In some cases, a T-cell multimeric polypeptide comprises: a) a first polypeptide comprising, in order from N-terminus to C-terminus: i) an epitope; ii) a first MHC polypeptide; and iii) an immunomodulatory domain; and b) a second polypeptide comprising, in order from N-terminus to C-terminus: i) a second MHC polypeptide; and ii) an Ig Fc polypeptide. In some cases, a T-cell multimeric polypeptide comprises: a) a first polypeptide comprising, in order from N-terminus to C-terminus: i) an epitope; and ii) a first MHC polypeptide; and b) a second polypeptide comprising, in order from N-terminus to C-terminus: i) an immunomodulatory domain; iii) a second MHC polypeptide; and ii) an Ig Fc polypeptide. In some cases, a T-cell multimeric polypeptide comprises: a) a first polypeptide comprising, in order from N-terminus to C-terminus: i) an epitope; and ii) a first MHC polypeptide; and b) a second polypeptide comprising, in order from N-terminus to C-terminus: i) a second MHC polypeptide; and ii) an Ig Fc polypeptide; and iii) an immunomodulatory ("MOD") domain. In some cases, a T-cell multimeric polypeptide comprises: a) a first polypeptide comprising, in order from N-terminus to C-terminus: i) an epitope; and ii) a first MHC polypeptide; and b) a second polypeptide comprising, in order from N-terminus to C-terminus: i) a second MHC polypeptide; and ii) an immunomodulatory domain. In some cases, a T-cell multimeric polypeptide comprises: a) a first polypeptide comprising, in order from N-terminus to C-terminus: i) an epitope; and ii) a first MHC polypeptide; and b) a second polypeptide comprising, in order from N-terminus to C-terminus: i) an immunomodulatory domain; and ii) a second MHC polypeptide. In some cases, a T-cell multimeric polypeptide comprises: a) a first polypeptide comprising, in order from N-terminus to C-terminus: i) an epitope; ii) a first MHC polypeptide; and iii) an immunomodulatory domain; and b) a second polypeptide comprising, in order from N-terminus to C-terminus: i) a second MHC polypeptide.

In some cases, a multimeric polypeptide comprises a non-Ig scaffold. For example, in some cases, the non-Ig scaffold is an XTEN polypeptide, a transferrin polypeptide, an Fc receptor polypeptide, an elastin-like polypeptide, a silk-like polypeptide, or a silk-elastin-like polypeptide.

In some cases, the first MHC polypeptide is a β2-microglobulin (β2M) polypeptide; and the second MHC polypeptide is an MHC class I heavy chain polypeptide. A suitable β2-M polypeptide comprises an amino acid sequence having at least 85%, at least 90%, at least 95%, at least 98%, at least 99%, or 100%, amino acid sequence identity to the amino acid sequence of a β2M polypeptide depicted in FIG. 6. In some cases, the MHC class I heavy chain polypeptide is an HLA-A, an HLA-B, or an HLA-C heavy chain. In some cases, the MHC class I heavy chain polypeptide comprises an amino acid sequence having at least 85%, at least 90%, at least 95%, at least 98%, at least 99%, or 100%, amino acid sequence identity to the amino acid sequence set forth in one of FIG. 5A-5C. In some cases, the first MHC polypeptide is an MHC Class II alpha chain polypeptide; and the second MHC polypeptide is an MHC class II beta chain polypeptide.

The epitope present in a multimeric polypeptide can be a T-cell epitope.

In some cases, a multimeric polypeptide comprises an Ig Fc polypeptide. In some cases, the Ig Fc polypeptide is an IgG1 Fc polypeptide, an IgG2 Fc polypeptide, an IgG3 Fc polypeptide, an IgG4 Fc polypeptide, an IgA Fc polypeptide, or an IgM Fc polypeptide. In some cases, the Ig Fc polypeptide comprises an amino acid sequence having at least 85%, at least 90%, at least 95%, at least 98%, at least 99%, or 100%, amino acid sequence identity to an amino acid sequence depicted in FIG. 4A-4C.

The first polypeptide and the second polypeptide of a multimeric polypeptide can be non-covalently associated. The first polypeptide and the second polypeptide of a multimeric polypeptide can be covalently linked. The first polypeptide and the second polypeptide of a multimeric polypeptide can be covalently linked, where the covalent linkage is via a disulfide bond. In some cases, the first MHC polypeptide or a linker between the epitope and the first MHC polypeptide comprises an amino acid substitution to provide a first Cys residue, and the second MHC polypeptide comprises an amino acid substitution to provide a second Cys residue, and wherein the disulfide linkage is between the first and the second Cys residues.

A multimeric polypeptide can include a linker between one or more of: the epitope and the first MHC polypeptide; two copies of the immunomodulatory ("MOD") polypeptide; the immunomodulatory polypeptide and the second MHC polypeptide; and the second MHC polypeptide and the Ig Fc polypeptide.

Immunomodulatory polypeptides suitable for inclusion in a T-cell multimeric polypeptide include, but are not limited to, a 4-1BBL polypeptide, a B7-1 polypeptide; a B7-2 polypeptide, an ICOS-L polypeptide, an OX-40L polypeptide, a CD80 polypeptide, a CD86 polypeptide, an IL-2 polypeptide, a PD-L1 polypeptide, a FasL polypeptide, and a PD-L2 polypeptide.

A multimeric polypeptide can include 2 or more immunomodulatory polypeptides. A multimeric polypeptide can include 2 immunomodulatory polypeptides. In some cases, the 2 immunomodulatory polypeptides are in tandem. A multimeric polypeptide can include 3 immunomodulatory polypeptides. In some cases, the 3 immunomodulatory polypeptides are in tandem.

A multimeric polypeptide can comprise a third polypeptide, where the third polypeptide comprises an immunomodulatory polypeptide comprising an amino acid sequence having at least 90%, amino acid sequence identity to the immunomodulatory polypeptide of the first polypeptide or the second polypeptide. In some cases, the third polypeptide is covalently linked to the first polypeptide.

Examples of suitable multimeric polypeptides are described in WO 2017/151940; WO 2017/201210; and PCT/US2017/067663. The disclosures of WO 2017/151940, WO 2017/201210, and PCT/US2017/067663 are incorporated by reference herein.

MHC Polypeptides

As noted above, a multimeric polypeptide of the present disclosure includes MHC polypeptides. For the purposes of the instant disclosure, the term "major histocompatibility complex (MHC) polypeptides" is meant to include MHC polypeptides of various species, including human MHC (also referred to as human leukocyte antigen (HLA)) polypeptides, rodent (e.g., mouse, rat, etc.) MHC polypeptides, and MHC polypeptides of other mammalian species (e.g., lagomorphs, non-human primates, canines, felines, ungulates (e.g., equines, bovines, ovines, caprines, etc.), and the like. The term "MHC polypeptide" is meant to include Class I MHC polypeptides (e.g., β-2 microglobulin and MHC class I heavy chain) and MHC Class II polypeptides (e.g., MHC Class II α polypeptide and MHC Class II β polypeptide).

As noted above, in some embodiments of a multimeric polypeptide of the present disclosure, the first and the second MHC polypeptides are Class I MHC polypeptides; e.g., in some cases, the first MHC polypeptide is an MHC Class I β2-microglobulin (β2M) polypeptide, and the second MHC polypeptide is an MHC Class I heavy chain (H chain). In other cases, the first and the second MHC polypeptides are Class II MHC polypeptides; e.g., in some cases, the first MHC polypeptide is an MHC Class II α-chain polypeptide, and the second MHC polypeptide is an MHC Class II β-chain polypeptide. In other cases, the first polypeptide is an MHC Class II β-chain polypeptide, and the second MHC polypeptide is an MHC Class II α-chain polypeptide.

In some cases, an MHC polypeptide of a multimeric polypeptide of the present disclosure is a human MHC polypeptide, where human MHC polypeptides are also referred to as "human leukocyte antigen" ("HLA") polypeptides. In some cases, an MHC polypeptide of a multimeric polypeptide of the present disclosure is a Class I HLA polypeptide, e.g., a β2-microglobulin polypeptide, or a Class I HLA heavy chain polypeptide. Class I HLA heavy chain polypeptides include HLA-A heavy chain polypeptides, HLA-B heavy chain polypeptides, HLA-C heavy chain polypeptides, HLA-E heavy chain polypeptides, HLA-F heavy chain polypeptides, and HLA-G heavy chain polypeptides. In some cases, an MHC polypeptide of a multimeric polypeptide of the present disclosure is a Class II HLA polypeptide, e.g., a Class II HLA a chain or a Class II HLA 13 chain. MHC Class II polypeptides include MCH Class II DP a and β polypeptides, DM α and β polypeptides, DOA α and β polypeptides, DOB α and β polypeptides, DQ α and β polypeptides, and DR α and β polypeptides.

In some cases, an MHC Class I heavy chain polypeptide of a multimeric polypeptide can comprise an amino acid sequence having at least 75%, at least 80%, at least 85%, at least 90%, at least 95%, at least 98%, at least 99%, or 100%, amino acid sequence identity to an amino acid sequence depicted in one of FIG. 5A-5C.

HLA-A

As an example, an MHC Class I heavy chain polypeptide of a multimeric polypeptide can comprise an amino acid sequence having at least 75%, at least 80%, at least 85%, at least 90%, at least 95%, at least 98%, at least 99%, or 100%, amino acid sequence identity to the following human HLA-A heavy chain amino acid sequence:

```
                                          (SEQ ID NO: 59)
GSHSMRYFFTSVSRPGRGEPRFIAVGYVDDTQFVRFDSDAASQR

MEPRAPWIEQEGPEYWDGETRKVKAHSQTHRVDLGTLRGYYNQS

EAGSHTVQRMYGCDVGSDWRFLRGYHQYAYDGKDYIALKEDLRS

WTAADMAAQTTKHKWEAAHVAEQLRAYLEGTCVEWLRRYLENGK

ETLQRTDAPKTHMTHHAVSDHEATLRCWALSFYPAEITLTWQRD

GEDQTQDTELVETRPAGDGTFQKWAAVVVPSGQEQRYTCHVQHE

GLPKPLTLRWEP.
```

HLA-A (Y84A; A236C)

In some cases, the MHC Class I heavy chain polypeptide comprises Y84A and A236C substitutions. For example, in some cases, the MHC Class I heavy chain polypeptide comprises an amino acid sequence having at least 75%, at least 80%, at least 85%, at least 90%, at least 95%, at least 98%, at least 99%, or 100%, amino acid sequence identity to the following human HLA-A heavy chain (Y84A; A236C) amino acid sequence:

```
                                          (SEQ ID NO: 50)
GSHSMRYFFTSVSRPGRGEPRFIAVGYVDDTQFVRFDSDAASQR

MEPRAPWIEQEGPEYWDGETRKVKAHSQTHRVDLGTLRGAYNQS

EAGSHTVQRMYGCDVGSDWRFLRGYHQYAYDGKDYIALKEDLRS

WTAADMAAQTTKHKWEAAHVAEQLRAYLEGTCVEWLRRYLENGK

ETLQRTDAPKTHMTHHAVSDHEATLRCWALSFYPAEITLTWQRD

GEDQTQDTELVETRPCGDGTFQKWAAVVVPSGQEQRYTCHVQHE

GLPKPLTLRWEP,
```

where amino acid 84 is Ala and amino acid 236 is Cys. In some cases, the Cys-236 forms an interchain disulfide bond with Cys-12 of a variant β2M polypeptide that comprises an R12C substitution.

HLA-A (Y84C; A139C)

In some cases, the MHC Class I heavy chain polypeptide comprises Y84C and A139C substitutions. For example, in some cases, the MHC Class I heavy chain polypeptide comprises an amino acid sequence having at least 75%, at least 80%, at least 85%, at least 90%, at least 95%, at least 98%, at least 99%, or 100%, amino acid sequence identity to the following human HLA-A heavy chain (Y84C; A139C) amino acid sequence:

```
                                          (SEQ ID NO: 196)
GSHSMRYFFTSVSRPGRGEPRFIAVGYVDDTQFVRFDSDAASQR

MEPRAPWIEQEGPEYWDGETRKVKAHSQTHRVDLGTLRGCYNQS

EAGSHTVQRMYGCDVGSDWRFLRGYHQYAYDGKDYIALKEDLRS

WTAADMCAQTTKHKWEAAHVAEQLRAYLEGTCVEWLRRYLENGK

ETLQRTDAPKTHMTHHAVSDHEATLRCWALSFYPAEITLTWQRD

GEDQTQDTELVETRPAGDGTFQKWAAVVVPSGQEQRYTCHVQHE

GLPKPLTLRWEP,
```

where amino acid 84 is Cys and amino acid 139 is Cys. In some cases, Cys-84 forms an intrachain disulfide bond with Cys-139.

HLA-A A11 (HLA-A11)

As one non-limiting example, an MHC Class I heavy chain polypeptide of a multimeric polypeptide can comprise an amino acid sequence having at least 75%, at least 80%, at least 85%, at least 90%, at least 95%, at least 98%, at least 99%, or 100%, amino acid sequence identity to the following human HLA-A A11 (also referred to as "HLA-A11") heavy chain amino acid sequence:

```
                                          (SEQ ID NO: 197)
GSHSMRYFYTSVSRPGRGEPRFIAVGYVDDTQFVRFDSDAASQ

RMEPRAPWIEQEGPEYWDQETRNVKAQSQTDRVDLGTLRGYYN

QSEDGSHTIQIMYGCDVGPDGRFLRGYRQDAYDGKDYIALNED

LRSWTAADMAAQITKRKWEAAHAAEQQRAYLEGTCVEWLRRYL

ENGKETLQRTDPPKTHMTHHPISDHEATLRCWALGFYPAEITL

TWQRDGEDQTQDTELVETRPAGDGTFQKWAAVVVPSGEEQRYT

CHVQHEGLPKPLTLRWE.
```

Such an MHC Class I heavy chain may be prominent in Asian populations, including populations of individuals of Asian descent.

HLA-A A11 (Y84A; A236C)

As one non-limiting example, in some cases, the MHC Class I heavy chain polypeptide is an HLA-A A11 allele that comprises Y84A and A236C substitutions. For example, in some cases, the MHC Class I heavy chain polypeptide comprises an amino acid sequence having at least 75%, at least 80%, at least 85%, at least 90%, at least 95%, at least 98%, at least 99%, or 100%, amino acid sequence identity to the following human HLA-A A11 heavy chain (Y84A; A236C) amino acid sequence:

(SEQ ID NO: 198)
GSHSMRYFYTSVSRPGRGEPRFIAVGYVDDTQFVRFDSDAASQ

RMEPRAPWIEQEGPEYWDQETRNVKAQSQTDRVDLGTLRGAYN

QSEDGSHTIQIMYGCDVGPDGRFLRGYRQDAYDGKDYIALNED

LRSWTAADMAAQITKRKWEAAHAAEQQRAYLEGTCVEWLRRYL

ENGKETLQRTDPPKTHMTHHPISDHEATLRCWALGFYPAEITL

TWQRDGEDQTQDTELVETRPCGDGTFQKWAAVVVPSGEEQRYT

CHVQHEGLPKPLTLRWE, where amino acid 84 is Ala and amino acid 236 is Cys. In some cases, the Cys-236 forms an interchain disulfide bond with Cys-12 of a variant β2M polypeptide that comprises an R12C substitution.

HLA-B

As another example, an MHC Class I heavy chain polypeptide of a multimeric polypeptide can comprise an amino acid sequence having at least 75%, at least 80%, at least 85%, at least 90%, at least 95%, at least 98%, at least 99%, or 100%, amino acid sequence identity to the following human HLA-B heavy chain amino acid sequence:

(SEQ ID NO: 199)
GSHSMRYFYTSVSRPGRGEPRFISVGYVDDTQFVRFDSDAA

SPREEPRAPWIEQEGPEYWDRNTQIYKAQAQTDRESLRNLR

GYYNQSEAGSHTLQSMYGCDVGPDGRLLRGHDQYAYDGKDY

IALNEDLRSWTAADTAAQITQRKWEAAREAEQRRAYLEGEC

VEWLRRYLENGKDKLERADPPKTHVTHHPISDHEATLRCWA

LGFYPAEITLTWQRDGEDQTQDTELVETRPAGDRTFQKWAA

VVVPSGEEQRYTCHVQHEGLPKPLTLRWEP.

HLA-B (Y84A; A236C)

As one non-limiting example, in some cases, the MHC Class I heavy chain polypeptide is an HLA-B polypeptide that comprises Y84A and A236C substitutions. For example, in some cases, the MHC Class I heavy chain polypeptide comprises an amino acid sequence having at least 75%, at least 80%, at least 85%, at least 90%, at least 95%, at least 98%, at least 99%, or 100%, amino acid sequence identity to the following human HLA-B heavy chain (Y84A; A236C) amino acid sequence:

(SEQ ID NO: 200)
GSHSMRYFYTSVSRPGRGEPRFISVGYVDDTQFVRFDSDAA

SPREEPRAPWIEQEGPEYWDRNTQIYKAQAQTDRESLRNLR

GAYNQSEAGSHTLQSMYGCDVGPDGRLLRGHDQYAYDGKDY

-continued

IALNEDLRSWTAADTAAQITQRKWEAAREAEQRRAYLEGEC

VEWLRRYLENGKDKLERADPPKTHVTHHPISDHEATLRCWA

LGFYPAEITLTWQRDGEDQTQDTELVETRPCGDRTFQKWAA

VVVPSGEEQRYTCHVQHEGLPKPLTLRWEP, where amino acid 84 is Ala and amino acid 236 is Cys. In some cases, the Cys-236 forms an interchain disulfide bond with Cys-12 of a variant β2M polypeptide that comprises an R12C substitution.

HLA-B (Y84C; A139C)

In some cases, the MHC Class I heavy chain polypeptide comprises Y84C and A139C substitutions. For example, in some cases, the MHC Class I heavy chain polypeptide comprises an amino acid sequence having at least 75%, at least 80%, at least 85%, at least 90%, at least 95%, at least 98%, at least 99%, or 100%, amino acid sequence identity to the following human HLA-B heavy chain (Y84C; A139C) amino acid sequence:

(SEQ ID NO: 201)
GSHSMRYFYTSVSRPGRGEPRFISVGYVDDTQFVRFDSDAA

SPREEPRAPWIEQEGPEYWDRNTQIYKAQAQTDRESLRNLR

GCYNQSEAGSHTLQSMYGCDVGPDGRLLRGHDQYAYDGKDY

IALNEDLRSWTAADTCAQITQRKWEAAREAEQRRAYLEGEC

VEWLRRYLENGKDKLERADPPKTHVTHHPISDHEATLRCWA

LGFYPAEITLTWQRDGEDQTQDTELVETRPAGDRTFQKWAA

VVVPSGEEQRYTCHVQHEGLPKPLTLRWEP, where amino acid 84 is Cys and amino acid 139 is Cys. In some cases, Cys-84 forms an intrachain disulfide bond with Cys-139.

HLA-C

As another example, an MHC Class I heavy chain polypeptide of a multimeric polypeptide can comprise an amino acid sequence having at least 75%, at least 80%, at least 85%, at least 90%, at least 95%, at least 98%, at least 99%, or 100%, amino acid sequence identity to the following human HLA-C heavy chain amino acid sequence:

(SEQ ID NO: 202)
CSHSMRYFDTAVSRPGRGEPRFISVGYVDDTQFVRFDSDAAS

PRGEPRAPWVEQEGPEYWDRETQNYKRQAQADRVSLRNLRGY

YNQSEDGSHTLQRMYGCDLGPDGRLLRGYDQSAYDGKDYIAL

NEDLRSWTAADTAAQITQRKLEAARAAEQLRAYLEGTCVEWL

RRYLENGKETLQRAEPPKTHVTHHPLSDHEATLRCWALGFYP

AEITLTWQRDGEDQTQDTELVETRPAGDGTFQKWAAVVVPSG

QEQRYTCHMQHEGLQEPLTLSWEP.

HLA-C(Y84A; A236C)

As one non-limiting example, in some cases, the MHC Class I heavy chain polypeptide is an HLA-C polypeptide that comprises Y84A and A236C substitutions. For example, in some cases, the MHC Class I heavy chain polypeptide comprises an amino acid sequence having at least 75%, at least 80%, at least 85%, at least 90%, at least 95%, at least 98%, at least 99%, or 100%, amino acid sequence identity to the following human HLA-C heavy chain (Y84A; A236C) amino acid sequence:

(SEQ ID NO: 203)

```
CSHSMRYFDTAVSRPGRGEPRFISVGYVDDTQFVRFDSDAAS
PRGEPRAPWVEQEGPEYWDRETQNYKRQAQADRVSLRNLRGA
YNQSEDGSHTLQRMYGCDLGPDGRLLRGYDQSAYDGKDYIAL
NEDLRSWTAADTAAQITQRKLEAARAAEQLRAYLEGTCVEWL
RRYLENGKETLQRAEPPKTHVTHHPLSDHEATLRCWALGFYP
AEITLTWQRDGEDQTQDTELVETRPCGDGTFQKWAAVVVPSG
QEQRYTCHMQHEGLQEPLTLSWEP,
```

where amino acid 84 is Ala and amino acid 236 is Cys. In some cases, the Cys-236 forms an interchain disulfide bond with Cys-12 of a variant β2M polypeptide that comprises an R12C substitution.

HLA-C(Y84C; A139C)

In some cases, the MHC Class I heavy chain polypeptide comprises Y84C and A139C substitutions. For example, in some cases, the MHC Class I heavy chain polypeptide comprises an amino acid sequence having at least 75%, at least 80%, at least 85%, at least 90%, at least 95%, at least 98%, at least 99%, or 100%, amino acid sequence identity to the following human HLA-C heavy chain (Y84C; A139C) amino acid sequence:

(SEQ ID NO: 204)

```
CSHSMRYFDTAVSRPGRGEPRFISVGYVDDTQFVRFDSDAAS
PRGEPRAPWVEQEGPEYWDRETQNYKRQAQADRVSLRNLRGC
YNQSEDGSHTLQRMYGCDLGPDGRLLRGYDQSAYDGKDYIAL
NEDLRSWTAADTCAQITQRKLEAARAAEQLRAYLEGTCVEWL
RRYLENGKETLQRAEPPKTHVTHHPLSDHEATLRCWALGFYP
AEITLTWQRDGEDQTQDTELVETRPAGDGTFQKWAAVVVPSG
QEQRYTCHMQHEGLQEPLTLSWEP,
```

where amino acid 84 is Cys and amino acid 139 is Cys. In some cases, Cys-84 forms an intrachain disulfide bond with Cys-139.

In some cases, an MHC Class I heavy chain polypeptide of a multimeric polypeptide can comprise an amino acid sequence having at least 75%, at least 80%, at least 85%, at least 90%, at least 95%, at least 98%, at least 99%, or 100%, amino acid sequence identity to an amino acid sequence depicted in one of FIG. 3A-3C.

As an example, an MHC Class I heavy chain polypeptide of a multimeric polypeptide can comprise an amino acid sequence having at least 75%, at least 80%, at least 85%, at least 90%, at least 95%, at least 98%, at least 99%, or 100%, amino acid sequence identity to amino acids 25-365 of the amino acid sequence of the human HLA-A heavy chain polypeptide depicted in FIG. 3A.

As another example, an MHC Class I heavy chain polypeptide of a multimeric polypeptide can comprise an amino acid sequence having at least 75%, at least 80%, at least 85%, at least 90%, at least 95%, at least 98%, at least 99%, or 100%, amino acid sequence identity to amino acids 25-362 of the amino acid sequence of the human HLA-B heavy chain polypeptide depicted in FIG. 3B.

As another example, an MHC Class I heavy chain polypeptide of a multimeric polypeptide can comprise an amino acid sequence having at least 75%, at least 80%, at least 85%, at least 90%, at least 95%, at least 98%, at least 99%, or 100%, amino acid sequence identity to amino acids 25-362 of the amino acid sequence of the human HLA-C heavy chain polypeptide depicted in FIG. 3C.

As another example, an MHC Class I heavy chain polypeptide of a multimeric polypeptide can comprise an amino acid sequence having at least 75%, at least 80%, at least 85%, at least 90%, at least 95%, at least 98%, at least 99%, or 100%, amino acid sequence identity to the following amino acid sequence:

(SEQ ID NO: 60)

```
GPHSLRYFVTAVSRPGLGEPRFIAVGYVDDTQFVRFDSDADN
PRFEPRAPWMEQEGPEYWEEQTQRAKSDEQWFRVSLRTAQRY
YNQSKGGSHTFQRMFGCDVGSDWRLLRGYQQFAYDGRDYIAL
NEDLKTWTAADTAALITRRKWEQAGDAEYYRAYLEGECVEWL
RRYLELGNETLLRTDSPKAHVTYHPRSQVDVTLRCWALGFYP
ADITLTWQLNGEDLTQDMELVETRPAGDGTFQKWAAVVVPLG
KEQNYTCHVHHKGLPEPLTLRW.
```

A β2-microglobulin (β2M) polypeptide of a multimeric polypeptide can be a human β2M polypeptide, a non-human primate β2M polypeptide, a murine β2M polypeptide, and the like. In some instances, a β2M polypeptide comprises an amino acid sequence having at least 75%, at least 80%, at least 85%, at least 90%, at least 95%, at least 98%, at least 99%, or 100%, amino acid sequence identity to a β2M amino acid sequence depicted in FIG. 6. In some instances, a β2M polypeptide comprises an amino acid sequence having at least 75%, at least 80%, at least 85%, at least 90%, at least 95%, at least 98%, at least 99%, or 100%, amino acid sequence identity to amino acids 21 to 119 of a β2M amino acid sequence depicted in FIG. 6.

In some cases, an MHC polypeptide comprises a single amino acid substitution relative to a reference MHC polypeptide (where a reference MHC polypeptide can be a wild-type MHC polypeptide), where the single amino acid substitution substitutes an amino acid with a cysteine (Cys) residue. Such cysteine residues, when present in an MHC polypeptide of a first polypeptide of a multimeric polypeptide of the present disclosure, can form a disulfide bond with a cysteine residue present in a second polypeptide chain of a multimeric polypeptide of the present disclosure.

In some cases, a first MHC polypeptide in a first polypeptide of a multimeric polypeptide, and/or the second MHC polypeptide in the second polypeptide of a multimeric polypeptide, includes an amino acid substitution to substitute an amino acid with a cysteine, where the substituted cysteine in the first MHC polypeptide forms a disulfide bond with a cysteine in the second MHC polypeptide, where a cysteine in the first MHC polypeptide forms a disulfide bond with the substituted cysteine in the second MHC polypeptide, or where the substituted cysteine in the first MHC polypeptide forms a disulfide bond with the substituted cysteine in the second MHC polypeptide.

For example, in some cases, one of following pairs of residues in an HLA β2-microglobulin and an HLA Class I heavy chain is substituted with cysteines (where residue numbers are those of the mature polypeptide): 1) β2M residue 12, HLA Class I heavy chain residue 236; 2) β2M residue 12, HLA Class I heavy chain residue 237; 3) β2M residue 8, HLA Class I heavy chain residue 234; 4) β2M residue 10, HLA Class I heavy chain residue 235; 5) β2M residue 24, HLA Class I heavy chain residue 236; 6) β2M residue 28, HLA Class I heavy chain residue 232; 7) β2M residue 98, HLA Class I heavy chain residue 192; 8) β2M residue 99, HLA Class I heavy chain residue 234; 9) β2M residue 3, HLA Class I heavy chain residue 120; 10) β2M residue 31, HLA Class I heavy chain residue 96; 11) β2M residue 53, HLA Class I heavy chain residue 35; 12) β2M residue 60, HLA Class I heavy chain residue 96; 13) β2M residue 60, HLA Class I heavy chain residue 122; 14) β2M residue 63, HLA Class I heavy chain residue 27; 15) β2M residue Arg3, HLA Class I heavy chain residue Gly120; 16) β2M residue His31, HLA Class I heavy chain residue Gln96; 17) β2M residue Asp53, HLA Class I heavy chain residue Arg35; 18) β2M residue Trp60, HLA Class I heavy chain residue Gln96; 19) β2M residue Trp60, HLA Class I heavy chain residue Asp122; 20) β2M residue Tyr63, HLA Class I heavy chain residue Tyr27; 21) β2M residue Lys6, HLA Class I heavy chain residue Glu232; 22) β2M residue Gln8, HLA Class I heavy chain residue Arg234; 23) β2M residue Tyr10, HLA Class I heavy chain residue Pro235; 24) β2M residue Ser11, HLA Class I heavy chain residue Gln242; 25) β2M residue Asn24, HLA Class I heavy chain residue Ala236; 26) β2M residue Ser28, HLA Class I heavy chain residue Glu232; 27) β2M residue Asp98, HLA Class I heavy chain residue His192; and 28) β2M residue Met99, HLA Class I heavy chain residue Arg234. The amino acid numbering of the MHC/HLA Class I heavy chain is in reference to the mature MHC/HLA Class I heavy chain, without a signal peptide. For example, in the amino acid sequence depicted in FIG. 5A, which includes a signal peptide, Gly120 is Gly144; Gln96 is Gln120; etc. In some cases, the β2M polypeptide comprises an R12C substitution, and the HLA Class I heavy chain comprises an A236C substitution; in such cases, a disulfide bond forms between Cys-12 of the β2M polypeptide and Cys-236 of the HLA Class I heavy chain. For example, in some cases, residue 236 of the mature HLA-A amino acid sequence (i.e., residue 260 of the amino acid sequence depicted in FIG. 5A) is substituted with a Cys. In some cases, residue 236 of the mature HLA-B amino acid sequence (i.e., residue 260 of the amino acid sequence depicted in FIG. 5B) is substituted with a Cys. In some cases, residue 236 of the mature HLA-C amino acid sequence (i.e., residue 260 of the amino acid sequence depicted in FIG. 5C) is substituted with a Cys. In some cases, residue 32 (corresponding to Arg-12 of mature β2M) of an amino acid sequence depicted in FIG. 6 is substituted with a Cys.

In some cases, a β2M polypeptide comprises the amino acid sequence: IQRTPKIQVY SRHPAENGKS NFLNCYVSGF HPSDIEVDLLKNGERIEKVE HSDLSFSKDW SFYLLYYTEF TPTEKDEYAC RVNHVTLSQP KIVKWDRDM (SEQ ID NO:61). In some cases, a β2M polypeptide comprises the amino acid sequence: IQRTPKIQVY S CHPAENGKS NFLNCYVSGF HPSDIEVDLLKNGERIEKVE HSDLSFSKDW SFYLLYYTEF TPTEKDEYAC RVNHVTLSQP KIVKWDRDM (SEQ ID NO:48).

In some cases, an HLA Class I heavy chain polypeptide comprises the amino acid sequence:

```
                                        (SEQ ID NO: 59)
GSHSMRYFFTSVSRPGRGEPRFIAVGYVDDTQFVRFDSDAAS
QRMEPRAPWIEQEGPEYWDGETRKVKAHSQTHRVDLGTLRGY
YNQSEAGSHTVQRMYGCDVGSDWRFLRGYHQYAYDGKDYIAL
```

-continued

```
KEDLRSWTAADMAAQTTKHKWEAAHVAEQLRAYLEGTCVEWL
RRYLENGKETLQRTDAPKTHMTHHAVSDHEATLRCWALSFYP
AEITLTWQRDGEDQTQDTELVETRPAGDGTFQKWAAVVVPSG
QEQRYTCHVQHEGLPKPLTLRWEP.
```

In some cases, an HLA Class I heavy chain polypeptide comprises the amino acid sequence:

```
                                        (SEQ ID NO: 62)
GSHSMRYFFTSVSRPGRGEPRFIAVGYVDDTQFVRFDSDAAS
QRMEPRAPWIEQEGPEYWDGETRKVKAHSQTHRVDLGTLRGY
YNQSEAGSHTVQRMYGCDVGSDWRFLRGYHQYAYDGKDYIAL
KEDLRSWTAADMAAQTTKHKWEAAHVAEQLRAYLEGTCVEWL
RRYLENGKETLQRTDAPKTHMTHHAVSDHEATLRCWALSFYP
AEITLTWQRDGEDQTQDTELVETRPCGDGTFQKWAAVVVPSG
QEQRYTCHVQHEGLPKPLTLRWEP.
```

In some cases, an HLA Class I heavy chain polypeptide comprises the amino acid sequence:

```
                                        (SEQ ID NO: 50)
GSHSMRYFFTSVSRPGRGEPRFIAVGYVDDTQFVRFDSDAAS
QRMEPRAPWIEQEGPEYWDGETRKVKAHSQTHRVDLGTLRGA
YNQSEAGSIITVQRMYGCDVGSDWRFLRGYHQYAYDGKDYIA
LKEDLRSWTAADMAAQTTKHKWEAAHVAEQLRAYLEGTCVEW
LRRYLENGKETLQRTDAPKTHMTHHAVSDHEATLRCWALSFY
PAEITLTWQRDGEDQTQDTELVETRPCGDGTFQKWAAVVVPS
GQEQRYTCHVQHEGLPKPLTLRWE.
```

In some cases, the β2M polypeptide comprises the following amino acid sequence:

IQRTPKIQVY SCHPAENGKS NFLNCYVSGF HPSDIEVDLLKNGERIEKVE HSDLSFSKDW SFYLLYYTEF TPTEKDEYAC RVNHVTLSQP KIVKWDRDM (SEQ ID NO:48); and the HLA ClassI heavy chain polypeptide of a multimeric polypeptide of the present disclosure comprises the following amino acid sequence:

```
                                        (SEQ ID NO: 62)
GSHSMRYFFTSVSRPGRGEPRFIAVGYVDDTQFVRFDSDAAS
QRMEPRAPWIEQEGPEYWDGETRKVKAHSQTHRVDLGTLRGY
YNQSEAGSHTVQRMYGCDVGSDWRFLRGYHQYAYDGKDYIAL
KEDLRSWTAADMAAQTTKHKWEAAHVAEQLRAYLEGTCVEWL
RRYLENGKETLQRTDAPKTHMTHHAVSDHEATLRCWALSFYP
AEITLTWQRDGEDQTQDTELVETRPCGDGTFQKWAAVVVPSG
QEQRYTCHVQHEGLPKPLTLRWEP,
```

where the Cys residues that are underlined and in bold form a disulfide bond with one another in the multimeric polypeptide.

In some cases, the β2M polypeptide comprises the amino acid sequence:

(SEQ ID NO: 48)
IQRTPKIQVYSCHPAENGKSNFLNCYVSGFHPSDIEVDLLKN

GERIEKVEHSDLSFSKDWSFYLLYYTEFTPTEKDEYACRVNH

VTLSQPKIVKWDRDM.

Scaffold Polypeptides

A T-cell modulatory multimeric polypeptide comprises an Fc polypeptide, or another suitable scaffold polypeptide.

Suitable scaffold polypeptides include antibody-based scaffold polypeptides and non-antibody-based scaffolds. Non-antibody-based scaffolds include, e.g., albumin, an XTEN (extended recombinant) polypeptide, transferrin, an Fc receptor polypeptide, an elastin-like polypeptide (see, e.g., Hassouneh et al. (2012) *Methods Enzymol.* 502:215; e.g., a polypeptide comprising a pentapeptide repeat unit of (Val-Pro-Gly-X-Gly; SEQ ID NO:212), where X is any amino acid other than proline), an albumin-binding polypeptide, a silk-like polypeptide (see, e.g., Valluzzi et al. (2002) *Philos Trans R Soc Lond B Biol Sci.* 357:165), a silk-elastin-like polypeptide (SELP; see, e.g., Megeed et al. (2002) *Adv Drug Deliv Rev.* 54:1075), and the like. Suitable XTEN polypeptides include, e.g., those disclosed in WO 2009/023270, WO 2010/091122, WO 2007/103515, US 2010/0189682, and US 2009/0092582; see also Schellenberger et al. (2009) Nat Biotechnol. 27:1186). Suitable albumin polypeptides include, e.g., human serum albumin.

Suitable scaffold polypeptides will in some cases be a half-life extending polypeptides. Thus, in some cases, a suitable scaffold polypeptide increases the in vivo half-life (e.g., the serum half-life) of the multimeric polypeptide, compared to a control multimeric polypeptide lacking the scaffold polypeptide. For example, in some cases, a scaffold polypeptide increases the in vivo half-life (e.g., the serum half-life) of the multimeric polypeptide, compared to a control multimeric polypeptide lacking the scaffold polypeptide, by at least about 10%, at least about 15%, at least about 20%, at least about 25%, at least about 50%, at least about 2-fold, at least about 2.5-fold, at least about 5-fold, at least about 10-fold, at least about 25-fold, at least about 50-fold, at least about 100-fold, or more than 100-fold. As an example, in some cases, an Fc polypeptide increases the in vivo half-life (e.g., the serum half-life) of the multimeric polypeptide, compared to a control multimeric polypeptide lacking the Fc polypeptide, by at least about 10%, at least about 15%, at least about 20%, at least about 25%, at least about 50%, at least about 2-fold, at least about 2.5-fold, at least about 5-fold, at least about 10-fold, at least about 25-fold, at least about 50-fold, at least about 100-fold, or more than 100-fold.

Fc Polypeptides

In some cases, the first and/or the second polypeptide chain of a multimeric polypeptide comprises an Fc polypeptide. The Fc polypeptide of a multimeric polypeptide can be a human IgG1 Fc, a human IgG2 Fc, a human IgG3 Fc, a human IgG4 Fc, etc. In some cases, the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to an amino acid sequence of an Fc region depicted in FIGS. 4A-C. In some cases, the Fc region comprises an amino acid sequence having at least about 70%, at least about 75%, at least about 80%, at least about 85%, at least about 90%, at least about 95%, at least about 98%, at least about 99%, or 100%, amino acid sequence identity to the human IgG1 Fc polypeptide depicted in FIG. 4A. In some cases, the Fc region comprises an amino acid sequence having at least about 70%, at least about 75%, at least about 80%, at least about 85%, at least about 90%, at least about 95%, at least about 98%, at least about 99%, or 100%, amino acid sequence identity to the human IgG1 Fc polypeptide depicted in FIG. 4A; and comprises a substitution of N77; e.g., the Fc polypeptide comprises an N77A substitution. In some cases, the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to the human IgG2 Fc polypeptide depicted in FIG. 4A; e.g., the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to amino acids 99-325 of the human IgG2 Fc polypeptide depicted in FIG. 4A. In some cases, the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to the human IgG3 Fc polypeptide depicted in FIG. 4A; e.g., the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to amino acids 19-246 of the human IgG3 Fc polypeptide depicted in FIG. 4A. In some cases, the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to the human IgM Fc polypeptide depicted in FIG. 4B; e.g., the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to amino acids 1-276 to the human IgM Fc polypeptide depicted in FIG. 4B. In some cases, the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to the human IgA Fc polypeptide depicted in FIG. 4C; e.g., the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to amino acids 1-234 to the human IgA Fc polypeptide depicted in FIG. 4C.

In some cases, the Fc polypeptide present in a multimeric polypeptide comprises the amino acid sequence depicted in FIG. 33A (human IgG1 Fc). In some cases, the Fc polypeptide present in a multimeric polypeptide of the present disclosure comprises the amino acid sequence depicted in FIG. 33A (human IgG1 Fc), except for a substitution of N297 with an amino acid other than asparagine. In some cases, the Fc polypeptide present in a multimeric polypeptide of the present disclosure comprises the amino acid sequence depicted in FIG. 33C (human IgG1 Fc comprising an N297A substitution). In some cases, the Fc polypeptide present in a multimeric polypeptide of the present disclosure comprises the amino acid sequence depicted in FIG. 33A (human IgG1 Fc), except for a substitution of L234 with an amino acid other than leucine. In some cases, the Fc polypeptide present in a multimeric polypeptide of the present disclosure comprises the amino acid sequence depicted in FIG. 33A (human IgG1 Fc), except for a substitution of L235 with an amino acid other than leucine. In some cases, the Fc polypeptide present in a multimeric polypeptide of the present disclosure comprises the amino acid sequence depicted in FIG. 33D (human IgG1 Fc comprising an L234A substitution and an L235A substitution). In some cases, the Fc polypeptide present in a multimeric polypeptide of the present disclosure comprises the amino acid sequence depicted in FIG. 33A (human IgG1 Fc), except for a substitution of P331 with an amino acid other than proline; in some cases, the substitution is a P331S substitution. In some cases, the Fc polypeptide present in a multimeric polypeptide of the present disclosure comprises the amino acid sequence depicted in FIG. 33A (human IgG1 Fc), except for substitutions at L234 and L235 with amino acids other than leucine. In some cases, the Fc polypeptide present in a multimeric polypeptide of the present disclosure comprises the amino acid sequence depicted in FIG. 33A (human IgG1 Fc), except for substitutions at L234 and L235 with amino acids other than leucine, and a substitution of P331 with an amino acid other than proline. In some cases, the Fc polypeptide present in a multimeric polypeptide of the present disclosure comprises the amino acid sequence depicted in FIG. 33B (human IgG1 Fc comprising L234F, L235E, and P331S substitutions). In some cases, the Fc polypeptide present in a multimeric polypeptide is an IgG1 Fc polypeptide that comprises L234A and L235A substitutions.

Linkers

A multimeric polypeptide can include linker peptides interposed between, e.g., an epitope and an MHC polypeptide; between an MHC polypeptide and an immunomodulatory polypeptide; between an MHC polypeptide and an Ig Fc polypeptide; between a first immunomodulatory polypeptide and a second immunomodulatory polypeptide; or a between a second immunomodulatory polypeptide and a third immunomodulatory polypeptide.

For example, a multimeric polypeptide can include linker peptides interposed between, e.g., an epitope and an MHC polypeptide; between an MHC polypeptide and an immunomodulatory polypeptide; between an MHC polypeptide and an Ig Fc polypeptide; between a first variant IL-2 polypeptide and a second variant IL-2 polypeptide; or a between a second variant IL-2 polypeptide and a third variant IL-2 polypeptide. As another example, a multimeric polypeptide can include linker peptides interposed between, e.g., an epitope and an MHC polypeptide; between an MHC polypeptide and an immunomodulatory polypeptide; between an MHC polypeptide and an Ig Fc polypeptide; between a first variant 4-1BBL polypeptide and a second variant 4-1BBL polypeptide; or a between a second variant 4-1BBL polypeptide and a third variant 4-1BBL polypeptide.

Suitable linkers (also referred to as "spacers") can be readily selected and can be of any of a number of suitable lengths, such as from 1 amino acid to 25 amino acids, from 3 amino acids to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids. A suitable linker can be 1, 2, 3, 4, 5, 6, 7, 8, 9, 10, 11, 12, 13, 14, 15, 16, 17, 18, 19, 20, 21, 22, 23, 24, or 25 amino acids in length.

Exemplary linkers include glycine polymers (G)., glycine-serine polymers (including, for example, $(GS)_n$, $(GSGGS)_n$ (SEQ ID NO:210) and $(GGGS)_n$ (SEQ ID NO:211), where n is an integer of at least one), glycine-alanine polymers, alanine-serine polymers, and other flexible linkers known in the art. Glycine and glycine-serine polymers can be used; both Gly and Ser are relatively unstructured, and therefore can serve as a neutral tether between components. Glycine polymers can be used; glycine accesses significantly more phi-psi space than even alanine, and is much less restricted than residues with longer side chains (see Scheraga, *Rev. Computational Chem.* 11173-142 (1992)).

Exemplary linkers can comprise amino acid sequences including, but not limited to, GGSG (SEQ ID NO:65), GGSGG (SEQ ID NO:66), GSGSG (SEQ ID NO:67), GSGGG (SEQ ID NO:68), GGGSG (SEQ ID NO:69), GSSSG (SEQ ID NO:70), and the like. Exemplary linkers can include, e.g., $Gly(Ser_4)n$, where n is 1, 2, 3, 4, 5, 6, 7, 8, 9, or 10. In some cases, a linker comprises the amino acid sequence (GSSSS)n (SEQ ID NO:71), where n is 4. In some cases, a linker comprises the amino acid sequence (GSSSS)n (SEQ ID NO:72), where n is 5. In some cases, a linker comprises the amino acid sequence (GGGGS)n (SEQ ID NO:205), where n is 1. In some cases, a linker comprises the amino acid sequence (GGGGS)n (SEQ ID NO:206), where n is 2. In some cases, a linker comprises the amino acid sequence (GGGGS)n (SEQ ID NO:207), where n is 3. In some cases, a linker comprises the amino acid sequence (GGGGS)n (SEQ ID NO:208), where n is 4. In some cases, a linker comprises the amino acid sequence (GGGGS)n (SEQ ID NO:209), where n is 5. In some cases, a linker comprises the amino acid sequence AAAGG (SEQ ID NO:73).

In some cases, a linker polypeptide, present in a first polypeptide of a multimeric polypeptide of the present disclosure, includes a cysteine residue that can form a disulfide bond with a cysteine residue present in a second polypeptide of a multimeric polypeptide of the present disclosure. In some cases, for example, a suitable linker comprises the amino acid sequence GCGASGGGGSGGGGS (SEQ ID NO:74).

Epitopes

An epitope (a peptide presenting one or more epitopes) present in a multimeric polypeptide of the present disclosure can have a length of from about 4 amino acids to about 25 amino acids, e.g., the epitope can have a length of from 4 amino acids (aa) to 10 aa, from 10 aa to 15 aa, from 15 aa to 20 aa, or from 20 aa to 25 aa. For example, an epitope present in a multimeric polypeptide of the present disclosure can have a length of 4 amino acids (aa), 5 aa, 6 aa, 7, aa, 8 aa, 9 aa, 10 aa, 11 aa, 12 aa, 13 aa, 14 aa, 15 aa, 16 aa, 17 aa, 18 aa, 19 aa, 20 aa, 21 aa, 22 aa, 23 aa, 24 aa, or 25 aa. In some cases, an epitope present in a multimeric polypeptide of the present disclosure has a length of from 5 amino acids to 10 amino acids, e.g., 5 aa, 6 aa, 7 aa, 8 aa, 9 aa, or 10 aa.

An epitope present in a multimeric polypeptide of the present disclosure is specifically bound by a T-cell, i.e., the epitope is specifically bound by an epitope-specific T cell. An epitope-specific T cell binds an epitope having a reference amino acid sequence, but does not substantially bind an epitope that differs from the reference amino acid sequence. For example, an epitope-specific T cell binds an epitope having a reference amino acid sequence, and binds an epitope that differs from the reference amino acid sequence, if at all, with an affinity that is less than $10^{-6}$ M, less than $10^{-5}$ M, or less than $10^{-4}$ M. An epitope-specific T cell can bind an epitope for which it is specific with an affinity of at least $10^{-7}$ M, at least $10^{-8}$M, at least $10^{-9}$ M, or at least $10^{-10}$ M.

Suitable epitopes include, but are not limited to, epitopes present in a cancer-associated antigen. Cancer-associated antigens include, but are not limited to, α-folate receptor; carbonic anhydrase IX (CAIX); CD19; CD20; CD22; CD30; CD33; CD44v7/8; carcinoembryonic antigen (CEA); epithelial glycoprotein-2 (EGP-2); epithelial glycoprotein-40 (EGP-40); folate binding protein (FBP); fetal acetylcholine receptor; ganglioside antigen GD2; Her2/neu; IL-13R-a2; kappa light chain; LeY; L1 cell adhesion molecule; melanoma-associated antigen (MAGE); MAGE-A1; mesothelin; MUC1; NKG2D ligands; oncofetal antigen (h5T4); prostate stem cell antigen (PSCA); prostate-specific membrane antigen (PSMA); tumor-associate glycoprotein-72 (TAG-72); and vascular endothelial growth factor receptor-2 (VEGF-R2). See, e.g., Vigneron et al. (2013) *Cancer Immunity* 13:15; and Vigneron (2015) *BioMed Res. Int'l Article ID* 948501. In some cases, the epitope is a human papilloma virus E7 antigen epitope; see, e.g., Ramos et al. (2013) *J. Immunother.* 36:66.

In some cases, the epitope is HPV16E7/82-90 (LLMGTLGIV; SEQ ID NO:75). In some cases, the epitope is HPV16E7/86-93 (TLGIVCPI; SEQ ID NO:76). In some cases, the epitope is HPV16E7/11-20 (YMLDLQPETT; SEQ ID NO:77). In some cases, the epitope is HPV16E7/11-19 (YMLDLQPET; SEQ ID NO:78). See, e.g., Ressing et al. ((1995) *J. Immunol.* 154:5934) for additional suitable HPV epitopes.

Immunomodulatory Polypeptides

Suitable immunomodulatory polypeptides include, but are not limited to, an IL-2 polypeptide, a 4-1BBL polypeptide, a B7-1 polypeptide; a B7-2 polypeptide, an ICOS-L polypeptide, an OX-40L polypeptide, a CD80 polypeptide, a CD86 polypeptide, a PD-L1 polypeptide, a FasL polypeptide, and a PD-L2 polypeptide.

In some cases, the immunomodulatory polypeptide comprises an amino acid sequence having at least 80%, at least 85%, at least 90%, at least 95%, at least 98%, at least 99%, or 100%, amino acid sequence identity with the amino acid sequence of a PD-L1 polypeptide depicted in FIG. 50A or FIG. 50B.

In some cases, the immunomodulatory polypeptide comprises an amino acid sequence having at least 80%, at least 85%, at least 90%, at least 95%, at least 98%, at least 99%, or 100%, amino acid sequence identity with the amino acid sequence of a CD80 polypeptide depicted in FIG. 51.

In some cases, the immunomodulatory polypeptide comprises an amino acid sequence having at least 80%, at least 85%, at least 90%, at least 95%, at least 98%, at least 99%, or 100%, amino acid sequence identity with the amino acid sequence of an ICOS-L polypeptide depicted in FIG. 51.

In some cases, the immunomodulatory polypeptide comprises an amino acid sequence having at least 80%, at least 85%, at least 90%, at least 95%, at least 98%, at least 99%, or 100%, amino acid sequence identity with the amino acid sequence of an OX40L polypeptide depicted in FIG. 53.

In some cases, the immunomodulatory polypeptide comprises an amino acid sequence having at least 80%, at least 85%, at least 90%, at least 95%, at least 98%, at least 99%, or 100%, amino acid sequence identity with the amino acid sequence of a PD-L2 polypeptide depicted in FIG. 54.

In some cases, the immunomodulatory polypeptide comprises an amino acid sequence having at least 80%, at least 85%, at least 90%, at least 95%, at least 98%, at least 99%, or 100%, amino acid sequence identity with the amino acid sequence of a CD86 polypeptide depicted in FIG. 55.

In some cases, the immunomodulatory polypeptide comprises an amino acid sequence having at least 80%, at least 85%, at least 90%, at least 95%, at least 98%, at least 99%, or 100%, amino acid sequence identity with the amino acid sequence of a FAS-L polypeptide depicted in FIG. 56.

In some cases, the immunomodulatory polypeptide present in a synTac exhibits reduced binding affinity to a cognate co-immunomodulatory polypeptide expressed on the surface of a T cell, compared to the binding affinity of a wild-type immunomodulatory polypeptide for the same cognate co-immunomodulatory polypeptide. In some cases, where a synTac comprises a reduced-affinity immunomodulatory polypeptide, the synTac polypeptide exhibits reduced binding to a cognate co-immunomodulatory polypeptide expressed on the surface of a T cell. For example, in some cases, a synTac polypeptide that comprises a reduced-affinity immunomodulatory polypeptid binds a cognate co-immunomodulatory polypeptide with a binding affinity that is at least 10%, at least 15%, at least 20%, at least 25%, at least 30%, at least 35%, at least 40%, at least 45%, at least 50% less, at least 55% less, at least 60% less, at least 65% less, at least 70% less, at least 75% less, at least 80% less, at least 85% less, at least 90% less, at least 95% less, or more than 95% less, than the binding affinity of a control synTac polypeptide comprising a wild-type immunomodulatory polypeptide for the same cognate co-immunomodulatory polypeptide.

Determining Binding Affinity

Binding affinity between an immunomodulatory polypeptide and its cognate co-immunomodulatory polypeptide can be determined by bio-layer interferometry (BLI) using purified immunomodulatory polypeptide and purified cognate co-immunomodulatory polypeptide. Binding affinity between a synTac of the present disclosure and its cognate co-immunomodulatory polypeptide can also be determined by BLI using purified synTac and the cognate co-immunomodulatory polypeptide. BLI methods are well known to those skilled in the art. See, e.g., Lad et al. (2015) *J. Biomol. Screen.* 20(4):498-507; and Shah and Duncan (2014) *J. Vis. Exp.* 18:e51383. The specific and relative binding affinities described in this disclosure between an immunomodulatory polypeptide and its cognate co-immunomodulatory polypeptide, or between a synTac and its cognate co-immunomodulatory polypeptide, can be determined using the following procedures.

To determine binding affinity between a synTac of the present disclosure and its cognate co-immunomodulatory polypeptide, a BLI assay can be carried out using an Octet RED 96 (Pal FortéBio) instrument, or a similar instrument, as follows. To determine binding affinity of a T-cell modulatory multimeric polypeptide (e.g., a synTac of the present disclosure; or a control T-cell modulatory multimeric polypeptide (where a control T-cell modulatory multimeric polypeptide comprises a wild-type immunomodulatory polypeptide)), the T-cell modulatory multimeric polypeptide is immobilized onto an insoluble support (a "biosensor"). The immobilized T-cell modulatory multimeric polypeptide is the "target" Immobilization can be effected by immobilizing a capture antibody onto the insoluble support, where the capture antibody immobilizes the T-cell modulatory multimeric polypeptide. For example, immobilization can be effected by immobilizing anti-Fc (e.g., anti-human IgG Fc)

antibodies onto the insoluble support, where the immobilized anti-Fc antibodies bind to and immobilize the T-cell modulatory multimeric polypeptide (where the T-cell modulatory multimeric polypeptide comprises an IgFc polypeptide). A co-immunomodulatory polypeptide is applied, at several different concentrations, to the immobilized T-cell modulatory multimeric polypeptide, and the instrument's response recorded. Assays are conducted in a liquid medium comprising 25 mM HEPES pH 6.8, 5% poly(ethylene glycol) 6000, 50 mM KCl, 0.1% bovine serum albumin, and 0.02% Tween 20 nonionic detergent. Binding of the co-immunomodulatory polypeptide to the immobilized T-cell modulatory multimeric polypeptide is conducted at 30° C. As a positive control for binding affinity, an anti-MHC Class I monoclonal antibody can be used. For example, anti-HLA Class I monoclonal antibody W6/32 (American Type Culture Collection No. HB-95; Parham et al. (1979) *J. Immunol.* 123:342), which has a $K_D$ of 7 nM, can be used. A standard curve can be generated using serial dilutions of the anti-MHC Class I monoclonal antibody. The co-immunomodulatory polypeptide, or the anti-MHC Class I mAb, is the "analyte." BLI analyzes the interference pattern of white light reflected from two surfaces: i) from the immobilized polypeptide ("target"); and ii) an internal reference layer. A change in the number of molecules ("analyte"; e.g., co-immunomodulatory polypeptide; anti-HLA antibody) bound to the biosensor tip causes a shift in the interference pattern; this shift in interference pattern can be measured in real time. The two kinetic terms that describe the affinity of the target/analyte interaction are the association constant ($k_a$) and dissociation constant ($k_d$). The ratio of these two terms ($k_{d/a}$) gives rise to the affinity constant $K_D$.

As noted above, determining binding affinity between an immunomodulatory polypeptide (e.g., IL-2 or an IL-2 variant) and its cognate co-immunomodulatory polypeptide (e.g., IL-2R) also can be determined by BLI. The assay is similar to that described above for the synTac multimeric polypeptide. A BLI assay can be carried out using an Octet RED 96 (Pal FortéBio) instrument, or a similar instrument, as follows. A component immunomodulatory polypeptide of a synTac of the present disclosure (e.g., a variant IL-2 polypeptide of the present disclosure); and a control immunomodulatory polypeptide (where a control immunomodulatory polypeptide comprises a wild-type immunomodulatory polypeptide, e.g. wild-type IL-2)) are immobilized onto an insoluble support (a "biosensor"). The immunomodulatory polypeptide is the "target" Immobilization can be effected by immobilizing a capture antibody onto the insoluble support, where the capture antibody immobilizes the immunomodulatory polypeptide. For example, if the target is fused to an immuno-affinity tag (e.g. FLAG, human IgG Fc) immobilization can be effected by immobilizing with the appropriate antibody to the immuno-affinity tag (e.g. anti-human IgG Fc) onto the insoluble support, where the immobilized antibodies bind to and immobilize the immunomodulatory polypeptide (where the immunomodulatory polypeptide comprises an IgFc polypeptide). A co-immunomodulatory polypeptide (or polypeptides) is applied, at several different concentrations, to the immobilized immunomodulatory polypeptide, and the instrument's response recorded. Alternatively, a co-immunomodulatory polypeptide (or polypeptides) is immobilized to the biosensor (e.g., for the IL-2 receptor heterotrimer, as a monomeric subunit, heterodimeric subcomplex, or the complete heterotrimer) and the immunomodulatory polypeptide is applied, at several different concentrations, to the immobilized coimmunomodulatory polypeptide(s), and the instrument's response is recorded. Assays are conducted in a liquid medium comprising 25 mM HEPES pH 6.8, 5% poly(ethylene glycol) 6000, 50 mM KCl, 0.1% bovine serum albumin, and 0.02% Tween 20 nonionic detergent. Binding of the co-immunomodulatory polypeptide to the immobilized immunomodulatory polypeptide is conducted at 30° C. As a positive control for binding affinity, an anti-MHC Class I monoclonal antibody can be used. For example, anti-HLA Class I monoclonal antibody W6/32 (American Type Culture Collection No. HB-95; Parham et al. (1979) *J. Immunol.* 123:342), which has a $K_D$ of 7 nM, can be used. A standard curve can be generated using serial dilutions of the anti-MHC Class I monoclonal antibody. The co-immunomodulatory polypeptide, or the anti-MHC Class I mAb, is the "analyte." BLI analyzes the interference pattern of white light reflected from two surfaces: i) from the immobilized polypeptide ("target"); and ii) an internal reference layer. A change in the number of molecules ("analyte"; e.g., co-immunomodulatory polypeptide; anti-HLA antibody) bound to the biosensor tip causes a shift in the interference pattern; this shift in interference pattern can be measured in real time. The two kinetic terms that describe the affinity of the target/analyte interaction are the association constant ($k_a$) and dissociation constant ($k_d$). The ratio of these two terms ($k_{d/a}$) gives rise to the affinity constant $K_D$. Determining the binding affinity of both a wild-type immunomodulatory polypeptide (e.g., IL-2) for its receptor (e.g., IL-2R) and a variant immunomodulatory polypeptide (e.g., an IL-2 variant as disclosed herein) for its cognate co-immunomodulatory polypeptide (e.g., its receptor) (e.g., IL-2R) thus allows one to determine the relative binding affinity of the variant co-immunomodulatory polypeptide, as compared to the wild-type co-immunomodulatory polypeptide, for the cognate co-immunomodulatory polypeptide. That is, one can determine whether the binding affinity of a variant immunomodulatory polypeptide for its receptor (its cognate co-immunomodulatory polypeptide) is reduced as compared to the binding affinity of the wild-type immunomodulatory polypeptide for the same cognate co-immunomodulatory polypeptide, and, if so, what is the percentage reduction from the binding affinity of the wild-type co-immunomodulatory polypeptide.

The BLI assay is carried out in a multi-well plate. To run the assay, the plate layout is defined, the assay steps are defined, and biosensors are assigned in Octet Data Acquisition software. The biosensor assembly is hydrated. The hydrated biosensor assembly and the assay plate are equilibrated for 10 minutes on the Octet instrument. Once the data are acquired, the acquired data are loaded into the Octet Data Analysis software. The data are processed in the Processing window by specifying method for reference subtraction, y-axis alignment, inter-step correction, and Savitzky-Golay filtering. Data are analyzed in the Analysis window by specifying steps to analyze (Association and Dissociation), selecting curve fit model (1:1), fitting method (global), and window of interest (in seconds). The quality of fit is evaluated. $K_D$ values for each data trace (analyte concentration) can be averaged if within a 3-fold range. $K_D$ error values should be within one order of magnitude of the affinity constant values; $R^2$ values should be above 0.95. See, e.g., Abdiche et al. (2008) *J. Anal. Biochem.* 377:209.

In some cases, the ratio of: i) the binding affinity of a control T-cell modulatory multimeric polypeptide (where the control comprises a wild-type immunomodulatory polypeptide, e.g., wild-type IL-2) to a cognate co-immunomodulatory polypeptide (e.g., IL-2R) to ii) the binding affinity of a T-cell modulatory multimeric polypeptide of the present disclosure comprising a variant of the wild-type immunomodulatory polypeptide (e.g., variant IL-2) to the cognate co-immunomodulatory polypeptide (e.g., IL-2R), when measured by BLI (as described above), is at least 1.5:1, at least 2:1, at least 5:1, at least 10:1, at least 15:1, at least 20:1, at least 25:1, at least 50:1, at least 100:1, at least 500:1, at least $10^2$:1, at least $5\times10^2$:1, at least $10^3$:1, at least $5\times10^3$:1, at least $10^4$:1, at least $10^5$:1, or at least $10^6$:1. In some cases, the ratio of: i) the binding affinity of a control T-cell modulatory multimeric polypeptide (where the control comprises a wild-type immunomodulatory polypeptide) to a cognate co-immunomodulatory polypeptide to ii) the binding affinity of a T-cell modulatory multimeric polypeptide of the present disclosure comprising a variant of the wild-type immunomodulatory polypeptide to the cognate co-immunomodulatory polypeptide, when measured by BLI, is in a range of from 1.5:1 to $10^6$:1, e.g., from 1.5:1 to 10:1, from 10:1 to 50:1, from 50:1 to $10^2$:1, from $10^2$:1 to $10^3$:1, from $10^3$:1 to $10^4$:1, from $10^4$:1 to $10^5$:1, or from $10^5$:1 to $10^6$:1.

In some cases, the ratio of: i) the binding affinity of a control immunomodulatory polypeptide (where the control comprises a wild-type immunomodulatory polypeptide, e.g., wild-type IL-2) to a cognate co-immunomodulatory polypeptide (e.g., IL-2R) to ii) the binding affinity of a immunomodulatory polypeptide of the present disclosure comprising a variant of the wild-type immunomodulatory polypeptide (e.g., variant IL-2) to the cognate co-immunomodulatory polypeptide (e.g., IL-2R), when measured by BLI (as described above), is at least 1.5:1, at least 2:1, at least 5:1, at least 10:1, at least 15:1, at least 20:1, at least 25:1, at least 50:1, at least 100:1, at least 500:1, at least $10^2$:1, at least $5\times10^2$:1, at least $10^3$:1, at least $5\times10^3$:1, at least $10^4$:1, at least $10^5$:1, or at least $10^6$:1. In some cases, the ratio of: i) the binding affinity of a control immunomodulatory polypeptide (where the control comprises a wild-type immunomodulatory polypeptide) to a cognate co-immunomodulatory polypeptide to ii) the binding affinity of a immunomodulatory polypeptide of the present disclosure comprising a variant of the wild-type immunomodulatory polypeptide to the cognate co-immunomodulatory polypeptide, when measured by BLI, is in a range of from 1.5:1 to $10^6$:1, e.g., from 1.5:1 to 10:1, from 10:1 to 50:1, from 50:1 to $10^2$:1, from $10^2$:1 to $10^3$:1, from $10^3$:1 to $10^4$:1, from $10^4$:1 to $10^5$:1, or from $10^5$:1 to $10^6$:1.

IL-2/synTac

In some cases, a multimeric polypeptide comprises a wild-type (naturally-occuring) IL-2 as the modulatory domain. In some cases, a multimeric polypeptide comprises a variant IL-2 polypeptide as the modulatory domain.

A T-cell modulatory multimeric polypeptide that comprises an IL-2 polypeptide as the modulatory ("MOD") domain is also referred to as an "IL-2/synTac," "an IL-2/synTac polypeptide" or an "IL-2/multimeric polypeptide."

In some cases, an IL-2/synTac polypeptide comprises a wild-type IL-2 polypeptide. In some cases, a synTac polypeptide comprises a single copy of a wild-type IL-2 polypeptide. In some cases, a synTac polypeptide comprises two copies of a wild-type IL-2 polypeptide. In some cases, a synTac polypeptide comprises three copies of a wild-type IL-2 polypeptide. In some cases, the wild-type IL-2 polypeptide comprises an amino acid sequence having at least 90%, at least 95%, at least 98%, or at least 99%, amino acid sequence identity to the amino acid sequence depicted in FIG. 2A. A wild-type amino acid sequence of a human IL2 polypeptide can be as follows: APTSSSTKKT QLQL EHLLLD LQMILNGINN YKNPKLTRML TFKF YMPKKA TELKHLQCLEEELKPLEEVL NLAQSKNFHL RPRDLISNIN VIVLELKGSE TTFMCEYADE TATIVEFLNRWITFCQSIIS TLT (SEQ ID NO:1).

In some cases, a synTac polypeptide comprises a variant IL-2 polypeptide. A variant IL-2 polypeptide present in a multimeric polypeptide exhibits reduced binding affinity to an IL2R, compared to the binding affinity of wild-type IL-2 to the IL2R. A multimeric polypeptide that comprises a variant IL-2 polypeptide also exhibits reduced binding affinity for an IL2R, compared to a control multimeric polypeptide comprising a wild-type IL-2 for IL2R (e.g., an IL2R comprising alpha, beta, and gamma polypeptides comprising the amino acid sequences (mature form) depicted in FIG. 3A-3C).

In some cases, an IL-2/synTac polypeptide exhibits reduced binding affinity to IL2R, compared to the binding affinity of an IL2 polypeptide comprising the amino acid sequence depicted in FIG. 2A for IL2R. For example, in some cases, an IL-2/synTac polypeptide binds IL2R with a binding affinity that is less than the binding affinity of a control synTac polypeptide comprising an IL2 polypeptide comprising the amino acid sequence depicted in FIG. 2A for an IL2R comprising alpha, beta, and gamma polypeptides comprising the amino acid sequences (mature form) depicted in FIG. 3A-3C. For example, in some cases, an IL-2/synTac polypeptide binds IL2R with a binding affinity that is at least 10%, at least 15%, at least 20%, at least 25%, at least 30%, at least 35%, at least 40%, at least 45%, at least 50% less, at least 55% less, at least 60% less, at least 65% less, at least 70% less, at least 75% less, at least 80% less, at least 85% less, at least 90% less, at least 95% less, or more than 95% less, than the binding affinity of a control synTac polypeptide comprising an IL-2 polypeptide comprising the amino acid sequence depicted in FIG. 2A for IL2R (e.g., an IL2R comprising alpha, beta, and gamma polypeptides comprising the amino acid sequences (mature form) depicted in FIG. 3A-3C).

In some cases, an IL-2/synTac polypeptide has a binding affinity for IL2R that is from 100 nm to about 100 μM. In some cases, an IL-2/synTac polypeptide has a binding affinity for IL2R that is from about 100 nM to 500 nM. For example, in some cases, an IL-2/synTac polypeptide has a binding affinity for IL2R (e.g., an IL2R comprising alpha, beta, and gamma polypeptides comprising the amino acid sequences (mature form) depicted in FIG. 3A-3C) that is from about 100 nM to about 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 450 nM, or from about 450 nM to about 500 nM. In some cases, an IL-2/synTac polypeptide has a binding affinity for IL2R (e.g., an IL2R comprising alpha, beta, and gamma polypeptides comprising the amino acid sequences (mature form) depicted in FIG. 3A-3C) that is from about 500 nM to 1 μM. For example, in some cases, an IL-2/synTac polypeptide has a binding affinity for IL2R (e.g., an IL2R comprising alpha, beta, and gamma polypeptides comprising the amino acid sequences (mature form) depicted in FIG. 3A-3C) that is from about 500 nM to about 600 nM, from about 600 nM to about 700 nM, from about 700 nM to about 800 nM, from about 800 nM to about 900 nM, or from about 900 nM to about 1 μM. In some cases, an IL-2/synTac polypeptide has a binding affinity for IL2R (e.g., an IL2R comprising alpha, beta, and gamma polypeptides comprising the amino acid sequences (mature form) depicted in FIG. 3A-3C) that is from about 1 μM to 10 μM. For example, in some cases, an IL-2/synTac polypeptide has a binding affinity for IL2R (e.g., an IL2R comprising alpha, beta, and gamma polypeptides comprising the amino acid sequences (mature form) depicted in FIG. 3A-3C) that is from about 1 μM to 2 μM, from about 2 μM to about 3 μM, from about 3 μM to about 4 μM, from about 4 μM to about 5 μM, from about 5 μM to about 6 μM, from about 6 μM to about 7 μM, from about 7 μM to about 8 μM, from about 8 μM to about 9 μM, or from about 9 μM to about 10 μM. In some cases, an IL-2/synTac polypeptide has a binding affinity for IL2R (e.g., an IL2R comprising alpha, beta, and gamma polypeptides comprising the amino acid sequences (mature form) depicted in FIG. 3A-3C) that is from about 10 μM to 100 μM. For example, in some cases, an IL-2/synTac polypeptide has a binding affinity for IL2R (e.g., an IL2R comprising alpha, beta, and gamma polypeptides comprising the amino acid sequences (mature form) depicted in FIG. 3A-3C) that is from about 10 μM to about 20 μM, from about 20 μM to about 30 μM, from about 30 μM to about 40 μM, from about 40 μM to about 50 μM, from about 50 μM to about 60 μM, from about 60 μM to about 70 μM, from about 70 μM to about 80 μM, from about 80 μM to about 90 μM, or from about 90 μM to about 100 μM.

A variant IL2 polypeptide present in an IL-2/synTac polypeptide can have a single amino acid substitution relative to a wild-type IL2 polypeptide (e.g., a IL2 polypeptide comprising the amino acid sequence depicted in FIG. 2A or as set forth in SEQ ID NO:1). In some cases, a variant IL2 polypeptide present in an IL-2/synTac polypeptide has from 2 to 10 amino acid substitutions relative to a wild-type IL2 polypeptide (e.g., a IL2 polypeptide comprising the amino acid sequence depicted in FIG. 2A or as set forth in SEQ ID NO:1). In some cases, a variant IL2 polypeptide present in a synTac polypeptide of the present disclosure has 2 amino acid substitutions relative to a wild-type IL2 polypeptide (e.g., a IL2 polypeptide comprising the amino acid sequence depicted in FIG. 2A or as set forth in SEQ ID NO:1). In some cases, a variant IL2 polypeptide present in a synTac polypeptide of the present disclosure has 3 amino acid substitutions relative to a wild-type IL2 polypeptide (e.g., a IL2 polypeptide comprising the amino acid sequence depicted in FIG. 2A or as set forth in SEQ ID NO:1). In some cases, a variant IL2 polypeptide present in a synTac polypeptide of the present disclosure has 4 amino acid substitutions relative to a wild-type IL2 polypeptide (e.g., a IL2 polypeptide comprising the amino acid sequence depicted in FIG. 2A or as set forth in SEQ ID NO:1). In some cases, a variant IL2 polypeptide present in a synTac polypeptide of the present disclosure has 5 amino acid substitutions relative to a wild-type IL2 polypeptide (e.g., a IL2 polypeptide comprising the amino acid sequence depicted in FIG. 2A or as set forth in SEQ ID NO:1). In some cases, a variant IL2 polypeptide present in a synTac polypeptide of the present disclosure has 6 amino acid substitutions relative to a wild-type IL2 polypeptide (e.g., a IL2 polypeptide comprising the amino acid sequence depicted in FIG. 2A or as set forth in SEQ ID NO:1). In some cases, a variant IL2 polypeptide present in a synTac polypeptide of the present disclosure has 7 amino acid substitutions relative to a wild-type IL2 polypeptide (e.g., a IL2 polypeptide comprising the amino acid sequence depicted in FIG. 2A or as set forth in SEQ ID NO:1). In some cases, a variant IL2 polypeptide present in a synTac polypeptide of the present disclosure has 8 amino acid substitutions relative to a wild-type IL2 polypeptide (e.g., a IL2 polypeptide comprising the amino acid sequence depicted in FIG. 2A or as set forth in SEQ ID NO:1). In some cases, a variant IL2 polypeptide present in a synTac polypeptide of the present disclosure has 9 amino acid substitutions relative to a wild-type IL2 polypeptide (e.g., a IL2 polypeptide comprising the amino acid sequence depicted in FIG. 2A or as set forth in SEQ ID NO:1). In some cases, a variant IL2 polypeptide present in a synTac polypeptide of the present disclosure has 10 amino acid substitutions relative to a wild-type IL2 polypeptide (e.g., a IL2 polypeptide comprising the amino acid sequence depicted in FIG. 2A or as set forth in SEQ ID NO:1).

In some cases, a multimeric polypeptide of the present disclosure comprises a first polypeptide and a second polypeptide, where the first polypeptide comprises, in order from amino terminus (N-terminus) to carboxyl terminus (C-terminus): a) an epitope (e.g., a T-cell epitope); b) a first major histocompatibility complex (MHC) polypeptide and c) an immunomodulatory polypeptide (e.g., a variant IL2 polypeptide of the present disclosure); and where the second polypeptide comprises, in order from N-terminus to C-terminus: a) a second MHC polypeptide; and b) an immunoglobulin (Ig) Fc polypeptide. In other cases, a multimeric polypeptide of the present disclosure comprises a first polypeptide and a second polypeptide, where the first polypeptide comprises, in order from N-terminus to C-terminus: a) an epitope (e.g., a T-cell epitope); and b) a first MHC polypeptide; and where the second polypeptide comprises, in order from N-terminus to C-terminus: a) an immunomodulatory polypeptide (e.g., a variant IL2 polypeptide of the present disclosure); b) a second MHC polypeptide; and c) an Ig Fc polypeptide. In some instances, the first and the second MHC polypeptides are Class I MHC polypeptides; e.g., in some cases, the first MHC polypeptide is an MHC Class I β2-microglobulin (B2M or β2M) polypeptide, and the second MHC polypeptide is an MHC Class I heavy chain (H chain); or the first MHC polypeptide is an MHC Class I H chain, and the second MHC polypeptide is an MHC Class I β2M polypeptide). In other cases, the first and the second MHC polypeptides are Class II MHC polypeptides; e.g., in some cases, the first MHC polypeptide is an MHC Class II α-chain polypeptide, and the second MHC polypeptide is an MHC Class II β-chain polypeptide. In other cases, the first polypeptide is an MHC Class II β-chain polypeptide, and the second MHC polypeptide is an MHC Class II α-chain polypeptide. In some cases, the multimeric polypeptide includes two or more immunomodulatory polypeptides, where at least one of the immunomodulatory polypeptides is a variant IL2 immunomodulatory polypeptide of the present disclosure. Where a multimeric polypeptide of the present disclosure includes two or more immunomodulatory polypeptides, in some cases, the two or more immunomodulatory polypeptides are present in the same polypeptide chain, and may be in tandem. Where a multimeric polypeptide of the present disclosure includes two or more immunomodulatory polypeptides, in some cases, the two or more immunomodulatory polypeptides are present in separate polypeptides. In some cases, a multimeric polypeptide of the present disclosure is a heterodimer. In some cases, a multimeric polypeptide of the present disclosure is a trimeric polypeptide.

In some cases, a multimeric polypeptide comprises: a) a first polypeptide comprising, in order from N-terminus to C-terminus: i) an epitope; and ii) a first MHC polypeptide; and b) a second polypeptide comprising, in order from N-terminus to C-terminus: i) a second MHC polypeptide; and ii) an Ig Fc polypeptide; and iii) an immunomodulatory domain (e.g., a variant IL2 polypeptide of the present disclosure). In some cases, a multimeric polypeptide of the present disclosure comprises: a) a first polypeptide comprising, in order from N-terminus to C-terminus: i) an epitope; and ii) a first MHC polypeptide; and b) a second polypeptide comprising, in order from N-terminus to C-terminus: i) a second MHC polypeptide; and ii) an immunomodulatory domain (e.g., a variant IL2 polypeptide of the present disclosure). In some cases, a multimeric polypeptide of the present disclosure comprises: a) a first polypeptide comprising, in order from N-terminus to C-terminus: i) an epitope; and ii) a first MHC polypeptide; and b) a second polypeptide comprising, in order from N-terminus to C-terminus: i) an immunomodulatory domain (e.g., a variant IL2 polypeptide of the present disclosure); and ii) a second MHC polypeptide. In some cases, a multimeric polypeptide of the present disclosure comprises: a) a first polypeptide comprising, in order from N-terminus to C-terminus: i) an epitope; ii) a first MHC polypeptide; and iii) an immunomodulatory domain (e.g., a variant IL2 polypeptide of the present disclosure); and b) a second polypeptide comprising, in order from N-terminus to C-terminus: i) a second MHC polypeptide. In some cases, where a multimeric polypeptide of the present disclosure comprises a non-Ig scaffold, the non-Ig scaffold is an XTEN peptide, a transferrin polypeptide, an Fc receptor polypeptide, an elastin-like polypeptide, a silk-like polypeptide, or a silk-elastin-like polypeptide.

In some cases, a multimeric polypeptide of the present disclosure is monovalent. In some cases, a multimeric polypeptide of the present disclosure is multivalent. In some cases, a multivalent multimeric polypeptide of the present disclosure comprises an immunoglobulin Fc polypeptide on one of the first or the second polypeptide. For example, depending on the Fc polypeptide present in a multimeric polypeptide of the present disclosure, the multimeric polypeptide can be a homodimer, where two molecules of the multimeric polypeptide are present in the homodimer, where the two molecules of the multimeric polypeptide can be disulfide linked to one another, e.g., via the Fc polypeptide present in the two molecules. As another example, a multimeric polypeptide of the present disclosure can comprise three, four, or five molecules of the multimeric polypeptide, where the molecules of the multimeric polypeptide can be disulfide linked to one another, e.g., via the Fc polypeptide present in the molecules.

In some cases, a multimeric polypeptide comprises: a) a first polypeptide comprising, in order from N-terminus to C-terminus: i) an epitope; ii) a β2M polypeptide; and iii) a variant IL2 polypeptide of the present disclosure; and b) a second polypeptide comprising, in order from N-terminus to C-terminus: i) a Class I MHC heavy chain; and ii) an Fc polypeptide. In some cases, a multimeric polypeptide of the present disclosure comprises: a) a first polypeptide comprising, in order from N-terminus to C-terminus: i) an epitope; and ii) a β2M polypeptide; and b) a second polypeptide comprising, in order from N-terminus to C-terminus: i) a variant IL2 polypeptide of the present disclosure; ii) a Class I MHC heavy chain; and iii) an Fc polypeptide. In some cases, a multimeric polypeptide of the present disclosure comprises: a) a first polypeptide comprising, in order from N-terminus to C-terminus: i) an epitope; ii) a β2M polypeptide; iii) a first variant IL2 polypeptide of the present disclosure; iv) a second variant IL2 polypeptide of the present disclosure; and v) a third variant IL2 polypeptide of the present disclosure; and b) a second polypeptide comprising, in order from N-terminus to C-terminus: i) a Class I MHC heavy chain; and ii) an Fc polypeptide. In some cases, the first, second, and third variant IL2 polypeptides have the same amino acid sequence. In some cases, the first, second, and third variant IL2 polypeptides differ from one another in amino acid sequence. In some cases, a multimeric polypeptide of the present disclosure comprises: a) a first polypeptide comprising, in order from N-terminus to C-terminus: i) an epitope; and ii) a β2M polypeptide; and b) a second polypeptide comprising, in order from N-terminus to C-terminus: i) a first variant IL2 polypeptide of the present disclosure; ii) a second variant IL2 polypeptide of the present disclosure; and iii) a third variant IL2 polypeptide of the present disclosure; iv) a Class I MHC heavy chain; and v) an Fc polypeptide. In some cases, the first, second, and third variant IL2 polypeptides have the same amino acid sequence. In some cases, the first, second, and third variant IL2 polypeptides differ from one another in amino acid sequence.

F42 Substitution

In some cases, a variant IL-2 polypeptide present in a multimeric polypeptide comprises an amino acid sequence having at least 90%, at least 95%, at least 98%, or at least 99%, amino acid sequence identity to the amino acid sequence depicted in FIG. 2B, where amino acid 42 is an amino acid other than a phenylalanine, e.g., where amino acid 42 is Gly, Ala, Val, Leu, Ile, Pro, Tyr, Trp, Ser, Thr, Cys, Met, Asn, Gln, Lys, Arg, His, Asp, or Glu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2B, where amino acid 42 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2B, where amino acid 42 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2B, where amino acid 42 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2B, where amino acid 42 is Val. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2B, where amino acid 42 is Leu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2B, where amino acid 42 is Ile. In some cases, a single copy of the variant IL-2 polypeptide is present in a multimeric polypeptide of the present disclosure. In some cases, a multimeric polypeptide of the present disclosure comprises two copies of the variant IL-2 polypeptide, e.g., where the two copies are in tandem with no linker between the two copies, or are in tandem and separated by a linker peptide. In some cases, a multimeric polypeptide of the present disclosure comprises three copies of the variant IL-2 polypeptide, e.g., where the three copies are in tandem with no linker between the three copies, or are in tandem and separated by a linker peptide. In some cases, where an IL-2/synTac of the present disclosure comprises HLA Class I heavy chain and β2M, the IL-2 polypeptide(s) is/are on the polypeptide chain comprising the HLA Class I heavy chain. In some cases, where an IL-2/synTac of the present disclosure comprises HLA Class I heavy chain and β2M, the IL-2 polypeptide(s) is/are on the polypeptide chain comprising the β2M polypeptide. In some cases, the variant IL-2 polypeptide, or the synTac comprising same, has a binding affinity for IL2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant IL-2 polypeptide present in a multimeric polypeptide of the present disclosure has a length of 133 amino acids.

Y45 Substitution

In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2F, where amino acid 45 is an amino acid other than a tyrosine, e.g., where amino acid 45 is Gly, Ala, Val, Leu, Ile, Pro, Phe, Trp, Ser, Thr, Cys, Met, Asn, Gln, Lys, Arg, His, Asp, or Glu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2F, where amino acid 45 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2F, where amino acid 45 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2F, where amino acid 45 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2F, where amino acid 45 is Val. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2F, where amino acid 45 is Leu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2F, where amino acid 45 is Ile. In some cases, a single copy of the variant IL-2 polypeptide is present in a multimeric polypeptide of the present disclosure. In some cases, a multimeric polypeptide of the present disclosure comprises two copies of the variant IL-2 polypeptide, e.g., where the two copies are in tandem with no linker between the two copies, or are in tandem and separated by a linker peptide. In some cases, a multimeric polypeptide of the present disclosure comprises three copies of the variant IL-2 polypeptide, e.g., where the three copies are in tandem with no linker between the three copies, or are in tandem and separated by a linker peptide. In some cases, where an IL-2/synTac of the present disclosure comprises HLA Class I heavy chain and β2M, the IL-2 polypeptide(s) is/are on the polypeptide chain comprising the HLA Class I heavy chain. In some cases, where an IL-2/synTac of the present disclosure comprises HLA Class I heavy chain and β2M, the IL-2 polypeptide(s) is/are on the polypeptide chain comprising the β2M polypeptide. In some cases, the variant IL-2 polypeptide, or the synTac comprising same, has a binding affinity for IL2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant IL-2 polypeptide present in a multimeric polypeptide of the present disclosure has a length of 133 amino acids.

Q126 Substitution

In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2G, where amino acid 126 is an amino acid other than a glutamine, e.g., where amino acid 126 is Gly, Ala, Val, Leu, Ile, Pro, Phe, Tyr, Trp, Ser, Thr, Cys, Met, Asn, Lys, Arg, His, Asp, or Glu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2G, where amino acid 126 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2G, where amino acid 126 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2G, where amino acid 126 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2G, where amino acid 126 is Val. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2G, where amino acid 126 is Leu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2G, where amino acid 126 is Ile. In some cases, a single copy of the variant IL-2 polypeptide is present in a multimeric polypeptide of the present disclosure. In some cases, a multimeric polypeptide of the present disclosure comprises two copies of the variant IL-2 polypeptide, e.g., where the two copies are in tandem with no linker between the two copies, or are in tandem and separated by a linker peptide. In some cases, a multimeric polypeptide of the present disclosure comprises three copies of the variant IL-2 polypeptide, e.g., where the three copies are in tandem with no linker between the three copies, or are in tandem and separated by a linker peptide. In some cases, where an IL-2/synTac of the present disclosure comprises HLA Class I heavy chain and β2M, the IL-2 polypeptide(s) is/are on the polypeptide chain comprising the HLA Class I heavy chain. In some cases, where an IL-2/synTac of the present disclosure comprises HLA Class I heavy chain and β2M, the IL-2 polypeptide(s) is/are on the polypeptide chain comprising the β2M polypeptide. In some cases, the variant IL-2 polypeptide, or a synTac comprising same, has a binding affinity for IL2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant IL-2 polypeptide present in a multimeric polypeptide of the present disclosure has a length of 133 amino acids.

F42 and H16 Substitutions

In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2H, where amino acid 42 is an amino acid other than a phenylalanine, e.g., where amino acid 42 is Gly, Ala, Val, Leu, Ile, Pro, Tyr, Trp, Ser, Thr, Cys, Met, Asn, Gln, Lys, Arg, His, Asp, or Glu; and where amino acid 16 is an amino acid other than a histidine, e.g., where amino acid 16 is Gly, Ala, Val, Leu, Ile, Pro, Phe, Tyr, Trp, Ser, Thr, Cys, Met, Asn, Gln, Lys, Arg, Asp, or Glu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2H, where amino acid 42 is Ala, Gly, Val, Leu, or Ile; and where amino acid 16 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2H, where amino acid 42 is Ala and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2H, where amino acid 42 is Ala and amino acid 16 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2H, where amino acid 42 is Val and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2H, where amino acid 42 is Leu, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2H, where amino acid 42 is Ile and amino acid 16 is Ala. In some cases, a single copy of the variant IL-2 polypeptide is present in a multimeric polypeptide of the present disclosure. In some cases, a multimeric polypeptide of the present disclosure comprises two copies of the variant IL-2 polypeptide, e.g., where the two copies are in tandem with no linker between the two copies, or are in tandem and separated by a linker peptide. In some cases, a multimeric polypeptide of the present disclosure comprises three copies of the variant IL-2 polypeptide, e.g., where the three copies are in tandem with no linker between the three copies, or are in tandem and separated by a linker peptide. In some cases, where an IL-2/synTac of the present disclosure comprises HLA Class I heavy chain and β2M, the IL-2 polypeptide(s) is/are on the polypeptide chain comprising the HLA Class I heavy chain. In some cases, where an IL-2/synTac of the present disclosure comprises HLA Class I heavy chain and β2M, the IL-2 polypeptide(s) is/are on the polypeptide chain comprising the β2M polypeptide. In some cases, a multimeric polypeptide of the present disclosure comprises 2 copies of the IL-2 variant comprising F42A and H16A substitutions, where the multimeric polypeptide comprises HLA Class I heavy chain and β2M polypeptides, and where the 2 copies of IL-2 (F42A, H16A) are on the polypeptide chain comprising the HLA Class I heavy chain. In some cases, the variant IL-2 polypeptide, or a synTac comprising same, has a binding affinity for IL2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant IL-2 polypeptide present in a multimeric polypeptide of the present disclosure has a length of 133 amino acids. In some cases, the variant IL-2 polypeptide comprises the amino acid sequence depicted in FIG. 34B (comprising H16A and F42A substitutions).

F42 and D20 Substitutions

In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 42 is an amino acid other than a phenylalanine, e.g., where amino acid 42 is Gly, Ala, Val, Leu, Ile, Pro, Tyr, Trp, Ser, Thr, Cys, Met, Asn, Gln, Lys, Arg, His, Asp, or Glu; and where amino acid 20 is an amino acid other than an aspartic acid, e.g., where amino acid 20 is Gly, Ala, Val, Leu, Ile, Pro, Phe, Tyr, Trp, Ser, Thr, Cys, Met, Asn, Gln, Lys, Arg, His, or Glu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ala, Gly, Val, Leu, or Ile; and where amino acid 20 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ala, Gly, Val, Leu, or Ile; and where amino acid 20 is Asn, Gln, Lys, Arg, or His. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ala and amino acid 20 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ala and amino acid 20 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 42 is Val and amino acid 20 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 42 is Leu, and amino acid 20 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ile and amino acid 20 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ala and amino acid 20 is Asn. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ala and amino acid 20 is Gln. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ala and amino acid 20 is Lys. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ala and amino acid 20 is Arg. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ala and amino acid 20 is His. In some cases, a single copy of the variant IL-2 polypeptide is present in a multimeric polypeptide of the present disclosure. In some cases, a multimeric polypeptide of the present disclosure comprises two copies of the variant IL-2 polypeptide, e.g., where the two copies are in tandem with no linker between the two copies, or are in tandem and separated by a linker peptide. In some cases, a multimeric polypeptide of the present disclosure comprises three copies of the variant IL-2 polypeptide, e.g., where the three copies are in tandem with no linker between the three copies, or are in tandem and separated by a linker peptide. In some cases, where an IL-2/synTac of the present disclosure comprises HLA Class I heavy chain and β2M, the IL-2 polypeptide(s) is/are on the polypeptide chain comprising the HLA Class I heavy chain. In some cases, where an IL-2/synTac of the present disclosure comprises HLA Class I heavy chain and β2M, the IL-2 polypeptide(s) is/are on the polypeptide chain comprising the β2M polypeptide. In some cases, the variant IL-2 polypeptide, or a synTac comprising same, has a binding affinity for IL2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant IL-2 polypeptide present in a multimeric polypeptide of the present disclosure has a length of 133 amino acids.

F42, D20, and E15 Substitutions

In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2J, where amino acid 42 is an amino acid other than a phenylalanine, e.g., where amino acid 42 is Gly, Ala, Val, Leu, Ile, Pro, Tyr, Trp, Ser, Thr, Cys, Met, Asn, Gln, Lys, Arg, His, Asp, or Glu; where amino acid 20 is an amino acid other than an aspartic acid, e.g., where amino acid 20 is Gly, Ala, Val, Leu, Ile, Pro, Phe, Tyr, Trp, Ser, Thr, Cys, Met, Asn, Gln, Lys, Arg, His, or Glu; and where amino acid 15 is an amino acid other than a glutamic acid, e.g., where amino acid 15 is Gly, Ala, Val, Leu, Ile, Pro, Phe, Tyr, Trp, Ser, Thr, Cys, Met, Asn, Gln, Lys, Arg, His, or Asp. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2J, where amino acid 42 is Ala, Gly, Val, Leu, or Ile; where amino acid 20 is Ala, Gly, Val, Leu, or Ile; and where amino acid 15 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2J, where amino acid 42 is Ala, Gly, Val, Leu, or Ile; where amino acid 20 is Asn, Gln, Lys, Arg, or His; and where amino acid 15 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2J, where amino acid 42 is Ala, amino acid 20 is Ala, and amino acid 15 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2J, where amino acid 42 is Ala, amino acid 20 is Gly, and amino acid 15 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2J, where amino acid 42 is Val, amino acid 20 is Ala, and amino acid 15 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2J, where amino acid 42 is Leu, amino acid 20 is Ala, and amino acid 15 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2J, where amino acid 42 is Ile, amino acid 20 is Ala, and amino acid 15 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2J, where amino acid 42 is Ala, amino acid 20 is Asn, and amino acid 15 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ala, amino acid 20 is Gln, and amino acid 15 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2J, where amino acid 42 is Ala, amino acid 20 is Lys, and amino acid 15 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2J, where amino acid 42 is Ala, amino acid 20 is Arg, and amino acid 15 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ala, amino acid 20 is His, and amino acid 15 is Ala. In some cases, a single copy of the variant IL-2 polypeptide is present in a multimeric polypeptide of the present disclosure. In some cases, a multimeric polypeptide of the present disclosure comprises two copies of the variant IL-2 polypeptide, e.g., where the two copies are in tandem with no linker between the two copies, or are in tandem and separated by a linker peptide. In some cases, where an IL-2/synTac of the present disclosure comprises HLA Class I heavy chain and β2M, the IL-2 polypeptide(s) is/are on the polypeptide chain comprising the HLA Class I heavy chain. In some cases, where an IL-2/synTac of the present disclosure comprises HLA Class I heavy chain and β2M, the IL-2 polypeptide(s) is/are on the polypeptide chain comprising the β2M polypeptide. In some cases, a multimeric polypeptide of the present disclosure comprises three copies of the variant IL-2 polypeptide, e.g., where the three copies are in tandem with no linker between the three copies, or are in tandem and separated by a linker peptide. In some cases, the variant IL-2 polypeptide, or a synTac comprising same, has a binding affinity for IL2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant IL-2 polypeptide present in a multimeric polypeptide of the present disclosure has a length of 133 amino acids.

F42, D20, and H16 Substitutions

In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 42 is an amino acid other than a phenylalanine, e.g., where amino acid 42 is Gly, Ala, Val, Leu, Ile, Pro, Tyr, Trp, Ser, Thr, Cys, Met, Asn, Gln, Lys, Arg, His, Asp, or Glu; where amino acid 20 is an amino acid other than an aspartic acid, e.g., where amino acid 20 is Gly, Ala, Val, Leu, Ile, Pro, Phe, Tyr, Trp, Ser, Thr, Cys, Met, Asn, Gln, Lys, Arg, His, or Glu; and where amino acid 16 is an amino acid other than a histidine, e.g., where amino acid 16 is Gly, Ala, Val, Leu, Ile, Pro, Phe, Tyr, Trp, Ser, Thr, Cys, Met, Asn, Gln, Lys, Arg, Asp, or Glu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 42 is Ala, Gly, Val, Leu, or Ile; where amino acid 20 is Ala, Gly, Val, Leu, or Ile; and where amino acid 16 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 42 is Ala, Gly, Val, Leu, or Ile; where amino acid 20 is Asn, Gln, Lys, Arg, or His; and where amino acid 16 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 42 is Ala, amino acid 20 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 42 is Ala, amino acid 20 is Gly, and amino acid 16 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 42 is Val, amino acid 20 is Ala, and amino acid 16 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 42 is Leu, amino acid 20 is Ala, and amino acid 16 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 42 is Ile, amino acid 20 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 42 is Ala, amino acid 20 is Asn, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 42 is Ala, amino acid 20 is Gln, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 42 is Ala, amino acid 20 is Lys, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 42 is Ala, amino acid 20 is Arg, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 42 is Ala, amino acid 20 is His, and amino acid 16 is Ala. In some cases, a single copy of the variant IL-2 polypeptide is present in a multimeric polypeptide of the present disclosure. In some cases, a multimeric polypeptide of the present disclosure comprises two copies of the variant IL-2 polypeptide, e.g., where the two copies are in tandem with no linker between the two copies, or are in tandem and separated by a linker peptide. In some cases, a multimeric polypeptide of the present disclosure comprises three copies of the variant IL-2 polypeptide, e.g., where the three copies are in tandem with no linker between the three copies, or are in tandem and separated by a linker peptide. In some cases, where an IL-2/synTac of the present disclosure comprises HLA Class I heavy chain and β2M, the IL-2 polypeptide(s) is/are on the polypeptide chain comprising the HLA Class I heavy chain. In some cases, where an IL-2/synTac of the present disclosure comprises HLA Class I heavy chain and β2M, the IL-2 polypeptide(s) is/are on the polypeptide chain comprising the β2M polypeptide. In some cases, the variant IL-2 polypeptide, or a synTac comprising same, has a binding affinity for IL2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant IL-2 polypeptide present in a multimeric polypeptide of the present disclosure has a length of 133 amino acids.

F42, D20, and Q126 Substitutions

In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 42 is an amino acid other than a phenylalanine, e.g., where amino acid 42 is Gly, Ala, Val, Leu, Ile, Pro, Tyr, Trp, Ser, Thr, Cys, Met, Asn, Gln, Lys, Arg, His, Asp, or Glu; where amino acid 20 is an amino acid other than an aspartic acid, e.g., where amino acid 20 is Gly, Ala, Val, Leu, Ile, Pro, Phe, Tyr, Trp, Ser, Thr, Cys, Met, Asn, Gln, Lys, Arg, His, or Glu; and where amino acid 126 is an amino acid other than a glutamine, e.g., where amino acid 126 is Gly, Ala, Val, Leu, Ile, Pro, Phe, Tyr, Trp, Ser, Thr, Cys, Met, Asn, Lys, Arg, His, Asp, or Glu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 42 is Ala, Gly, Val, Leu, or Ile; where amino acid 20 is Ala, Gly, Val, Leu, or Ile; and where amino acid 126 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 42 is Ala, Gly, Val, Leu, or Ile; where amino acid 20 is Asn, Gln, Lys, Arg, or His; and where amino acid 126 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 42 is Ala, amino acid 20 is Ala, and amino acid 126 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 42 is Ala, amino acid 20 is Gly, and amino acid 126 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 42 is Val, amino acid 20 is Ala, and amino acid 126 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 42 is Leu, amino acid 20 is Ala, and amino acid 126 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 42 is Ile, amino acid 20 is Ala, and amino acid 126 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 42 is Ala, amino acid 20 is Asn, and amino acid 126 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 42 is Ala, amino acid 20 is Gln, and amino acid 126 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 42 is Ala, amino acid 20 is Lys, and amino acid 126 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 42 is Ala, amino acid 20 is Arg, and amino acid 126 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 42 is Ala, amino acid 20 is His, and amino acid 126 is Ala. In some cases, a single copy of the variant IL-2 polypeptide is present in a multimeric polypeptide of the present disclosure. In some cases, a multimeric polypeptide of the present disclosure comprises two copies of the variant IL-2 polypeptide, e.g., where the two copies are in tandem with no linker between the two copies, or are in tandem and separated by a linker peptide. In some cases, a multimeric polypeptide of the present disclosure comprises three copies of the variant IL-2 polypeptide, e.g., where the three copies are in tandem with no linker between the three copies, or are in tandem and separated by a linker peptide. In some cases, where an IL-2/synTac of the present disclosure comprises HLA Class I heavy chain and β2M, the IL-2 polypeptide(s) is/are on the polypeptide chain comprising the HLA Class I heavy chain. In some cases, where an IL-2/synTac of the present disclosure comprises HLA Class I heavy chain and β2M, the IL-2 polypeptide(s) is/are on the polypeptide chain comprising the β2M polypeptide. In some cases, the variant IL-2 polypeptide, or a synTac comprising same, has a binding affinity for IL2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant IL-2 polypeptide present in a multimeric polypeptide of the present disclosure has a length of 133 amino acids.

F42, D20, and Y45 Substitutions

In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 42 is an amino acid other than a phenylalanine, e.g., where amino acid 42 is Gly, Ala, Val, Leu, Ile, Pro, Tyr, Trp, Ser, Thr, Cys, Met, Asn, Gln, Lys, Arg, His, Asp, or Glu; where amino acid 20 is an amino acid other than an aspartic acid, e.g., where amino acid 20 is Gly, Ala, Val, Leu, Ile, Pro, Phe, Tyr, Trp, Ser, Thr, Cys, Met, Asn, Gln, Lys, Arg, His, or Glu; and where amino acid 45 is an amino acid other than a tyrosine, e.g., where amino acid 45 is Gly, Ala, Val, Leu, Ile, Pro, Phe, Trp, Ser, Thr, Cys, Met, Asn, Gln, Lys, Arg, His, Asp, or Glu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 42 is Ala, Gly, Val, Leu, or Ile; where amino acid 20 is Ala, Gly, Val, Leu, or Ile; and where amino acid 45 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 42 is Ala, Gly, Val, Leu, or Ile; where amino acid 20 is Asn, Gln, Lys, Arg, or His; and where amino acid 45 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 42 is Ala, amino acid 20 is Ala, and amino acid 45 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 42 is Ala, amino acid 20 is Gly, and amino acid 45 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 42 is Val, amino acid 20 is Ala, and amino acid 45 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 42 is Leu, amino acid 20 is Ala, and amino acid 45 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 42 is Ile, amino acid 20 is Ala, and amino acid 45 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 42 is Ala, amino acid 20 is Asn, and amino acid 45 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 42 is Ala, amino acid 20 is Gln, and amino acid 45 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 42 is Ala, amino acid 20 is Lys, and amino acid 45 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 42 is Ala, amino acid 20 is Arg, and amino acid 45 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 42 is Ala, amino acid 20 is His, and amino acid 45 is Ala. In some cases, a single copy of the variant IL-2 polypeptide is present in a multimeric polypeptide of the present disclosure. In some cases, a multimeric polypeptide of the present disclosure comprises two copies of the variant IL-2 polypeptide, e.g., where the two copies are in tandem with no linker between the two copies, or are in tandem and separated by a linker peptide. In some cases, a multimeric polypeptide of the present disclosure comprises three copies of the variant IL-2 polypeptide, e.g., where the three copies are in tandem with no linker between the three copies, or are in tandem and separated by a linker peptide. In some cases, where an IL-2/synTac of the present disclosure comprises HLA Class I heavy chain and β2M, the IL-2 polypeptide(s) is/are on the polypeptide chain comprising the HLA Class I heavy chain. In some cases, where an IL-2/synTac of the present disclosure comprises HLA Class I heavy chain and β2M, the IL-2 polypeptide(s) is/are on the polypeptide chain comprising the β2M polypeptide. In some cases, the variant IL-2 polypeptide, or a synTac comprising same, has a binding affinity for IL2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant IL-2 polypeptide present in a multimeric polypeptide of the present disclosure has a length of 133 amino acids.

F4, D20, Y45, and H16 Substitutions

In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2N, where amino acid 42 is an amino acid other than a phenylalanine, e.g., where amino acid 42 is Gly, Ala, Val, Leu, Ile, Pro, Tyr, Trp, Ser, Thr, Cys, Met, Asn, Gln, Lys, Arg, His, Asp, or Glu; where amino acid 20 is an amino acid other than an aspartic acid, e.g., where amino acid 20 is Gly, Ala, Val, Leu, Ile, Pro, Phe, Tyr, Trp, Ser, Thr, Cys, Met, Asn, Gln, Lys, Arg, His, or Glu; where amino acid 45 is an amino acid other than a tyrosine, e.g., where amino acid 45 is Gly, Ala, Val, Leu, Ile, Pro, Phe, Trp, Ser, Thr, Cys, Met, Asn, Gln, Lys, Arg, His, Asp, or Glu; and where amino acid 16 is an amino acid other than a histidine, e.g., where amino acid 16 is Gly, Ala, Val, Leu, Ile, Pro, Phe, Tyr, Trp, Ser, Thr, Cys, Met, Asn, Gln, Lys, Arg, Asp, or Glu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2N, where amino acid 42 is Ala, Gly, Val, Leu, or Ile; where amino acid 20 is Ala, Gly, Val, Leu, or Ile; where amino acid 45 is Ala, Gly, Val, Leu, or Ile; and where amino acid 16 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2N, where amino acid 42 is Ala, Gly, Val, Leu, or Ile; where amino acid 20 is Asn, Gln, Lys, Arg, or His; where amino acid 45 is Ala, Gly, Val, Leu, or Ile; and where amino acid 16 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2N, where amino acid 42 is Ala, amino acid 20 is Ala, amino acid 45 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2N, where amino acid 42 is Ala, amino acid 20 is Gly, amino acid 45 is Gly, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2N, where amino acid 42 is Val, amino acid 20 is Ala, amino acid 45 is Gly, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2N, where amino acid 42 is Leu, amino acid 20 is Ala, amino acid 45 is Gly, and amino acid 16 is Val. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2N, where amino acid 42 is Ile, amino acid 20 is Ala, amino acid 45 is Ala, and amino acid 16 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2N, where amino acid 42 is Ala, amino acid 20 is Asn, amino acid 45 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2N, where amino acid 42 is Ala, amino acid 20 is Gln, amino acid 45 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2N, where amino acid 42 is Ala, amino acid 20 is Lys, amino acid 45 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2N, where amino acid 42 is Ala, amino acid 20 is Arg, amino acid 45 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2N, where amino acid 42 is Ala, amino acid 20 is His, amino acid 45 is Ala, and amino acid 16 is Ala. In some cases, a single copy of the variant IL-2 polypeptide is present in a multimeric polypeptide of the present disclosure. In some cases, a multimeric polypeptide of the present disclosure comprises two copies of the variant IL-2 polypeptide, e.g., where the two copies are in tandem with no linker between the two copies, or are in tandem and separated by a linker peptide. In some cases, a multimeric polypeptide of the present disclosure comprises three copies of the variant IL-2 polypeptide, e.g., where the three copies are in tandem with no linker between the three copies, or are in tandem and separated by a linker peptide. In some cases, where an IL-2/synTac of the present disclosure comprises HLA Class I heavy chain and β2M, the IL-2 polypeptide(s) is/are on the polypeptide chain comprising the HLA Class I heavy chain. In some cases, where an IL-2/synTac of the present disclosure comprises HLA Class I heavy chain and β2M, the IL-2 polypeptide(s) is/are on the polypeptide chain comprising the β2M polypeptide. In some cases, the variant IL-2 polypeptide, or a synTac comprising same, has a binding affinity for IL2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant IL-2 polypeptide present in a multimeric polypeptide of the present disclosure has a length of 133 amino acids.

F42, D20, Y45, and Q126 Substitutions

In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2O, where amino acid 42 is an amino acid other than a phenylalanine, e.g., where amino acid 42 is Gly, Ala, Val, Leu, Ile, Pro, Tyr, Trp, Ser, Thr, Cys, Met, Asn, Gln, Lys, Arg, His, Asp, or Glu; where amino acid 20 is an amino acid other than an aspartic acid, e.g., where amino acid 20 is Gly, Ala, Val, Leu, Ile, Pro, Phe, Tyr, Trp, Ser, Thr, Cys, Met, Asn, Gln, Lys, Arg, His, or Glu; where amino acid 45 is an amino acid other than a tyrosine, e.g., where amino acid 45 is Gly, Ala, Val, Leu, Ile, Pro, Phe, Trp, Ser, Thr, Cys, Met, Asn, Gln, Lys, Arg, His, Asp, or Glu; and where amino acid 126 is an amino acid other than a glutamine, e.g., where amino acid 126 is Gly, Ala, Val, Leu, Ile, Pro, Phe, Tyr, Trp, Ser, Thr, Cys, Met, Asn, Lys, Arg, His, Asp, or Glu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2O, where amino acid 42 is Ala, Gly, Val, Leu, or Ile; where amino acid 20 is Ala, Gly, Val, Leu, or Ile; where amino acid 45 is Ala, Gly, Val, Leu, or Ile; and where amino acid 126 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2O, where amino acid 42 is Ala, Gly, Val, Leu, or Ile; where amino acid 20 is Asn, Gln, Lys, Arg, or His; where amino acid 45 is Ala, Gly, Val, Leu, or Ile; and where amino acid 126 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2O, where amino acid 42 is Ala, amino acid 20 is Ala, amino acid 45 is Ala, and amino acid 126 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2O, where amino acid 42 is Ala, amino acid 20 is Gly, amino acid 45 is Gly, and amino acid 126 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2O, where amino acid 42 is Val, amino acid 20 is Ala, amino acid 45 is Gly, and amino acid 126 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2O, where amino acid 42 is Leu, amino acid 20 is Ala, amino acid 45 is Gly, and amino acid 126 is Val. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2O, where amino acid 42 is Ile, amino acid 20 is Ala, amino acid 45 is Ala, and amino acid 126 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2O, where amino acid 42 is Ala, amino acid 20 is Asn, amino acid 45 is Ala, and amino acid 126 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2O, where amino acid 42 is Ala, amino acid 20 is Gln, amino acid 45 is Ala, and amino acid 126 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2O, where amino acid 42 is Ala, amino acid 20 is Lys, amino acid 45 is Ala, and amino acid 126 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2O, where amino acid 42 is Ala, amino acid 20 is Arg, amino acid 45 is Ala, and amino acid 126 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2O, where amino acid 42 is Ala, amino acid 20 is His, amino acid 45 is Ala, and amino acid 126 is Ala. In some cases, a single copy of the variant IL-2 polypeptide is present in a multimeric polypeptide of the present disclosure. In some cases, a multimeric polypeptide of the present disclosure comprises two copies of the variant IL-2 polypeptide, e.g., where the two copies are in tandem with no linker between the two copies, or are in tandem and separated by a linker peptide. In some cases, a multimeric polypeptide of the present disclosure comprises three copies of the variant IL-2 polypeptide, e.g., where the three copies are in tandem with no linker between the three copies, or are in tandem and separated by a linker peptide. In some cases, where an IL-2/synTac of the present disclosure comprises HLA Class I heavy chain and β2M, the IL-2 polypeptide(s) is/are on the polypeptide chain comprising the HLA Class I heavy chain. In some cases, where an IL-2/synTac of the present disclosure comprises HLA Class I heavy chain and β2M, the IL-2 polypeptide(s) is/are on the polypeptide chain comprising the β2M polypeptide. In some cases, the variant IL-2 polypeptide, or a synTac comprising same, has a binding affinity for IL2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant IL-2 polypeptide present in a multimeric polypeptide of the present disclosure has a length of 133 amino acids.

F42, D20, Y45, H16, and Q126 Substitutions

In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2P, where amino acid 42 is an amino acid other than a phenylalanine, e.g., where amino acid 42 is Gly, Ala, Val, Leu, Ile, Pro, Tyr, Trp, Ser, Thr, Cys, Met, Asn, Gln, Lys, Arg, His, Asp, or Glu; where amino acid 20 is an amino acid other than an aspartic acid, e.g., where amino acid 20 is Gly, Ala, Val, Leu, Ile, Pro, Phe, Tyr, Trp, Ser, Thr, Cys, Met, Asn, Gln, Lys, Arg, His, or Glu; where amino acid 45 is an amino acid other than a tyrosine, e.g., where amino acid 45 is Gly, Ala, Val, Leu, Ile, Pro, Phe, Trp, Ser, Thr, Cys, Met, Asn, Gln, Lys, Arg, His, Asp, or Glu; where amino acid 126 is an amino acid other than a glutamine, e.g., where amino acid 126 is Gly, Ala, Val, Leu, Ile, Pro, Phe, Tyr, Trp, Ser, Thr, Cys, Met, Asn, Lys, Arg, His, Asp, or Glu; and where amino acid 16 is an amino acid other than a histidine, e.g., where amino acid 16 is Gly, Ala, Val, Leu, Ile, Pro, Phe, Tyr, Trp, Ser, Thr, Cys, Met, Asn, Gln, Lys, Arg, Asp, or Glu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2P, where amino acid 42 is Ala, Gly, Val, Leu, or Ile; where amino acid 20 is Ala, Gly, Val, Leu, or Ile; where amino acid 45 is Ala, Gly, Val, Leu, or Ile; where amino acid 126 is Ala, Gly, Val, Leu, or Ile; and where amino acid 16 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2P, where amino acid 42 is Ala, Gly, Val, Leu, or Ile; where amino acid 20 is Asn, Gln, Lys, Arg, or His; where amino acid 45 is Ala, Gly, Val, Leu, or Ile; where amino acid 126 is Ala, Gly, Val, Leu, or Ile; and where amino acid 16 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2P, where amino acid 42 is Ala, amino acid 20 is Ala, amino acid 45 is Ala, amino acid 126 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2P, where amino acid 42 is Ala, amino acid 20 is Gly, amino acid 45 is Gly, amino acid 126 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2P, where amino acid 42 is Val, amino acid 20 is Ala, amino acid 45 is Gly, amino acid 126 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2P, where amino acid 42 is Leu, amino acid 20 is Ala, amino acid 45 is Gly, amino acid 126 is Val, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2P, where amino acid 42 is Ile, amino acid 20 is Ala, amino acid 45 is Ala, amino acid 126 is Gly, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2P, where amino acid 42 is Ala, amino acid 20 is Asn, amino acid 45 is Ala, amino acid 126 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2P, where amino acid 42 is Ala, amino acid 20 is Gln, amino acid 45 is Ala, amino acid 126 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2P, where amino acid 42 is Ala, amino acid 20 is Lys, amino acid 45 is Ala, amino acid 126 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2P, where amino acid 42 is Ala, amino acid 20 is Arg, amino acid 45 is Ala, amino acid 126 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2P, where amino acid 42 is Ala, amino acid 20 is His, amino acid 45 is Ala, amino acid 126 is Ala, and amino acid 16 is Ala. In some cases, a single copy of the variant IL-2 polypeptide is present in a multimeric polypeptide of the present disclosure. In some cases, a multimeric polypeptide of the present disclosure comprises two copies of the variant IL-2 polypeptide, e.g., where the two copies are in tandem with no linker between the two copies, or are in tandem and separated by a linker peptide. In some cases, a multimeric polypeptide of the present disclosure comprises three copies of the variant IL-2 polypeptide, e.g., where the three copies are in tandem with no linker between the three copies, or are in tandem and separated by a linker peptide. In some cases, where an IL-2/synTac of the present disclosure comprises HLA Class I heavy chain and β2M, the IL-2 polypeptide(s) is/are on the polypeptide chain comprising the HLA Class I heavy chain. In some cases, where an IL-2/synTac of the present disclosure comprises HLA Class I heavy chain and β2M, the IL-2 polypeptide(s) is/are on the polypeptide chain comprising the β2M polypeptide. In some cases, the variant IL-2 polypeptide, or a synTac comprising same, has a binding affinity for IL2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant IL-2 polypeptide present in a multimeric polypeptide of the present disclosure has a length of 133 amino acids.

F42, Q126, and H16 Substitutions

In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 42 is an amino acid other than a phenylalanine, e.g., where amino acid 42 is Gly, Ala, Val, Leu, Ile, Pro, Tyr, Trp, Ser, Thr, Cys, Met, Asn, Gln, Lys, Arg, His, Asp, or Glu; where amino acid 126 is an amino acid other than a glutamine, e.g., where amino acid 126 is Gly, Ala, Val, Leu, Ile, Pro, Phe, Tyr, Trp, Ser, Thr, Cys, Met, Asn, Lys, Arg, His, Asp, or Glu; and where amino acid 16 is an amino acid other than a histidine, e.g., where amino acid 16 is Gly, Ala, Val, Leu, Ile, Pro, Phe, Tyr, Trp, Ser, Thr, Cys, Met, Asn, Gln, Lys, Arg, Asp, or Glu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Ala, Gly, Val, Leu, or Ile; where amino acid 126 is Ala, Gly, Val, Leu, or Ile; and where amino acid 16 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Ala, Gly, Val, Leu, or Ile; where amino acid 126 is Asn, Gln, Lys, Arg, or His; and where amino acid 16 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Ala, amino acid 126 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Ala, amino acid 126 is Gly, and amino acid 16 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Val, amino acid 126 is Ala, and amino acid 16 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Leu, amino acid 126 is Ala, and amino acid 16 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Ile, amino acid 126 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Ala, amino acid 126 is Asn, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Ala, amino acid 126 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Ala, amino acid 126 is Lys, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Ala, amino acid 126 is Arg, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Ala, amino acid 126 is His, and amino acid 16 is Ala. In some cases, a single copy of the variant IL-2 polypeptide is present in a multimeric polypeptide of the present disclosure. In some cases, a multimeric polypeptide of the present disclosure comprises two copies of the variant IL-2 polypeptide, e.g., where the two copies are in tandem with no linker between the two copies, or are in tandem and separated by a linker peptide. In some cases, a multimeric polypeptide of the present disclosure comprises three copies of the variant IL-2 polypeptide, e.g., where the three copies are in tandem with no linker between the three copies, or are in tandem and separated by a linker peptide. In some cases, where an IL-2/synTac of the present disclosure comprises HLA Class I heavy chain and β2M, the IL-2 polypeptide(s) is/are on the polypeptide chain comprising the HLA Class I heavy chain. In some cases, where an IL-2/synTac of the present disclosure comprises HLA Class I heavy chain and β2M, the IL-2 polypeptide(s) is/are on the polypeptide chain comprising the β2M polypeptide. In some cases, the variant IL-2 polypeptide, or a synTac comprising the variant IL-2 polypeptide, has a binding affinity for IL2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant IL-2 polypeptide has a length of 133 amino acids.

4-1BBL

In some cases, a synTac suitable for use in a method of the present disclosure comprises a 4-1BBL polypeptide as the immunomodulatory domain(s). Suitable 4-1BBL immunomodulatory domains include a wild-type 4-1BBL immunomodulatory domain, and a variant 4-1BBL immunomodulatory domain.

A wild-type human 4-1BBL amino acid sequence is provided in FIG. 36A. The tumor necrosis factor (TNF) homology domain (THD) of human 4-1BBL comprises amino acids 81-254, amino acids 80-254, or amino acids 80-246 of the amino acid sequence depicted in FIG. 36A. Thus, a wild-type amino acid sequence of the THD of human 4-1BBL can be, e.g., one of SEQ ID NOs: 213-215, as follows:

```
                                        (SEQ ID NO: 213)
PAGLLDLRQG MFAQLVAQNV LLIDGPLSWY SDPGLAGVSL
TGGLSYKEDT KELVVAKAGV YYVFFQLELR RVVAGEGSGS
VSLALHLQPL RSAAGAAALA LTVDLPPASS EARNSAFGFQ
GRLLHLSAGQ RLGVHLHTEA RARHAWQLTQ GATVLGLFRV
TPEIPAGLPS PRSE.

                                        (SEQ ID NO: 214)
D PAGLLDLRQG MFAQLVAQNV LLIDGPLSWY SDPGLAGVSL
TGGLSYKEDT KELVVAKAGV YYVFFQLELR RVVAGEGSGS
VSLALHLQPL RSAAGAAALA LTVDLPPASS EARNSAFGFQ
GRLLHLSAGQ RLGVHLHTEA RARHAWQLTQ GATVLGLFRV
TPEIPAGLPS PRSE.

                                        (SEQ ID NO: 215)
D PAGLLDLRQG MFAQLVAQNV LLIDGPLSWY SDPGLAGVSL
TGGLSYKEDT KELVVAKAGV YYVFFQLELR RVVAGEGSGS
VSLALHLQPL RSAAGAAALA LTVDLPPASS EARNSAFGFQ
GRLLHLSAGQ RLGVHLHTEA RARHAWQLTQ GATVLGLFRV
TPEIPA.
```

Wild-type 4-1BBL binds to 4-1BB (CD137). An amino acid sequences of 4-1BB is provided in FIG. 37. A variant 4-1BBL polypeptide of the present disclosure binds to 4-1BB with reduced affinity compared to binding of wild-type 4-1BBL to 4-1BB.

Variant 4-1BBL polypeptides include those having an amino acid sequence that has at least 80%, at least 85%, at least 90%, at least 95%, or at least 99% amino acid sequence identity to a corresponding wild-type 4-1BBL polypeptide, and include variant 4-1BBL polypeptides that differ by 1, 2, 3, 4, 5, 6, 7, 8, 9, 10, 11, 12, 13, 14, or 15 amino acids, or more than 15 amino acids, relative to a corresponding wild-type 4-1BBL polypeptide. In some cases, a variant 4-1BBL polypeptide differs in amino acid sequence from a wild-type 4-1BBL polypeptide by only a single amino acid. In some cases, a variant 4-1BBL polypeptide differs in amino acid sequence from a wild-type 4-1BBL polypeptide by no more than 2 amino acids. In some cases, a variant 4-1BBL polypeptide differs in amino acid sequence from a wild-type 4-1BBL polypeptide by no more than 3 amino acids. In some cases, a variant 4-1BBL polypeptide differs in amino acid sequence from a wild-type 4-1BBL polypeptide by no more than 4 amino acids. In some cases, a variant 4-1BBL polypeptide differs in amino acid sequence from a wild-type 4-1BBL polypeptide by no more than 5 amino acids.

In some cases, the variant 4-1BBL polypeptide present in a multimeric polypeptide of the present disclosure exhibits reduced binding affinity to 4-1BB, compared to the binding affinity of a 4-1BBL polypeptide comprising the amino acid sequence depicted in FIG. 36A for 4-1BB. For example, in some cases, the variant 4-1BBL polypeptide present in a multimeric polypeptide of the present disclosure binds 4-1BB with a binding affinity that is less than the binding affinity of a 4-1BBL polypeptide comprising the amino acid sequence depicted in FIG. 36A for a 4-1BB polypeptide comprising the amino acid sequence depicted in FIG. 37. For example, in some cases, the variant 4-1BBL polypeptide present in a multimeric polypeptide of the present disclosure binds 4-1BB with a binding affinity that is at least 10% less, at least 15% less, at least 20% less, at least 25% less, at least 30% less, at least 35% less, at least 40% less, at least 45% less, at least 50% less, at least 55% less, at least 60% less, at least 65% less, at least 70% less, at least 75% less, at least 80% less, at least 85% less, at least 90% less, at least 95% less, or more than 95% less, than the binding affinity of a 4-1BBL polypeptide comprising the amino acid sequence depicted in FIG. 36A for 4-1BB (e.g., a 4-1BB polypeptide comprising the amino acid sequence depicted in FIG. 37).

In some cases, the variant 4-1BBL polypeptide present in a multimeric polypeptide of the present disclosure exhibits reduced binding affinity to 4-1BB, compared to the binding affinity of a 4-1BBL polypeptide comprising the amino acid sequence depicted in SEQ ID NO:213 for 4-1BB. For example, in some cases, the variant 4-1BBL polypeptide present in a multimeric polypeptide of the present disclosure binds 4-1BB with a binding affinity that is less than the binding affinity of a 4-1BBL polypeptide comprising the amino acid sequence depicted in SEQ ID NO:213 for a 4-1BB polypeptide comprising the amino acid sequence depicted in one of FIG. 37A-37C. For example, in some cases, the variant 4-1BBL polypeptide present in a multimeric polypeptide of the present disclosure binds 4-1BB with a binding affinity that is at least 10% less, at least 15% less, at least 20% less, at least 25% less, at least 30% less, at least 35% less, at least 40% less, at least 45% less, at least 50% less, at least 55% less, at least 60% less, at least 65% less, at least 70% less, at least 75% less, at least 80% less, at least 85% less, at least 90% less, at least 95% less, or more than 95% less, than the binding affinity of a 4-1BBL polypeptide comprising the amino acid sequence depicted in SEQ ID NO:213 for 4-1BB (e.g., a 4-1BB polypeptide comprising the amino acid sequence depicted in FIG. 37).

In some cases, a variant 4-1BBL polypeptide present in a multimeric polypeptide of the present disclosure has a binding affinity to 4-1BB that is from 100 nM to 100 μM. As another example, in some cases, a variant 4-1BBL polypeptide present in a multimeric polypeptide of the present disclosure has a binding affinity for 4-1BB (e.g., a 4-1BB polypeptide comprising the amino acid sequence depicted in FIG. 37) that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM.

In some cases, a variant 4-1BBL polypeptide present in a multimeric polypeptide of the present disclosure exhibits increased production in a mammalian host cell, compared to the production in the same mammalian host cell of a control multimeric polypeptide comprising a wild-type 4-1BBL polypeptide (e.g., a 4-1BBL polypeptide comprising the amino acid sequence depicted in FIG. 36A or as set forth in SEQ ID NO:213). For example, in some cases, a variant 4-1BBL polypeptide present in a multimeric polypeptide, when expressed in a mammalian host cell, is produced in an amount that is from 25% higher to about 50% higher, from about 50% higher to about 75% higher, from about 75% higher to about 2-fold higher, from about 2-fold higher to about 5-fold higher, from about 5-fold higher to about 10-fold higher, from about 10-fold higher to about 20-fold higher, from about 20-fold higher to about 30-fold higher, from about 30-fold higher to about 40-fold higher, from about 40-fold higher to about 50-fold higher, from abouat 50-fold higher to about 75-fold higher, from about 75-fold higher to about 100-fold higher, or more than 100-fold higher, than the amount of a control multimeric polypeptide comprising a wild-type 4-1BBL polypeptide (e.g., a 4-1BBL polypeptide comprising the amino acid sequence depicted in FIG. 36A or as set forth in SEQ ID NO:213) produced in the same mammalian host cell.

In some cases, a variant 4-1BBL polypeptide present in a multimeric polypeptide is produced in a mammalian host cell in an amount of from about 50 mg/L to about 75 mg/L, from about 75 mg/L to about 100 mg/L, from about 100 mg/L to about 150 mg/L, from about 150 mg/L to about 200 mg/L, from about 200 mg/L to about 250 mg/L, from about 250 mg/L to about 500 mg/L, or more than 500 mg/L. In some cases, a variant 4-1BBL polypeptide present in a multimeric polypeptide is produced in a mammalian host cell in an amount of from about 10 mg/L to about 15 mg/L, from about 15 mg/L to about 20 mg/L, from about 20 mg/L to about 25 mg/L, from about 25 mg/L to about 30 mg/L, from about 35 mg/L to about 40 mg/L, from about 40 mg/L to about 45 mg/L, or from about 45 mg/L to about 50 mg/L.

A variant 4-1BBL polypeptide present in a multimeric polypeptide can have a single amino acid substitution relative to a wild-type 4-1BBL polypeptide (e.g., a 4-1BBL polypeptide comprising the amino acid sequence depicted in FIG. 36A or as set forth in SEQ ID NO:213). In some cases, a variant 4-1BBL polypeptide present in a multimeric polypeptide of the present disclosure has from 2 to 10 amino acid substitutions relative to a wild-type 4-1BBL polypeptide (e.g., a 4-1BBL polypeptide comprising the amino acid sequence depicted in FIG. 36A or as set forth in SEQ ID NO:213). In some cases, a variant 4-1BBL polypeptide present in a multimeric polypeptide of the present disclosure has 2 amino acid substitutions relative to a wild-type 4-1BBL polypeptide (e.g., a 4-1BBL polypeptide comprising the amino acid sequence depicted in FIG. 36A or as set forth in SEQ ID NO:213). In some cases, a variant 4-1BBL polypeptide present in a multimeric polypeptide of the present disclosure has 3 amino acid substitutions relative to a wild-type 4-1BBL polypeptide (e.g., a 4-1BBL polypeptide comprising the amino acid sequence depicted in FIG. 36A or as set forth in SEQ ID NO:213). In some cases, a variant 4-1BBL polypeptide present in a multimeric polypeptide of the present disclosure has 4 amino acid substitutions relative to a wild-type 4-1BBL polypeptide (e.g., a 4-1BBL polypeptide comprising the amino acid sequence depicted in FIG. 36A or as set forth in SEQ ID NO:213). In some cases, a variant 4-1BBL polypeptide present in a multimeric polypeptide of the present disclosure has 5 amino acid substitutions relative to a wild-type 4-1BBL polypeptide (e.g., a 4-1BBL polypeptide comprising the amino acid sequence depicted in FIG. 36A or as set forth in SEQ ID NO:213). In some cases, a variant 4-1BBL polypeptide present in a multimeric polypeptide of the present disclosure has 6 amino acid substitutions relative to a wild-type 4-1BBL polypeptide (e.g., a 4-1BBL polypeptide comprising the amino acid sequence depicted in FIG. 36A or as set forth in SEQ ID NO:213). In some cases, a variant 4-1BBL polypeptide of the present disclosure has 7 amino acid substitutions relative to a wild-type 4-1BBL polypeptide (e.g., a 4-1BBL polypeptide comprising the amino acid sequence depicted in FIG. 36A or as set forth in SEQ ID NO:213). In some cases, a variant 4-1BBL polypeptide present in a multimeric polypeptide of the present disclosure has 8 amino acid substitutions relative to a wild-type 4-1BBL polypeptide (e.g., a 4-1BBL polypeptide comprising the amino acid sequence depicted in FIG. 36A or as set forth in SEQ ID NO:213). In some cases, a variant 4-1BBL polypeptide present in a multimeric polypeptide of the present disclosure has 9 amino acid substitutions relative to a wild-type 4-1BBL polypeptide (e.g., a 4-1BBL polypeptide comprising the amino acid sequence depicted in FIG. 36A or as set forth in SEQ ID NO:213). In some cases, a variant 4-1BBL polypeptide present in a multimeric polypeptide of the present disclosure has 10 amino acid substitutions relative to a wild-type 4-1BBL polypeptide (e.g., a 4-1BBL polypeptide comprising the amino acid sequence depicted in FIG. 36A or as set forth in SEQ ID NO:213).

In some cases, a variant 4-1BBL polypeptide present in a multimeric polypeptide of the present disclosure has from 11 to 50 amino acid substitutions relative to a wild-type 4-1BBL polypeptide (e.g., a 4-1BBL polypeptide comprising the amino acid sequence depicted in FIG. 36A or as set forth in SEQ ID NO:213). For example, in some cases, a variant 4-1BBL polypeptide present in a multimeric polypeptide of the present disclosure has from 11 to 15, from 15 to 20, from 20 to 25, from 25 to 30, from 30 to 35, from 35 to 40, from 40 to 45, or from 45 to 50, amino acid substitutions relative to a wild-type 4-1BBL polypeptide (e.g., a 4-1BBL polypeptide comprising the amino acid sequence depicted in FIG. 36A or as set forth in SEQ ID NO:213).

Suitable variant 4-1BBL polypeptides that can be included in a multimeric polypeptide of the present disclosure include those described above.

4-1BBL with K127 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 47 is an amino acid other than a lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at K48. In some cases, a variant 4-1BBL polypeptide present in a multimeric polypeptide of the present disclosure comprises the amino acid sequence set forth in SEQ ID NO:214, with an amino acid substitution at K48. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at K48. In some cases, a variant 4-1BBL polypeptide present in a multimeric polypeptide of the present disclosure comprises the amino acid sequence set forth in SEQ ID NO:215, with an amino acid substitution at K48.

K127+M91 Substitutions

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at M91, where amino acid 91 is Gly, Ala, Val, Leu, Ile, Pro, Phe, Tyr, Trp, Ser, Thr, Cys, Asn, Gln, Lys, Arg, His, Asp, or Glu. In some cases, amino acid 127 is Ala; and amino acid 91 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than a lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 11 is other than methionine, e.g., where amino acid 11 is Gly, Ala, Val, Leu, Ile, Pro, Phe, Tyr, Trp, Ser, Thr, Cys, Asn, Gln, Lys, Arg, His, Asp, or Glu. In some cases, amino acid 47 is Ala; and amino acid 11 is Ala.

K127+F92 Substitutions

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at F92, where amino acid 92 is Gly, Ala, Val, Leu, Ile, Pro, Tyr, Trp, Ser, Thr, Cys, Met, Asn, Gln, Lys, Arg, His, Asp, or Glu. In some cases, amino acid 127 is Ala; and amino acid 92 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than a lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 12 is other than phenylalanine, e.g., where amino acid 12 is Gly, Ala, Val, Leu, Ile, Pro, Tyr, Trp, Ser, Thr, Cys, Met, Asn, Gln, Lys, Arg, His, Asp, or Glu. In some cases, amino acid 47 is Ala; and amino acid 12 is Ala.

K127+Q94 Substitutions

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at Q94, where amino acid 94 is Gly, Ala, Val, Leu, Ile, Pro, Phe, Tyr, Trp, Ser, Thr, Cys, Met, Asn, Lys, Arg, His, Asp, or Glu. In some cases, amino acid 127 is Ala; and amino acid 94 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than a lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 14 is other than glutamine, e.g., where amino acid 14 is Gly, Ala, Val, Leu, Ile, Pro, Phe, Tyr, Trp, Ser, Thr, Cys, Met, Asn, Lys, Arg, His, Asp, or Glu. In some cases, amino acid 47 is Ala; and amino acid 14 is Ala.

K127+L95 Substitutions

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at L95, where amino acid 95 is Gly, Ala, Val, Ile, Pro, Phe, Tyr, Trp, Ser, Thr, Cys, Met, Asn, Gln, Lys, Arg, His, Asp, or Glu. In some cases, amino acid 127 is Ala; and amino acid 95 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than a lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 15 is other than leucine, e.g., where amino acid 15 is Gly, Ala, Val, Ile, Pro, Phe, Tyr, Trp, Ser, Thr, Cys, Met, Asn, Gln, Lys, Arg, His, Asp, or Glu. In some cases, amino acid 47 is Ala; and amino acid 15 is Ala.

K127+V96 Substitutions

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at V96, where amino acid 96 is Gly, Ala, Leu, Ile, Pro, Phe, Tyr, Trp, Ser, Thr, Cys, Met, Asn, Gln, Lys, Arg, His, Asp, or Glu. In some cases, amino acid 127 is Ala; and amino acid 96 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than a lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 16 is other than a valine, e.g., where amino acid 16 is Gly, Ala, Leu, Ile, Pro, Phe, Tyr, Trp, Ser, Thr, Cys, Met, Asn, Gln, Lys, Arg, His, Asp, or Glu. In some cases, amino acid 47 is Ala; and amino acid 16 is Ala.

K127+Q98 Substitutions

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at Q98, where amino acid 98 is Gly, Ala, Val, Leu, Ile, Pro, Phe, Tyr, Trp, Ser, Thr, Cys, Met, Asn, Lys, Arg, His, Asp, or Glu. In some cases, amino acid 127 is Ala; and amino acid 98 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than a lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 18 is other than glutamine, e.g., where amino acid 18 is Gly, Ala, Val, Leu, Ile, Pro, Phe, Tyr, Trp, Ser, Thr, Cys, Met, Asn, Lys, Arg, His, Asp, or Glu. In some cases, amino acid 47 is Ala; and amino acid 18 is Ala.

K127+N99 Substitutions

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at N99, where amino acid 99 is Gly, Ala, Val, Leu, Ile, Pro, Phe, Tyr, Trp, Ser, Thr, Cys, Met, Gln, Lys, Arg, His, Asp, or Glu. In some cases, amino acid 127 is Ala; and amino acid 99 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than a lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 19 is other than an asparagine, e.g., where amino acid 19 is Gly, Ala, Val, Leu, Ile, Pro, Phe, Tyr, Trp, Ser, Thr, Cys, Met, Gln, Lys, Arg, His, Asp, or Glu. In some cases, amino acid 47 is Ala; and amino acid 19 is Ala.

K127+V100 Substitutions

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at V100, where amino acid 100 is Gly, Ala, Leu, Ile, Pro, Phe, Tyr, Trp, Ser, Thr, Cys, Met, Asn, Gln, Lys, Arg, His, Asp, or Glu. In some cases, amino acid 127 is Ala; and amino acid 100 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than a lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 20 is other than a valine, e.g., where amino acid 20 is Gly, Ala, Leu, Ile, Pro, Phe, Tyr, Trp, Ser, Thr, Cys, Met, Asn, Gln, Lys, Arg, His, Asp, or Glu. In some cases, amino acid 47 is Ala; and amino acid 20 is Ala.

K127+L101 Substitutions

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at L101, where amino acid 101 is Gly, Ala, Val, Ile, Pro, Phe, Tyr, Trp, Ser, Thr, Cys, Met, Asn, Gln, Lys, Arg, His, Asp, or Glu. In some cases, amino acid 127 is Ala; and amino acid 101 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than a lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 21 is other than leucine, e.g., where amino acid 21 is Gly, Ala, Val, Ile, Pro, Phe, Tyr, Trp, Ser, Thr, Cys, Met, Asn, Gln, Lys, Arg, His, Asp, or Glu. In some cases, amino acid 47 is Ala; and amino acid 21 is Ala.

K127+L102 Substitutions

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at L102, where amino acid 102 is Gly, Ala, Val, Ile, Pro, Phe, Tyr, Trp, Ser, Thr, Cys, Met, Asn, Gln, Lys, Arg, His, Asp, or Glu. In some cases, amino acid 127 is Ala; and amino acid 102 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than a lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 22 is other than leucine, e.g., where amino acid 22 is Gly, Ala, Val, Ile, Pro, Phe, Tyr, Trp, Ser, Thr, Cys, Met, Asn, Gln, Lys, Arg, His, Asp, or Glu. In some cases, amino acid 47 is Ala; and amino acid 22 is Ala.

K127+I103 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at I103, where amino acid 103 is Gly, Ala, Val, Leu, Pro, Phe, Tyr, Trp, Ser, Thr, Cys, Met, Asn, Gln, Lys, Arg, His, Asp, or Glu. In some cases, amino acid 127 is Ala; and amino acid 103 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than a lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 23 is other than isoleucine, e.g., where amino acid 23 is Gly, Ala, Val, Leu, Pro, Phe, Tyr, Trp, Ser, Thr, Cys, Met, Asn, Gln, Lys, Arg, His, Asp, or Glu. In some cases, amino acid 47 is Ala; and amino acid 23 is Ala.

K127+D104 Substitutions

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at D104, where amino acid 104 is Gly, Ala, Val, Leu, Ile, Pro, Phe, Tyr, Trp, Ser, Thr, Cys, Met, Asn, Gln, Lys, Arg, His, or Glu. In some cases, amino acid 127 is Ala; and amino acid 104 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 24 is other than aspartic acid, e.g., where amino acid 24 is Gly, Ala, Val, Leu, Ile, Pro, Phe, Tyr, Trp, Ser, Thr, Cys, Met, Asn, Gln, Lys, Arg, His, or Glu. In some cases, amino acid 47 is Ala; and amino acid 24 is Ala.

K127+G105 Substitutions

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at G105, where amino acid 105 is Ala, Val, Leu, Ile, Pro, Phe, Tyr, Trp, Ser, Thr, Cys, Met, Asn, Gln, Lys, Arg, His, Asp, or Glu. In some cases, amino acid 127 is Ala; and amino acid 105 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than a lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 25 is other than glycine, e.g., where amino acid 25 is Ala, Val, Leu, Ile, Pro, Phe, Tyr, Trp, Ser, Thr, Cys, Met, Asn, Gln, Lys, Arg, His, Asp, or Glu. In some cases, amino acid 47 is Ala; and amino acid 25 is Ala.

K127+P106 Substitutions

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at P106, where amino acid 106 is Gly, Ala, Val, Leu, Ile, Phe, Tyr, Trp, Ser, Thr, Cys, Met, Asn, Gln, Lys, Arg, His, Asp, or Glu. In some cases, amino acid 127 is Ala; and amino acid 106 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than a lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 26 is other than proline, e.g., where amino acid 26 is Gly, Ala, Val, Leu, Ile, Phe, Tyr, Trp, Ser, Thr, Cys, Met, Asn, Gln, Lys, Arg, His, Asp, or Glu. In some cases, amino acid 47 is Ala; and amino acid 26 is Ala.

K127+L107 Substitutions

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at L107, where amino acid 107 is Gly, Ala, Val, Ile, Pro, Phe, Tyr, Trp, Ser, Thr, Cys, Met, Asn, Gln, Lys, Arg, His, Asp, or Glu. In some cases, amino acid 127 is Ala; and amino acid 107 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than a lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 27 is other than leucine, e.g., where amino acid 27 is Gly, Ala, Val, Ile, Pro, Phe, Tyr, Trp, Ser, Thr, Cys, Met, Asn, Gln, Lys, Arg, His, Asp, or Glu. In some cases, amino acid 47 is Ala; and amino acid 27 is Ala.

K127+S108 Substitutions

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at S108, where amino acid 108 is Gly, Ala, Val, Leu, Ile, Pro, Phe, Tyr, Trp, Thr, Cys, Met, Asn, Gln, Lys, Arg, His, Asp, or Glu. In some cases, amino acid 127 is Ala; and amino acid 108 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than a lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 28 is other than serine, e.g., where amino acid 28 is Gly, Ala, Val, Leu, Ile, Pro, Phe, Tyr, Trp, Thr, Cys, Met, Asn, Gln, Lys, Arg, His, Asp, or Glu. In some cases, amino acid 47 is Ala; and amino acid 28 is Ala.

K127+W109 Substitutions

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at W109, where amino acid 109 is Gly, Ala, Val, Leu, Ile, Pro, Phe, Tyr, Ser, Thr, Cys, Met, Asn, Gln, Lys, Arg, His, Asp, or Glu. In some cases, amino acid 127 is Ala; and amino acid 109 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than a lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 29 is other than tryptophan, e.g., where amino acid 29 is Gly, Ala, Val, Leu, Ile, Pro, Phe, Tyr, Ser, Thr, Cys, Met, Asn, Gln, Lys, Arg, His, Asp, or Glu. In some cases, amino acid 47 is Ala; and amino acid 29 is Ala.

K127+Y110 Substitutions

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at Y110, where amino acid 110 is Gly, Ala, Val, Leu, Ile, Pro, Phe, Trp, Ser, Thr, Cys, Met, Asn, Gln, Lys, Arg, His, Asp, or Glu. In some cases, amino acid 127 is Ala; and amino acid 110 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than a lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 30 is other than tyrosine, e.g., where amino acid 30 is Gly, Ala, Val, Leu, Ile, Pro, Phe, Trp, Ser, Thr, Cys, Met, Asn, Gln, Lys, Arg, His, Asp, or Glu. In some cases, amino acid 47 is Ala; and amino acid 30 is Ala.

K127+S111 Substitutions

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at 5111, where amino acid 111 is Gly, Ala, Val, Leu, Ile, Pro, Phe, Tyr, Trp, Thr, Cys, Met, Asn, Gln, Lys, Arg, His, Asp, or Glu. In some cases, amino acid 127 is Ala; and amino acid 111 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than a lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 31 is other than serine, e.g., where amino acid 31 is Gly, Ala, Val, Leu, Ile, Pro, Phe, Tyr, Trp, Thr, Cys, Met, Asn, Gln, Lys, Arg, His, Asp, or Glu. In some cases, amino acid 47 is Ala; and amino acid 31 is Ala.

K127+D112 Substitutions

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at D112, where amino acid 112 is Gly, Ala, Val, Leu, Ile, Pro, Phe, Tyr, Trp, Ser, Thr, Cys, Met, Asn, Gln, Lys, Arg, His, or Glu. In some cases, amino acid 127 is Ala; and amino acid 112 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 32 is other than aspartic acid, e.g., where amino acid 32 is Gly, Ala, Val, Leu, Ile, Pro, Phe, Tyr, Trp, Ser, Thr, Cys, Met, Asn, Gln, Lys, Arg, His, or Glu. In some cases, amino acid 47 is Ala; and amino acid 32 is Ala.

K127+P113 Substitutions

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at P113, where amino acid 113 is Gly, Ala, Val, Leu, Ile, Phe, Tyr, Trp, Ser, Thr, Cys, Met, Asn, Gln, Lys, Arg, His, Asp, or Glu. In some cases, amino acid 127 is Ala; and amino acid 113 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than a lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 33 is other than proline, e.g., where amino acid 33 is Gly, Ala, Val, Leu, Ile, Phe, Tyr, Trp, Ser, Thr, Cys, Met, Asn, Gln, Lys, Arg, His, Asp, or Glu. In some cases, amino acid 47 is Ala; and amino acid 33 is Ala.

K127+G114 Substitutions

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at G114, where amino acid 114 is Ala, Val, Leu, Ile, Pro, Phe, Tyr, Trp, Ser, Thr, Cys, Met, Asn, Gln, Lys, Arg, His, Asp, or Glu. In some cases, amino acid 127 is Ala; and amino acid 114 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than a lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 34 is other than glycine, e.g., where amino acid 34 is Ala, Val, Leu, Ile, Pro, Phe, Tyr, Trp, Ser, Thr, Cys, Met, Asn, Gln, Lys, Arg, His, Asp, or Glu. In some cases, amino acid 47 is Ala; and amino acid 34 is Ala.

K127+L115 Substitutions

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at L115, where amino acid 115 is Gly, Ala, Val, Ile, Pro, Phe, Tyr, Trp, Ser, Thr, Cys, Met, Asn, Gln, Lys, Arg, His, Asp, or Glu. In some cases, amino acid 127 is Ala; and amino acid 115 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than a lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 35 is other than leucine, e.g., where amino acid 35 is Gly, Ala, Val, Ile, Pro, Phe, Tyr, Trp, Ser, Thr, Cys, Met, Asn, Gln, Lys, Arg, His, Asp, or Glu. In some cases, amino acid 47 is Ala; and amino acid 35 is Ala.

4-1BBL with Q227 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36D where amino acid 227 (indicated by an "x") is an amino acid other than a glutamine, e.g., where amino acid 227 is Gly, Ala, Val, Leu, Ile, Pro, Phe, Tyr, Trp, Ser, Thr, Cys, Met, Asn, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 147 is other than glutamine, e.g., where amino acid 147 is Gly, Ala, Val, Leu, Ile, Pro, Phe, Tyr, Trp, Ser, Thr, Cys, Met, Asn, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at Q148. In some cases, a variant 4-1BBL polypeptide present in a multimeric polypeptide of the present disclosure comprises the amino acid sequence set forth in SEQ ID NO:214, with an amino acid substitution at Q148. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at Q148. In some cases, a variant 4-1BBL polypeptide present in a multimeric polypeptide of the present disclosure comprises the amino acid sequence set forth in SEQ ID NO:215, with an amino acid substitution at Q148.

4-1BBL with M91 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36E, where amino acid 91 (indicated by an "x") is an amino acid other than a methionine, e.g., where amino acid 91 is Gly, Ala, Val, Leu, Ile, Pro, Phe, Tyr, Trp, Ser, Thr, Cys, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 11 is other than a methionine, e.g., where amino acid 11 is Gly, Ala, Val, Leu, Ile, Pro, Phe, Tyr, Trp, Ser, Thr, Cys, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at M12. In some cases, a variant 4-1BBL polypeptide present in a multimeric polypeptide of the present disclosure comprises the amino acid sequence set forth in SEQ ID NO:214, with an amino acid substitution at M12. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at M12. In some cases, a variant 4-1BBL polypeptide present in a multimeric polypeptide of the present disclosure comprises the amino acid sequence set forth in SEQ ID NO:215, with an amino acid substitution at M12.

4-1BBL with F92 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36F, where amino acid 92 (indicated by an "x") is an amino acid other than a phenylalanine, e.g., where amino acid 92 is Gly, Ala, Val, Leu, Ile, Pro, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 12 is other than a phenylalanine, e.g., where amino acid 12 is Gly, Ala, Val, Leu, Ile, Pro, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at F13. In some cases, a variant 4-1BBL polypeptide present in a multimeric polypeptide of the present disclosure comprises the amino acid sequence set forth in SEQ ID NO:214, with an amino acid substitution at F13. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at F13. In some cases, a variant 4-1BBL polypeptide present in a multimeric polypeptide of the present disclosure comprises the amino acid sequence set forth in SEQ ID NO:215, with an amino acid substitution at F13.

4-1BBL with Q94 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36G, where amino acid 94 (indicated by an "x") is an amino acid other than a glutamine, e.g., where amino acid 94 is Gly, Ala, Val, Leu, Ile, Pro, Phe, Tyr, Trp, Ser, Thr, Cys, Met, Asn, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 14 is other than a glutamine, e.g., where amino acid 14 is Gly, Ala, Val, Leu, Ile, Pro, Phe, Tyr, Trp, Ser, Thr, Cys, Met, Asn, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at Q15. In some cases, a variant 4-1BBL polypeptide present in a multimeric polypeptide of the present disclosure comprises the amino acid sequence set forth in SEQ ID NO:214, with an amino acid substitution at Q15. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at Q15. In some cases, a variant 4-1BBL polypeptide present in a multimeric polypeptide of the present disclosure comprises the amino acid sequence set forth in SEQ ID NO:215, with an amino acid substitution at Q15.

4-1BBL with L95 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36H, where amino acid 95 (indicated by an "x") is an amino acid other than a leucine, e.g., where amino acid 95 is Gly, Ala, Val, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 15 is other than a leucine, e.g., where amino acid 15 is Gly, Ala, Val, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at L16. In some cases, a variant 4-1BBL polypeptide present in a multimeric polypeptide of the present disclosure comprises the amino acid sequence set forth in SEQ ID NO:214, with an amino acid substitution at L16. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at L16. In some cases, a variant 4-1BBL polypeptide present in a multimeric polypeptide of the present disclosure comprises the amino acid sequence set forth in SEQ ID NO:215, with an amino acid substitution at L16.

4-1BBL with V96 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36I, where amino acid 96 (indicated by an "x") is an amino acid other than a valine, e.g., where amino acid 96 is Gly, Ala, Leu, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 16 is other than a valine, e.g., where amino acid 16 is Gly, Ala, Leu, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at V17. In some cases, a variant 4-1BBL polypeptide present in a multimeric polypeptide of the present disclosure comprises the amino acid sequence set forth in SEQ ID NO:214, with an amino acid substitution at V17. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at V17. In some cases, a variant 4-1BBL polypeptide present in a multimeric polypeptide of the present disclosure comprises the amino acid sequence set forth in SEQ ID NO:215, with an amino acid substitution at V17.

4-1BBL with Q98 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36J, where amino acid 98 (indicated by an "x") is an amino acid other than a glutamine, e.g., where amino acid 98 is Gly, Ala, Val, Leu, Ile, Pro, Phe, Tyr, Trp, Ser, Thr, Cys, Met, Asn, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 18 is other than a glutamine, e.g., where amino acid 18 is Gly, Ala, Val, Leu, Ile, Pro, Phe, Tyr, Trp, Ser, Thr, Cys, Met, Asn, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at Q19. In some cases, a variant 4-1BBL polypeptide present in a multimeric polypeptide of the present disclosure comprises the amino acid sequence set forth in SEQ ID NO:214, with an amino acid substitution at Q19. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at Q19. In some cases, a variant 4-1BBL polypeptide present in a multimeric polypeptide of the present disclosure comprises the amino acid sequence set forth in SEQ ID NO:215, with an amino acid substitution at Q19.

4-1BBL with N99 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36K, where amino acid 99 (indicated by an "x") is an amino acid other than an asparagine, e.g., where amino acid 99 is Gly, Ala, Val, Leu, Ile, Pro, Phe, Tyr, Trp, Ser, Thr, Cys, Met, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 19 is other than an asparagine, e.g., where amino acid 19 is Gly, Ala, Val, Leu, Ile, Pro, Phe, Tyr, Trp, Ser, Thr, Cys, Met, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at N20. In some cases, a variant 4-1BBL polypeptide present in a multimeric polypeptide of the present disclosure comprises the amino acid sequence set forth in SEQ ID NO:214, with an amino acid substitution at N20. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at N20. In some cases, a variant 4-1BBL polypeptide present in a multimeric polypeptide of the present disclosure comprises the amino acid sequence set forth in SEQ ID NO:215, with an amino acid substitution at N20.

4-1BBL with V100 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36L, where amino acid 100 (indicated by an "x") is an amino acid other than a valine, e.g., where amino acid 100 is Gly, Ala, Leu, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 20 is other than a valine, e.g., where amino acid 20 is Gly, Ala, Leu, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at V21. In some cases, a variant 4-1BBL polypeptide present in a multimeric polypeptide of the present disclosure comprises the amino acid sequence set forth in SEQ ID NO:214, with an amino acid substitution at V21. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at V21. In some cases, a variant 4-1BBL polypeptide present in a multimeric polypeptide of the present disclosure comprises the amino acid sequence set forth in SEQ ID NO:215, with an amino acid substitution at V21.

4-1BBL with L101 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36M, where amino acid 101 (indicated by an "x") is an amino acid other than a leucine, e.g., where amino acid 101 is Gly, Ala, Val, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 21 is other than a leucine, e.g., where amino acid 21 is Gly, Ala, Val, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at L22. In some cases, a variant 4-1BBL polypeptide present in a multimeric polypeptide of the present disclosure comprises the amino acid sequence set forth in SEQ ID NO:214, with an amino acid substitution at L22. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at L22. In some cases, a variant 4-1BBL polypeptide present in a multimeric polypeptide of the present disclosure comprises the amino acid sequence set forth in SEQ ID NO:215, with an amino acid substitution at L22.

4-1BBL with L102 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36N, where amino acid 102 (indicated by an "x") is an amino acid other than a leucine, e.g., where amino acid 102 is Gly, Ala, Val, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 22 is other than a leucine, e.g., where amino acid 22 is Gly, Ala, Val, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at L23. In some cases, a variant 4-1BBL polypeptide present in a multimeric polypeptide of the present disclosure comprises the amino acid sequence set forth in SEQ ID NO:214, with an amino acid substitution at L23. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID N0:215, with an amino acid substitution at L23. In some cases, a variant 4-1BBL polypeptide present in a multimeric polypeptide of the present disclosure comprises the amino acid sequence set forth in SEQ ID N0:215, with an amino acid substitution at L23.

4-1BBL with I103 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36O, where amino acid 103 (indicated by an "x") is an amino acid other than an isoleucine, e.g., where amino acid 103 is Gly, Ala, Val, Leu, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID N0:213, where amino acid 23 is other than an isoleucine, e.g., where amino acid 23 is Gly, Ala, Val, Leu, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at 124. In some cases, a variant 4-1BBL polypeptide present in a multimeric polypeptide of the present disclosure comprises the amino acid sequence set forth in SEQ ID NO:214, with an amino acid substitution at 124. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at 124. In some cases, a variant 4-1BBL polypeptide present in a multimeric polypeptide of the present disclosure comprises the amino acid sequence set forth in SEQ ID NO:215, with an amino acid substitution at 124.

4-1BBL with D104 substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36P, where amino acid 104 (indicated by an "x") is an amino acid other than an aspartic acid, e.g., where amino acid 104 is Gly, Ala, Val, Leu, Ile, Pro, Phe, Tyr, Trp, Ser, Thr, Cys, Met, Asn, Gln, Lys, Arg, His, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 24 is other than an aspartic acid, e.g., where amino acid 24 is Gly, Ala, Val, Leu, Ile, Pro, Phe, Tyr, Trp, Ser, Thr, Cys, Met, Asn, Gln, Lys, Arg, His, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at D25. In some cases, a variant 4-1BBL polypeptide present in a multimeric polypeptide of the present disclosure comprises the amino acid sequence set forth in SEQ ID NO:214, with an amino acid substitution at D25. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at D25. In some cases, a variant 4-1BBL polypeptide present in a multimeric polypeptide of the present disclosure comprises the amino acid sequence set forth in SEQ ID NO:215, with an amino acid substitution at D25.

4-1BBL with G105 substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36Q, where amino acid 105 (indicated by an "x") is an amino acid other than a glycine, e.g., where amino acid 105 is Ala, Val, Leu, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 25 is other than a glycine, e.g., where amino acid 25 is Ala, Val, Leu, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at G26. In some cases, a variant 4-1BBL polypeptide present in a multimeric polypeptide of the present disclosure comprises the amino acid sequence set forth in SEQ ID NO:214, with an amino acid substitution at G26. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at G26. In some cases, a variant 4-1BBL polypeptide present in a multimeric polypeptide of the present disclosure comprises the amino acid sequence set forth in SEQ ID NO:215, with an amino acid substitution at G26.

4-1BBL with P106 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36R, where amino acid 106 (indicated by an "x") is an amino acid other than a proline, e.g., where amino acid 106 is Gly, Ala, Val, Leu, Ile, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 26 is other than a proline, e.g., where amino acid 26 is Gly, Ala, Val, Leu, Ile, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at P27. In some cases, a variant 4-1BBL polypeptide present in a multimeric polypeptide of the present disclosure comprises the amino acid sequence set forth in SEQ ID NO:214, with an amino acid substitution at P27. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at P27. In some cases, a variant 4-1BBL polypeptide present in a multimeric polypeptide of the present disclosure comprises the amino acid sequence set forth in SEQ ID NO:215, with an amino acid substitution at P27.

4-1BBL with L107 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36S, where amino acid 107 (indicated by an "x") is an amino acid other than a leucine, e.g., where amino acid 107 is Gly, Ala, Val, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 27 is other than a leucine, e.g., where amino acid 27 is Gly, Ala, Val, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at L28. In some cases, a variant 4-1BBL polypeptide present in a multimeric polypeptide of the present disclosure comprises the amino acid sequence set forth in SEQ ID NO:214, with an amino acid substitution at L28. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at L28. In some cases, a variant 4-1BBL polypeptide present in a multimeric polypeptide of the present disclosure comprises the amino acid sequence set forth in SEQ ID NO:215, with an amino acid substitution at L28.

4-1BBL with S108 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36T, where amino acid 108 (indicated by an "x") is an amino acid other than a serine, e.g., where amino acid 108 is Gly, Ala, Val, Leu, Ile, Pro, Phe, Tyr, Trp, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 28 is other than a serine, e.g., where amino acid 28 is Gly, Ala, Val, Leu, Ile, Pro, Phe, Tyr, Trp, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at S29. In some cases, a variant 4-1BBL polypeptide present in a multimeric polypeptide of the present disclosure comprises the amino acid sequence set forth in SEQ ID NO:214, with an amino acid substitution at S29. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at S29. In some cases, a variant 4-1BBL polypeptide present in a multimeric polypeptide of the present disclosure comprises the amino acid sequence set forth in SEQ ID NO:215, with an amino acid substitution at S29.

4-1BBL with W109 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36U, where amino acid 109 (indicated by an "x") is an amino acid other than a tryptophan, e.g., where amino acid 109 is Gly, Ala, Val, Leu, Ile, Pro, Phe, Tyr, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 29 is other than a tryptophan, e.g., where amino acid 29 is Gly, Ala, Val, Leu, Ile, Pro, Phe, Tyr, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at W30. In some cases, a variant 4-1BBL polypeptide present in a multimeric polypeptide of the present disclosure comprises the amino acid sequence set forth in SEQ ID NO:214, with an amino acid substitution at W30. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at W30. In some cases, a variant 4-1BBL polypeptide present in a multimeric polypeptide of the present disclosure comprises the amino acid sequence set forth in SEQ ID NO:215, with an amino acid substitution at W30.

4-1BBL with Y110 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36V, where amino acid 110 (indicated by an "x") is an amino acid other than a tyrosine, e.g., where amino acid 110 is Gly, Ala, Val, Leu, Ile, Pro, Phe, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 30 is other than a tyrosine, e.g., where amino acid 30 is Gly, Ala, Val, Leu, Ile, Pro, Phe, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at Y31. In some cases, a variant 4-1BBL polypeptide present in a multimeric polypeptide of the present disclosure comprises the amino acid sequence set forth in SEQ ID NO:214, with an amino acid substitution at Y31. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at Y31. In some cases, a variant 4-1BBL polypeptide present in a multimeric polypeptide of the present disclosure comprises the amino acid sequence set forth in SEQ ID NO:215, with an amino acid substitution at Y31.

4-1BBL with S111 substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36W, where amino acid 111 (indicated by an "x") is an amino acid other than a serine, e.g., where amino acid 111 is Gly, Ala, Val, Leu, Ile, Pro, Phe, Tyr, Trp, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 31 is other than a serine, e.g., where amino acid 31 is Gly, Ala, Val, Leu, Ile, Pro, Phe, Tyr, Trp, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at S32. In some cases, a variant 4-1BBL polypeptide present in a multimeric polypeptide of the present disclosure comprises the amino acid sequence set forth in SEQ ID NO:214, with an amino acid substitution at S32. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at S32. In some cases, a variant 4-1BBL polypeptide present in a multimeric polypeptide of the present disclosure comprises the amino acid sequence set forth in SEQ ID NO:215, with an amino acid substitution at S32.

4-1BBL with D112 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36X, where amino acid 112 (indicated by an "x") is an amino acid other than an aspartic acid, e.g., where amino acid 112 is Gly, Ala, Val, Leu, Ile, Pro, Phe, Tyr, Trp, Ser, Thr, Cys, Met, Asn, Gln, Lys, Arg, His, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 32 is other than an aspartic acid, e.g., where amino acid 32 is Gly, Ala, Val, Leu, Ile, Pro, Phe, Tyr, Trp, Ser, Thr, Cys, Met, Asn, Gln, Lys, Arg, His, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at D33. In some cases, a variant 4-1BBL polypeptide present in a multimeric polypeptide of the present disclosure comprises the amino acid sequence set forth in SEQ ID NO:214, with an amino acid substitution at D33. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at D33. In some cases, a variant 4-1BBL polypeptide present in a multimeric polypeptide of the present disclosure comprises the amino acid sequence set forth in SEQ ID NO:215, with an amino acid substitution at D33.

4-1BBL with P113 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36Y, where amino acid 113 (indicated by an "x") is an amino acid other than a proline, e.g., where amino acid 113 is Gly, Ala, Val, Leu, Ile, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 33 is other than a proline, e.g., where amino acid 33 is Gly, Ala, Val, Leu, Ile, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at P34. In some cases, a variant 4-1BBL polypeptide present in a multimeric polypeptide of the present disclosure comprises the amino acid sequence set forth in SEQ ID NO:214, with an amino acid substitution at P34. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at P34. In some cases, a variant 4-1BBL polypeptide present in a multimeric polypeptide of the present disclosure comprises the amino acid sequence set forth in SEQ ID NO:215, with an amino acid substitution at P34.

4-1BBL with G114 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36Z, where amino acid 114 (indicated by an "x") is an amino acid other than a glycine, e.g., where amino acid 114 is Ala, Val, Leu, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 34 is other than a glycine, e.g., where amino acid 34 is Ala, Val, Leu, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at G35. In some cases, a variant 4-1BBL polypeptide present in a multimeric polypeptide of the present disclosure comprises the amino acid sequence set forth in SEQ ID NO:214, with an amino acid substitution at G35. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at G35. In some cases, a variant 4-1BBL polypeptide present in a multimeric polypeptide of the present disclosure comprises the amino acid sequence set forth in SEQ ID NO:215, with an amino acid substitution at G35.

4-1BBL with L115 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36AA, where amino acid 115 (indicated by an "x") is an amino acid other than a leucine, e.g., where amino acid 115 is Gly, Ala, Val, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 35 is other than a leucine, e.g., where amino acid 35 is Gly, Ala, Val, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at L36. In some cases, a variant 4-1BBL polypeptide present in a multimeric polypeptide of the present disclosure comprises the amino acid sequence set forth in SEQ ID NO:214, with an amino acid substitution at L36. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at L36. In some cases, a variant 4-1BBL polypeptide present in a multimeric polypeptide of the present disclosure comprises the amino acid sequence set forth in SEQ ID NO:215, with an amino acid substitution at L36.

4-1BBL with G117 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36BB, where amino acid 117 (indicated by an "x") is an amino acid other than a glycine, e.g., where amino acid 117 is Ala, Val, Leu, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 37 is other than a glycine, e.g., where amino acid 37 is Ala, Val, Leu, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at G38. In some cases, a variant 4-1BBL polypeptide present in a multimeric polypeptide of the present disclosure comprises the amino acid sequence set forth in SEQ ID NO:214, with an amino acid substitution at G38. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at G38. In some cases, a variant 4-1BBL polypeptide present in a multimeric polypeptide of the present disclosure comprises the amino acid sequence set forth in SEQ ID NO:215, with an amino acid substitution at G38.

4-1BBL with V118 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36CC, where amino acid 118 (indicated by an "x") is an amino acid other than a valine, e.g., where amino acid 118 is Gly, Ala, Leu, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 38 is other than a valine, e.g., where amino acid 38 is Gly, Ala, Leu, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at V39. In some cases, a variant 4-1BBL polypeptide present in a multimeric polypeptide of the present disclosure comprises the amino acid sequence set forth in SEQ ID NO:214, with an amino acid substitution at V39. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at V39. In some cases, a variant 4-1BBL polypeptide present in a multimeric polypeptide of the present disclosure comprises the amino acid sequence set forth in SEQ ID NO:215, with an amino acid substitution at V39.

4-1BBL with S119 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36DD, where amino acid 119 (indicated by an "x") is an amino acid other than a serine, e.g., where amino acid 119 is Gly, Ala, Val, Leu, Ile, Pro, Phe, Tyr, Trp, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 39 is other than a serine, e.g., where amino acid 39 is Gly, Ala, Val, Leu, Ile, Pro, Phe, Tyr, Trp, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at S40. In some cases, a variant 4-1BBL polypeptide present in a multimeric polypeptide of the present disclosure comprises the amino acid sequence set forth in SEQ ID NO:214, with an amino acid substitution at S40. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at S40. In some cases, a variant 4-1BBL polypeptide present in a multimeric polypeptide of the present disclosure comprises the amino acid sequence set forth in SEQ ID NO:215, with an amino acid substitution at S40.

4-1BBL with L120 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36EE, where amino acid 120 (indicated by an "x") is an amino acid other than a leucine, e.g., where amino acid 120 is Gly, Ala, Val, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 40 is other than a leucine, e.g., where amino acid 40 is Gly, Ala, Val, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at L41. In some cases, a variant 4-1BBL polypeptide present in a multimeric polypeptide of the present disclosure comprises the amino acid sequence set forth in SEQ ID NO:214, with an amino acid substitution at L41. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at L41. In some cases, a variant 4-1BBL polypeptide present in a multimeric polypeptide of the present disclosure comprises the amino acid sequence set forth in SEQ ID NO:215, with an amino acid substitution at L41.

4-1BBL with T121 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36FF, where amino acid 121 (indicated by an "x") is an amino acid other than a threonine, e.g., where amino acid 121 is Gly, Ala, Val, Leu, Ile, Pro, Phe, Tyr, Trp, Ser, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 41 is other than a threonine, e.g., where amino acid 41 is Gly, Ala, Val, Leu, Ile, Pro, Phe, Tyr, Trp, Ser, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at T42. In some cases, a variant 4-1BBL polypeptide present in a multimeric polypeptide of the present disclosure comprises the amino acid sequence set forth in SEQ ID NO:214, with an amino acid substitution at T42. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at T42. In some cases, a variant 4-1BBL polypeptide present in a multimeric polypeptide of the present disclosure comprises the amino acid sequence set forth in SEQ ID NO:215, with an amino acid substitution at T42.

4-1BBL with G122 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36GG, where amino acid 122 (indicated by an "x") is an amino acid other than a glycine, e.g., where amino acid 122 is Ala, Val, Leu, Ile, Pro, Phe, Tyr, Trp, Ser, Thr, Cys, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 42 is other than a glycine, e.g., where amino acid 42 is Ala, Val, Leu, Ile, Pro, Phe, Tyr, Trp, Ser, Thr, Cys, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at G43. In some cases, a variant 4-1BBL polypeptide present in a multimeric polypeptide of the present disclosure comprises the amino acid sequence set forth in SEQ ID NO:214, with an amino acid substitution at G43. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at G43. In some cases, a variant 4-1BBL polypeptide present in a multimeric polypeptide of the present disclosure comprises the amino acid sequence set forth in SEQ ID NO:215, with an amino acid substitution at G43.

4-1BBL with G123 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36HH, where amino acid 123 (indicated by an "x") is an amino acid other than a glycine, e.g., where amino acid 123 is Ala, Val, Leu, Ile, Pro, Phe, Tyr, Trp, Ser, Thr, Cys, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 43 is other than a glycine, e.g., where amino acid 43 is Ala, Val, Leu, Ile, Pro, Phe, Tyr, Trp, Ser, Thr, Cys, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at G44. In some cases, a variant 4-1BBL polypeptide present in a multimeric polypeptide of the present disclosure comprises the amino acid sequence set forth in SEQ ID NO:214, with an amino acid substitution at G44. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at G44. In some cases, a variant 4-1BBL polypeptide present in a multimeric polypeptide of the present disclosure comprises the amino acid sequence set forth in SEQ ID NO:215, with an amino acid substitution at G44.

4-1BBL with L124 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36II, where amino acid 124 (indicated by an "x") is an amino acid other than a leucine, e.g., where amino acid 124 is Gly, Ala, Val, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 44 is other than a leucine, e.g., where amino acid 44 is Gly, Ala, Val, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at L45. In some cases, a variant 4-1BBL polypeptide present in a multimeric polypeptide of the present disclosure comprises the amino acid sequence set forth in SEQ ID NO:214, with an amino acid substitution at L45. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at L45. In some cases, a variant 4-1BBL polypeptide present in a multimeric polypeptide of the present disclosure comprises the amino acid sequence set forth in SEQ ID NO:215, with an amino acid substitution at L45.

4-1BBL with S125 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36JJ, where amino acid 125 (indicated by an "x") is an amino acid other than a serine, e.g., where amino acid 125 is Gly, Ala, Val, Leu, Ile, Pro, Phe, Tyr, Trp, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 45 is other than a serine, e.g., where amino acid 45 is Gly, Ala, Val, Leu, Ile, Pro, Phe, Tyr, Trp, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at S46. In some cases, a variant 4-1BBL polypeptide present in a multimeric polypeptide of the present disclosure comprises the amino acid sequence set forth in SEQ ID NO:214, with an amino acid substitution at S46. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at S46. In some cases, a variant 4-1BBL polypeptide present in a multimeric polypeptide of the present disclosure comprises the amino acid sequence set forth in SEQ ID NO:215, with an amino acid substitution at S46.

4-1BBL with Y126 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36KK, where amino acid 126 (indicated by an "x") is an amino acid other than a tyrosine, e.g., where amino acid 126 is Gly, Ala, Val, Leu, Ile, Pro, Phe, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 46 is other than a tyrosine, e.g., where amino acid 46 is Gly, Ala, Val, Leu, Ile, Pro, Phe, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at Y47. In some cases, a variant 4-1BBL polypeptide present in a multimeric polypeptide of the present disclosure comprises the amino acid sequence set forth in SEQ ID NO:214, with an amino acid substitution at Y47. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at Y47. In some cases, a variant 4-1BBL polypeptide present in a multimeric polypeptide of the present disclosure comprises the amino acid sequence set forth in SEQ ID NO:215, with an amino acid substitution at Y47.

4-1BBL with E128 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36LL, where amino acid 128 (indicated by an "x") is an amino acid other than a glutamic acid, e.g., where amino acid 128 is Gly, Ala, Val, Leu, Ile, Pro, Phe, Tyr, Trp, Ser, Thr, Cys, Met, Asn, Gln, Lys, Arg, His, or Asp. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 48 is other than a glutamic acid, e.g., where amino acid 48 is Gly, Ala, Val, Leu, Ile, Pro, Phe, Tyr, Trp, Ser, Thr, Cys, Met, Asn, Gln, Lys, Arg, His, or Asp.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at E49. In some cases, a variant 4-1BBL polypeptide present in a multimeric polypeptide of the present disclosure comprises the amino acid sequence set forth in SEQ ID NO:214, with an amino acid substitution at E49. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at E49. In some cases, a variant 4-1BBL polypeptide present in a multimeric polypeptide of the present disclosure comprises the amino acid sequence set forth in SEQ ID NO:215, with an amino acid substitution at E49.

4-1BBL with D129 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36MM, where amino acid 129 (indicated by an "x") is an amino acid other than an aspartic acid, e.g., where amino acid 129 is Gly, Ala, Val, Leu, Ile, Pro, Phe, Tyr, Trp, Ser, Thr, Cys, Met, Asn, Gln, Lys, Arg, His, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 49 is other than an aspartic acid, e.g., where amino acid 49 is Gly, Ala, Val, Leu, Ile, Pro, Phe, Tyr, Trp, Ser, Thr, Cys, Met, Asn, Gln, Lys, Arg, His, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at D50. In some cases, a variant 4-1BBL polypeptide present in a multimeric polypeptide of the present disclosure comprises the amino acid sequence set forth in SEQ ID NO:214, with an amino acid substitution at D50. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at D50. In some cases, a variant 4-1BBL polypeptide present in a multimeric polypeptide of the present disclosure comprises the amino acid sequence set forth in SEQ ID NO:215, with an amino acid substitution at D50.

4-1BBL with T130 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36NN, where amino acid 130 (indicated by an "x") is an amino acid other than a threonine, e.g., where amino acid 130 is Gly, Ala, Val, Leu, Ile, Pro, Phe, Tyr, Trp, Ser, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 50 is other than a threonine, e.g., where amino acid 50 is Gly, Ala, Val, Leu, Ile, Pro, Phe, Tyr, Trp, Ser, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at T51. In some cases, a variant 4-1BBL polypeptide present in a multimeric polypeptide of the present disclosure comprises the amino acid sequence set forth in SEQ ID NO:214, with an amino acid substitution at T51. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID N0:215, with an amino acid substitution at T51. In some cases, a variant 4-1BBL polypeptide present in a multimeric polypeptide of the present disclosure comprises the amino acid sequence set forth in SEQ ID N0:215, with an amino acid substitution at T51.

4-1BBL with K131 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36OO, where amino acid 131 (indicated by an "x") is an amino acid other than a lysine, e.g., where amino acid 131 is Gly, Ala, Val, Leu, Ile, Pro, Phe, Tyr, Trp, Ser, Thr, Cys, Met, Asn, Gln, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID N0:213, where amino acid 51 is other than a lysine, e.g., where amino acid 51 is Gly, Ala, Val, Leu, Ile, Pro, Phe, Tyr, Trp, Ser, Thr, Cys, Met, Asn, Gln, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at K52. In some cases, a variant 4-1BBL polypeptide present in a multimeric polypeptide of the present disclosure comprises the amino acid sequence set forth in SEQ ID NO:214, with an amino acid substitution at K52. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at K52. In some cases, a variant 4-1BBL polypeptide present in a multimeric polypeptide of the present disclosure comprises the amino acid sequence set forth in SEQ ID NO:215, with an amino acid substitution at K52.

4-1BBL with E132 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36PP, where amino acid 132 (indicated by an "x") is an amino acid other than a glutamic acid, e.g., where amino acid 132 is Gly, Ala, Val, Leu, Ile, Pro, Phe, Tyr, Trp, Ser, Thr, Cys, Met, Asn, Gln, Lys, Arg, His, or Asp. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 52 is other than a glutamic acid, e.g., where amino acid 52 is Gly, Ala, Val, Leu, Ile, Pro, Phe, Tyr, Trp, Ser, Thr, Cys, Met, Asn, Gln, Lys, Arg, His, or Asp.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at E53. In some cases, a variant 4-1BBL polypeptide present in a multimeric polypeptide of the present disclosure comprises the amino acid sequence set forth in SEQ ID NO:214, with an amino acid substitution at E53. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at E53. In some cases, a variant 4-1BBL polypeptide present in a multimeric polypeptide of the present disclosure comprises the amino acid sequence set forth in SEQ ID NO:215, with an amino acid substitution at E53.

4-1BBL with F144 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36QQ, where amino acid 144 (indicated by an "x") is an amino acid other than a phenylalanine, e.g., where amino acid 144 is Gly, Ala, Val, Leu, Ile, Pro, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 64 is other than a phenylalanine, e.g., where amino acid 64 is Gly, Ala, Val, Leu, Ile, Pro, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at F65. In some cases, a variant 4-1BBL polypeptide present in a multimeric polypeptide of the present disclosure comprises the amino acid sequence set forth in SEQ ID NO:214, with an amino acid substitution at F65. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at F65. In some cases, a variant 4-1BBL polypeptide present in a multimeric polypeptide of the present disclosure comprises the amino acid sequence set forth in SEQ ID NO:215, with an amino acid substitution at F65.

4-1BBL with F145 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36RR, where amino acid 145 (indicated by an "x") is an amino acid other than a phenylalanine, e.g., where amino acid 145 is Gly, Ala, Val, Leu, Ile, Pro, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 65 is other than a phenylalanine, e.g., where amino acid 65 is Gly, Ala, Val, Leu, Ile, Pro, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at F66. In some cases, a variant 4-1BBL polypeptide present in a multimeric polypeptide of the present disclosure comprises the amino acid sequence set forth in SEQ ID NO:214, with an amino acid substitution at F66. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at F66. In some cases, a variant 4-1BBL polypeptide present in a multimeric polypeptide of the present disclosure comprises the amino acid sequence set forth in SEQ ID NO:215, with an amino acid substitution at F66.

4-1BBL with Q146 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36SS, where amino acid 146 (indicated by an "x") is an amino acid other than a glutamine, e.g., where amino acid 146 is Gly, Ala, Val, Leu, Ile, Pro, Phe, Tyr, Trp, Ser, Thr, Cys, Met, Asn, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 66 is other than a glutamine, e.g., where amino acid 66 is Gly, Ala, Val, Leu, Ile, Pro, Phe, Tyr, Trp, Ser, Thr, Cys, Met, Asn, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at Q67. In some cases, a variant 4-1BBL polypeptide present in a multimeric polypeptide of the present disclosure comprises the amino acid sequence set forth in SEQ ID NO:214, with an amino acid substitution at Q67. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at Q67. In some cases, a variant 4-1BBL polypeptide present in a multimeric polypeptide of the present disclosure comprises the amino acid sequence set forth in SEQ ID NO:215, with an amino acid substitution at Q67.

4-1BBL with L147 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36TT, where amino acid 147 (indicated by an "x") is an amino acid other than a leucine, e.g., where amino acid 147 is Gly, Ala, Val, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 67 is other than a leucine, e.g., where amino acid 67 is Gly, Ala, Val, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at L68. In some cases, a variant 4-1BBL polypeptide present in a multimeric polypeptide of the present disclosure comprises the amino acid sequence set forth in SEQ ID NO:214, with an amino acid substitution at L68. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at L68. In some cases, a variant 4-1BBL polypeptide present in a multimeric polypeptide of the present disclosure comprises the amino acid sequence set forth in SEQ ID NO:215, with an amino acid substitution at L68.

4-1BBL with E148 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36UU, where amino acid 148 (indicated by an "x") is an amino acid other than a glutamic acid, e.g., where amino acid 148 is Gly, Ala, Val, Leu, Ile, Pro, Phe, Tyr, Trp, Ser, Thr, Cys, Met, Asn, Gln, Lys, Arg, His, or Asp. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 68 is other than a glutamic acid, e.g., where amino acid 68 is Gly, Ala, Val, Leu, Ile, Pro, Phe, Tyr, Trp, Ser, Thr, Cys, Met, Asn, Gln, Lys, Arg, His, or Asp.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at E69. In some cases, a variant 4-1BBL polypeptide present in a multimeric polypeptide of the present disclosure comprises the amino acid sequence set forth in SEQ ID NO:214, with an amino acid substitution at E69. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at E69. In some cases, a variant 4-1BBL polypeptide present in a multimeric polypeptide of the present disclosure comprises the amino acid sequence set forth in SEQ ID NO:215, with an amino acid substitution at E69.

4-1BBL with L149 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36VV, where amino acid 149 (indicated by an "x") is an amino acid other than a leucine, e.g., where amino acid 149 is Gly, Ala, Val, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 69 is other than a leucine, e.g., where amino acid 69 is Gly, Ala, Val, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at L70. In some cases, a variant 4-1BBL polypeptide present in a multimeric polypeptide of the present disclosure comprises the amino acid sequence set forth in SEQ ID NO:214, with an amino acid substitution at L70. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at L70. In some cases, a variant 4-1BBL polypeptide present in a multimeric polypeptide of the present disclosure comprises the amino acid sequence set forth in SEQ ID NO:215, with an amino acid substitution at L70.

4-1BBL with R150 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36WW, where amino acid 150 (indicated by an "x") is an amino acid other than an arginine, e.g., where amino acid 150 is Gly, Ala, Val, Leu, Ile, Pro, Phe, Tyr, Trp, Ser, Thr, Cys, Met, Asn, Gln, Lys, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 70 is other than an arginine, e.g., where amino acid 70 is Gly, Ala, Val, Leu, Ile, Pro, Phe, Tyr, Trp, Ser, Thr, Cys, Met, Asn, Gln, Lys, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at R71. In some cases, a variant 4-1BBL polypeptide present in a multimeric polypeptide of the present disclosure comprises the amino acid sequence set forth in SEQ ID NO:214, with an amino acid substitution at R71. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at R71. In some cases, a variant 4-1BBL polypeptide present in a multimeric polypeptide of the present disclosure comprises the amino acid sequence set forth in SEQ ID NO:215, with an amino acid substitution at R71.

4-1BBL with R151 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36XX, where amino acid 151 (indicated by an "x") is an amino acid other than an arginine, e.g., where amino acid 151 is Gly, Ala, Val, Leu, Ile, Pro, Phe, Tyr, Trp, Ser, Thr, Cys, Met, Asn, Gln, Lys, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 71 is is other than an arginine, e.g., where amino acid 71 is Gly, Ala, Val, Leu, Ile, Pro, Phe, Tyr, Trp, Ser, Thr, Cys, Met, Asn, Gln, Lys, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at R72. In some cases, a variant 4-1BBL polypeptide present in a multimeric polypeptide of the present disclosure comprises the amino acid sequence set forth in SEQ ID NO:214, with an amino acid substitution at R72. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at R72. In some cases, a variant 4-1BBL polypeptide present in a multimeric polypeptide of the present disclosure comprises the amino acid sequence set forth in SEQ ID NO:215, with an amino acid substitution at R72.

4-1BBL with V152 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36YY, where amino acid 152 (indicated by an "x") is an amino acid other than a valine, e.g., where amino acid 152 is Gly, Ala, Leu, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 72 is other than a valine, e.g., where amino acid 72 is Gly, Ala, Leu, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at V73. In some cases, a variant 4-1BBL polypeptide present in a multimeric polypeptide of the present disclosure comprises the amino acid sequence set forth in SEQ ID NO:214, with an amino acid substitution at V73. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at V73. In some cases, a variant 4-1BBL polypeptide present in a multimeric polypeptide of the present disclosure comprises the amino acid sequence set forth in SEQ ID NO:215, with an amino acid substitution at V73.

4-1BBL with V153 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36ZZ, where amino acid 153 (indicated by an "x") is an amino acid other than a valine, e.g., where amino acid 153 is Gly, Ala, Leu, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 73 is other than a valine, e.g., where amino acid 73 is Gly, Ala, Leu, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at V74. In some cases, a variant 4-1BBL polypeptide present in a multimeric polypeptide of the present disclosure comprises the amino acid sequence set forth in SEQ ID NO:214, with an amino acid substitution at V74. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at V74. In some cases, a variant 4-1BBL polypeptide present in a multimeric polypeptide of the present disclosure comprises the amino acid sequence set forth in SEQ ID NO:215, with an amino acid substitution at V74.

4-1BBL with G155 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36AAA, where amino acid 155 (indicated by an "x") is an amino acid other than a glycine, e.g., where amino acid 155 is Ala, Val, Leu, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 75 is other than a glycine, e.g., where amino acid 75 is Ala, Val, Leu, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at G76. In some cases, a variant 4-1BBL polypeptide present in a multimeric polypeptide of the present disclosure comprises the amino acid sequence set forth in SEQ ID NO:214, with an amino acid substitution at G76. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at G76. In some cases, a variant 4-1BBL polypeptide present in a multimeric polypeptide of the present disclosure comprises the amino acid sequence set forth in SEQ ID NO:215, with an amino acid substitution at G76.

4-1BBL with E156 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36BBB, where amino acid 156 (indicated by an "x") is an amino acid other than a glutamic acid, e.g., where amino acid 156 is Gly, Ala, Val, Leu, Ile, Pro, Phe, Tyr, Trp, Ser, Thr, Cys, Met, Asn, Gln, Lys, Arg, His, or Asp. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 76 is other than a glutamic acid, e.g., where amino acid 76 is Gly, Ala, Val, Leu, Ile, Pro, Phe, Tyr, Trp, Ser, Thr, Cys, Met, Asn, Gln, Lys, Arg, His, or Asp.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at E77. In some cases, a variant 4-1BBL polypeptide present in a multimeric polypeptide of the present disclosure comprises the amino acid sequence set forth in SEQ ID NO:214, with an amino acid substitution at E77. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at E77. In some cases, a variant 4-1BBL polypeptide present in a multimeric polypeptide of the present disclosure comprises the amino acid sequence set forth in SEQ ID NO:215, with an amino acid substitution at E77.

4-1BBL with G157 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36CCC, where amino acid 157 (indicated by an "x") is an amino acid other than a glycine, e.g., where amino acid 157 is Ala, Val, Leu, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 77 is other than a glycine, e.g., where amino acid 77 is Ala, Val, Leu, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at G78. In some cases, a variant 4-1BBL polypeptide present in a multimeric polypeptide of the present disclosure comprises the amino acid sequence set forth in SEQ ID NO:214, with an amino acid substitution at G78. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at G78. In some cases, a variant 4-1BBL polypeptide present in a multimeric polypeptide of the present disclosure comprises the amino acid sequence set forth in SEQ ID NO:215, with an amino acid substitution at G78.

4-1BBL with S158 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36DDD, where amino acid 158 (indicated by an "x") is an amino acid other than a serine, e.g., where amino acid 158 is Gly, Ala, Val, Leu, Ile, Pro, Phe, Tyr, Trp, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 78 is other than a serine, e.g., where amino acid 78 is Gly, Ala, Val, Leu, Ile, Pro, Phe, Tyr, Trp, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at S79. In some cases, a variant 4-1BBL polypeptide present in a multimeric polypeptide of the present disclosure comprises the amino acid sequence set forth in SEQ ID NO:214, with an amino acid substitution at S79. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at S79. In some cases, a variant 4-1BBL polypeptide present in a multimeric polypeptide of the present disclosure comprises the amino acid sequence set forth in SEQ ID NO:215, with an amino acid substitution at S79.

4-1BBL with D184 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36EEE, where amino acid 184 (indicated by an "x") is an amino acid other than an aspartic acid, e.g., where amino acid 184 is Gly, Ala, Val, Leu, Ile, Pro, Phe, Tyr, Trp, Ser, Thr, Cys, Met, Asn, Gln, Lys, Arg, His, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 104 is other than an aspartic acid, e.g., where amino acid 104 is Gly, Ala, Val, Leu, Ile, Pro, Phe, Tyr, Trp, Ser, Thr, Cys, Met, Asn, Gln, Lys, Arg, His, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at D105. In some cases, a variant 4-1BBL polypeptide present in a multimeric polypeptide of the present disclosure comprises the amino acid sequence set forth in SEQ ID NO:214, with an amino acid substitution at D105. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at D105. In some cases, a variant 4-1BBL polypeptide present in a multimeric polypeptide of the present disclosure comprises the amino acid sequence set forth in SEQ ID NO:215, with an amino acid substitution at D105.

4-1BBL with L185 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36FFF, where amino acid 185 (indicated by an "x") is an amino acid other than a leucine, e.g., where amino acid 185 is Gly, Ala, Val, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 105 is other than a leucine, e.g., where amino acid 105 is Gly, Ala, Val, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at L106. In some cases, a variant 4-1BBL polypeptide present in a multimeric polypeptide of the present disclosure comprises the amino acid sequence set forth in SEQ ID NO:214, with an amino acid substitution at L106. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at L106. In some cases, a variant 4-1BBL polypeptide present in a multimeric polypeptide of the present disclosure comprises the amino acid sequence set forth in SEQ ID NO:215, with an amino acid substitution at L106.

4-1BBL with P186 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36GGG, where amino acid 186 (indicated by an "x") is an amino acid other than a proline, e.g., where amino acid 186 is Gly, Ala, Val, Leu, Ile, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 106 is other than a proline, e.g., where amino acid 106 is Gly, Ala, Val, Leu, Ile, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at P107. In some cases, a variant 4-1BBL polypeptide present in a multimeric polypeptide of the present disclosure comprises the amino acid sequence set forth in SEQ ID NO:214, with an amino acid substitution at P107. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at P107. In some cases, a variant 4-1BBL polypeptide present in a multimeric polypeptide of the present disclosure comprises the amino acid sequence set forth in SEQ ID NO:215, with an amino acid substitution at P107.

4-1BBL with P187 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36HHH, where amino acid 187 (indicated by an "x") is an amino acid other than a proline, e.g., where amino acid 187 is Gly, Ala, Val, Leu, Ile, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 107 is other than a proline, e.g., where amino acid 107 is Gly, Ala, Val, Leu, Ile, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at P108. In some cases, a variant 4-1BBL polypeptide present in a multimeric polypeptide of the present disclosure comprises the amino acid sequence set forth in SEQ ID NO:214, with an amino acid substitution at P108. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at P108. In some cases, a variant 4-1BBL polypeptide present in a multimeric polypeptide of the present disclosure comprises the amino acid sequence set forth in SEQ ID NO:215, with an amino acid substitution at P108.

4-1BBL with S189 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36III, where amino acid 189 (indicated by an "x") is an amino acid other than a serine, e.g., where amino acid 189 is Gly, Ala, Val, Leu, Ile, Pro, Phe, Tyr, Trp, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 109 is other than a serine, e.g., where amino acid 109 is Gly, Ala, Val, Leu, Ile, Pro, Phe, Tyr, Trp, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at 5110. In some cases, a variant 4-1BBL polypeptide present in a multimeric polypeptide of the present disclosure comprises the amino acid sequence set forth in SEQ ID NO:214, with an amino acid substitution at 5110. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at 5110. In some cases, a variant 4-1BBL polypeptide present in a multimeric polypeptide of the present disclosure comprises the amino acid sequence set forth in SEQ ID NO:215, with an amino acid substitution at 5110.

4-1BBL with S190 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36JJJ, where amino acid 190 (indicated by an "x") is an amino acid other than a serine, e.g., where amino acid 190 is Gly, Ala, Val, Leu, Ile, Pro, Phe, Tyr, Trp, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 110 is other than a serine, e.g., where amino acid 110 is Gly, Ala, Val, Leu, Ile, Pro, Phe, Tyr, Trp, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at 5111. In some cases, a variant 4-1BBL polypeptide present in a multimeric polypeptide of the present disclosure comprises the amino acid sequence set forth in SEQ ID NO:214, with an amino acid substitution at 5111. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at 5111. In some cases, a variant 4-1BBL polypeptide present in a multimeric polypeptide of the present disclosure comprises the amino acid sequence set forth in SEQ ID NO:215, with an amino acid substitution at 5111.

4-1BBL with E191 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36KKK, where amino acid 191 (indicated by an "x") is an amino acid other than a glutamic acid, e.g., where amino acid 191 is Gly, Ala, Val, Leu, Ile, Pro, Phe, Tyr, Trp, Ser, Thr, Cys, Met, Asn, Gln, Lys, Arg, His, or Asp. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 111 is other than a glutamic acid, e.g., where amino acid 111 is Gly, Ala, Val, Leu, Ile, Pro, Phe, Tyr, Trp, Ser, Thr, Cys, Met, Asn, Gln, Lys, Arg, His, or Asp.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at E112. In some cases, a variant 4-1BBL polypeptide present in a multimeric polypeptide of the present disclosure comprises the amino acid sequence set forth in SEQ ID NO:214, with an amino acid substitution at E112. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at E112. In some cases, a variant 4-1BBL polypeptide present in a multimeric polypeptide of the present disclosure comprises the amino acid sequence set forth in SEQ ID NO:215, with an amino acid substitution at E112.

4-1BBL with R193 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36LLL, where amino acid 193 (indicated by an "x") is an amino acid other than an arginine, e.g., where amino acid 193 is Gly, Ala, Val, Leu, Ile, Pro, Phe, Tyr, Trp, Ser, Thr, Cys, Met, Asn, Gln, Lys, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 113 is other than arginine, e.g., where amino acid 113 is Gly, Ala, Val, Leu, Ile, Pro, Phe, Tyr, Trp, Ser, Thr, Cys, Met, Asn, Gln, Lys, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at R114. In some cases, a variant 4-1BBL polypeptide present in a multimeric polypeptide of the present disclosure comprises the amino acid sequence set forth in SEQ ID NO:214 with an amino acid substitution at R114. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at R114. In some cases, a variant 4-1BBL polypeptide present in a multimeric polypeptide of the present disclosure comprises the amino acid sequence set forth in SEQ ID NO:215, with an amino acid substitution at R114.

4-1BBL with N194 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36MMM, where amino acid 194 (indicated by an "x") is an amino acid other than a asparagine, e.g., where amino acid 194 is Gly, Ala, Val, Leu, Ile, Pro, Phe, Tyr, Trp, Ser, Thr, Cys, Met, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 114 is other than a asparagine, e.g., where amino acid 114 is Gly, Ala, Val, Leu, Ile, Pro, Phe, Tyr, Trp, Ser, Thr, Cys, Met, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at N115. In some cases, a variant 4-1BBL polypeptide present in a multimeric polypeptide of the present disclosure comprises the amino acid sequence set forth in SEQ ID NO:214 with an amino acid substitution at N115. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at N115. In some cases, a variant 4-1BBL polypeptide present in a multimeric polypeptide of the present disclosure comprises the amino acid sequence set forth in SEQ ID NO:215, with an amino acid substitution at N115.

4-1BBL with S195 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36NNN, where amino acid 195 (indicated by an "x") is an amino acid other than a serine, e.g., where amino acid 195 is Gly, Ala, Val, Leu, Ile, Pro, Phe, Tyr, Trp, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 115 is other than a serine, e.g., where amino acid 115 is Gly, Ala, Val, Leu, Ile, Pro, Phe, Tyr, Trp, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at 5116. In some cases, a variant 4-1BBL polypeptide present in a multimeric polypeptide of the present disclosure comprises the amino acid sequence set forth in SEQ ID NO:214 with an amino acid substitution at 5116. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID N0:215, with an amino acid substitution at 5116. In some cases, a variant 4-1BBL polypeptide present in a multimeric polypeptide of the present disclosure comprises the amino acid sequence set forth in SEQ ID N0:215, with an amino acid substitution at 5116.

4-1BBL with F197 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36OOO, where amino acid 197 (indicated by an "x") is an amino acid other than a phenylalanine, e.g., where amino acid 197 is Gly, Ala, Val, Leu, Ile, Pro, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID N0:213, where amino acid 117 is other than a phenylalanine, e.g., where amino acid 117 is Gly, Ala, Val, Leu, Ile, Pro, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at F118. In some cases, a variant 4-1BBL polypeptide present in a multimeric polypeptide of the present disclosure comprises the amino acid sequence set forth in SEQ ID NO:214 with an amino acid substitution at F118. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at F118. In some cases, a variant 4-1BBL polypeptide present in a multimeric polypeptide of the present disclosure comprises the amino acid sequence set forth in SEQ ID NO:215, with an amino acid substitution at F118.

4-1BBL with Q210 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36PPP, where amino acid 210 (indicated by an "x") is an amino acid other than a glutamine, e.g., where amino acid 210 is Gly, Ala, Val, Leu, Ile, Pro, Phe, Tyr, Trp, Ser, Thr, Cys, Met, Asn, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 130 is other than a glutamine, e.g., where amino acid 130 is Gly, Ala, Val, Leu, Ile, Pro, Phe, Tyr, Trp, Ser, Thr, Cys, Met, Asn, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at Q131. In some cases, a variant 4-1BBL polypeptide present in a multimeric polypeptide of the present disclosure comprises the amino acid sequence set forth in SEQ ID NO:214 with an amino acid substitution at Q131. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at Q131. In some cases, a variant 4-1BBL polypeptide present in a multimeric polypeptide of the present disclosure comprises the amino acid sequence set forth in SEQ ID NO:215, with an amino acid substitution at Q131.

4-1BBL with R211 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36QQQ, where amino acid 211 (indicated by an "x") is an amino acid other than an arginine, e.g., where amino acid 211 is Gly, Ala, Val, Leu, Ile, Pro, Phe, Tyr, Trp, Ser, Thr, Cys, Met, Asn, Gln, Lys, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 131 is other than an arginine, e.g., where amino acid 131 is Gly, Ala, Val, Leu, Ile, Pro, Phe, Tyr, Trp, Ser, Thr, Cys, Met, Asn, Gln, Lys, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at R132. In some cases, a variant 4-1BBL polypeptide present in a multimeric polypeptide of the present disclosure comprises the amino acid sequence set forth in SEQ ID NO:214 with an amino acid substitution at R132. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at R132. In some cases, a variant 4-1BBL polypeptide present in a multimeric polypeptide of the present disclosure comprises the amino acid sequence set forth in SEQ ID NO:215, with an amino acid substitution at R132.

4-1BBL with L212 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36RRR, where amino acid 212 (indicated by an "x") is an amino acid other than a leucine, e.g., where amino acid 212 is Gly, Ala, Val, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 132 is other than a leucine, e.g., where amino acid 132 is Gly, Ala, Val, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at L133. In some cases, a variant 4-1BBL polypeptide present in a multimeric polypeptide of the present disclosure comprises the amino acid sequence set forth in SEQ ID NO:214 with an amino acid substitution at L133. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at L133. In some cases, a variant 4-1BBL polypeptide present in a multimeric polypeptide of the present disclosure comprises the amino acid sequence set forth in SEQ ID NO:215, with an amino acid substitution at L133.

4-1BBL with G213 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36SSS, where amino acid 213 (indicated by an "x") is an amino acid other than a glycine, e.g., where amino acid 213 is Ala, Val, Leu, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 133 is other than a glycine, e.g., where amino acid 133 is Ala, Val, Leu, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at G134. In some cases, a variant 4-1BBL polypeptide present in a multimeric polypeptide of the present disclosure comprises the amino acid sequence set forth in SEQ ID NO:214 with an amino acid substitution at G134. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at G134. In some cases, a variant 4-1BBL polypeptide present in a multimeric polypeptide of the present disclosure comprises the amino acid sequence set forth in SEQ ID NO:215, with an amino acid substitution at G134.

4-1BBL with V214 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36TTT, where amino acid 214 (indicated by an "x") is an amino acid other than a valine, e.g., where amino acid 214 is Gly, Ala, Leu, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 134 is other than a valine, e.g., where amino acid 134 is Gly, Ala, Leu, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at V135. In some cases, a variant 4-1BBL polypeptide present in a multimeric polypeptide of the present disclosure comprises the amino acid sequence set forth in SEQ ID NO:214 with an amino acid substitution at V135. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at V135. In some cases, a variant 4-1BBL polypeptide present in a multimeric polypeptide of the present disclosure comprises the amino acid sequence set forth in SEQ ID NO:215, with an amino acid substitution at V135.

4-1BBL with H215 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36UUU, where amino acid 215 (indicated by an "x") is an amino acid other than a histidine, e.g., where amino acid 215 is Gly, Ala, Val, Leu, Ile, Pro, Phe, Tyr, Trp, Ser, Thr, Cys, Met, Asn, Gln, Lys, Arg, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 135 is other than a histidine, e.g., where amino acid 135 is Gly, Ala, Val, Leu, Ile, Pro, Phe, Tyr, Trp, Ser, Thr, Cys, Met, Asn, Gln, Lys, Arg, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at H136. In some cases, a variant 4-1BBL polypeptide present in a multimeric polypeptide of the present disclosure comprises the amino acid sequence set forth in SEQ ID NO:214 with an amino acid substitution at H136. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at H136. In some cases, a variant 4-1BBL polypeptide present in a multimeric polypeptide of the present disclosure comprises the amino acid sequence set forth in SEQ ID NO:215, with an amino acid substitution at H136.

4-1BBL with L216 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36VVV, where amino acid 216 (indicated by an "x") is an amino acid other than a leucine, e.g., where amino acid 216 is Gly, Ala, Val, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 136 is other than a leucine, e.g., where amino acid 136 is Gly, Ala, Val, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at L137. In some cases, a variant 4-1BBL polypeptide present in a multimeric polypeptide of the present disclosure comprises the amino acid sequence set forth in SEQ ID NO:214 with an amino acid substitution at L137. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at L137. In some cases, a variant 4-1BBL polypeptide present in a multimeric polypeptide of the present disclosure comprises the amino acid sequence set forth in SEQ ID NO:215, with an amino acid substitution at L137.

4-1BBL with H217 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36WWW, where amino acid 217 (indicated by an "x") is an amino acid other than a histidine, e.g., where amino acid 217 is Gly, Ala, Val, Leu, Ile, Pro, Phe, Tyr, Trp, Ser, Thr, Cys, Met, Asn, Gln, Lys, Arg, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 137 is other than a histidine, e.g., where amino acid 137 is Gly, Ala, Val, Leu, Ile, Pro, Phe, Tyr, Trp, Ser, Thr, Cys, Met, Asn, Gln, Lys, Arg, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at H138. In some cases, a variant 4-1BBL polypeptide present in a multimeric polypeptide of the present disclosure comprises the amino acid sequence set forth in SEQ ID NO:214 with an amino acid substitution at H138. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at H138. In some cases, a variant 4-1BBL polypeptide present in a multimeric polypeptide of the present disclosure comprises the amino acid sequence set forth in SEQ ID NO:215, with an amino acid substitution at H138.

4-1BBL with T218 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36XXX, where amino acid 218 (indicated by an "x") is an amino acid other than a threonine, e.g., where amino acid 218 is Gly, Ala, Val, Leu, Ile, Pro, Phe, Tyr, Trp, Ser, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 138 is other than a threonine, e.g., where amino acid 138 is Gly, Ala, Val, Leu, Ile, Pro, Phe, Tyr, Trp, Ser, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at T139. In some cases, a variant 4-1BBL polypeptide present in a multimeric polypeptide of the present disclosure comprises the amino acid sequence set forth in SEQ ID NO:214 with an amino acid substitution at T139. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at T139. In some cases, a variant 4-1BBL polypeptide present in a multimeric polypeptide of the present disclosure comprises the amino acid sequence set forth in SEQ ID NO:215, with an amino acid substitution at T139.

4-1BBL with E219 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36YYY, where amino acid 219 (indicated by an "x") is an amino acid other than a glutamic acid, e.g., where amino acid 219 is Gly, Ala, Val, Leu, Ile, Pro, Phe, Tyr, Trp, Ser, Thr, Cys, Met, Asn, Gln, Lys, Arg, His, or Asp. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 139 is other than a glutamic acid, e.g., where amino acid 139 is Gly, Ala, Val, Leu, Ile, Pro, Phe, Tyr, Trp, Ser, Thr, Cys, Met, Asn, Gln, Lys, Arg, His, or Asp.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at E140. In some cases, a variant 4-1BBL polypeptide present in a multimeric polypeptide of the present disclosure comprises the amino acid sequence set forth in SEQ ID NO:214 with an amino acid substitution at E140. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at E140. In some cases, a variant 4-1BBL polypeptide present in a multimeric polypeptide of the present disclosure comprises the amino acid sequence set forth in SEQ ID NO:215, with an amino acid substitution at E140.

4-1BBL with 8221 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36ZZZ, where amino acid 221 (indicated by an "x") is an amino acid other than an arginine, e.g., where amino acid 221 is Gly, Ala, Val, Leu, Ile, Pro, Phe, Tyr, Trp, Ser, Thr, Cys, Met, Asn, Gln, Lys, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 141 is other than an arginine, e.g., where amino acid 141 is Gly, Ala, Val, Leu, Ile, Pro, Phe, Tyr, Trp, Ser, Thr, Cys, Met, Asn, Gln, Lys, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at R142. In some cases, a variant 4-1BBL polypeptide present in a multimeric polypeptide of the present disclosure comprises the amino acid sequence set forth in SEQ ID NO:214 with an amino acid substitution at R142. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at R142. In some cases, a variant 4-1BBL polypeptide present in a multimeric polypeptide of the present disclosure comprises the amino acid sequence set forth in SEQ ID NO:215, with an amino acid substitution at R142.

4-1BBL with 8223 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36AAAA, where amino acid 223 (indicated by an "x") is an amino acid other than an arginine, e.g., where amino acid 223 is Gly, Ala, Val, Leu, Ile, Pro, Phe, Tyr, Trp, Ser, Thr, Cys, Met, Asn, Gln, Lys, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 143 is other than an arginine, e.g., where amino acid 143 is Gly, Ala, Val, Leu, Ile, Pro, Phe, Tyr, Trp, Ser, Thr, Cys, Met, Asn, Gln, Lys, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at R144. In some cases, a variant 4-1BBL polypeptide present in a multimeric polypeptide of the present disclosure comprises the amino acid sequence set forth in SEQ ID NO:214 with an amino acid substitution at R144. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at R144. In some cases, a variant 4-1BBL polypeptide present in a multimeric polypeptide of the present disclosure comprises the amino acid sequence set forth in SEQ ID NO:215, with an amino acid substitution at R144.

4-1BBL with H224 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36BBBB, where amino acid 224 (indicated by an "x") is an amino acid other than a histidine, e.g., where amino acid 224 is Gly, Ala, Val, Leu, Ile, Pro, Phe, Tyr, Trp, Ser, Thr, Cys, Met, Asn, Gln, Lys, Arg, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 144 is other than a histidine, e.g., where amino acid 144 is Gly, Ala, Val, Leu, Ile, Pro, Phe, Tyr, Trp, Ser, Thr, Cys, Met, Asn, Gln, Lys, Arg, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at H145. In some cases, a variant 4-1BBL polypeptide present in a multimeric polypeptide of the present disclosure comprises the amino acid sequence set forth in SEQ ID NO:214 with an amino acid substitution at H145. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at H145. In some cases, a variant 4-1BBL polypeptide present in a multimeric polypeptide of the present disclosure comprises the amino acid sequence set forth in SEQ ID NO:215, with an amino acid substitution at H145.

4-1BBL with W226 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36CCCC, where amino acid 226 (indicated by an "x") is an amino acid other than a tryptophan, e.g., where amino acid 226 is Gly, Ala, Val, Leu, Ile, Pro, Phe, Tyr, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 146 is other than a tryptophan, e.g., where amino acid 146 is Gly, Ala, Val, Leu, Ile, Pro, Phe, Tyr, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at W147. In some cases, a variant 4-1BBL polypeptide present in a multimeric polypeptide of the present disclosure comprises the amino acid sequence set forth in SEQ ID NO:214 with an amino acid substitution at W147. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at W147. In some cases, a variant 4-1BBL polypeptide present in a multimeric polypeptide of the present disclosure comprises the amino acid sequence set forth in SEQ ID NO:215, with an amino acid substitution at W147.

4-1BBL with L228 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36DDDD, where amino acid 228 (indicated by an "x") is an amino acid other than a leucine, e.g., where amino acid 228 is Gly, Ala, Val, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 148 is other than a leucine, e.g., where amino acid 148 is Gly, Ala, Val, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at L149. In some cases, a variant 4-1BBL polypeptide present in a multimeric polypeptide of the present disclosure comprises the amino acid sequence set forth in SEQ ID NO:214 with an amino acid substitution at L149. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at L149. In some cases, a variant 4-1BBL polypeptide present in a multimeric polypeptide of the present disclosure comprises the amino acid sequence set forth in SEQ ID NO:215, with an amino acid substitution at L149.

4-1BBL with T229 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36EEEE, where amino acid 229 (indicated by an "x") is an amino acid other than a threonine, e.g., where amino acid 229 is Gly, Ala, Val, Leu, Ile, Pro, Phe, Tyr, Trp, Ser, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 149 is other than a threonine, e.g., where amino acid 149 is Gly, Ala, Val, Leu, Ile, Pro, Phe, Tyr, Trp, Ser, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at T150. In some cases, a variant 4-1BBL polypeptide present in a multimeric polypeptide of the present disclosure comprises the amino acid sequence set forth in SEQ ID NO:214 with an amino acid substitution at T150. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at T150. In some cases, a variant 4-1BBL polypeptide present in a multimeric polypeptide of the present disclosure comprises the amino acid sequence set forth in SEQ ID NO:215, with an amino acid substitution at T150.

4-1BBL with Q230 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36FFFF, where amino acid 230 (indicated by an "x") is an amino acid other than a glutamine, e.g., where amino acid 230 is Gly, Ala, Val, Leu, Ile, Pro, Phe, Tyr, Trp, Ser, Thr, Cys, Met, Asn, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 150 is other than a glutamine, e.g., where amino acid 150 is Gly, Ala, Val, Leu, Ile, Pro, Phe, Tyr, Trp, Ser, Thr, Cys, Met, Asn, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at Q151. In some cases, a variant 4-1BBL polypeptide present in a multimeric polypeptide of the present disclosure comprises the amino acid sequence set forth in SEQ ID NO:214 with an amino acid substitution at Q151. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at Q151. In some cases, a variant 4-1BBL polypeptide present in a multimeric polypeptide of the present disclosure comprises the amino acid sequence set forth in SEQ ID NO:215, with an amino acid substitution at Q151.

4-1BBL with G231 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36GGGG, where amino acid 231 (indicated by an "x") is an amino acid other than a glycine, e.g., where amino acid 231 is Ala, Val, Leu, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 151 is other than a glycine, e.g., where amino acid 151 is Ala, Val, Leu, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at G152. In some cases, a variant 4-1BBL polypeptide present in a multimeric polypeptide of the present disclosure comprises the amino acid sequence set forth in SEQ ID NO:214 with an amino acid substitution at G152. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at G152. In some cases, a variant 4-1BBL polypeptide present in a multimeric polypeptide of the present disclosure comprises the amino acid sequence set forth in SEQ ID NO:215, with an amino acid substitution at G152.

4-1BBL with T233 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36HHHH, where amino acid 233 (indicated by an "x") is an amino acid other than a threonine, e.g., where amino acid 233 is Gly, Ala, Val, Leu, Ile, Pro, Phe, Tyr, Trp, Ser, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 153 is other than a threonine, e.g., where amino acid 153 is Gly, Ala, Val, Leu, Ile, Pro, Phe, Tyr, Trp, Ser, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at T154. In some cases, a variant 4-1BBL polypeptide present in a multimeric polypeptide of the present disclosure comprises the amino acid sequence set forth in SEQ ID NO:214 with an amino acid substitution at T154. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at T154. In some cases, a variant 4-1BBL polypeptide present in a multimeric polypeptide of the present disclosure comprises the amino acid sequence set forth in SEQ ID NO:215, with an amino acid substitution at T154.

4-1BBL with V234 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36IIII, where amino acid 234 (indicated by an "x") is an amino acid other than a valine, e.g., where amino acid 234 is Gly, Ala, Leu, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 154 is other than a valine, e.g., where amino acid 154 is Gly, Ala, Leu, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at V155. In some cases, a variant 4-1BBL polypeptide present in a multimeric polypeptide of the present disclosure comprises the amino acid sequence set forth in SEQ ID NO:214 with an amino acid substitution at V155. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at V155. In some cases, a variant 4-1BBL polypeptide present in a multimeric polypeptide of the present disclosure comprises the amino acid sequence set forth in SEQ ID NO:215, with an amino acid substitution at V155.

Exemplary Multimeric Polypeptides Comprising 4-1BBL Immunomodulatory Polypeptide Exemplary multimeric polypeptides that are suitable for use in a method of the present disclosure are described below.

K127

In some cases, a multimeric polypeptide of the present disclosure comprises: a) a first polypeptide comprising, in order from N-terminus to C-terminus: i) an epitope; ii) a β2M polypeptide; and iii) a variant 4-1BBL polypeptide comprising an amino acid sequence having at least 90%, at least 95%, at least 98%, or at least 99%, amino acid sequence identity to the amino acid sequence depicted in FIG. 36B, where amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; or a variant 4-1BBL polypeptide of the present disclosure comprising an amino acid sequence having at least 90%, at least 95%, at least 98%, or at least 99%, amino acid sequence identity to the amino acid sequence set forth in SEQ ID NO:213, with an amino acid substitution at K47, e.g., where amino acid 47 is Gly, Ala, Val, Leu, Ile, Pro, Phe, Tyr, Trp, Ser, Thr, Cys, Met, Asn, Gln, Arg, His, Asp, or Glu; and b) a second polypeptide comprising, in order from N-terminus to C-terminus: i) a Class I MHC heavy chain; and ii) an Fc polypeptide. In some cases, a multimeric polypeptide of the present disclosure comprises: a) a first polypeptide comprising, in order from N-terminus to C-terminus: i) an epitope; and ii) a β2M polypeptide; and b) a second polypeptide comprising, in order from N-terminus to C-terminus: i) a variant 4-1BBL polypeptide comprising an amino acid sequence having at least 90%, at least 95%, at least 98%, or at least 99%, amino acid sequence identity to the amino acid sequence depicted in FIG. 36B, where amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; or a variant 4-1BBL polypeptide of the present disclosure comprising an amino acid sequence having at least 90%, at least 95%, at least 98%, or at least 99%, amino acid sequence identity to the amino acid sequence set forth in SEQ ID NO:213, with an amino acid substitution at K47, e.g., where amino acid 47 is Gly, Ala, Val, Leu, Ile, Pro, Phe, Tyr, Trp, Ser, Thr, Cys, Met, Asn, Gln, Arg, His, Asp, or Glu; ii) a Class I MHC heavy chain; and iii) an Fc polypeptide. In some cases, a multimeric polypeptide of the present disclosure comprises: a) a first polypeptide comprising, in order from N-terminus to C-terminus: i) an epitope; ii) a β2M polypeptide; iii) a first variant 4-1BBL polypeptide of the present disclosure; iv) a second variant 4-1BBL polypeptide of the present disclosure; and v) a third variant 4-1BBL polypeptide of the present disclosure; and b) a second polypeptide comprising, in order from N-terminus to C-terminus: i) a Class I MHC heavy chain; and ii) an Fc polypeptide. In some cases, each of the first, second, and third variant 4-1BBL polypeptides comprises an amino acid sequence having at least 90%, at least 95%, at least 98%, or at least 99%, amino acid sequence identity to the amino acid sequence depicted in FIG. 36B, where amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; e.g., each of the first, second, and third variant 4-1BBL polypeptides comprises an amino acid sequence having at least 90%, at least 95%, at least 98%, or at least 99%, amino acid sequence identity to the amino acid sequence set forth in SEQ ID NO:213, with an amino acid substitution at K47, e.g., where amino acid 47 is Gly, Ala, Val, Leu, Ile, Pro, Phe, Tyr, Trp, Ser, Thr, Cys, Met, Asn, Gln, Arg, His, Asp, or Glu. In some cases, a multimeric polypeptide of the present disclosure comprises: a) a first polypeptide comprising, in order from N-terminus to C-terminus: i) an epitope; and ii) a β2M polypeptide; and b) a second polypeptide comprising, in order from N-terminus to C-terminus: i) a first variant 4-1BBL polypeptide of the present disclosure; ii) a second variant 4-1BBL polypeptide of the present disclosure; and iii) a third variant 4-1BBL polypeptide of the present disclosure; iv) a Class I MHC heavy chain; and v) an Fc polypeptide. In some cases, each of the first, second, and third variant 4-1BBL polypeptides comprises an amino acid sequence having at least 90%, at least 95%, at least 98%, or at least 99%, amino acid sequence identity to the amino acid sequence depicted in FIG. 36B, where amino acid 127 (indicated by an “x”) is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; e.g., each of the first, second, and third variant 4-1BBL polypeptides comprises an amino acid sequence having at least 90%, at least 95%, at least 98%, or at least 99%, amino acid sequence identity to the amino acid sequence set forth in SEQ ID NO:213, with an amino acid substitution at K47, e.g., where amino acid 47 is Gly, Ala, Val, Leu, Ile, Pro, Phe, Tyr, Trp, Ser, Thr, Cys, Met, Asn, Gln, Arg, His, Asp, or Glu. In some cases, the variant 4-1BBL polypeptide comprises a K127 substitution and an M91 substitution (based on the numbering depicted in FIG. 36A). In some cases, the variant 4-1BBL polypeptide comprises a K127 substitution and an F92 substitution (based on the numbering depicted in FIG. 36A). In some cases, the variant 4-1BBL polypeptide comprises a K127 substitution and a Q94 substitution (based on the numbering depicted in FIG. 36A). In some cases, the variant 4-1BBL polypeptide comprises a K127 substitution and an L95 substitution (based on the numbering depicted in FIG. 36A). In some cases, the variant 4-1BBL polypeptide comprises a K127 substitution and a V96 substitution (based on the numbering depicted in FIG. 36A). In some cases, the variant 4-1BBL polypeptide comprises a K127 substitution and a Q98 substitution (based on the numbering depicted in FIG. 36A). In some cases, the variant 4-1BBL polypeptide comprises a K127 substitution and an N99 substitution (based on the numbering depicted in FIG. 36A). In some cases, the variant 4-1BBL polypeptide comprises a K127 substitution and a V100 substitution (based on the numbering depicted in FIG. 36A). In some cases, the variant 4-1BBL polypeptide comprises a K127 substitution and an L101 substitution (based on the numbering depicted in FIG. 36A). In some cases, the variant 4-1BBL polypeptide comprises a K127 substitution and an L102 substitution (based on the numbering depicted in FIG. 36A). In some cases, the variant 4-1BBL polypeptide comprises a K127 substitution and an 1103 substitution (based on the numbering depicted in FIG. 36A). In some cases, the variant 4-1BBL polypeptide comprises a K127 substitution and a D104 substitution (based on the numbering depicted in FIG. 36A). In some cases, the variant 4-1BBL polypeptide comprises a K127 substitution and a G105 substitution (based on the numbering depicted in FIG. 36A). In some cases, the variant 4-1BBL polypeptide comprises a K127 substitution and a P106 substitution (based on the numbering depicted in FIG. 36A). In some cases, the variant 4-1BBL polypeptide comprises a K127 substitution and an L107 substitution (based on the numbering depicted in FIG. 36A). In some cases, the variant 4-1BBL polypeptide comprises a K127 substitution and an 5108 substitution (based on the numbering depicted in FIG. 36A). In some cases, the variant 4-1BBL polypeptide comprises a K127 substitution and a W109 substitution (based on the numbering depicted in FIG. 36A). In some cases, the variant 4-1BBL polypeptide comprises a K127 substitution and a Y110 substitution (based on the numbering depicted in FIG. 36A). In some cases, the variant 4-1BBL polypeptide comprises a K127 substitution and an 5111 substitution (based on the numbering depicted in FIG. 36A). In some cases, the variant 4-1BBL polypeptide comprises a K127 substitution and a D112 substitution (based on the numbering depicted in FIG. 36A). In some cases, the variant 4-1BBL polypeptide comprises a K127 substitution and a P113 substitution (based on the numbering depicted in FIG. 36A). In some cases, the variant 4-1BBL polypeptide comprises a K127 substitution and a G114 substitution (based on the numbering depicted in FIG. 36A). In some cases, the variant 4-1BBL polypeptide comprises a K127 substitution and an L115 substitution (based on the numbering depicted in FIG. 36A).

In some cases, a multimeric polypeptide of the present disclosure comprises: a) a first polypeptide comprising, in order from N-terminus to C-terminus: i) an epitope; and ii) a β2M polypeptide; and b) a second polypeptide comprising, in order from N-terminus to C-terminus: i) a first variant 4-1BBL polypeptide of the present disclosure; ii) a linker; iii) a second variant 4-1BBL polypeptide of the present disclosure; iv) a linker; v) a third variant 4-1BBL polypeptide of the present disclosure; vi) a Class I MHC heavy chain; and vii) an Fc polypeptide. In some cases, each of the first, second, and third variant 4-1BBL polypeptides comprises an amino acid sequence having at least 90%, at least 95%, at least 98%, or at least 99%, amino acid sequence identity to the amino acid sequence depicted in FIG. 36B, where amino acid 127 (indicated by an “x”) is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; e.g., each of the first, second, and third variant 4-1BBL polypeptides comprises an amino acid sequence having at least 90%, at least 95%, at least 98%, or at least 99%, amino acid sequence identity to the amino acid sequence set forth in SEQ ID NO:213, with an amino acid substitution at K47, e.g., where amino acid 47 is Gly, Ala, Val, Leu, Ile, Pro, Phe, Tyr, Trp, Ser, Thr, Cys, Met, Asn, Gln, Arg, His, Asp, or Glu. In some cases, the linker comprises a (GSSSS)n (SEQ ID NO:131) sequence, where n is 1, 2, 3, 4, or 5. In some cases, n is 4. In some cases, n is 5. In some cases, the variant 4-1BBL polypeptide comprises a K127 substitution and an M91 substitution (based on the numbering depicted in FIG. 36A). In some cases, the variant 4-1BBL polypeptide comprises a K127 substitution and an F92 substitution (based on the numbering depicted in FIG. 36A). In some cases, the variant 4-1BBL polypeptide comprises a K127 substitution and a Q94 substitution (based on the numbering depicted in FIG. 36A). In some cases, the variant 4-1BBL polypeptide comprises a K127 substitution and an L95 substitution (based on the numbering depicted in FIG. 36A). In some cases, the variant 4-1BBL polypeptide comprises a K127 substitution and a V96 substitution (based on the numbering depicted in FIG. 36A). In some cases, the variant 4-1BBL polypeptide comprises a K127 substitution and a Q98 substitution (based on the numbering depicted in FIG. 36A). In some cases, the variant 4-1BBL polypeptide comprises a K127 substitution and an N99 substitution (based on the numbering depicted in FIG. 36A). In some cases, the variant 4-1BBL polypeptide comprises a K127 substitution and a V100 substitution (based on the numbering depicted in FIG. 36A). In some cases, the variant 4-1BBL polypeptide comprises a K127 substitution and an L101 substitution (based on the numbering depicted in FIG. 36A). In some cases, the variant 4-1BBL polypeptide comprises a K127 substitution and an L102 substitution (based on the numbering depicted in FIG. 36A). In some cases, the variant 4-1BBL polypeptide comprises a K127 substitution and an 1103 substitution (based on the numbering depicted in FIG. 36A). In some cases, the variant 4-1BBL polypeptide comprises a K127 substitution and a D104 substitution (based on the numbering depicted in FIG. 36A). In some cases, the variant 4-1BBL polypeptide comprises a K127 substitution and a G105 substitution (based on the numbering depicted in FIG. 36A). In some cases, the variant 4-1BBL polypeptide comprises a K127 substitution and a P106 substitution (based on the numbering depicted in FIG. 36A). In some cases, the variant 4-1BBL polypeptide comprises a K127 substitution and an L107 substitution (based on the numbering depicted in FIG. 36A). In some cases, the variant 4-1BBL polypeptide comprises a K127 substitution and an 5108 substitution (based on the numbering depicted in FIG. 36A). In some cases, the variant 4-1BBL polypeptide comprises a K127 substitution and a W109 substitution (based on the numbering depicted in FIG. 36A). In some cases, the variant 4-1BBL polypeptide comprises a K127 substitution and a Y110 substitution (based on the numbering depicted in FIG. 36A). In some cases, the variant 4-1BBL polypeptide comprises a K127 substitution and an 5111 substitution (based on the numbering depicted in FIG. 36A). In some cases, the variant 4-1BBL polypeptide comprises a K127 substitution and a D112 substitution (based on the numbering depicted in FIG. 36A). In some cases, the variant 4-1BBL polypeptide comprises a K127 substitution and a P113 substitution (based on the numbering depicted in FIG. 36A). In some cases, the variant 4-1BBL polypeptide comprises a K127 substitution and a G114 substitution (based on the numbering depicted in FIG. 36A). In some cases, the variant 4-1BBL polypeptide comprises a K127 substitution and an L115 substitution (based on the numbering depicted in FIG. 36A).

Q227

In some cases, a multimeric polypeptide of the present disclosure comprises: a) a first polypeptide comprising, in order from N-terminus to C-terminus: i) an epitope; ii) a β2M polypeptide; and iii) a variant 4-1BBL polypeptide comprising an amino acid sequence having at least 90%, at least 95%, at least 98%, or at least 99%, amino acid sequence identity to the amino acid sequence depicted in FIG. 36D, where amino acid 227 (indicated by an "x") is an amino acid other than a glutamine, e.g., where amino acid 227 is Gly, Ala, Val, Leu, Ile, Pro, Phe, Tyr, Trp, Ser, Thr, Cys, Met, Asn, Lys, Arg, His, Asp, or Glu; or a variant 4-1BBL polypeptide of the present disclosure comprising an amino acid sequence having at least 90%, at least 95%, at least 98%, or at least 99%, amino acid sequence identity to the amino acid sequence set forth in SEQ ID NO:213, with an amino acid substitution at Q147, e.g., where amino acid 147 is Gly, Ala, Val, Leu, Ile, Pro, Phe, Tyr, Trp, Ser, Thr, Cys, Met, Asn, Lys, Arg, His, Asp, or Glu; and b) a second polypeptide comprising, in order from N-terminus to C-terminus: i) a Class I MHC heavy chain; and ii) an Fc polypeptide. In some cases, a multimeric polypeptide of the present disclosure comprises: a) a first polypeptide comprising, in order from N-terminus to C-terminus: i) an epitope; and ii) a β2M polypeptide; and b) a second polypeptide comprising, in order from N-terminus to C-terminus: i) a variant 4-1BBL polypeptide comprising an amino acid sequence having at least 90%, at least 95%, at least 98%, or at least 99%, amino acid sequence identity to the amino acid sequence depicted in FIG. 36D, where amino acid 227 (indicated by an "x") is an amino acid other than a glutamine, e.g., where amino acid 227 is Gly, Ala, Val, Leu, Ile, Pro, Phe, Tyr, Trp, Ser, Thr, Cys, Met, Asn, Lys, Arg, His, Asp, or Glu; or a variant 4-1BBL polypeptide of the present disclosure comprising an amino acid sequence having at least 90%, at least 95%, at least 98%, or at least 99%, amino acid sequence identity to the amino acid sequence set forth in SEQ ID NO:213, with an amino acid substitution at Q147, e.g., where amino acid 147 is Gly, Ala, Val, Leu, Ile, Pro, Phe, Tyr, Trp, Ser, Thr, Cys, Met, Asn, Lys, Arg, His, Asp, or Glu; ii) a Class I MHC heavy chain; and iii) an Fc polypeptide. In some cases, a multimeric polypeptide of the present disclosure comprises: a) a first polypeptide comprising, in order from N-terminus to C-terminus: i) an epitope; ii) a β2M polypeptide; iii) a first variant 4-1BBL polypeptide of the present disclosure; iv) a second variant 4-1BBL polypeptide of the present disclosure; and v) a third variant 4-1BBL polypeptide of the present disclosure; and b) a second polypeptide comprising, in order from N-terminus to C-terminus: i) a Class I MHC heavy chain; and ii) an Fc polypeptide. In some cases, each of the first, second, and third variant 4-1BBL polypeptides comprises an amino acid sequence having at least 90%, at least 95%, at least 98%, or at least 99%, amino acid sequence identity to the amino acid sequence depicted in FIG. 36D, where amino acid 227 (indicated by an "x") is an amino acid other than a glutamine, e.g., where amino acid 227 is Gly, Ala, Val, Leu, Ile, Pro, Phe, Tyr, Trp, Ser, Thr, Cys, Met, Asn, Lys, Arg, His, Asp, or Glu; or each of the first, second, and third variant 4-1BBL polypeptides comprises an amino acid sequence having at least 90%, at least 95%, at least 98%, or at least 99%, amino acid sequence identity to the amino acid sequence set forth in SEQ ID NO:213, with an amino acid substitution at Q147, e.g., where amino acid 147 is Gly, Ala, Val, Leu, Ile, Pro, Phe, Tyr, Trp, Ser, Thr, Cys, Met, Asn, Lys, Arg, His, Asp, or Glu. In some cases, a multimeric polypeptide of the present disclosure comprises: a) a first polypeptide comprising, in order from N-terminus to C-terminus: i) an epitope; and ii) a β2M polypeptide; and b) a second polypeptide comprising, in order from N-terminus to C-terminus: i) a first variant 4-1BBL polypeptide of the present disclosure; ii) a second variant 4-1BBL polypeptide of the present disclosure; and iii) a third variant 4-1BBL polypeptide of the present disclosure; iv) a Class I MHC heavy chain; and v) an Fc polypeptide. In some cases, each of the first, second, and third variant 4-1BBL polypeptides comprises an amino acid sequence having at least 90%, at least 95%, at least 98%, or at least 99%, amino acid sequence identity to the amino acid sequence depicted in FIG. 36D, where amino acid 227 (indicated by an "x") is an amino acid other than a glutamine, e.g., where amino acid 227 is Gly, Ala, Val, Leu, Ile, Pro, Phe, Tyr, Trp, Ser, Thr, Cys, Met, Asn, Lys, Arg, His, Asp, or Glu; or each of the first, second, and third variant 4-1BBL polypeptides comprises an amino acid sequence having at least 90%, at least 95%, at least 98%, or at least 99%, amino acid sequence identity to the amino acid sequence set forth in SEQ ID NO:213, with an amino acid substitution at Q147, e.g., where amino acid 147 is Gly, Ala, Val, Leu, Ile, Pro, Phe, Tyr, Trp, Ser, Thr, Cys, Met, Asn, Lys, Arg, His, Asp, or Glu.

In some cases, a multimeric polypeptide of the present disclosure comprises: a) a first polypeptide comprising, in order from N-terminus to C-terminus: i) an epitope; and ii) a β2M polypeptide; and b) a second polypeptide comprising, in order from N-terminus to C-terminus: i) a first variant 4-1BBL polypeptide of the present disclosure; ii) a linker; iii) a second variant 4-1BBL polypeptide of the present disclosure; iv) a linker; v) a third variant 4-1BBL polypeptide of the present disclosure; vi) a Class I MHC heavy chain; and vii) an Fc polypeptide. In some cases, each of the first, second, and third variant 4-1BBL polypeptides comprises an amino acid sequence having at least 90%, at least 95%, at least 98%, or at least 99%, amino acid sequence identity to the amino acid sequence depicted in FIG. 36D, where amino acid 227 (indicated by an "x") is an amino acid other than a glutamine, e.g., where amino acid 227 is Gly, Ala, Val, Leu, Ile, Pro, Phe, Tyr, Trp, Ser, Thr, Cys, Met, Asn, Lys, Arg, His, Asp, or Glu; or each of the first, second, and third variant 4-1BBL polypeptides comprises an amino acid sequence having at least 90%, at least 95%, at least 98%, or at least 99%, amino acid sequence identity to the amino acid sequence set forth in SEQ ID NO:213, with an amino acid substitution at Q147, e.g., where amino acid 147 is Gly, Ala, Val, Leu, Ile, Pro, Phe, Tyr, Trp, Ser, Thr, Cys, Met, Asn, Lys, Arg, His, Asp, or Glu. In some cases, the linker comprises a (GSSSS)n (SEQ ID NO:131) sequence, where n is 1, 2, 3, 4, or 5. In some cases, the linker comprises a (GSSSS)n (SEQ ID NO:131) sequence, where n is 4. In some cases, the linker comprises a (GSSSS)n (SEQ ID NO:131) sequence, where n is 5. In some cases, the linker comprises a (GGGGS)n sequence, where n is 1, 2, 3, 4, 5, 6, 7, 8, 9, or 10. In some cases, the linker comprises a (GGGGS)n sequence, where n is 2. In some cases, the linker comprises a (GGGGS)n sequence, where n is 3. In some cases, the linker comprises a (GGGGS)n sequence, where n is 4. In some cases, the linker comprises a (GGGGS)n sequence, where n is 5.

Multiple Immunomodulatory Domains

As noted above, in some cases, a multimeric polypeptide comprises two or more immunomodulatory polypeptides. In some cases, at least one of the two or more immunomodulatory polypeptide is a variant immunomodulatory polypeptide. For example, in the case of an IL-2/synTac, in some cases, at least one of the two or more immunomodulatory polypeptide is a variant IL-2 polypeptide. As another example, in the case of a 4-1BBL/synTac, in some cases, at least one of the two or more immunomodulatory polypeptide is a variant 4-1BBL polypeptide.

In some cases, a multimeric polypeptide comprises two or more copies of a variant IL-2 polypeptide of the present disclosure. In some cases, the two or more variant IL-2 polypeptides are on the same polypeptide chain of a multimeric polypeptide. In some cases, the two or more variant IL-2 polypeptides are on separate polypeptide chains of a multimeric polypeptide.

In some cases, a multimeric polypeptide comprises a first immunomodulatory polypeptide, and at least a second immunomodulatory polypeptide, where the first immunomodulatory polypeptide is a variant IL-2 polypeptide of the present disclosure, and the second immunomodulatory polypeptide is not an IL-2 polypeptide. For example, in some cases, the second immunomodulatory polypeptide is a member of the tumor necrosis factor (TNF) superfamily; e.g., a FasL polypeptide, a 4-1BBL polypeptide, a CD40 polypeptide, an OX40L polypeptide, a CD30L polypeptide, a CD70 polypeptide, etc. In some cases, the second immunomodulatory polypeptide of a multimeric polypeptide is a T-cell co-stimulatory polypeptide and is a member of the immunoglobulin (Ig) superfamily; e.g., a CD7 polypeptide, a CD86 polypeptide, an ICAM polypeptide, etc. In some cases, the second immunomodulatory polypeptide is 4-1BBL, OX40L, ICOS-L, ICAM, PD-L1, CD86, FasL, and PD-L2. Suitable immunomodulatory polypeptides of a multimeric polypeptide of the present disclosure include, e.g., CD7, CD30L, CD40, CD70, CD83, HLA-G, MICA, MICB, HVEM, lymphotoxin beta receptor, 3/TR6, ILT3, ILT4, or HVEM.

Further T cell modulatory domains (MODs) that can be included in a multimeric polypeptide of the present disclosure include naturally occurring or synthetic human gene products (protein), affinity reagents (e.g., an antibody, antibody fragment, single chain Fvs, aptamers, nanobody) targeting a human gene product, including, but not limited to all secreted proteins arising from classical and non-classical (e.g., FGF2, Ill, S100A4) secretion mechanisms, and ecto-domains of all cell surface proteins anchored by naturally occurring genetically encoded protein segments (single or multiple membrane spans) or post-translational modifications such as GPI linkages). Any naturally occurring or synthetic affinity reagent (e.g., antibody, antibody fragment, single chain Fvs, aptamer, nanobody, lectin, etc) targeting a cell surface glycan or other post-translational modification (e.g., sulfation). Examples include, but are not limited to, members of the TNF/TNFR family (OX40L, ICOSL, FASL, LTA, LTB TRAIL, CD153, TNFSF9, RANKL, TWEAK, TNFSF13, TNFSF13b, TNFSF14, TNFSF15, TNFSF18, CD40LG, CD70) or affinity reagents directed at the TNF/TNFR family members; members of the Immunoglobulin superfamily (VISTA, PD1, PD-L1, PD-L2, B71, B72, CTLA4, CD28, TIM3, CD4, CD8, CD19, T cell receptor chains, ICOS, ICOS ligand, HHLA2, butyrophilins, BTLA, B7-H3, B7-H4, CD3, CD79a, CD79b, IgSF CAMS (including CD2, CD58, CD48, CD150, CD229, CD244, ICAM-1), Leukocyte immunoglobulin like receptors (LILR), killer cell immunoglobulin like receptors (KIR)), lectin superfamily members, selectins, cytokines/chemokine and cytokine/chemokine receptors, growth factors and growth factor receptors), adhesion molecules (integrins, fibronectins, cadherins), or ecto-domains of multi-span integral membrane protein, or affinity reagents directed at the Immunoglobulin superfamily and listed gene products. In addition, active homologs/orthologs of these gene products, including but not limited to, viral sequences (e.g., CMV, EBV), bacterial sequences, fungal sequences, eukaryotic pathogens (e.g., *Schistosoma, Plasmodium, Babesia, Eimeria, Theileria, Toxoplasma, Entamoeba, Leishmania*, and *Trypanosoma*), and mammalian-derived coding regions. In addition, a MOD may comprise a small molecules drug targeting a human gene product.

Additional Polypeptides

A polypeptide chain of a multimeric polypeptide can include one or more polypeptides in addition to those described above. Suitable additional polypeptides include epitope tags and affinity domains. The one or more additional polypeptide can be included at the N-terminus of a polypeptide chain of a multimeric polypeptide, at the C-terminus of a polypeptide chain of a multimeric polypeptide, or internally within a polypeptide chain of a multimeric polypeptide.

Epitope Tag

Suitable epitope tags include, but are not limited to, hemagglutinin (HA; e.g., YPYDVPDYA (SEQ ID NO:79); FLAG (e.g., DYKDDDDK (SEQ ID NO:80); c-myc (e.g., EQKLISEEDL; SEQ ID NO:81), and the like.

Affinity Domain

Affinity domains include peptide sequences that can interact with a binding partner, e.g., such as one immobilized on a solid support, useful for identification or purification. DNA sequences encoding multiple consecutive single amino acids, such as histidine, when fused to the expressed protein, may be used for one-step purification of the recombinant protein by high affinity binding to a resin column, such as nickel sepharose. Exemplary affinity domains include His5 (HHHHH) (SEQ ID NO:82), HisX6 (HHHHHH) (SEQ ID NO:83), C-myc (EQKLISEEDL) (SEQ ID NO:81), Flag (DYKDDDDK) (SEQ ID NO:80), StrepTag (WSHPQFEK) (SEQ ID NO:84), hemagglutinin, e.g., HA Tag (YPYDVPDYA) (SEQ ID NO:79), glutathione-S-transferase (GST), thioredoxin, cellulose binding domain, RYIRS (SEQ ID NO:85), Phe-His-His-Thr (SEQ ID NO:86), chitin binding domain, S-peptide, T7 peptide, SH2 domain, C-end RNA tag, WEAAAREACCRECCARA (SEQ ID NO:87), metal binding domains, e.g., zinc binding domains or calcium binding domains such as those from calcium-binding proteins, e.g., calmodulin, troponin C, calcineurin B, myosin light chain, recoverin, S-modulin, visinin, VILIP, neurocalcin, hippocalcin, frequenin, caltractin, calpain large-subunit, S100 proteins, parvalbumin, calbindin D9K, calbindin D28K, and calretinin, inteins, biotin, streptavidin, MyoD, Id, leucine zipper sequences, and maltose binding protein.

Examples of IL-2/Multimeric Polypeptides

The following are non-limiting embodiments of an IL-2/synTac multimeric polypeptide suitable for use in a treatment method of the present disclosure.

In some cases, an IL-2/synTac multimeric polypeptide comprises: a) a first polypeptide comprising, in order from N-terminus to C-terminus: i) an epitope; ii) a β2-microglobulin (β2M) polypeptide comprising the amino acid sequence depicted in FIG. 34A; and b) a second polypeptide comprising, in order from N-terminus to C-terminus: i) a variant IL-2 polypeptide of the present disclosure; ii) a major histocompatibility complex (MHC) heavy chain polypeptide comprising the amino acid sequence depicted in FIG. 34C; and iii) an IgG1 Fc polypeptide comprising one or more amino acid substitutions selected from N297A, L234A, L235A, L234F, L235E, and P331S. In some cases, the variant IL-2 polypeptide comprises an H16A and an F42A substitution. In some cases, the IgG1 Fc polypeptide comprises an N297A substitution. In some cases, the IgG1 Fc polypeptide comprises an L234A substitution and an L235A substitution. In some cases, the IgG1 Fc polypeptide comprises an L234F substitution and an L235E substitution. In some cases, the IgG1 Fc polypeptide comprises an L234F substitution, an L235E substitution, and a P331S substitution. In some cases, the second polypeptide comprises two copies of the variant IL-2 polypeptide. In some cases, the first polypeptide comprises a peptide linker between the epitope and the β2M polypeptide. In some cases, the second polypeptide comprises a peptide linker between one or more of: a) a first copy of the variant IL-2 polypeptide and a second copy of the variant IL-2 polypeptide; b) the variant IL-2 polypeptide and the MHC heavy chain polypeptide; and c) between the MHC heavy chain polypeptide and the IgG1 Fc polypeptide. In some cases, the peptide linker is selected from $(GGGGS)_3$ (SEQ ID NO:207), $(GGGGS)_4$ (SEQ ID NO:208), and AAAGG (SEQ ID NO:73). In some cases, the IgG1 Fc polypeptide comprises the amino acid sequence depicted in FIG. 33B. In some cases, the IgG1 Fc polypeptide comprises the amino acid sequence depicted in FIG. 33C. In some cases, the IgG1 Fc polypeptide comprises the amino acid sequence depicted in FIG. 33D.

In some cases, a multimeric polypeptide comprises: a) a first polypeptide comprising, in order from N-terminus to C-terminus: i) an epitope; ii) a β2-microglobulin polypeptide comprising the amino acid sequence depicted in FIG. 34A; and b) a second polypeptide comprising, in order from N-terminus to C-terminus: i) a variant IL-2 polypeptide comprising the amino acid sequence depicted in FIG. 34B; ii) a major histocompatibility complex (MHC) heavy chain polypeptide comprising the amino acid sequence depicted in FIG. 34C; and iii) an IgG1 Fc polypeptide comprising one or more amino acid substitutions selected from N297A, L234A, L235A, L234F, L235E, and P331S. In some cases, the IgG1 Fc polypeptide comprises an N297A substitution. In some cases, the IgG1 Fc polypeptide comprises an L234A substitution and an L235A substitution. In some cases, the IgG1 Fc polypeptide comprises an L234F substitution and an L235E substitution. In some cases, the IgG1 Fc polypeptide comprises an L234F substitution, an L235E substitution, and a P331S substitution. In some cases, the IgG1 Fc polypeptide comprises the amino acid sequence depicted in FIG. 33B. In some cases, the IgG1 Fc polypeptide comprises the amino acid sequence depicted in FIG. 33C. In some cases, the IgG1 Fc polypeptide comprises the amino acid sequence depicted in FIG. 33D. In some cases, in the second polypeptide comprises two copies of the variant IL-2 polypeptide. In some cases, the first polypeptide comprises a peptide linker between the epitope and the β2M polypeptide. In some cases, the second polypeptide comprises a peptide linker between one or more of: a) a first copy of the variant IL-2 polypeptide and a second copy of the variant IL-2 polypeptide; b) the variant IL-2 polypeptide and the MHC heavy chain polypeptide; and c) between the MHC heavy chain polypeptide and the IgG1 Fc polypeptide. In some cases, the peptide linker is selected from $(GGGGS)_3$ (SEQ ID NO:207), $(GGGGS)_4$ (SEQ ID NO:208), and AAAGG (SEQ ID NO:73).

In some cases, multimeric polypeptide comprises: a) a first polypeptide comprising, in order from N-terminus to C-terminus: i) an epitope comprising the amino acid sequence YMLDLQPETT (SEQ ID NO:77); ii) a β2-microglobulin polypeptide comprising the amino acid sequence depicted in FIG. 34A; and b) a second polypeptide comprising, in order from N-terminus to C-terminus: i) a variant IL-2 polypeptide comprising the amino acid sequence depicted in FIG. 34B; ii) a major histocompatibility complex (MHC) heavy chain polypeptide comprising the amino acid sequence depicted in FIG. 34C; and iii) an IgG1 Fc polypeptide comprising the amino acid sequence depicted in FIG. 33A, 33B, 33C, or 33D. In some cases, the IgG1 Fc polypeptide comprises the amino acid sequence depicted in FIG. 33B. In some cases, the IgG1 Fc polypeptide comprises the amino acid sequence depicted in FIG. 33C. In some cases, the IgG1 Fc polypeptide comprises the amino acid sequence depicted in FIG. 33D. In some cases, the second polypeptide comprises two copies of the variant IL-2 polypeptide. In some cases, the first polypeptide comprises a peptide linker between the epitope and the β2M polypeptide. In some cases, the second polypeptide comprises a peptide linker between one or more of: a) a first copy of the variant IL-2 polypeptide and a second copy of the variant IL-2 polypeptide; b) the variant IL-2 polypeptide and the MHC heavy chain polypeptide; and c) between the MHC heavy chain polypeptide and the IgG1 Fc polypeptide. In some cases, the peptide linker is selected from $(GGGGS)_3$ (SEQ ID NO:207), $(GGGGS)_4$ (SEQ ID NO:208), and AAAGG (SEQ ID NO:73). In some cases, the IgG1 Fc polypeptide comprises the amino acid sequence depicted in FIG. 33B. In some cases, the IgG1 Fc polypeptide comprises the amino acid sequence depicted in FIG. 33C. In some cases, the IgG1 Fc polypeptide comprises the amino acid sequence depicted in FIG. 33D.

In some cases, a multimeric polypeptide comprises: a) a first polypeptide comprising the amino acid sequence depicted in FIG. 31; and b) a second polypeptide comprising the amino acid sequence depicted in FIG. 22.

In some cases, a multimeric polypeptide comprises: a) a first polypeptide comprising the amino acid sequence depicted in FIG. 31; and b) a second polypeptide comprising the amino acid sequence depicted in FIG. 25.

In some cases, a multimeric polypeptide comprises: a) a first polypeptide comprising the amino acid sequence depicted in FIG. 31; and ab) a second polypeptide comprising the amino acid sequence depicted in FIG. 28.

Formulations, Doses, and Routes of Administration

In carrying out a treatment method of the present disclosure, a synTac can be formulated in a composition comprising a pharmaceutically acceptable excipient, and an immune checkpoint inhibitor can be formulated in a composition comprising a pharmaceutically acceptable excipient. For simplicity, the term "active agent" is used below to refer to a synTac or an immune checkpoint inhibitor. In general, the synTac and the immune checkpoint inhibitor are present in separate compositions.

The composition may comprise a pharmaceutically acceptable excipient, a variety of which are known in the art and need not be discussed in detail herein. Pharmaceutically acceptable excipients have been amply described in a variety of publications, including, for example, "Remington: The Science and Practice of Pharmacy", $19^{th}$ Ed. (1995), or latest edition, Mack Publishing Co; A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

A pharmaceutical composition can comprise a synTac or an immune checkpoint inhibitor, and a pharmaceutically acceptable excipient. In some cases, a pharmaceutical composition will be suitable for administration to a subject, e.g., will be sterile. For example, in some cases, a pharmaceutical composition will be suitable for administration to a human subject, e.g., where the composition is sterile and is free of detectable pyrogens and/or other toxins.

The compositions may comprise other components, such as pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate, hydrochloride, sulfate salts, solvates (e.g., mixed ionic salts, water, organics), hydrates (e.g., water), and the like.

For example, compositions may include aqueous solution, powder form, granules, tablets, pills, suppositories, capsules, suspensions, sprays, and the like. The composition may be formulated according to the various routes of administration described below.

Where an active agent (a synTac or an immune checkpoint inhibitor) is administered as an injectable (e.g. subcutaneously, intraperitoneally, intramuscularly, and/or intravenously) directly into a tissue, a formulation can be provided as a ready-to-use dosage form, or as non-aqueous form (e.g. a reconstitutable storage-stable powder) or aqueous form, such as liquid composed of pharmaceutically acceptable carriers and excipients. The formulations may also be provided so as to enhance serum half-life of an active agent following administration. For example, the protein may be provided in a liposome formulation, prepared as a colloid, or other conventional techniques for extending serum half-life. A variety of methods are available for preparing liposomes, as described in, e.g., Szoka et al. 1980 *Ann. Rev. Biophys. Bioeng.* 9:467, U.S. Pat. Nos. 4,235,871, 4,501,728 and 4,837,028. The preparations may also be provided in controlled release or slow-release forms.

Other examples of formulations suitable for parenteral administration include isotonic sterile injection solutions, anti-oxidants, bacteriostats, and solutes that render the formulation isotonic with the blood of the intended recipient, suspending agents, solubilizers, thickening agents, stabilizers, and preservatives. For example, a subject pharmaceutical composition can be present in a container, e.g., a sterile container, such as a syringe. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

The concentration of an active agent (a synTac or an immune checkpoint inhibitor) in a formulation can vary widely (e.g., from less than about 0.1%, usually at or at least about 2% to as much as 20% to 50% or more by weight) and will usually be selected primarily based on fluid volumes, viscosities, and patient-based factors in accordance with the particular mode of administration selected and the patient's needs.

The present disclosure provides a container comprising an active agent (a synTac or an immune checkpoint inhibitor), e.g., a container comprising a liquid composition comprising an active agent. The container can be, e.g., a syringe, an ampoule, and the like. In some cases, the container is sterile. In some cases, both the container and the composition are sterile.

The present disclosure provides compositions, including pharmaceutical compositions, comprising an active agent (a synTac or an immune checkpoint inhibitor). A composition can comprise: a) an active agent (a synTac or an immune checkpoint inhibitor); and b) an excipient, as described above. In some cases, the excipient is a pharmaceutically acceptable excipient.

Compositions Comprising a Nucleic Acid or a Recombinant Expression Vector

In some cases, a synTac is administered as a multimeric polypeptide per se. In other instances, one or more nucleic acids comprising nucleotide sequences encoding a synTac are administered, instead of administering a synTac as a multimeric polypeptide per se. The nucleic acid(s) can be present in a pharmaceutical composition. A pharmaceutical composition can comprise one or more recombinant expression vectors comprising the one or more nucleic acids. A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

A pharmaceutical formulation can include a nucleic acid or recombinant expression vector of the present disclosure in an amount of from about 0.001% to about 90% (w/w). In the description of formulations, below, "nucleic acid or recombinant expression vector" will be understood to include a nucleic acid or recombinant expression vector comprising nucleotide sequences encoding a synTac.

A nucleic acid or recombinant expression vector can be admixed, encapsulated, conjugated or otherwise associated with other compounds or mixtures of compounds; such compounds can include, e.g., liposomes or receptor-targeted molecules. A nucleic acid or recombinant expression vector can be combined in a formulation with one or more components that assist in uptake, distribution and/or absorption.

A nucleic acid or recombinant expression vector composition can be formulated into any of many possible dosage forms such as, but not limited to, tablets, capsules, gel capsules, liquid syrups, soft gels, suppositories, and enemas. A nucleic acid or recombinant expression vector composition can also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

A formulation comprising a nucleic acid or recombinant expression vector can be a liposomal formulation. As used herein, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes that can interact with negatively charged DNA molecules to form a stable complex. Liposomes that are pH sensitive or negatively charged are believed to entrap DNA rather than complex with it. Both cationic and noncationic liposomes can be used to deliver a subject nucleic acid or recombinant expression vector.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein by reference in its entirety.

The formulations and compositions of the present disclosure may also include surfactants. The use of surfactants in drug products, formulations and in emulsions is well known in the art. Surfactants and their uses are further described in U.S. Pat. No. 6,287,860.

In one embodiment, various penetration enhancers are included, to effect the efficient delivery of nucleic acids. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein by reference in its entirety.

Compositions and formulations for oral administration include powders or granules, microparticulates, nanoparticulates, suspensions or solutions in water or non-aqueous media, capsules, gel capsules, sachets, tablets, or minitablets. Thickeners, flavoring agents, diluents, emulsifiers, dispersing aids or binders may be desirable. Suitable oral formulations include those in which a subject antisense nucleic acid is administered in conjunction with one or more penetration enhancers surfactants and chelators. Suitable surfactants include, but are not limited to, fatty acids and/or esters or salts thereof, bile acids and/or salts thereof. Suitable bile acids/salts and fatty acids and their uses are further described in U.S. Pat. No. 6,287,860. Also suitable are combinations of penetration enhancers, for example, fatty acids/salts in combination with bile acids/salts. An exemplary suitable combination is the sodium salt of lauric acid, capric acid, and UDCA. Further penetration enhancers include, but are not limited to, polyoxyethylene-9-lauryl ether, and polyoxyethylene-20-cetyl ether. Suitable penetration enhancers also include propylene glycol, dimethylsulfoxide, triethanoiamine, N,N-dimethylacetamide, N,N-dimethylformamide, 2-pyrrolidone and derivatives thereof, tetrahydrofurfuryl alcohol, and AZONE™.

Treatment Methods

The present disclosure provides a treatment method, comprising administering a synTac and an immune checkpoint inhibitor. In some cases, the method comprises administering to an individual in need thereof: a) a first composition comprising a synTac; and b) a second composition comprising an immune checkpoint inhibitor. In some cases, a treatment method of the present disclosure comprises administering to an individual in need thereof: a) a first composition comprising one or more recombinant expression vectors comprising nucleotide sequences encoding a synTac; and b) a second composition comprising an immune checkpoint inhibitor. In some cases, a treatment method of the present disclosure comprises administering to an individual in need thereof: a) a first composition comprising one or more mRNA molecules comprising nucleotide sequences encoding a multimeric polypeptide; and b) a second composition comprising an immune checkpoint inhibitor. In some cases, the immune checkpoint inhibitor is an antibody specific for an immune checkpoint polypeptide.

Thus, for example, a treatment method of the present disclosure can comprise co-administration of a synTac (e.g., a 4-1BBL synTac, IL-2 synTac, etc., as described above) and an antibody specific for an immune checkpoint. By "co-administration" is meant that both a synTac (e.g., a 4-1BBL synTac, IL-2 synTac, etc., as described above) and an antibody specific for an immune checkpoint are administered to an individual, although not necessarily at the same time, in order to achieve a therapeutic effect that is the result of having administered both the synTac and the immune checkpoint inhibitor. The administration of the synTac (e.g., a 4-1BBL synTac, IL-2 synTac, etc.) and the antibody specific for an immune checkpoint can be substantially simultaneous, e.g., the synTac (e.g., a 4-1BBL synTac, IL-2 synTac, etc.) can be administered to an individual within about 1 minute to about 24 hours (e.g., within about 1 minute, within about 5 minutes, within about 15 minutes, within about 30 minutes, within about 1 hour, within about 4 hours, within about 8 hours, within about 12 hours, or within about 24 hours) of administration of the antibody specific for an immune checkpoint. In some cases, a synTac (e.g., a 4-1BBL synTac, IL-2 synTac, etc.) is administered to an individual who is undergoing treatment with an antibody specific for an immune checkpoint. The administration of the synTac (e.g., a 4-1BBL synTac, IL-2 synTac, etc.) and the antibody specific for an immune checkpoint can occur at different times and/or at different frequencies.

Thus, for example, a treatment method of the present disclosure can comprise co-administration of a 4-1BBL synTac and an antibody specific for an immune checkpoint. By "co-administration" is meant that both a 4-1BBL synTac and an antibody specific for an immune checkpoint are administered to an individual, although not necessarily at the same time, in order to achieve a therapeutic effect that is the result of having administered both the synTac and the immune checkpoint inhibitor. The administration of the 4-1BBL synTac and the antibody specific for an immune checkpoint can be substantially simultaneous, e.g., the 4-1BBL synTac can be administered to an individual within about 1 minute to about 24 hours (e.g., within about 1 minute, within about 5 minutes, within about 15 minutes, within about 30 minutes, within about 1 hour, within about 4 hours, within about 8 hours, within about 12 hours, or within about 24 hours) of administration of the antibody specific for an immune checkpoint. In some cases, a 4-1BBL synTac is administered to an individual who is undergoing treatment with an antibody specific for an immune checkpoint. The administration of the 4-1BBL synTac and the antibody specific for an immune checkpoint can occur at different times and/or at different frequencies.

As another example, a treatment method of the present disclosure can comprise co-administration of a synTac (e.g., an IL-2 synTac, as described above) and an antibody specific for an immune checkpoint. By "co-administration" is meant that both an IL-2 synTac and an antibody specific for an immune checkpoint are administered to an individual, although not necessarily at the same time, in order to achieve a therapeutic effect that is the result of having administered both the synTac and the immune checkpoint inhibitor. The administration of the IL-2 synTac and the antibody specific for an immune checkpoint can be substantially simultaneous, e.g., the IL-2 synTac can be administered to an individual within about 1 minute to about 24 hours (e.g., within about 1 minute, within about 5 minutes, within about 15 minutes, within about 30 minutes, within about 1 hour, within about 4 hours, within about 8 hours, within about 12 hours, or within about 24 hours) of administration of the antibody specific for an immune checkpoint. In some cases, an IL-2 synTac is administered to an individual who is undergoing treatment with an antibody specific for an immune checkpoint. The administration of the IL-2 synTac and the antibody specific for an immune checkpoint can occur at different times and/or at different frequencies.

The present disclosure provides a treatment method, comprising administering a synTac and an immune checkpoint inhibitor. A treatment method of the present disclosure can modulate an activity of a target T cell. In some cases, e.g., where the target T cell is a $CD8^+$ T cell, the multimeric polypeptide comprises Class I MHC polypeptides (e.g., β2-microglobulin and Class I MHC heavy chain). In some cases, e.g., where the target T cell is a $CD4^+$ T cell, the multimeric polypeptide comprises Class II MHC polypeptides (e.g., Class II MHC a chain; Class II MHC chain).

Where a multimeric polypeptide includes an immunomodulatory polypeptide that is an activating polypeptide, a method of the present disclosure activates the epitope-specific T cell. In some instances, the epitope-specific T cell is a T cell that is specific for an epitope present on a cancer cell, and contacting the epitope-specific T cell with the multimeric polypeptide increases cytotoxic activity of the T cell toward the cancer cell. In some instances, the epitope-specific T cell is a T cell that is specific for an epitope present on a cancer cell, and a method of the present disclosure increases the number of the epitope-specific T cells.

In some instances, the epitope-specific T cell is a T cell that is specific for an epitope present on a virus-infected cell, and a method of the present disclosure increases cytotoxic activity of the T cell toward the virus-infected cell. In some instances, the epitope-specific T cell is a T cell that is specific for an epitope present on a virus-infected cell, and a method of the present disclosure increases the number of the epitope-specific T cells.

Where a multimeric polypeptide of the present disclosure includes an immunomodulatory polypeptide that is an inhibiting polypeptide, a method of the present disclosure inhibits the epitope-specific T cell. In some instances, the epitope-specific T cell is a self-reactive T cell that is specific for an epitope present in a self antigen, and a method of the present disclosure reduces the number of the self-reactive T cells.

In some cases, the immunomodulatory polypeptide is an activating polypeptide, and the multimeric polypeptide activates the epitope-specific T cell. In some cases, the epitope is a cancer-associated epitope, and the multimeric polypeptide increases the activity of a T cell specific for the cancer-associate epitope.

In some cases, a treatment method of the present disclosure treats a cancer in an individual having the cancer. Thus, the present disclosure provides a method of treating cancer in an individual, the method comprising administering to the individual: a) a multimeric polypeptide of the present disclosure, or one or more nucleic acids (e.g., expression vectors; mRNA; etc.) comprising nucleotide sequences encoding the multimeric polypeptide, where the multimeric polypeptide comprises a T-cell epitope that is a cancer epitope, and where the multimeric polypeptide comprises a stimulatory immunomodulatory polypeptide; and b) an immune checkpoint inhibitor. In some cases, "effective amounts" of a multimeric polypeptide and an immune checkpoint inhibitor are amounts that, when administered in one or more doses to an individual in need thereof, reduce the number of cancer cells in the individual. For example, in some cases, "effective amounts" of a multimeric polypeptide and an immune checkpoint inhibitor are amounts that, when administered in one or more doses to an individual in need thereof, reduce the number of cancer cells in the individual by at least 10%, at least 15%, at least 20%, at least 25%, at least 30%, at least 40%, at least 50%, at least 60%, at least 70%, at least 80%, at least 90%, or at least 95%, compared to the number of cancer cells in the individual before administration of the multimeric polypeptide and the immune checkpoint inhibitor, or in the absence of administration with the multimeric polypeptide and the immune checkpoint inhibitor. In some cases, "effective amounts" of a multimeric polypeptide and an immune checkpoint inhibitor are amounts that, when administered in one or more doses to an individual in need thereof, reduce the number of cancer cells in the individual to undetectable levels. In some cases, "effective amounts" of a multimeric polypeptide and an immune checkpoint inhibitor are amounts that, when administered in one or more doses to an individual in need thereof, reduce the tumor mass in the individual. For example, in some cases, "effective amounts" of a multimeric polypeptide and an immune checkpoint inhibitor are amounts that, when administered in one or more doses to an individual in need thereof, reduce the tumor mass in the individual by at least 10%, at least 15%, at least 20%, at least 25%, at least 30%, at least 40%, at least 50%, at least 60%, at least 70%, at least 80%, at least 90%, or at least 95%, compared to the tumor mass in the individual before administration of the multimeric polypeptide and the immune checkpoint inhibitor, or in the absence of administration with the multimeric polypeptide and the immune checkpoint inhibitor. In some cases, "effective amounts" of a multimeric polypeptide and an immune checkpoint inhibitor are amounts that, when administered in one or more doses to an individual in need thereof, increase survival time of the individual. For example, in some cases, "effective amounts" of a multimeric polypeptide and an immune checkpoint inhibitor are amounts that, when administered in one or more doses to an individual in need thereof, increase survival time of the individual by at least 1 month, at least 2 months, at least 3 months, from 3 months to 6 months, from 6 months to 1 year, from 1 year to 2 years, from 2 years to 5 years, from 5 years to 10 years, or more than 10 years, compared to the expected survival time of the individual in the absence of administration with the multimeric polypeptide and the immune checkpoint inhibitor.

In some instances, the epitope-specific T cell is a T cell that is specific for an epitope present on a virus-infected cell, and a method of the present disclosure increases cytotoxic activity of the T cell toward the virus-infected cell. In some instances, the epitope-specific T cell is a T cell that is specific for an epitope present on a virus-infected cell, and a method of the present disclosure increases the number of the epitope-specific T cells.

As noted above, in some cases, in carrying out a subject treatment method, a multimeric polypeptide is administered to an individual in need thereof, as the polypeptide per se. In other instances, in carrying out a subject treatment method, one or more nucleic acids comprising nucleotide sequences encoding a multimeric polypeptide is/are administering to an individual in need thereof. Thus, in other instances, one or more nucleic acids encoding a synTac is/are administered to an individual in need thereof.

Dosages—synTac

A suitable dosage of a synTac can be determined by an attending physician or other qualified medical personnel, based on various clinical factors. As is well known in the medical arts, dosages for any one patient depend upon many factors, including the patient's size, body surface area, age, the particular polypeptide or nucleic acid to be administered, sex of the patient, time, and route of administration, general health, and other drugs being administered concurrently. A multimeric polypeptide (synTac) may be administered in amounts between 1 ng/kg body weight and 20 mg/kg body weight per dose, e.g. between 0.1 mg/kg body weight to 10 mg/kg body weight, e.g. between 0.5 mg/kg body weight to 5 mg/kg body weight; however, doses below or above this exemplary range are envisioned, especially considering the aforementioned factors. If the regimen is a continuous infusion, it can also be in the range of 1 μg to 10 mg per kilogram of body weight per minute. A multimeric polypeptide can be administered in an amount of from about 1 mg/kg body weight to 50 mg/kg body weight, e.g., from about 1 mg/kg body weight to about 5 mg/kg body weight, from about 5 mg/kg body weight to about 10 mg/kg body weight, from about 10 mg/kg body weight to about 15 mg/kg body weight, from about 15 mg/kg body weight to about 20 mg/kg body weight, from about 20 mg/kg body weight to about 25 mg/kg body weight, from about 25 mg/kg body weight to about 30 mg/kg body weight, from about 30 mg/kg body weight to about 35 mg/kg body weight, from about 35 mg/kg body weight to about 40 mg/kg body weight, or from about 40 mg/kg body weight to about 50 mg/kg body weight.

In some cases, a suitable dose of a multimeric polypeptide is from 0.01 μg to 100 g per kg of body weight, from 0.1 μg to 10 g per kg of body weight, from 1 μg to 1 g per kg of body weight, from 10 μg to 100 mg per kg of body weight, from 100 μg to 10 mg per kg of body weight, or from 100 μg to 1 mg per kg of body weight. Persons of ordinary skill in the art can easily estimate repetition rates for dosing based on measured residence times and concentrations of the administered agent in bodily fluids or tissues. Following successful treatment, it may be desirable to have the patient undergo maintenance therapy to prevent the recurrence of the disease state, wherein a multimeric polypeptide is administered in maintenance doses, ranging from 0.01 μg to 100 g per kg of body weight, from 0.1 μg to 10 g per kg of body weight, from 1 μg to 1 g per kg of body weight, from 10 μg to 100 mg per kg of body weight, from 100 μg to 10 mg per kg of body weight, or from 100 μg to 1 mg per kg of body weight.

Those of skill will readily appreciate that dose levels can vary as a function of the specific multimeric polypeptide, the severity of the symptoms and the susceptibility of the subject to side effects. Preferred dosages for a given compound are readily determinable by those of skill in the art by a variety of means.

In some embodiments, multiple doses of a multimeric polypeptide (or a nucleic acid or a recombinant expression vector encoding same) are administered. The frequency of administration of a multimeric polypeptide can vary depending on any of a variety of factors, e.g., severity of the symptoms, etc. For example, in some embodiments, a multimeric polypeptide is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

The duration of administration of a multimeric polypeptide, e.g., the period of time over which a multimeric polypeptide is administered, can vary, depending on any of a variety of factors, e.g., patient response, etc. For example, a multimeric polypeptide can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

A suitable dosage of a synTac can be determined by an attending physician or other qualified medical personnel, based on various clinical factors. As is well known in the medical arts, dosages for any one patient depend upon many factors, including the patient's size, body surface area, age, the particular polypeptide or nucleic acid to be administered, sex of the patient, time, and route of administration, general health, and other drugs being administered concurrently. A multimeric polypeptide (synTac) may be administered in amounts between 1 ng/kg body weight and 20 mg/kg body weight per dose, e.g. between 0.1 mg/kg body weight to 10 mg/kg body weight, e.g. between 0.5 mg/kg body weight to 5 mg/kg body weight; however, doses below or above this exemplary range are envisioned, especially considering the aforementioned factors. If the regimen is a continuous infusion, it can also be in the range of 1 μg to 10 mg per kilogram of body weight per minute. A multimeric polypeptide can be administered in an amount of from about 1 mg/kg body weight to 50 mg/kg body weight, e.g., from about 1 mg/kg body weight to about 5 mg/kg body weight, from about 5 mg/kg body weight to about 10 mg/kg body weight, from about 10 mg/kg body weight to about 15 mg/kg body weight, from about 15 mg/kg body weight to about 20 mg/kg body weight, from about 20 mg/kg body weight to about 25 mg/kg body weight, from about 25 mg/kg body weight to about 30 mg/kg body weight, from about 30 mg/kg body weight to about 35 mg/kg body weight, from about 35 mg/kg body weight to about 40 mg/kg body weight, or from about 40 mg/kg body weight to about 50 mg/kg body weight.

In some cases, a suitable dose of a multimeric polypeptide is from 0.01 μg to 100 g per kg of body weight, from 0.1 μg to 10 g per kg of body weight, from 1 μg to 1 g per kg of body weight, from 10 μg to 100 mg per kg of body weight, from 100 μg to 10 mg per kg of body weight, or from 100 μg to 1 mg per kg of body weight. Persons of ordinary skill in the art can easily estimate repetition rates for dosing based on measured residence times and concentrations of the administered agent in bodily fluids or tissues. Following successful treatment, it may be desirable to have the patient undergo maintenance therapy to prevent the recurrence of the disease state, wherein a multimeric polypeptide is administered in maintenance doses, ranging from 0.01 μg to 100 g per kg of body weight, from 0.1 μg to 10 g per kg of body weight, from 1 μg to 1 g per kg of body weight, from 10 μg to 100 mg per kg of body weight, from 100 μg to 10 mg per kg of body weight, or from 100 μg to 1 mg per kg of body weight.

Those of skill will readily appreciate that dose levels can vary as a function of the specific multimeric polypeptide, the severity of the symptoms and the susceptibility of the subject to side effects. Preferred dosages for a given compound are readily determinable by those of skill in the art by a variety of means.

In some embodiments, multiple doses of a multimeric polypeptide (or a nucleic acid or a recombinant expression vector encoding same) are administered. The frequency of administration of a multimeric polypeptide can vary depending on any of a variety of factors, e.g., severity of the symptoms, etc. For example, in some embodiments, a multimeric polypeptide is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

The duration of administration of a multimeric polypeptide, e.g., the period of time over which a multimeric polypeptide is administered, can vary, depending on any of a variety of factors, e.g., patient response, etc. For example, a multimeric polypeptide can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

Dosages—Immune Checkpoint Inhibitor

A suitable dosage of an immune checkpoint inhibitor can be determined by an attending physician or other qualified medical personnel, based on various clinical factors. As is well known in the medical arts, dosages for any one patient depend upon many factors, including the patient's size, body surface area, age, the particular polypeptide or nucleic acid to be administered, sex of the patient, time, and route of administration, general health, and other drugs being administered concurrently. An immune checkpoint inhibitor may be administered in amounts between 1 ng/kg body weight and 20 mg/kg body weight per dose, e.g. between 0.1 mg/kg body weight to 10 mg/kg body weight, e.g. between 0.5 mg/kg body weight to 5 mg/kg body weight; however, doses below or above this exemplary range are envisioned, especially considering the aforementioned factors. If the regimen is a continuous infusion, it can also be in the range of 1 μg to 10 mg per kilogram of body weight per minute. An immune checkpoint inhibitor can be administered in an amount of from about 1 mg/kg body weight to 50 mg/kg body weight, e.g., from about 1 mg/kg body weight to about 5 mg/kg body weight, from about 5 mg/kg body weight to about 10 mg/kg body weight, from about 10 mg/kg body weight to about 15 mg/kg body weight, from about 15 mg/kg body weight to about 20 mg/kg body weight, from about 20 mg/kg body weight to about 25 mg/kg body weight, from about 25 mg/kg body weight to about 30 mg/kg body weight, from about 30 mg/kg body weight to about 35 mg/kg body weight, from about 35 mg/kg body weight to about 40 mg/kg body weight, or from about 40 mg/kg body weight to about 50 mg/kg body weight.

In some cases, a suitable dose of an immune checkpoint inhibitor is from 0.01 μg to 100 g per kg of body weight, from 0.1 μg to 10 g per kg of body weight, from 1 μg to 1 g per kg of body weight, from 10 μg to 100 mg per kg of body weight, from 100 μg to 10 mg per kg of body weight, or from 100 μg to 1 mg per kg of body weight. Persons of ordinary skill in the art can easily estimate repetition rates for dosing based on measured residence times and concentrations of the administered agent in bodily fluids or tissues. Following successful treatment, it may be desirable to have the patient undergo maintenance therapy to prevent the recurrence of the disease state, wherein an immune checkpoint inhibitor is administered in maintenance doses, ranging from 0.01 μg to 100 g per kg of body weight, from 0.1 μg to 10 g per kg of body weight, from 1 μg to 1 g per kg of body weight, from 10 μg to 100 mg per kg of body weight, from 100 μg to 10 mg per kg of body weight, or from 100 μg to 1 mg per kg of body weight.

Those of skill will readily appreciate that dose levels can vary as a function of the specific immune checkpoint inhibitor, the severity of the symptoms and the susceptibility of the subject to side effects. Preferred dosages for a given compound are readily determinable by those of skill in the art by a variety of means.

In some embodiments, multiple doses of an immune checkpoint inhibitor are administered. The frequency of administration an immune checkpoint inhibitor can vary depending on any of a variety of factors, e.g., severity of the symptoms, etc. For example, in some embodiments, a multimeric polypeptide is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

The duration of administration of an immune checkpoint inhibitor, e.g., the period of time over which an immune checkpoint inhibitor is administered, can vary, depending on any of a variety of factors, e.g., patient response, etc. For example, an immune checkpoint inhibitor can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

The following are non-limiting examples.

Pembrolizumab can be administered to an individual in need thereof in an amount of 2 mg/kg every 3 weeks. Pembrolizumab can be administered to an individual in need thereof in an amount of 200 mg every 3 weeks. In some cases, a method of the present disclosure provides for a reduced amount of an anti-PD1 that needs to be administered to achieve clinical benefit. For example, in some cases, the amount of pembrolizumab that needs to be administered to achieve clinical benefit can be reduced by from 10% to 50%, or more than 50%, compared to the amount of pembrolizumab that needs to be administered to achieve clinical benefit in the absence of treatment with a synTac.

Nivolumab can be administered to an individual in need thereof in an amount of 3 mg/kg every 2 weeks. Nivolumab can be administered to an individual in need thereof in an amount of 240 mg every 2 weeks. In some cases, a method of the present disclosure provides for a reduced amount of an anti-PD1 that needs to be administered to achieve clinical benefit. For example, in some cases, the amount of nivolumab that needs to be administered to achieve clinical benefit can be reduced by from 10% to 50%, or more than 50%, compared to the amount of nivolumab that needs to be administered to achieve clinical benefit in the absence of treatment with a synTac.

Atezolizumab can be administered to an individual in need thereof in an amount of 1200 mg every 3 weeks. In some cases, a method of the present disclosure provides for a reduced amount of an anti-PD1 that needs to be administered to achieve clinical benefit. For example, in some cases, the amount of atezolizumab that needs to be administered to achieve clinical benefit can be reduced by from 10% to 50%, or more than 50%, compared to the amount of atezolizumab that needs to be administered to achieve clinical benefit in the absence of treatment with a synTac.

Ipilimumab can be administered to an individual in need thereof in an amount of 3 mg/kg every 3 weeks. Ipilimumab can be administered to an individual in need thereof in an amount of 10 mg/kg every 3 weeks. Ipilimumab can be administered to an individual in need thereof in an amount of 10 mg/kg every 12 weeks. In some cases, a method of the present disclosure provides for a reduced amount of an anti-PD1 that needs to be administered to achieve clinical benefit. For example, in some cases, the amount of ipilimumab that needs to be administered to achieve clinical benefit can be reduced by from 10% to 50%, or more than 50%, compared to the amount of ipilimumab that needs to be administered to achieve clinical benefit in the absence of treatment with a synTac.

Routes of Administration

An active agent (a multimeric polypeptide; an immune checkpoint inhibitor) is administered to an individual using any available method and route suitable for drug delivery, including in vivo and ex vivo methods, as well as systemic and localized routes of administration. In some cases, a synTac is administered by a first route of administration; and an immune checkpoint inhibitor is administered by a second route of administration that is different from the first route of administration. In some cases, a synTac and an immune checkpoint inhibitor are administered by the same routes of administration.

Conventional and pharmaceutically acceptable routes of administration include intratumoral, peritumoral, intramuscular, intratracheal, intracranial, subcutaneous, intradermal, topical application, intravenous, intraarterial, rectal, nasal, oral, and other enteral and parenteral routes of administration. Routes of administration may be combined, if desired, or adjusted depending upon the multimeric polypeptide, the immune checkpoint inhibitor and/or the desired effect.

In some cases, a multimeric polypeptide is administered intravenously; and an immune checkpoint inhibitor intravenously. In some cases, a multimeric polypeptide is administered intramuscularly; and an immune checkpoint inhibitor intramuscularly. In some cases, a multimeric polypeptide is administered locally; and an immune checkpoint inhibitor locally. In some cases, a multimeric polypeptide is administered intratumorally; and an immune checkpoint inhibitor intratumorally. In some cases, a multimeric polypeptide is administered peritumorally; and an immune checkpoint inhibitor peritumorally. In some cases, a multimeric polypeptide is administered intracranially; and an immune checkpoint inhibitor intracranially. In some cases, a multimeric polypeptide is administered subcutaneously; and an immune checkpoint inhibitor subcutaneously.

In some cases, a multimeric polypeptide is administered intravenously; and an immune checkpoint inhibitor peritumorally. In some cases, a multimeric polypeptide is administered intramuscularly; and an immune checkpoint inhibitor intravenously. In some cases, a multimeric polypeptide is administered systemically; and an immune checkpoint inhibitor locally. In some cases, a multimeric polypeptide is administered intratumorally; and an immune checkpoint inhibitor intravenously. In some cases, a multimeric polypeptide is administered systemically; and an immune checkpoint inhibitor peritumorally. In some cases, a multimeric polypeptide is administered intravenously; and an immune checkpoint inhibitor intracranially. In some cases, a multimeric polypeptide is administered subcutaneously; and an immune checkpoint inhibitor intravenously.

A multimeric polypeptide and an immune checkpoint inhibitor can be administered to a host using any available conventional methods and routes suitable for delivery of conventional drugs, including systemic or localized routes. In general, routes of administration contemplated for use in a method of the present disclosure include, but are not necessarily limited to, enteral, parenteral, and inhalational routes.

Parenteral routes of administration other than inhalation administration include, but are not necessarily limited to, topical, transdermal, subcutaneous, intramuscular, intraorbital, intracapsular, intraspinal, intrasternal, intratumoral, peritumoral, and intravenous routes, i.e., any route of administration other than through the alimentary canal. Parenteral administration can be carried to effect systemic or local delivery of an active agent (a synTac or an immune checkpoint inhibitor). Where systemic delivery is desired, administration can involve intravenous delivery.

Subjects Suitable for Treatment

Subjects suitable for treatment with a method of the present disclosure include individuals who have cancer, including individuals who have been diagnosed as having cancer, individuals who have been treated for cancer but who failed to respond to the treatment, and individuals who have been treated for cancer and who initially responded but subsequently became refractory to the treatment. Subjects suitable for treatment with a method of the present disclosure include individuals who have an infection (e.g., an infection with a pathogen such as a bacterium, a virus, a protozoan, etc.), including individuals who have been diagnosed as having an infection, and individuals who have been treated for an infection but who failed to respond to the treatment. Subjects suitable for treatment with a method of the present disclosure include individuals who have bacterial infection, including individuals who have been diagnosed as having a bacterial infection, and individuals who have been treated for a bacterial infection but who failed to respond to the treatment. Subjects suitable for treatment with a method of the present disclosure include individuals who have a viral infection, including individuals who have been diagnosed as having a viral infection, and individuals who have been treated for a viral infection but who failed to respond to the treatment. Subjects suitable for treatment with a method of the present disclosure include individuals who have an autoimmune disease, including individuals who have been diagnosed as having an autoimmune disease, and individuals who have been treated for a autoimmune disease but who failed to respond to the treatment.

In some cases, a method of the present disclosure comprises administering a synTac to an individual who is undergoing treatment with an immune checkpoint inhibitor. In some cases, a method of the present disclosure comprises administering a synTac to an individual who is undergoing treatment with an anti-PD1 antibody. For example, in some cases, a method of the present disclosure comprises administering a synTac to an individual who is undergoing treatment with pembrolizumab. As another example, in some cases, a method of the present disclosure comprises administering a synTac to an individual who is undergoing treatment with nivolumab. In some cases, a method of the present disclosure comprises administering a synTac to an individual who is undergoing treatment with an anti-PD-L1 antibody. For example, in some cases, a method of the present disclosure comprises administering a synTac to an individual who is undergoing treatment with atezolizumab. In some cases, a method of the present disclosure comprises administering a synTac to an individual who is undergoing treatment with an anti-CTLA4 antibody. For example, in some cases, a method of the present disclosure comprises administering a synTac to an individual who is undergoing treatment with ipilimumab. As another example, in some cases, a method of the present disclosure comprises administering a synTac to an individual who is undergoing treatment with tremelimumab.

In some cases, e.g., where the epitope is an HPV epitope, a subject suitable for treatment with a method of the present disclosure is an individual who has been diagnosed as having an HPV-associated cancer or an HPV-attributable cancer. HPV-associated and HPV-attributable cancers include, e.g., head and neck cancer; cervical cancer; and genitoanal cancer.

Methods of Selectively Delivering a Costimulatory Polypeptide Together with an Immune Checkpoint Inhibitor to an Individual The present disclosure thus provides a method of delivering a costimulatory polypeptide such as IL-2, or a reduced-affinity variant of a naturally occurring costimulatory polypeptide such as an IL-2 variant disclosed herein, to a selected T cell or a selected T cell population, e.g., in a manner such that a TCR specific for a given epitope is targeted, together with co-administration of a checkpoint inhibitor so as to provide the patient with the therapeutic effect of both the selective delivery of the costimulatory polypeptide and the checkpoint inhibitor. The present disclosure provides a method of delivering a costimulatory polypeptide such as IL-2, or a reduced-affinity variant of a naturally occurring costimulatory polypeptide such as an IL-2 variant disclosed herein, selectively to a target T cell bearing a TCR specific for the epitope present in a multimeric polypeptide of the present disclosure, together with co-administration of a checkpoint inhibitor so as to provide the patient with the therapeutic effect of both the selective delivery of the costimulatory polypeptide and the checkpoint inhibitor. The method comprises contacting a population of T cells with a multimeric polypeptide of the present disclosure. The population of T cells can be a mixed population that comprises: i) the target T cell; and ii) non-target T cells that are not specific for the epitope (e.g., T cells that are specific for an epitope(s) other than the epitope to which the epitope-specific T cell binds). The epitope-specific T cell is specific for the epitope-presenting peptide present in the multimeric polypeptide, and binds to the peptide HLA complex or peptide MHC complex provided by the multimeric polypeptide. Contacting the population of T cells with the multimeric polypeptide delivers the costimulatory polypeptide (e.g., IL-2 or a reduced-affinity variant of IL-2) present in the multimeric polypeptide selectively to the T cell(s) that are specific for the epitope present in the multimeric polypeptide. The checkpoint inhibitor is co-administered with the multimeric polypeptide (either together or at different times before and/or after administration of the multimeric polypeptide) so as to provide the patient with the therapeutic effect of both the selective delivery of the costimulatory polypeptide and the checkpoint inhibitor.

Thus, the present disclosure provides a method of delivering to a patient (i) a checkpoint inhibitor as described above and (ii) a costimulatory polypeptide such as IL-2, or a reduced-affinity variant of a naturally occurring costimulatory polypeptide such as an IL-2 variant disclosed herein, or a combination of both, selectively to a target T cell, the method comprising contacting a mixed population of T cells with a multimeric polypeptide of the present disclosure. The mixed population of T cells comprises the target T cell and non-target T cells. The target T cell is specific for the epitope present within the multimeric polypeptide. Contacting the mixed population of T cells with a multimeric polypeptide of the present disclosure delivers the costimulatory polypeptide(s) present within the multimeric polypeptide to the target T cell. The co-administration of the checkpoint inhibitor with the multimeric polypeptide (either together or at different times before and/or after administration of the multimeric polypeptide) thus provides the patient with the therapeutic effect of both the selective delivery of the costimulatory polypeptide and the checkpoint inhibitor.

For example, a multimeric polypeptide of the present disclosure is contacted with a population of T cells comprising: i) a target T cell(s) that is specific for the epitope present in the multimeric polypeptide; and ii) a non-target T cell(s), e.g., a T cell(s) that is specific for a second epitope(s) that is not the epitope present in the multimeric polypeptide. Contacting the population results in selective delivery of the costimulatory polypeptide(s) (e.g., naturally-occurring costimulatory polypeptide (e.g., naturally occurring IL-2) or reduced-affinity variant of a naturally occurring costimulatory polypeptide (e.g., an IL-2 variant disclosed herein)), which is present in the multimeric polypeptide, to the target T cell. Thus, e.g., less than 50%, less than 40%, less than 30%, less than 25%, less than 20%, less than 15%, less than 10%, less than 5%, or less than 4%, 3%, 2% or 1%, of the non-target T cells bind the multimeric polypeptide and, as a result, the costimulatory polypeptide (e.g., IL-2 or IL-2 variant) present in the multimeric polypeptides is substantially not delivered to the non-target T cells. The co-administration of the checkpoint inhibitor with the multimeric polypeptide (either together or at different times before and/or after administration of the multimeric polypeptide) thus provides the patient with the therapeutic effect of both the selective delivery of the costimulatory polypeptide and the checkpoint inhibitor.

In some cases, the population of T cells is in vitro. In some cases, the population of T cells is in vitro, and a biological response (e.g., T cell activation and/or expansion and/or phenotypic differentiation) of the target T cell population to the multimeric polypeptide of the present disclosure is elicited in the context of an in vitro culture. For example, a mixed population of T cells can be obtained from an individual, and can be contacted with the multimeric polypeptide in vitro. Such contacting can comprise single or multiple exposures of the population of T cells to a defined dose(s) and/or exposure schedule(s). In some cases, said contacting results in selectively binding/activating and/or expanding target T cells within the population of T cells, and results in generation of a population of activated and/or expanded target T cells. As an example, a mixed population of T cells can be peripheral blood mononuclear cells (PBMC). For example, PBMC from a patient can be obtained by standard blood drawing and PBMC enrichment techniques before being exposed to 0.1-1000 nM of a multimeric polypeptide of the present disclosure under standard lymphocyte culture conditions. At time points before, during, and after exposure of the mixed T cell population at a defined dose and schedule, the abundance of target T cells in the in vitro culture can be monitored by specific peptide-MHC multimers and/or phenotypic markers and/or functional activity (e.g. cytokine ELISpot assays). In some cases, upon achieving an optimal abundance and/or phenotype of antigen specific cells in vitro, all or a portion of the population of activated and/or expanded target T cells is administered to the individual (the individual from whom the mixed population of T cells was obtained), which individual already has received administration of a checkpoint inhibitor prior to the administration of the target T cells and/or will receive administration of a checkpoint inhibitor after the administration of target T cells.

In some cases, the population of T cells is in vitro. For example, a mixed population of T cells is obtained from an individual, and is contacted with a multimeric polypeptide of the present disclosure in vitro. Such contacting, which can comprise single or multiple exposures of the T cells to a defined dose(s) and/or exposure schedule(s) in the context of in vitro cell culture, can be used to determine whether the mixed population of T cells includes T cells that are specific for the epitope presented by the multimeric polypeptide. The presence of T cells that are specific for the epitope of the multimeric polypeptide can be determined by assaying a sample comprising a mixed population of T cells, which population of T cells comprises T cells that are not specific for the epitope (non-target T cells) and may comprise T cells that are specific for the epitope (target T cells). Known assays can be used to detect activation and/or proliferation of the target T cells, thereby providing an ex vivo assay that can determine whether a particular multimeric polypeptide (synTac) possesses an epitope that binds to T cells present in the individual and thus whether the multimeric polypeptide has potential use as a therapeutic composition for that individual. Suitable known assays for detection of activation and/or proliferation of target T cells include, e.g., flow cytometric characterization of T cell phenotype and/or antigen specificity and/or proliferation. Such an assay to detect the presence of epitope-specific T cells, e.g., a companion diagnostic, can further include additional assays (e.g. effector cytokine ELISpot assays) and/or appropriate controls (e.g. antigen-specific and antigen-nonspecific multimeric peptide-HLA staining reagents) to determine whether the multimeric polypeptide is selectively binding/activating and/or expanding the target T cell. Thus, for example, the present disclosure provides a method of detecting, in a mixed population of T cells obtained from an individual, the presence of a target T cell that binds an epitope of interest, the method comprising: a) contacting in vitro the mixed population of T cells with a multimeric polypeptide of the present disclosure, wherein the multimeric polypeptide comprises the epitope of interest; and b) detecting activation and/or proliferation of T cells in response to said contacting, wherein activated and/or proliferated T cells indicates the presence of the target T cell. Alternatively, and/or in addition, if activation and/or expansion (proliferation) of the desired T cell population is obtained using the multimeric polypeptide, then all or a portion of the population of T cells comprising the activated/expanded T cells can be administered back to the individual (who has received administration of a checkpoint inhibitor before administration of the T cells and/or will receive administration of a checkpoint inhibitor after administration of the T cells) as a therapy.

In some instances, the population of T cells is in vivo in an individual. In such instances, a method of the present disclosure for selectively delivering a costimulatory polypeptide (e.g., IL-2 or a reduced-affinity IL-2) to an epitope-specific T cell comprises administering the multimeric polypeptide to the individual.

The epitope-specific T cell to which a costimulatory polypeptide (e.g., IL-2 or a reduced-affinity IL-2) is being selectively delivered is also referred to herein as a "target T cell." In some cases, the target T cell is a regulatory T cell (Treg). In some cases, the Treg inhibits or suppresses activity of an autoreactive T cell.

In some cases, the target T cell is a cytotoxic T cell. For example, the target T cell can be a cytotoxic T cell specific for a cancer epitope (e.g., an epitope presented by a cancer cell).

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure designated Aspects 1-122, Aspects A-Z, Aspects AA-ZZ, and Aspects AAA-BBB, are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A variant IL-2 polypeptide comprising an amino acid sequence having at least 85% amino acid sequence identity to set forth in SEQ ID NO:1, wherein the variant IL-2 polypeptide has one or more amino acid substitutions relative to set forth in SEQ ID NO:1, and wherein the variant IL-2 polypeptide exhibits reduced binding affinity to an IL-2 receptor (IL2R) comprising alpha, beta, and gamma polypeptides having amino acid sequences depicted in FIG. 3A-3C, compared to the binding affinity of the IL-2 amino acid sequence set forth in one of SEQ ID NO:1 for the IL2R.

Aspect 2. The variant IL2 polypeptide of aspect 1, wherein the variant comprises a substitution of one or more of E15, H16, D20, F42, Y45, and Q126.

Aspect 3. The variant IL2 polypeptide of aspect 1 or aspect 2, wherein the variant immunomodulatory polypeptide exhibits from less than 10% to less than 50% of the binding affinity exhibited by the IL2 amino acid sequence set forth in SEQ ID NO:1 for the IL2R.

Aspect 4. The variant IL2 polypeptide of any one of aspects 1-3, wherein the variant comprises substitutions of F42 with Ala, Gly, Val, Ile, or Leu.

Aspect 5. The variant IL2 polypeptide of any one of aspects 1-3, wherein the variant comprises substitutions of F42 and D20.

Aspect 6. The variant IL2 polypeptide of any one of aspects 1-3, wherein the variant comprises substitutions of F42 and H16.

Aspect 7. The variant IL2 polypeptide of any one of aspects 1-3, wherein the variant comprises substitutions of F42, D20, and Y45; or wherein the variant comprises substitutions of F42, H16, and Q126.

Aspect 8. A multimeric polypeptide comprising:

a) a first polypeptide comprising, in order from N-terminus to C-terminus:

i) an epitope;

ii) a first major histocompatibility complex (MHC) polypeptide; and b) a second polypeptide comprising, in order from N-terminus to C-terminus:

i) a second MHC polypeptide; and ii) optionally an immunoglobulin (Ig) Fc polypeptide or a non-Ig scaffold, wherein the multimeric polypeptide comprises one or more immunomodulatory domains, wherein the one or more immunomodulatory domain is:

A) at the C-terminus of the first polypeptide;

B) at the N-terminus of the second polypeptide;

C) at the C-terminus of the second polypeptide; or

D) at the C-terminus of the first polypeptide and at the N-terminus of the second polypeptide, wherein at least one of the one or more immunomodulatory domains is a variant IL2 polypeptide of any one of aspects 1-7, and wherein the multimeric polypeptide exhibits reduced binding affinity to an IL-2 receptor (IL2R) comprising alpha, beta, and gamma polypeptides having amino acid sequences depicted in FIG. 3A-3C, compared to the binding affinity of a control multimeric polypeptide comprising the IL2 amino acid sequence set forth in SEQ ID NO:1 for the IL2R polypeptide.

Aspect 9. The multimeric polypeptide of aspect 8, wherein:

a) the first polypeptide comprises, in order from N-terminus to C-terminus:

i) the epitope;

ii) the first MHC polypeptide; and iii) the variant IL2 polypeptide; and b) the second polypeptide comprises, in order from N-terminus to C-terminus:

i) the second MHC polypeptide; and ii) the Ig Fc polypeptide.

Aspect 10. The multimeric polypeptide of aspect 8, wherein:

a) the first polypeptide comprises, in order from N-terminus to C-terminus:

i) the epitope; and ii) the first MHC polypeptide; and b) the second polypeptide comprises, in order from N-terminus to C-terminus:

i) the variant IL2 polypeptide;

ii) the second MHC polypeptide; and iii) the Ig Fc polypeptide.

Aspect 11. The multimeric polypeptide of aspect 8, wherein:

a) the first polypeptide comprises, in order from N-terminus to C-terminus:

i) the epitope; and ii) the first MHC polypeptide; and b) the second polypeptide comprises, in order from N-terminus to C-terminus:

i) the second MHC polypeptide; and ii) the variant IL2 polypeptide.

Aspect 12. The multimeric polypeptide of aspect 8, wherein:

a) the first polypeptide comprises, in order from N-terminus to C-terminus:

i) the epitope; and ii) the first MHC polypeptide; and b) second polypeptide comprising, in order from N-terminus to C-terminus:

i) the variant IL2 polypeptide; and ii) the second MHC polypeptide.

Aspect 13. The multimeric polypeptide of aspect 8, wherein:

a) the first polypeptide comprises, in order from N-terminus to C-terminus:

i) the epitope;

ii) the first MHC polypeptide; and iii) the variant IL2 polypeptide; and b) the second polypeptide comprises the second MHC polypeptide.

Aspect 14. The multimeric polypeptide of aspect 8, wherein the non-Ig scaffold is an XTEN polypeptide, a transferrin polypeptide, an elastin-like polypeptide, a silk-like polypeptide, or a silk-elastin-like polypeptide.

Aspect 15. The multimeric polypeptide of any one of aspects 8-14, wherein the first MHC polypeptide is a β2-microglobulin polypeptide; and wherein the second MHC polypeptide is an MHC class I heavy chain polypeptide.

Aspect 16. The multimeric polypeptide of aspect 15, wherein the β2-microglobulin polypeptide comprises an amino acid sequence having at least 85% amino acid sequence identity to one of the amino acid sequences set forth in FIG. 6.

Aspect 17. The multimeric polypeptide of aspect 15, wherein the MHC class I heavy chain polypeptide is an HLA-A, an HLA-B, or an HLA-C heavy chain.

Aspect 18. The multimeric polypeptide of aspect 15, wherein the MHC class I heavy chain polypeptide comprises an amino acid sequence having at least 85% amino acid sequence identity to the amino acid sequence set forth in one of FIG. 5A-5C.

Aspect 19. The multimeric polypeptide of any one of aspects 8-14, wherein the first MHC polypeptide is an MHC Class II alpha chain polypeptide; and wherein the second MHC polypeptide is an MHC class II beta chain polypeptide.

Aspect 20. The multimeric polypeptide of any one of aspects 8-19, wherein the epitope is a T-cell epitope.

Aspect 21. The multimeric polypeptide of any one of aspects 8-13 and 15-20, wherein multimeric polypeptide comprises an Fc polypeptide, and wherein the Ig Fc polypeptide is an IgG1 Fc polypeptide, an IgG2 Fc polypeptide, an IgG3 Fc polypeptide, an IgG4 Fc polypeptide, an IgA Fc polypeptide, or an IgM Fc polypeptide.

Aspect 22. The multimeric polypeptide of aspect 21, wherein the Ig Fc polypeptide comprises an amino acid sequence having at least 85% amino acid sequence identity to an amino acid sequence depicted in FIG. 4A-4C.

Aspect 23. The multimeric polypeptide of any one of aspects 8-22, wherein the first polypeptide and the second polypeptide are non-covalently associated.

Aspect 24. The multimeric polypeptide of any one of aspects 8-22, wherein the first polypeptide and the second polypeptide are covalently linked to one another.

Aspect 25. The multimeric polypeptide of aspect 24, wherein the covalent linkage is via a disulfide bond.

Aspect 26. The multimeric polypeptide of aspect 25, wherein the first MHC polypeptide or a linker between the epitope and the first MHC polypeptide comprises an amino acid substitution to provide a first Cys residue, and the second MHC polypeptide comprises an amino acid substitution to provide a second Cys residue, and wherein the disulfide linkage is between the first and the second Cys residues.

Aspect 27. The multimeric polypeptide of any one of aspects 8-26, comprising a linker interposed between the epitope and the first MHC polypeptide.

Aspect 28. The multimeric polypeptide of any one of aspects 8-26, comprising a linker interposed between the MHC polypeptide and the immunomodulatory polypeptide.

Aspect 29. The multimeric polypeptide of any one of aspects 8-28, comprising 2 variant IL2 polypeptides.

Aspect 30. The multimeric polypeptide of any one of aspects 8-28, comprising 3 variant IL2 polypeptides.

Aspect 31. The multimeric polypeptide of aspect 29 or aspect 30, wherein the 2 or 3 variant IL2 polypeptides are in tandem, and wherein the multimeric polypeptide comprises a linker between the variant IL2 polypeptides.

Aspect 32. The multimeric polypeptide of any one of aspects 8-28, wherein the variant IL2 comprises a substitution of one or more of E15, H16, D20, F42, Y45, and Q126/

Aspect 33. The multimeric polypeptide of any one of aspects 8-28, wherein the variant IL2 comprises a substitution of F42 with Ala, Gly, Val, Ile, or Leu.

Aspect 34. The multimeric polypeptide of aspect 33, wherein the variant IL2 comprises substitutions of F42 and D20.

Aspect 35. The multimeric polypeptide of aspect 33, wherein the variant IL2 comprises substitutions of F42 and H16.

Aspect 36. The multimeric polypeptide of aspect 33, wherein the variant IL2 comprises substitutions of F42, D20, and Y45; or wherein the variant IL-2 comprising substitutions of F42, H16, and Q126.

Aspect 37. A nucleic acid comprising a nucleotide sequence encoding a recombinant polypeptide, i) wherein the recombinant polypeptide comprises, in order from N-terminus to C-terminus:

a) an epitope;

b) a first major histocompatibility complex (MHC) polypeptide;

c) an immunomodulatory polypeptide;

d) a proteolytically cleavable linker or a ribosome skipping signal;

e) a second MHC polypeptide; and f) an immunoglobulin (Ig) Fc polypeptide;

wherein the immunomodulatory polypeptide is a variant immunomodulatory polypeptide of any one of aspects 1-7; or ii) wherein the recombinant polypeptide comprises, in order from N-terminus to C-terminus:

a) an epitope;

b) a first MHC polypeptide;

c) a proteolytically cleavable linker or a ribosome skipping signal;

d) an immunomodulatory polypeptide e) a second MHC polypeptide; and f) an Ig Fc polypeptide, wherein the immunomodulatory polypeptide is a variant immunomodulatory polypeptide of any one of aspects 1-7.

Aspect 38. The nucleic acid of aspect 37, wherein the first MHC polypeptide is a β2-microglobulin polypeptide; and wherein the second MHC polypeptide is an MHC class I heavy chain polypeptide.

Aspect 39. The nucleic acid of aspect 38, wherein the β2-microglobulin polypeptide comprises an amino acid sequence having at least 85% amino acid sequence identity to one of the amino acid sequences set forth in FIG. 6.

Aspect 40. The nucleic acid of aspect 38, wherein the MHC class I heavy chain polypeptide is an HLA-A, HLA-B, or HLA-C heavy chain.

Aspect 41. The nucleic acid of aspect 40, wherein the MHC class I heavy chain polypeptide comprises an amino acid sequence having at least 85% amino acid sequence identity to the amino acid sequence set forth in any one of FIG. 5A-5C.

Aspect 42. The nucleic acid of aspect 37, wherein the first MHC polypeptide is an MHC Class II alpha chain polypeptide; and wherein the second MHC polypeptide is an MHC class II beta chain polypeptide.

Aspect 43. The nucleic acid of any one of aspects 37-43, wherein the epitope is a T-cell epitope.

Aspect 44. The nucleic acid of any one of aspects 37-43, wherein the Ig Fc polypeptide is an IgG1 Fc polypeptide, an IgG2 Fc polypeptide, an IgG3 Fc polypeptide, an IgG4 Fc polypeptide, an IgA Fc polypeptide, or an IgM Fc polypeptide.

Aspect 45. The nucleic acid of aspect 44, wherein the Ig Fc polypeptide comprises an amino acid sequence having at least 85% amino acid sequence identity to an amino acid sequence depicted in FIGS. 4A-4C.

Aspect 46. The nucleic acid of any one of aspects 37-45, wherein the variant IL2 immunomodulatory polypeptide comprises a substitution of one or more of E15, H16, D20, F42, Y45, and Q126.

Aspect 47. The nucleic acid of any one of aspects 37-46, wherein the multimeric polypeptide comprises a second immunomodulatory polypeptide selected from a CD7, CD30L, CD40, CD70, CD83, HLA-G, MICA, MICB, HVEM, lymphotoxin beta receptor, 3/TR6, ILT3, ILT4, and HVEM.

Aspect 48. The nucleic acid of any one of aspects 37-47, wherein the proteolytically cleavable linker or ribosome skipping signal comprises an amino acid sequence selected from:

a)

(SEQ ID NO: 88)

LEVLFQGP;

-continued b)
(SEQ ID NO: 90)
ENLYTQS;

c) a furin cleavage site;

d)
(SEQ ID NO: 89)
LVPR;

e)
(SEQ ID NO: 91)
GSGATNFSLLKQAGDVEENPGP;

f)
(SEQ ID NO: 92)
GSGEGRGSLLTCGDVEENPGP;

g)
(SEQ ID NO: 93)
GSGQCTNYALLKLAGDVESNPGP;
and h)
(SEQ ID NO: 94)
GSGVKQTLNFDLLKLAGDVESNPGP.

Aspect 49. The nucleic acid of aspect 31, wherein the recombinant polypeptide comprises, in order from N-terminus to C-terminus:

a) a first leader peptide;

b) the epitope;

c) the first MHC polypeptide;

d) the immunomodulatory polypeptide;

e) the proteolytically cleavable linker or ribosome skipping signal;

f) a second leader peptide;

g) the second MHC polypeptide; and h) the immunoglobulin (Ig) Fc polypeptide.

Aspect 50. The nucleic acid of aspect 49, wherein the first leader peptide and the second leader peptide is a β2-M leader peptide.

Aspect 51. The nucleic acid of any one of aspects 37-50, wherein the nucleotide sequence is operably linked to a transcriptional control element.

Aspect 52. The nucleic acid of aspect 51, wherein the transcriptional control element is a promoter that is functional in a eukaryotic cell.

Aspect 53. The nucleic acid of any one of aspects 37-52, wherein the first MHC polypeptide or a linker between the epitope and the first MHC polypeptide comprises an amino acid substitution to provide a first Cys residue, and the second MHC polypeptide comprises an amino acid substitution to provide a second Cys residue, and wherein the first and the second Cys residues provide for a disulfide linkage between the first MHC polypeptide and the second MHC polypeptide.

Aspect 54. A recombinant expression vector comprising the nucleic acid of any one of aspects 37-52.

Aspect 55. The recombinant expression vector of aspect 54, wherein the vector is a viral vector or a non-viral vector.

Aspect 56. A host cell genetically modified with the recombinant expression vector of aspect 48-55.

Aspect 57. The host cell of aspect 56, wherein the host cell is in vitro.

Aspect 58. The host cell of aspect 57, wherein the host cell is genetically modified such that the cell does not produce an endogenous MHC β2-microglobulin polypeptide.

Aspect 59. A composition comprising:

a) a first nucleic acid comprising a nucleotide sequence encoding a first polypeptide comprising, in order from N-terminus to C-terminus:

i) an epitope;

ii) a first MHC polypeptide; and iii) an immunomodulatory domain, wherein the immunomodulatory domain is a variant IL2 polypeptide of any one of aspects 1-7; and b) a first nucleic acid comprising a nucleotide sequence encoding a second polypeptide comprising, in order from N-terminus to C-terminus:

i) a second MHC polypeptide; and ii) an Ig Fc polypeptide.

Aspect 60. A composition comprising:

a) a first nucleic acid comprising a nucleotide sequence encoding a first polypeptide comprising, in order from N-terminus to C-terminus:

i) an epitope; and ii) a first MHC polypeptide; and b) a first nucleic acid comprising a nucleotide sequence encoding a second polypeptide comprising, in order from N-terminus to C-terminus:

i) an immunomodulatory domain, wherein the immunomodulatory domain is a variant IL2 polypeptide of any one of aspects 1-7;

ii) a second MHC polypeptide; and iii) an Ig Fc polypeptide.

Aspect 61. The composition of aspect 59 or aspect 60, wherein the first and/or the second nucleic acid is present in a recombinant expression vector.

Aspect 62. A host cell genetically modified with the composition of any one of aspects 59-61.

Aspect 63. A method of producing the multimeric polypeptide of any one of aspects 8-36, the method comprising:

a) culturing the host cell of any one of aspects 56-58 and 62 in vitro in a culture medium under conditions such that the host cell synthesizes the multimeric polypeptide; and b) isolating the multimeric polypeptide from the host cell and/or from the culture medium.

Aspect 64. The method of aspect 63, wherein the second polypeptide comprises an affinity tag, and wherein said isolating comprises contacting the multimeric polypeptide produced by the cell with a binding partner for the affinity tag, wherein the binding partner is immobilized, thereby immobilizing the multimeric polypeptide.

Aspect 65. The method of aspect 64, comprising eluting the immobilized multimeric polypeptide.

Aspect 66. A method of selectively activating an epitope-specific T cell, the method comprising contacting the T cell with the multimeric polypeptide of any one of aspects 8-36, wherein said contacting selectively activates the epitope-specific T cell.

Aspect 67. The method of aspect 66, wherein said contacting is in vitro.

Aspect 68. The method of aspect 66, wherein said contacting is in vivo.

Aspect 69. The method of aspect 66, wherein the epitope is a cancer-associated epitope, and wherein said administering selectively increases the activity of a T cell specific for the cancer-associate epitope.

Aspect 70. A method of treating cancer in an individual, the method comprising administering to the individual an effective amount of:

a) the multimeric polypeptide of any one of aspects 8-36; or b) one or more recombinant expression vectors comprising nucleotide sequences encoding the multimeric polypeptide of any one of aspects 8-36; or c) one or more mRNAs comprising nucleotide sequences encoding the multimeric polypeptide of any one of aspects 8-36, wherein the epitope is a cancer-associated epitope, and wherein said administering effective to selectively activate a cancer epitope-specific T cell in an individual.

Aspect 71. The method of aspect 70, wherein said administering is subcutaneous.

Aspect 72. The method of aspect 70, wherein said administering is intravenous.

Aspect 73. The method of aspect 70, wherein said administering is peritumoral.

Aspect 74. The method of aspect 70, wherein said administering is systemic.

Aspect 75. The method of aspect 70, wherein said administering is distal to a treatment site.

Aspect 76. The method of aspect 70, wherein said administering is local.

Aspect 77. The method of aspect 70, wherein said administering is at or near a treatment site.

Aspect 78. A composition comprising:

a) the multimeric polypeptide of any one of aspects 8-36; and b) a pharmaceutically acceptable excipient.

Aspect 79. A composition comprising:

a) the nucleic acid of any one of aspects 37-53 or the recombinant expression vector of aspect 54 or 55; and b) a pharmaceutically acceptable excipient.

Aspect 80. A multimeric polypeptide comprising:

a) a first polypeptide comprising, in order from N-terminus to C-terminus:

i) an epitope;

ii) a β2-microglobulin (β2M) polypeptide comprising the amino acid sequence depicted in FIG. 34A; and b) a second polypeptide comprising, in order from N-terminus to C-terminus:

i) a variant IL-2 polypeptide of any one of aspects 1-7;

ii) a major histocompatibility comples (MHC) heavy chain polypeptide comprising the amino acid sequence depicted in FIG. 34C; and iii) an IgG1 Fc polypeptide comprising one or more amino acid substitutions selected from N297A, L234A, L235A, L234F, L235E, and P331S (N77A, L14A, L15A, L14F, L15E, and P111S, respectively, based on the amino acid numbering depicted in FIG. 33A).

Aspect 81. The multimeric polypeptide of aspect 80, wherein the IgG1 Fc polypeptide comprises an N297A substitution (N77A based on the amino acid numbering depicted in FIG. 33A).

Aspect 82. The multimeric polypeptide of aspect 80, wherein the IgG1 Fc polypeptide comprises an L234A substitution and an L235A substitution (L14A and L15A based on the amino acid numbering depicted in FIG. 33A).

Aspect 83. The multimeric polypeptide of aspect 80, wherein the IgG1 Fc polypeptide comprises an L234F substitution and an L235E substitution (L14F and L15E based on the amino acid numbering depicted in FIG. 33A).

Aspect 84. The multimeric polypeptide of aspect 80, wherein the IgG1 Fc polypeptide comprises an L234F substitution, an L235E substitution, and a P331S (L14F, L15E, and P111S substitutions based on the amino acid numbering depicted in FIG. 33A).

Aspect 85. The multimeric polypeptide of any one of aspects 80-84, wherein the second polypeptide comprises two copies of the variant IL-2 polypeptide.

Aspect 86. The multimeric polypeptide of any one of aspects 80-85, wherein the first polypeptide comprises a peptide linker between the epitope and the β2M polypeptide.

Aspect 87. The multimeric polypeptide of any one of aspects 80-86, wherein the second polypeptide comprises a peptide linker between one or more of:

a) a first copy of the variant IL-2 polypeptide and a second copy of the variant IL-2 polypeptide;

b) the variant IL-2 polypeptide and the MHC heavy chain polypeptide; and c) between the MHC heavy chain polypeptide and the IgG1 Fc polypeptide.

Aspect 88. The multimeric polypeptide of aspect 86 or aspect 87, wherein the peptide linker is selected from $(GGGGS)_3$, $(GGGGS)_4$, and AAAGG.

Aspect 89. A multimeric polypeptide comprising:

a) a first polypeptide comprising, in order from N-terminus to C-terminus:

i) an epitope;

ii) a β2-microglobulin polypeptide comprising the amino acid sequence depicted in FIG. 34A; and b) a second polypeptide comprising, in order from N-terminus to C-terminus:

i) a variant IL-2 polypeptide comprising the amino acid sequence depicted in FIG. 34B;

ii) a major histocompatibility comples (MHC) heavy chain polypeptide comprising the amino acid sequence depicted in FIG. 34C; and iii) an IgG1 Fc polypeptide comprising one or more amino acid substitutions selected from N297A, L234A, L235A, L234F, L235E, and P331S (N77A, L14A, L15A, L14F, L15E, and P111S, respectively, based on the amino acid numbering depicted in FIG. 33A).

Aspect 90. The multimeric polypeptide of aspect 89, wherein the IgG1 Fc polypeptide comprises an N297A substitution (N77A based on the amino acid numbering depicted in FIG. 33A).

Aspect 91. The multimeric polypeptide of aspect 89, wherein the IgG1 Fc polypeptide comprises an L234A substitution and an L235A substitution (L14A and L15A based on the amino acid numbering depicted in FIG. 33A).

Aspect 92. The multimeric polypeptide of aspect 89, wherein the IgG1 Fc polypeptide comprises an L234F substitution and an L235E substitution (L14F and L15E based on the amino acid numbering depicted in FIG. 33A).

Aspect 93. The multimeric polypeptide of aspect 89, wherein the IgG1 Fc polypeptide comprises an L234F substitution, an L235E substitution, and a P331S substitution (L14F, L15E, and P111S based on the amino acid numbering depicted in FIG. 33A).

Aspect 94. The multimeric polypeptide of any one of aspects 89-93, wherein the second polypeptide comprises two copies of the variant IL-2 polypeptide.

Aspect 95. The multimeric polypeptide of any one of aspects 89-94, wherein the first polypeptide comprises a peptide linker between the epitope and the β2M polypeptide.

Aspect 96. The multimeric polypeptide of any one of aspects 89-95, wherein the second polypeptide comprises a peptide linker between one or more of:

a) a first copy of the variant IL-2 polypeptide and a second copy of the variant IL-2 polypeptide;

b) the variant IL-2 polypeptide and the MHC heavy chain polypeptide; and c) between the MHC heavy chain polypeptide and the IgG1 Fc polypeptide.

Aspect 97. The multimeric polypeptide of aspect 95 or aspect 96, wherein the peptide linker is selected from $(GGGGS)_3$, $(GGGGS)_4$, and AAAGG.

Aspect 98. A multimeric polypeptide comprising:

a) a first polypeptide comprising, in order from N-terminus to C-terminus:

i) an epitope comprising the amino acid sequence YMIDLQPETT (SEQ ID NO:77);

ii) a β2-microglobulin polypeptide comprising the amino acid sequence depicted in FIG. 34A; and b) a second polypeptide comprising, in order from N-terminus to C-terminus:

i) a variant IL-2 polypeptide comprising the amino acid sequence depicted in FIG. 34B;

ii) a major histocompatibility comples (MHC) heavy chain polypeptide comprising the amino acid sequence depicted in FIG. 34C; and iii) an IgG1 Fc polypeptide comprising the amino acid sequence depicted in FIG. 33A, 33B, 33C, or 33D.

Aspect 99. The multimeric polypeptide of aspect 98, wherein the IgG1 Fc polypeptide comprises the amino acid sequence depicted in FIG. 33B.

Aspect 100. The multimeric polypeptide of aspect 98, wherein the IgG1 Fc polypeptide comprises the amino acid sequence depicted in FIG. 33C.

Aspect 101. The multimeric polypeptide of aspect 98, wherein the IgG1 Fc polypeptide comprises the amino acid sequence depicted in FIG. 33D.

Aspect 102. The multimeric polypeptide of any one of aspects 98-101, wherein the second polypeptide comprises two copies of the variant IL-2 polypeptide.

Aspect 103. The multimeric polypeptide of any one of aspects 98-102, wherein the first polypeptide comprises a peptide linker between the epitope and the β2M polypeptide.

Aspect 104. The multimeric polypeptide of any one of aspects 98-103, wherein the second polypeptide comprises a peptide linker between one or more of:

a) a first copy of the variant IL-2 polypeptide and a second copy of the variant IL-2 polypeptide;

b) the variant IL-2 polypeptide and the MHC heavy chain polypeptide; and c) between the MHC heavy chain polypeptide and the IgG1 Fc polypeptide.

Aspect 105. The multimeric polypeptide of aspect 103 or aspect 104, wherein the peptide linker is selected from $(GGGGS)_3$, $(GGGGS)_4$, and AAAGG.

Aspect 106. A multimeric polypeptide comprising:

a) a first polypeptide comprising the amino acid sequence depicted in FIG. 31;

b) a second polypeptide comprising the amino acid sequence depicted in FIG. 22.

Aspect 107. A multimeric polypeptide comprising:

a) a first polypeptide comprising the amino acid sequence depicted in FIG. 31;

b) a second polypeptide comprising the amino acid sequence depicted in FIG. 25.

Aspect 108. A multimeric polypeptide comprising:

a) a first polypeptide comprising the amino acid sequence depicted in FIG. 31;

b) a second polypeptide comprising the amino acid sequence depicted in FIG. 28.

Aspect 109. A pharmaceutical composition comprising:

a) a multimeric polypeptide according to any one of aspects 80-108; and b) a pharmaceutically acceptable excipient.

Aspect 110. One or more nucleic acids comprising nucleotide sequences encoding the first and/or the second polypeptide of the multimeric polypeptide according to any one of aspects 80-108.

Aspect 111. The one or more nucleic acids of aspect 110, wherein the nucleic acid(s) is/are present in recombinant expression vectors.

Aspect 112. A method of selectively activating an epitope-specific T cell, the method comprising contacting the T cell with the multimeric polypeptide of any one of aspects 80-108, wherein said contacting selectively activates the epitope-specific T cell.

Aspect 113. The method of aspect 112, wherein said contacting is in vitro.

Aspect 114. The method of aspect 112, wherein said contacting is in vivo.

Aspect 115. A method comprising administering to an individual an effective amount of:

a) the multimeric polypeptide of any one of aspects 80-108; or b) one or more recombinant expression vectors comprising nucleotide sequences encoding the multimeric polypeptide of any one of aspects 80-108; or c) one or more mRNAs comprising nucleotide sequences encoding the multimeric polypeptide of any one of aspects 80-108, wherein said administering induces a T cell response to epitope in the individual.

Aspect 116. The method of aspect 115, wherein said administering is subcutaneous.

Aspect 117. The method of aspect 115, wherein said administering is intravenous.

Aspect 118. The method of aspect 115, wherein said administering is systemic.

Aspect 119. The method of aspect 115, wherein said administering is intramuscular.

Aspect 120. The method of aspect 115, wherein said administering is distal to a treatment site.

Aspect 121. The method of aspect 115, wherein said administering is local.

Aspect 122. The method of aspect 115, wherein said administering is at or near a treatment site.

Aspect A. A method of modulating an immune response an individual in need thereof, the method comprising administering to the individual a multimeric polypeptide and an immune checkpoint inhibitor, wherein the multimeric polypeptide comprises:

a) a first polypeptide comprising, in order from N-terminus to C-terminus:

i) an epitope;

ii) a first major histocompatibility complex (MHC) polypeptide; and b) a second polypeptide comprising, in order from N-terminus to C-terminus:

i) a second MHC polypeptide; and ii) optionally an immunoglobulin (Ig) Fc polypeptide or a non-Ig scaffold, wherein the multimeric polypeptide comprises one or more immunomodulatory polypeptides, wherein the one or more immunomodulatory polypeptides is:

A) at the C-terminus of the first polypeptide;

B) at the N-terminus of the second polypeptide;

C) at the C-terminus of the second polypeptide; or

D) at the C-terminus of the first polypeptide and at the N-terminus of the second polypeptide; and wherein said administering modulates the immune response in the individual.

Aspect B. A treatment method comprising administering to an individual a multimeric polypeptide and an immune checkpoint inhibitor, wherein the multimeric polypeptide comprises:

a) a first polypeptide comprising, in order from N-terminus to C-terminus:

i) an epitope;

ii) a first major histocompatibility complex (MHC) polypeptide; and b) a second polypeptide comprising, in order from N-terminus to C-terminus:

i) a second MHC polypeptide; and ii) optionally an immunoglobulin (Ig) Fc polypeptide or a non-Ig scaffold, wherein the multimeric polypeptide comprises one or more immunomodulatory polypeptides, wherein the one or more immunomodulatory polypeptides is:

A) at the C-terminus of the first polypeptide;

B) at the N-terminus of the second polypeptide;

C) at the C-terminus of the second polypeptide; or

D) at the C-terminus of the first polypeptide and at the N-terminus of the second polypeptide; and wherein said administering treats the individual.

Aspect C. A method of treating cancer in an individual, the method comprising administering to the individual a multimeric polypeptide and an immune checkpoint inhibitor, wherein the multimeric polypeptide comprises:

a) a first polypeptide comprising, in order from N-terminus to C-terminus:

i) an epitope;

ii) a first major histocompatibility complex (MHC) polypeptide; and b) a second polypeptide comprising, in order from N-terminus to C-terminus:

i) a second MHC polypeptide; and ii) optionally an immunoglobulin (Ig) Fc polypeptide or a non-Ig scaffold, wherein the multimeric polypeptide comprises one or more immunomodulatory polypeptides, wherein the one or more immunomodulatory polypeptides is:

A) at the C-terminus of the first polypeptide;

B) at the N-terminus of the second polypeptide;

C) at the C-terminus of the second polypeptide; or

D) at the C-terminus of the first polypeptide and at the N-terminus of the second polypeptide; and wherein said administering treats the cancer in the individual.

Aspect D. A treatment method comprising administering to an individual a multimeric polypeptide, where the individual is undergoing treatment with an immune checkpoint inhibitor, wherein the multimeric polypeptide comprises:

a) a first polypeptide comprising, in order from N-terminus to C-terminus:

i) an epitope;

ii) a first major histocompatibility complex (MHC) polypeptide; and b) a second polypeptide comprising, in order from N-terminus to C-terminus:

i) a second MHC polypeptide; and ii) optionally an immunoglobulin (Ig) Fc polypeptide or a non-Ig scaffold, wherein the multimeric polypeptide comprises one or more immunomodulatory polypeptides, wherein the one or more immunomodulatory polypeptides is:

A) at the C-terminus of the first polypeptide;

B) at the N-terminus of the second polypeptide;

C) at the C-terminus of the second polypeptide; or

D) at the C-terminus of the first polypeptide and at the N-terminus of the second polypeptide; and wherein said administering treats the individual.

Aspect E. The method of any one of Aspects A-D, wherein the multimeric polypeptide comprises:

a) a first polypeptide comprising, in order from N-terminus to C-terminus:

i) an epitope;

ii) a first MHC polypeptide; and iii) an immunomodulatory domain; and b) a second polypeptide comprising, in order from N-terminus to C-terminus:

i) a second MHC polypeptide; and ii) an Ig Fc polypeptide.

Aspect F. The method of any one of Aspects A-D, wherein the multimeric polypeptide comprises:

a) a first polypeptide comprising, in order from N-terminus to C-terminus:

i) an epitope; and ii) a first MHC polypeptide; and b) a second polypeptide comprising, in order from N-terminus to C-terminus:

i) an immunomodulatory domain;

iii) a second MHC polypeptide; and ii) an immunoglobulin (Ig) Fc polypeptide.

Aspect G. The method of any one of Aspects A-D, wherein the multimeric polypeptide comprises:

a) a first polypeptide comprising, in order from N-terminus to C-terminus:

i) an epitope; and ii) a first MHC polypeptide; and b) a second polypeptide comprising, in order from N-terminus to C-terminus:

i) a second MHC polypeptide; and ii) an Ig Fc polypeptide; and iii) an immunomodulatory domain Aspect H. The method of any one of Aspects A-D, wherein the multimeric polypeptide comprises:

a) a first polypeptide comprising, in order from N-terminus to C-terminus:

i) an epitope; and ii) a first MHC polypeptide; and b) a second polypeptide comprising, in order from N-terminus to C-terminus:

i) a second MHC polypeptide; and ii) an immunomodulatory domain.

Aspect I. The method of any one of Aspects A-D, wherein the multimeric polypeptide comprises:

a) a first polypeptide comprising, in order from N-terminus to C-terminus:

i) an epitope; and ii) a first MHC polypeptide; and b) a second polypeptide comprising, in order from N-terminus to C-terminus:

i) an immunomodulatory domain; and ii) a second MHC polypeptide.

Aspect J. The method of any one of Aspects A-D, wherein the multimeric polypeptide comprises:

a) a first polypeptide comprising, in order from N-terminus to C-terminus:

i) an epitope;

ii) a first MHC polypeptide; and iii) an immunomodulatory domain; and b) a second polypeptide comprising, in order from N-terminus to C-terminus:

i) a second MHC polypeptide.

Aspect K. The method of any one of Aspects A-D, wherein the non-Ig scaffold of the multimeric polypeptide is an XTEN polypeptide, a transferrin polypeptide, an Fc receptor polypeptide, an elastin-like polypeptide, a silk-like polypeptide, or a silk-elastin-like polypeptide.

Aspect L. The method of any one of aspects A-K, wherein the first MHC polypeptide of the multimeric polypeptide is a β2-microglobulin polypeptide; and wherein the second MHC polypeptide is an MHC class I heavy chain polypeptide.

Aspect M. The method of aspect L, wherein the β2-microglobulin polypeptide of the multimeric polypeptide comprises an amino acid sequence having at least 85% amino acid sequence identity to one of the amino acid sequences set forth in FIG. 6.

Aspect N. The method of aspect L, wherein the MHC class I heavy chain polypeptide of the multimeric polypeptide is an HLA-A, an HLA-B, or an HLA-C heavy chain.

Aspect O. The method of aspect 11, wherein the MHC class I heavy chain polypeptide comprises an amino acid sequence having at least 85% amino acid sequence identity to the amino acid sequence set forth in one of FIG. 5A-5C.

Aspect P. The method of any one of aspects A-K, wherein the first MHC polypeptide of the multimeric polypeptide is an MHC Class II alpha chain polypeptide; and wherein the second MHC polypeptide is an MHC class II beta chain polypeptide.

Aspect Q. The method of any one of aspects A-P, wherein the epitope is a T-cell epitope.

Aspect R. The method of any one of aspects A-J, wherein multimeric polypeptide of the multimeric polypeptide comprises an Fc polypeptide, and wherein the Ig Fc polypeptide is an IgG1 Fc polypeptide, an IgG2 Fc polypeptide, an IgG3 Fc polypeptide, an IgG4 Fc polypeptide, an IgA Fc polypeptide, or an IgM Fc polypeptide.

Aspect S. The method of aspect R, wherein the Ig Fc polypeptide comprises an amino acid sequence having at least 85% amino acid sequence identity to an amino acid sequence depicted in FIG. 4A-4C.

Aspect T. The method of any one of aspects A-S, wherein the first polypeptide and the second polypeptide of the multimeric polypeptide are non-covalently associated.

Aspect U. The method of any one of aspects A-S, wherein the first polypeptide and the second polypeptide of the multimeric polypeptide are covalently linked.

Aspect V. The method of aspect U, wherein the covalent linkage is via a disulfide bond.

Aspect W. The method of aspect V, wherein the first MHC polypeptide or a linker between the epitope and the first MHC polypeptide of the multimeric polypeptide comprises an amino acid substitution to provide a first Cys residue, and the second MHC polypeptide of the multimeric polypeptide comprises an amino acid substitution to provide a second Cys residue, and wherein the disulfide linkage is between the first and the second Cys residues.

Aspect X. The method of any one of aspects A-K, wherein the multimeric polypeptide comprises a linker between the epitope and the first MHC polypeptide, between the immunomodulatory polypeptide and the MHC polypeptide, or between the MHC polypeptide and the Ig Fc.

Aspect Y. The method of any one of aspects A-K, wherein the immunomodulatory polypeptide of the multimeric polypeptide is selected from a 4-1BBL polypeptide, a B7-1 polypeptide; a B7-2 polypeptide, an ICOS-L polypeptide, an OX-40L polypeptide, a CD80 polypeptide, a CD86 polypeptide, a PD-L1 polypeptide, a FasL polypeptide, and a PD-L2 polypeptide.

Aspect Z. The method of any one of aspects A-Y, wherein the multimeric polypeptide comprises 2 or more immunomodulatory polypeptides.

Aspect AA. The method of aspect Z, wherein the 2 or more immunomodulatory polypeptides are in tandem.

Aspect BB. The method of any one of aspects A-Z and AA, wherein the immunomodulatory polypeptide is selected from a 4-1BBL polypeptide, a CD80 polypeptide, a CD86 polypeptide, an IL-2 polypeptide, a B7-1 polypeptide; a B7-2 polypeptide, an ICOS-L polypeptide, an OX-40L polypeptide, a CD86 polypeptide, a PD-L1 polypeptide, a FasL polypeptide, and a PD-L2 polypeptide.

Aspect CC. The method of any one of aspects A-Z and AA-BB, wherein the immunomodulatory polypeptide is a variant immunomodulatory polypeptide has one or more amino acid substitutions relative to the naturally occurring form of the immunomodulatory polypeptide, and wherein the variant immunomodulatory polypeptide exhibits reduced binding affinity to a co-modulatory polypeptide to which the naturally occurring form of the immunomodulatory polypeptide binds.

Aspect DD. The method of any one of aspects A-Z and AA-BB, wherein the immunomodulatory polypeptide is a variant IL-2 polypeptide comprising an amino acid sequence having at least 85% amino acid sequence identity to set forth in SEQ ID NO:1, wherein the variant IL-2 polypeptide has one or more amino acid substitutions relative to set forth in SEQ ID NO:1, and wherein the variant IL-2 polypeptide exhibits reduced binding affinity to an IL-2 receptor (IL2R) comprising alpha, beta, and gamma polypeptides having amino acid sequences depicted in FIG. 3A-3C, compared to the binding affinity of the IL-2 amino acid sequence set forth in one of SEQ ID NO:1 for the IL2R.

Aspect EE. The method of aspect DD, wherein the variant IL-2 polypeptide comprises a substitution of one or more of E15, H16, D20, F42, Y45, and Q126.

Aspect FF. The method of aspect EE, wherein the variant IL-2 polypeptide comprises:

a) substitutions of F42 and D20;

b) substitutions of F42 and H16;

c) substitutions of F42, D20, and Y45; or d) substitutions of F42, H16, and Q126.

Aspect GG. The method of any one of aspects A-Z and AA-FF, wherein the multimeric polypeptide comprises an Ig Fc polypeptide comprising one or more amino acid substitutions selected from N297A, L234A, L235A, L234F, L235E, and P331S.

Aspect HH. The method of aspect GG, wherein the Ig Fc polypeptide comprises:

a) an N297A substitution;

b) an L234A substitution and an L235A substitution;

c) an L234F substitution and an L235E substitution; or d) an L234F substitution, an L235E substitution, and a P331S substitution.

Aspect II. The method of any one of aspects A-Z and AA-HH, wherein the epitope of the multimeric polypeptide comprises the amino acid sequence YMLDLQPETT (SEQ ID NO:77).

Aspect JJ. The method of any one of aspects A-Z and AA-HH, wherein the β2-microglobulin polypeptide of the multimeric polypeptide comprises the amino acid sequence depicted in FIG. 34A.

Aspect KK. The method of any one of aspects A-Z and AA-JJ, wherein the major histocompatibility complex (MHC) heavy chain polypeptide of the multimeric polypeptide comprises the amino acid sequence depicted in FIG. 34C.

Aspect LL. The method of any one of aspects A-Z and AA-KK, wherein the immune checkpoint inhibitor is an antibody specific for the immune checkpoint inhibitor.

Aspect MM. The method of aspect LL, wherein the antibody is a monoclonal antibody.

Aspect NN. The method of aspect KK or aspect LL, wherein the antibody comprises at least one humanized light chain and/or heavy chain framework region.

Aspect OO. The method of aspect LL, wherein the antibody comprises an Fc polypeptide, and wherein the Ig Fc polypeptide is an IgG1 Fc polypeptide, an IgG2 Fc polypeptide, an IgG3 Fc polypeptide, an IgG4 Fc polypeptide, an IgA Fc polypeptide, or an IgM Fc polypeptide.

Aspect PP. The method of aspect LL, wherein the antibody is an Fv fragment, a nanobody, or a Fab fragment.

Aspect QQ. The method of any one of aspects LL-PP, wherein the immune checkpoint inhibitor is an antibody specific for an immune checkpoint inhibitor selected from CD27, CD28, CD40, CD122, CD96, CD73, CD47, OX40, GITR, CSF1R, JAK, PI3K delta, PI3K gamma, TAM, arginase, CD137 (also known as 4-1BB), ICOS, A2AR, B7-H3, B7-H4, BTLA, CTLA-4, LAG3, TIM3, VISTA, CD96, TIGIT, CD122, PD-1, PD-L1 and PD-L2.

Aspect RR. The method of any one of aspects LL-PP, wherein the immune checkpoint inhibitor is an antibody specific for PD1.

Aspect SS. The method of aspect RR, wherein the antibody is pembrolizumab, nivolumab, pidilizumab, or BMS-39886.

Aspect TT. The method of any one of aspects LL-PP, wherein the immune checkpoint inhibitor is an antibody specific for PD-L1.

Aspect UU. The method of aspect TT, wherein the antibody is durvalumab, atezolizumab, KN035, or avelumab.

Aspect VV. The method of any one of aspects LL-PP, wherein the immune checkpoint inhibitor is an antibody specific for CTLA4.

Aspect WW. The method of aspect VV, wherein the antibody is ipilimumab or tremelimumab.

Aspect XX. The method of any one of aspects A-Z and AA-WW, wherein the multimeric polypeptide and the immune checkpoint inhibitor are administered by the same route of administration.

Aspect YY. The method of any one of aspects A-Z and AA-WW, wherein the multimeric polypeptide and the immune checkpoint inhibitor are administered by different routes of administration.

Aspect ZZ. The method of any one of aspects A-Z and AA-YY, wherein the multimeric polypeptide is administered by a route of administration selected from subcutaneous, intravenous, peritumoral, and intramuscular.

Aspect AAA. The method of any one of aspects A-Z and AA-YY, wherein the immune checkpoint inhibitor is administered by a route of administration selected from subcutaneous, intravenous, peritumoral, and intramuscular.

Aspect BBB. The method of any one of aspects A-Z, AA-ZZ, and AAA, wherein the individual is a human

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); kiloDalton(s), kDa; i.m., intramuscular (ly); i.p., intraperitoneal(ly); s.c., subcutaneous(ly); and the like.

Example 1: Production of IL-2/synTac

Figure 7A:
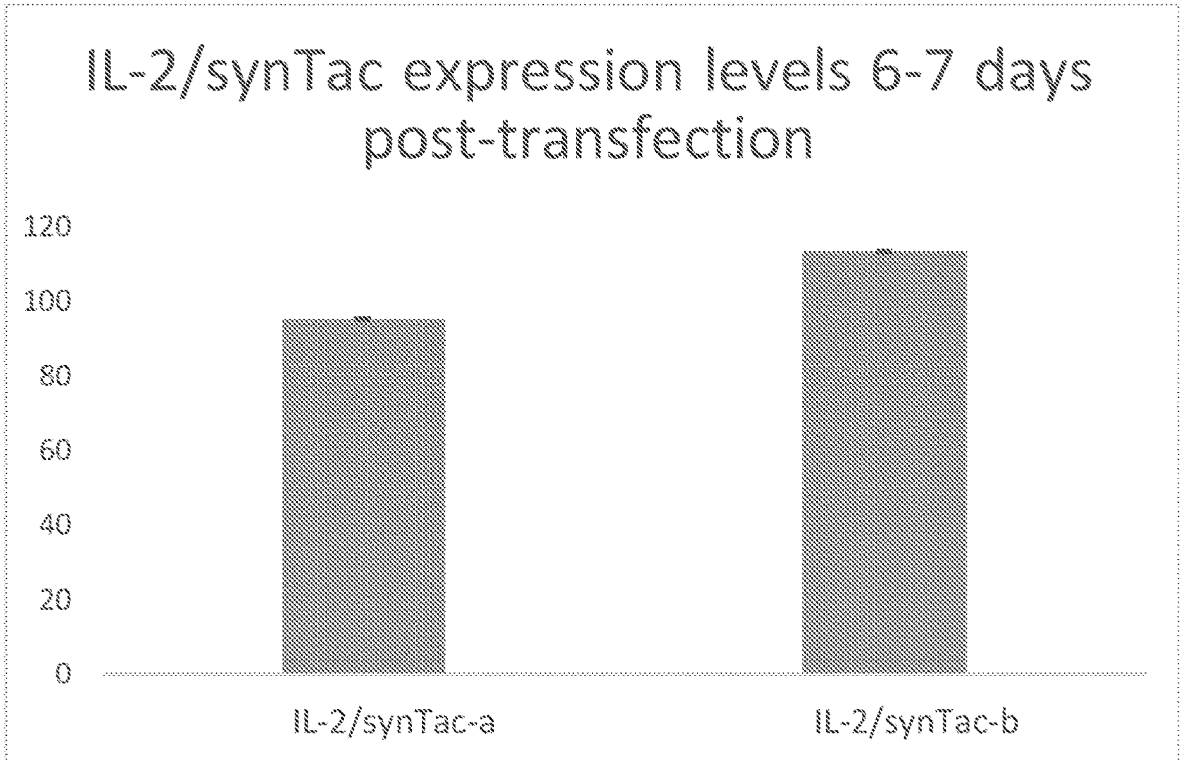
FIG. 7A-7B depict production of IL-2/synTacs ("Cue-IL-2-a" and Cue-IL-2-b") of the present disclosure following transient transfection.

Production of IL-2/synTac by transiently transfected mammalian cells was analyzed. As shown in FIG. 7A, production levels (in mg/L culture medium) of two different IL-2/synTacs, 6-7 days following transient transfection of the cells, was greater than 90 mg/L.

Figure 7B:
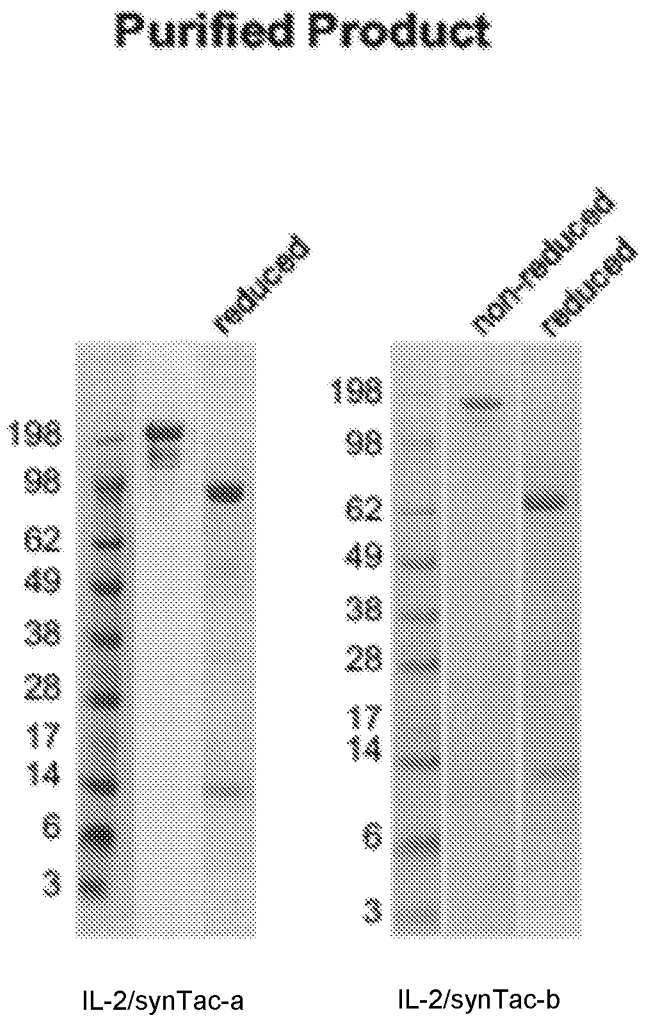

The IL-2/synTacs produced by the mammalian cells was purified, and subjected to reducing and non-reducing polyacrylamide gel electrophoresis. The results are depicted in FIG. 7B. Sizes are given in kDa.

IL-2/synTacs were generated, in which the IL-2 polypeptide was in the "light chain" (i.e., the polypeptide comprising MHC Class I light chain; e.g., β2M) or in the "heavy chain" (i.e., the polypeptide comprising MHC Class I heavy chain). Expression levels and stability of the IL-2/synTacs were analyzed.

Figure 8A:
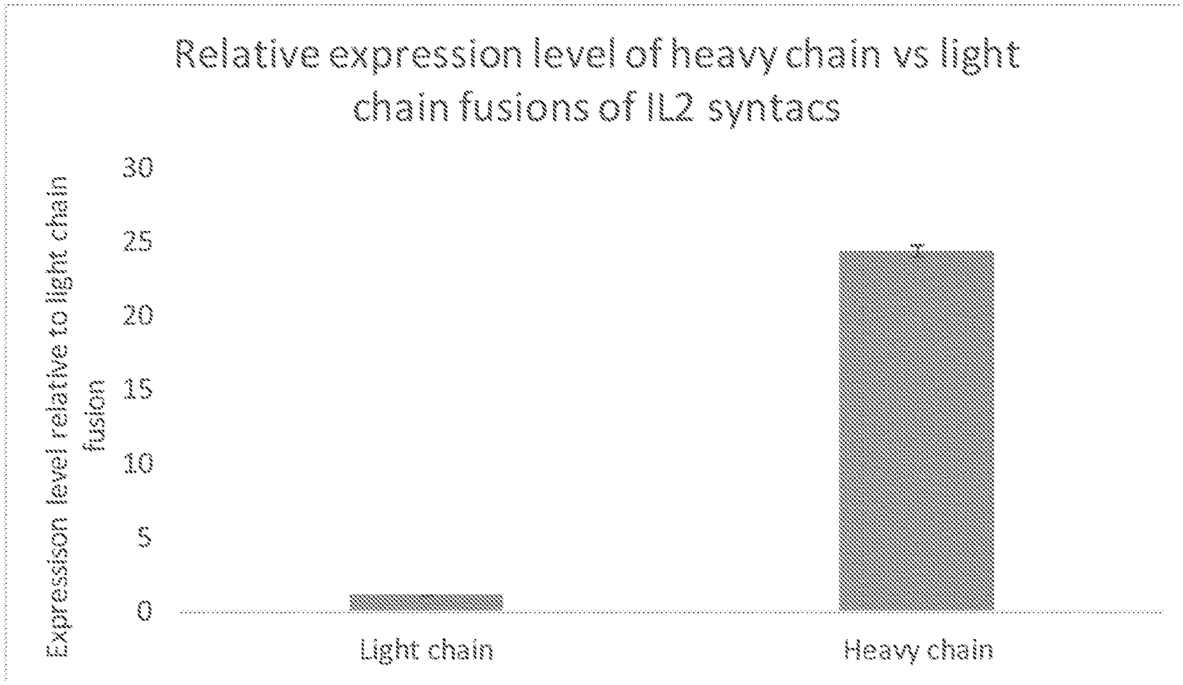
FIG. 8A-8B depict production of IL-2/synTacs of the present disclosure, in which the IL-2 polypeptide is present on the light chain (the polypeptide chain with the light chain (e.g., β2M) of an MHC Class I molecule) or on the heavy chain (the polypeptide chain with the heavy chain of an MHC Class I molecule).

The synTacs were produced in mammalian cells. As shown in FIG. 8A, the IL-2/synTac comprising IL-2 on the heavy chain was produced at levels about 25-fold higher than the level of the IL-2/synTac comprising IL-2 on the light chain.

Figure 8B:
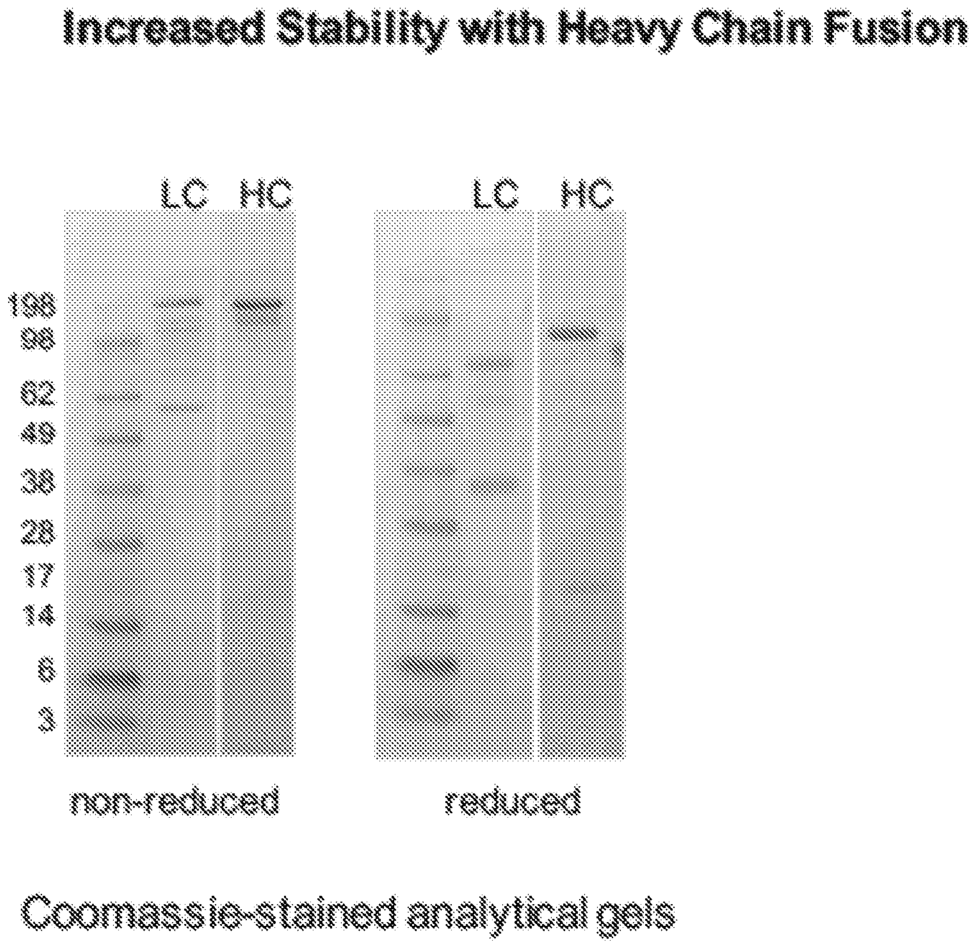

The IL-2/synTacs produced by mammalian cells were subjected to reducing and non-reducing polyacrylamide gel electrophoresis; and the gels were stained with Coomassie blue. As shown in FIG. 8B, the IL-2/synTac comprising IL-2 on the heavy chain was more stable than the IL-2/synTac comprising IL-2 on the light chain. Sizes are given in kDa.

Figure 9:
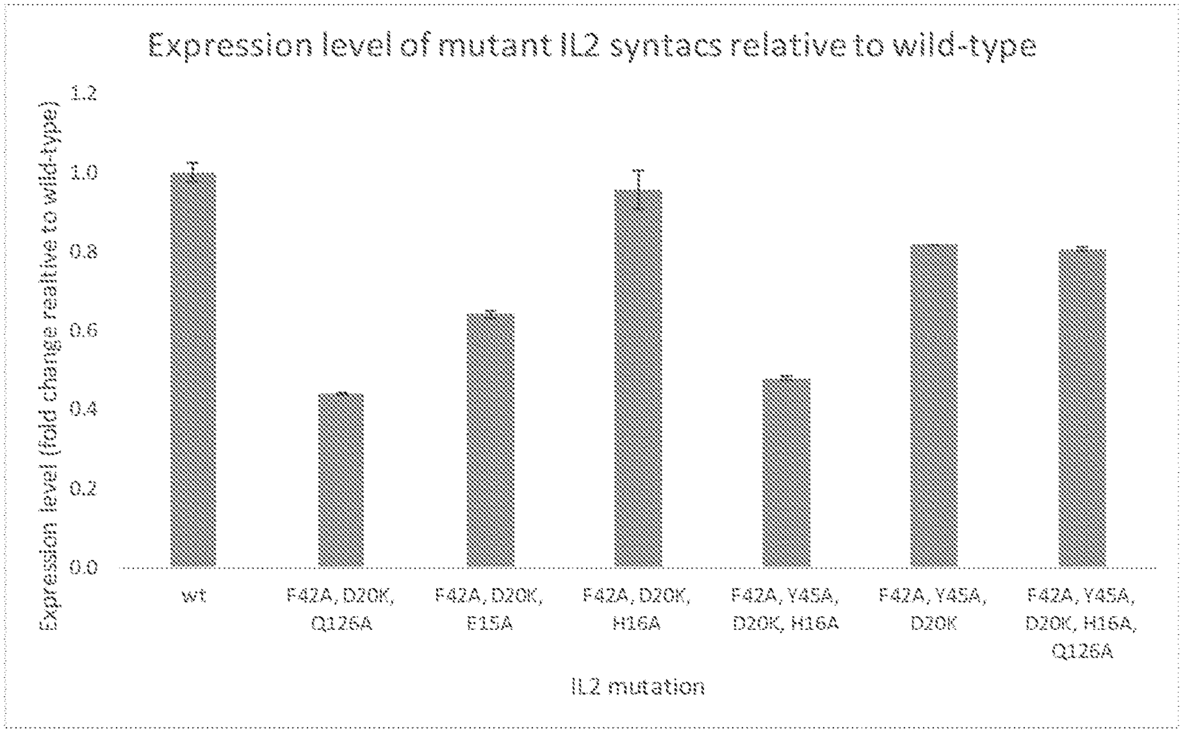
FIG. 9 depicts the expression level of IL-2/syn-Tacs, in which the IL-2 is wild-type (wt), or comprises various combinations of F42A, D20K, Q126A, E15A, Y45A, and H16A.

Expression levels of IL-2/synTacs comprising variant IL-2 were assessed. FIG. 9 depicts the expression level of IL-2/syn-Tacs, in which the IL-2 is wild-type (wt), or comprises various combinations of F42A, D20K, Q126A, E15A, Y45A, and H16A. The expression levels are expressed as percent change relative to expression levels of a synTac with wild-type IL-2.

Figure 10:
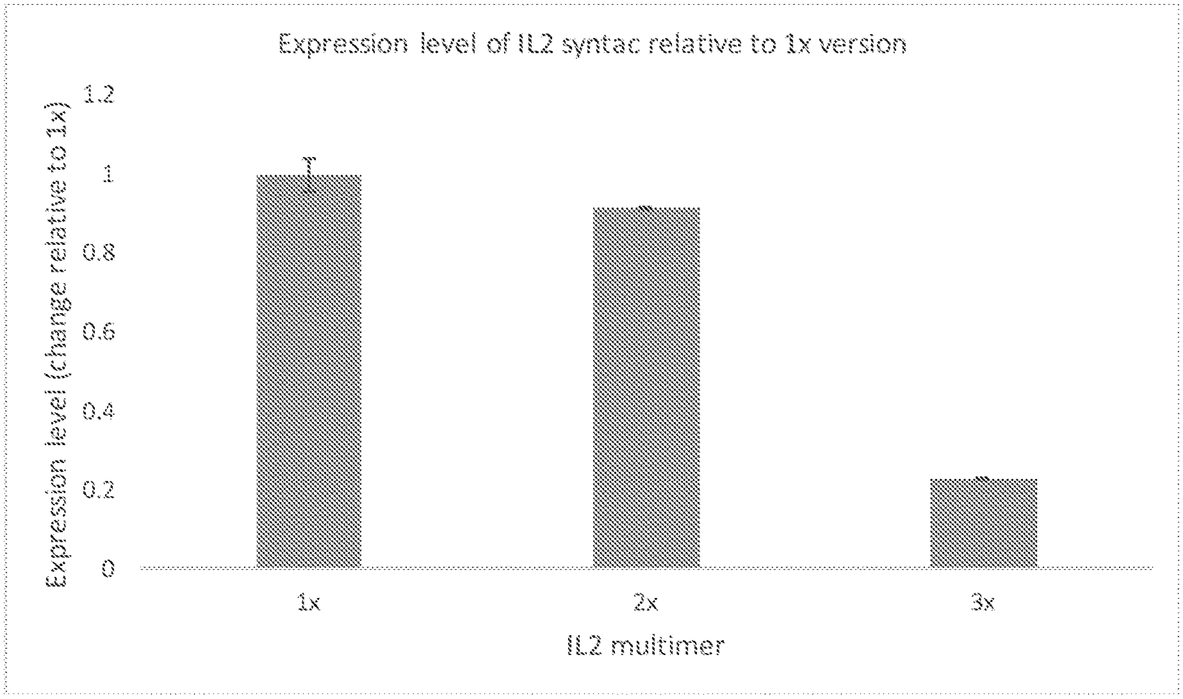
FIG. 10 depicts expression of IL-2/synTacs of the present disclosure, in which the IL-2 is present in one copy (1×), two copies (2×) or three copies (3×) in the synTac.

The effect of the copy number of IL-2 in an IL-2/synTac on expression levels was evaluated. IL-2/synTacs comprising one copy (1×), two copies (2×) or three copies (3×) in the synTac. The various IL-2/synTacs were produced in mammalian cells, and expression levels were assayed. The data are depicted in FIG. 10. IL-2/synTacs with one or two copies of IL-2 exhibit similar expression levels, while an IL-2/synTac with three copies of IL-2 exhibited lower expression levels. Expression levels are expressed as fold change relative to the expression level of the IL-2/synTac with a single copy of IL-2.

Example 2: In Vitro Activity of IL-2/synTac

To achieve maximal specificity of targeting through a T-cell receptor, the affinity of the co-stimulatory polypeptide for its ligand should be lower than the affinity of MHC for the TCR. The peptide/MHC affinity for TCR can be about 10 μM.

An IL-2/synTac was generated, comprising two copies of a variant IL-2 comprising F42A and H16A substitutions. Costimulatory signaling induced by the IL-2/synTac was tested on antigen-specific $CD8^+$ T cells and non-specific $CD8^+$ T cells. Antigen-specific $CD8^+$ T cells and non-specific $CD8^+$ T cells were contacted with various concentrations of the IL-2/synTac.

Figure 11:
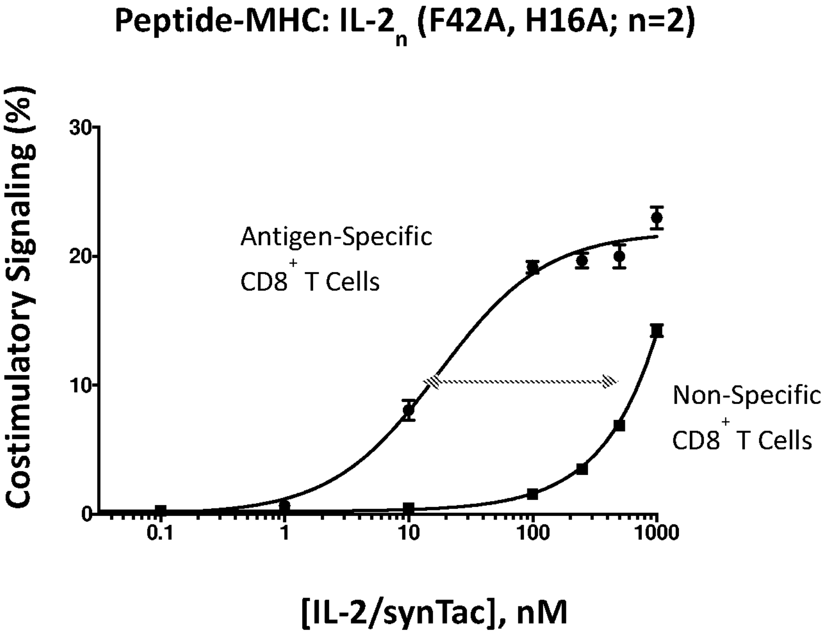
FIG. 11 depicts in vitro stimulation of antigen-specific $CD8^+$ T cells and non-specific $CD8^+$ T cells by an IL-2/synTac of the present disclosure, where the IL-2 variant comprising F42A and H16A substitutions is present in the synTac in two copies.

As shown in FIG. 11, the IL-2/synTac induced costimulatory signaling in antigen-specific $CD8^+$ T cells at a much lower concentration than in non-specific $CD8^+$ T cells.

Selectivity of IL-2/synTac binding was tested. $CD8^+$ T cells were isolated from spleens of LCMV or OT1 mice. The $CD8^+$ T cells were incubated with IL-2/synTacs at various concentrations, and allowed to bind for 20 minutes. The IL-2/synTacs comprise IgG2a Fc. Binding of IL-2/synTacs to the $CD8^+$ T cells was detected using phycoerythrin (PE)-labeled anti-IgG2a antibody. PE fluorescence was detected using flow cytometry to determine the percent of cells bound to IL-2/synTac.

Figure 12:
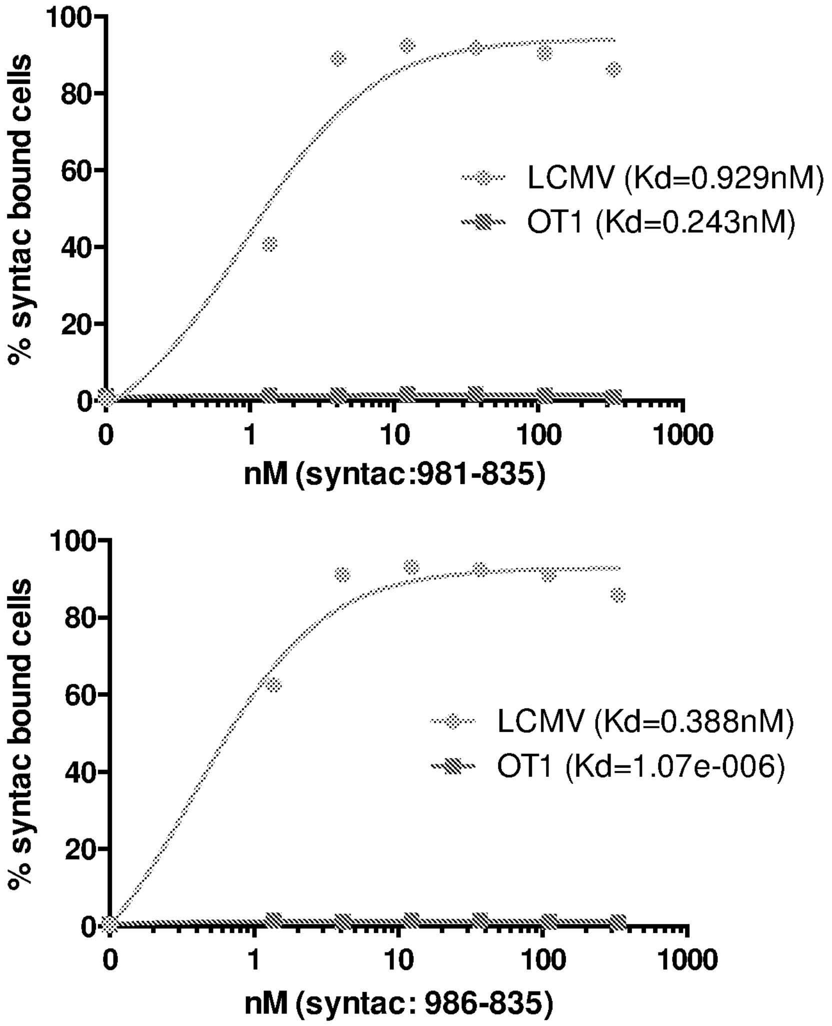
FIG. 12 depicts IL-2/synTac binding to specific (lymphocytic choriomeningitis virus; LCMV) or non-specific (OT1; recognizing ovalbumin) $CD8^+$ T cells.

As shown in FIG. 12, IL-2/synTac binds in an antigen-specific manner to LCMV $CD8^+$ T cells, but does not exhibit significant binding to OT1 $CD8^+$ T cells. Thus, IL-2/synTac selectively binds to $CD8^+$ T cells specific for the epitope present in the IL-2/synTac.

It was determined whether an IL-2/synTac selectively activates target T cells. $CD8^+$ T cells were isolated from spleens of LCMV or OT1 mice. The IL-2/synTacs used included either the F42A single amino acid substitution, or the F42A and H16A substitutions. The $CD8^+$ T cells were stimulated with IL-2/synTacs at various concentrations for 20 minutes. The cells were then stained with PE-labelled anti-phospho-STAT5 antibody. PE fluorescence was detected using flow cytometry to determine the percent of cells that are phospho-STAT5 positive, where phospho-STAT5 is a marker of activation.

Figure 13:
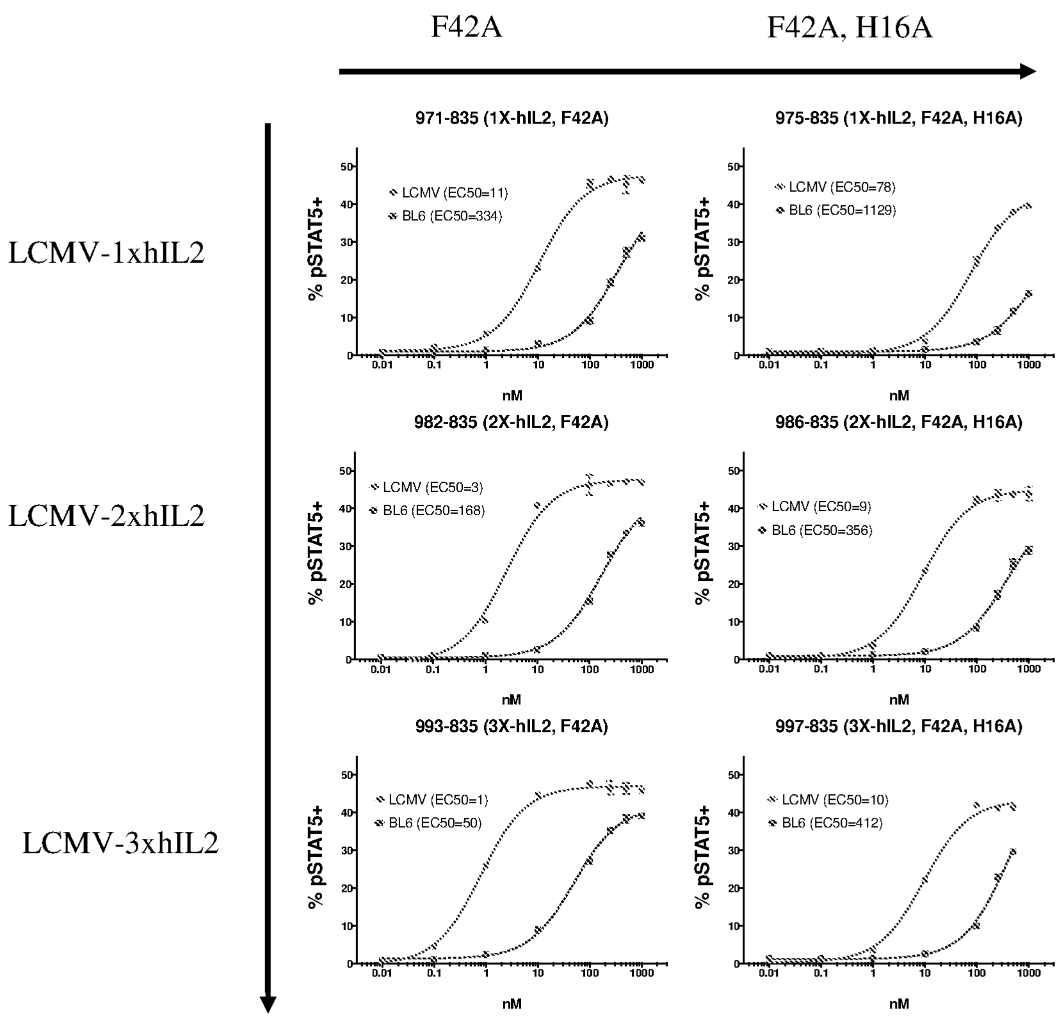
FIG. 13 depicts IL-2/synTac-mediated signaling in antigen-specific (LCMV) or non-specific (BL6) $CD8^+$ T cells.

As shown in FIG. 13, IL-2/synTac induced $CD8^+$ stimulation (as indicated by teh % phospho-STAT5-positive cells) in antigen-specific (LCMV) $CD8^+$ T cells at much lower concentrations than in non-specific (BL6) $CD8^+$ T cells.

The specific activity of various IL-2/synTacs was analyzed. IL-2/synTacs comprising a single copy of IL-2, two copies of IL-2, or three copies of IL-2, where the IL-2 comprised various combinations of F42A, D20K, Q126A, E15A, H16A, and Y45A substitutions, were tested at various concentrations for stimulation of $CD8^+$ antigen-specific (LCMV) or non-specific (BL6) cells. The percent phospho-signal transducer and activator of transcription 5 (pSTAT5)-positive was determined. The data are depicted in FIG. 14A-14F.

Example 3: In Vivo Activity of IL-2/synTac

Figure 15:
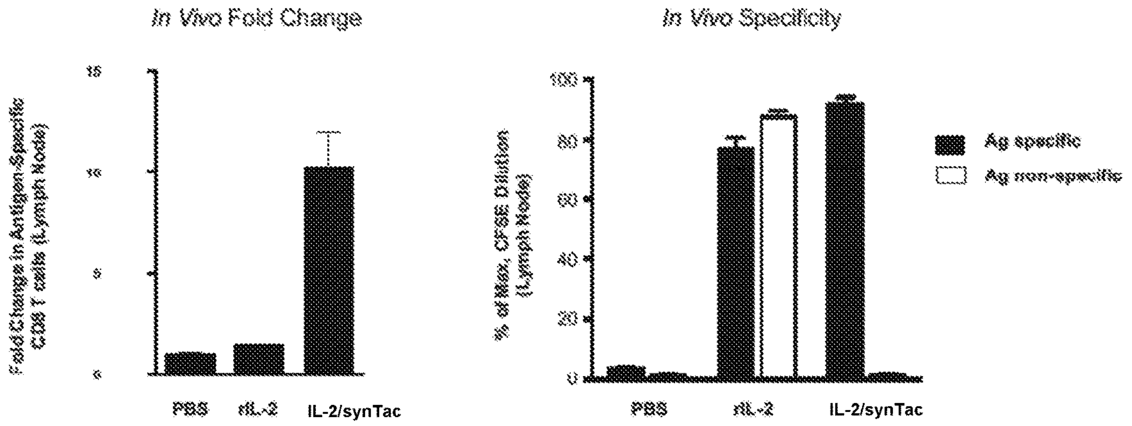
FIG. 15 depicts in vivo activity of an IL-2/synTac of the present disclosure. The left panel depicts the fold change in the number of antigen-specific $CD8^+$ T cells following administration of phosphate buffered saline (PBS), recombinant IL-2 (rIL-2), or an IL-2/synTac of the present disclosure. The right panel depicts antigen-specific and non-antigen-specific responses following administration of PBS, rIL-2, or an IL-2/synTac of the present disclosure.

The in vivo activity of IL-2/synTac was tested. The in vivo fold change in antigen-specific $CD8^+$ T cells was tested, following administration of phosphate buffered saline (PBS), recombinant IL-2 (rIL-2), or an IL-2/synTac of the present disclosure. The data are shown in FIG. 15, left panel. The data indicate that IL-2/synTac is 10 times more potent than rIL-2.

The in vivo specificity of IL-2/synTac was tested. Antigen-specific and non-antigen-specific responses following administration of PBS, rIL-2, or IL-2/synTac was assessed. The data are expressed as percent of lymph node cells that were antigen-specific or antigen non-specific following administration of PBS, rIL-2, or IL-2/synTac. As depicted in FIG. 15, right panel, IL-2/synTac induced an antigen-specific response (expressed as % maximum dilution of carboxyfluorescein succinimidyl ester (CFSE), an index of T cell proliferation). In contrast, the response induced by rIL-2 was not antigen-specific.

Figure 16A:
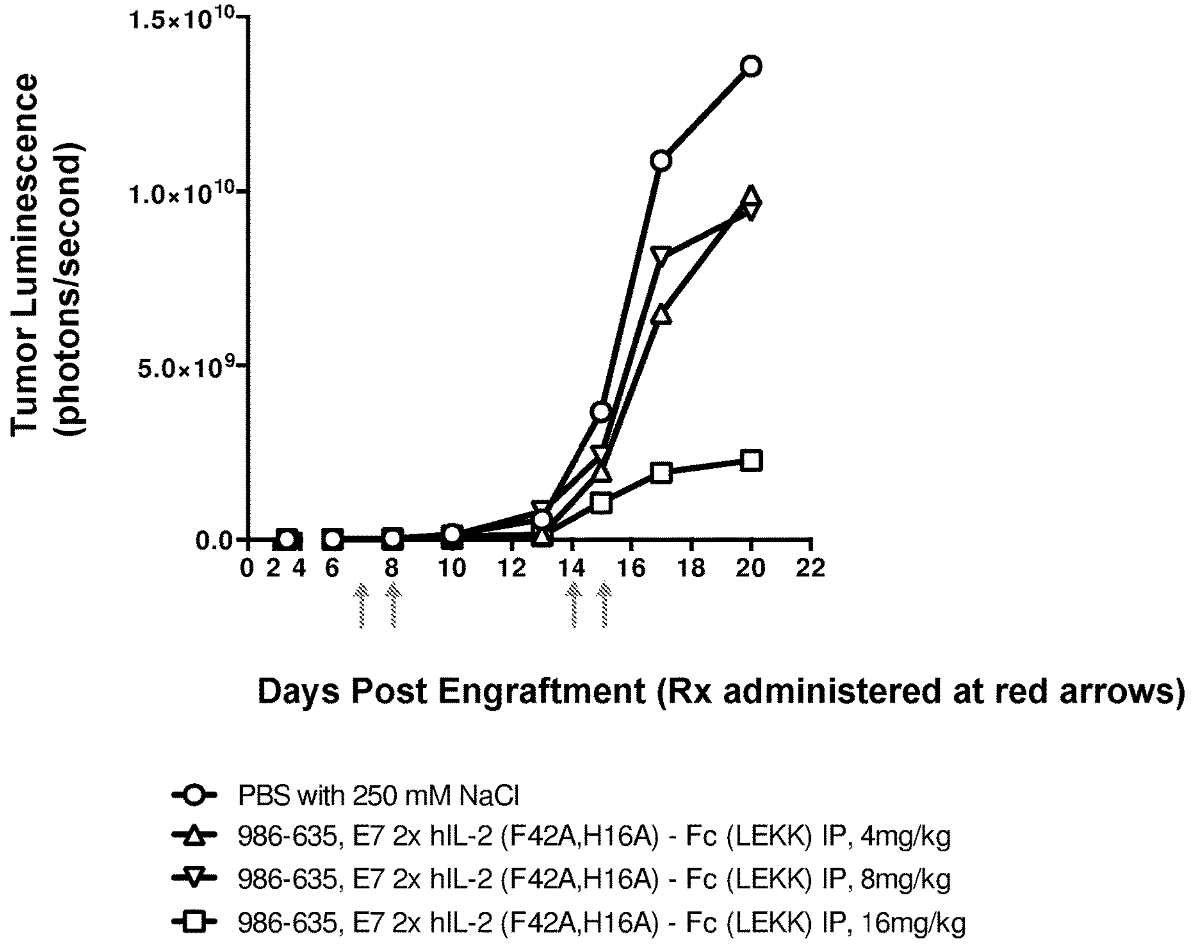
FIG. 16A-16B depict dose escalation (FIG. 16A) and route of administration (FIG. 16B) effects.

A dose response assay was conducted. IL-2/synTac (F42A, H16A) was administered intraperitoneally at concentrations of 4 mg/kg, 8 mg/kg, and 16 mg/kg. The results are shown in FIG. 16A. As shown in FIG. 16A, IL-2/synTac administered at 4 mg/kg or 8 mg/kg gave similar results; IL-2/synTac administered at 16 mg/kg induced the most potent immunostimulatory activity.

Figure 16B:
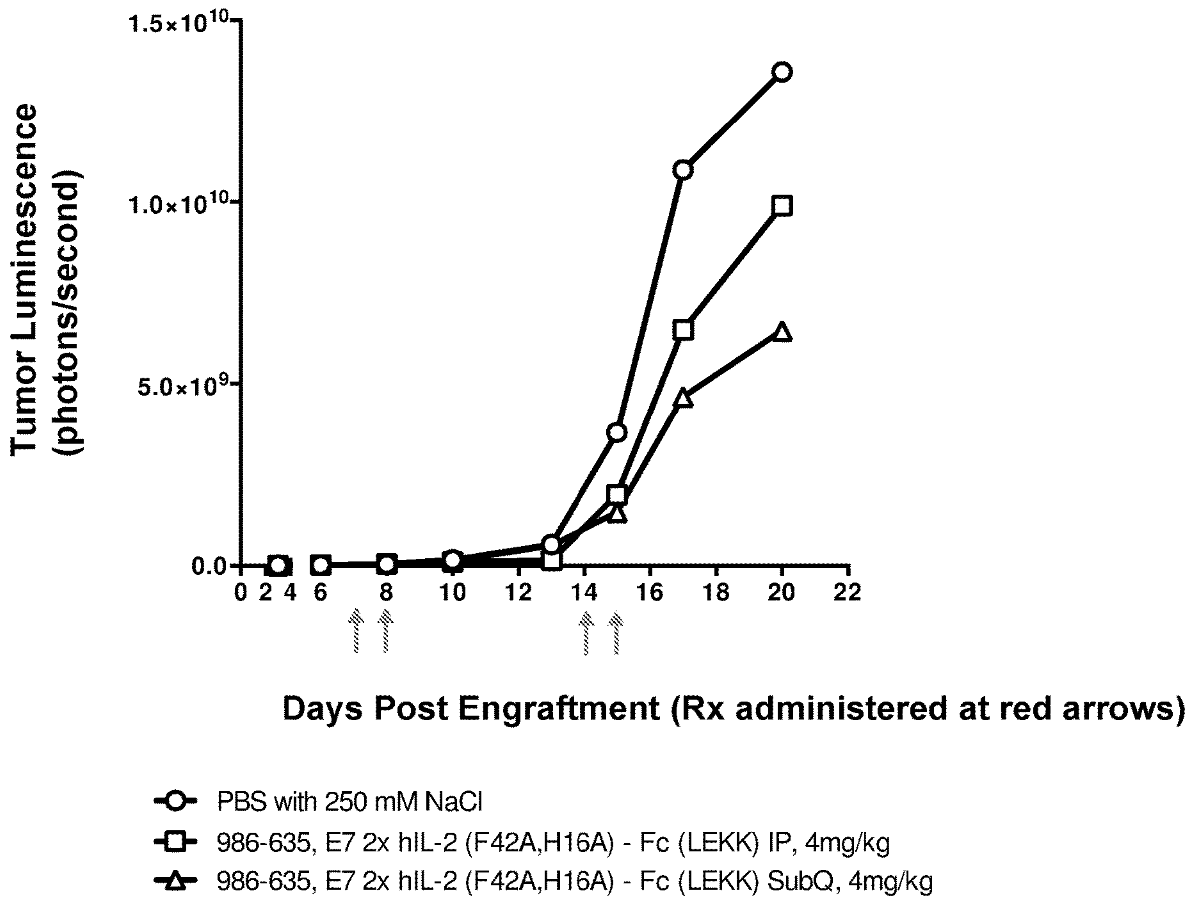

The effect of route of administration of IL-2/synTac was tested. IL-2/synTac (F42A, H16A) was administered at 4 mg/kg, either subcutaneously (SubQ) or intraperitoneally (IP). As shown in FIG. 16B, subcutaneous administration resulted in a more potent immunostimulatory activity than IP administration.

Figure 17A:
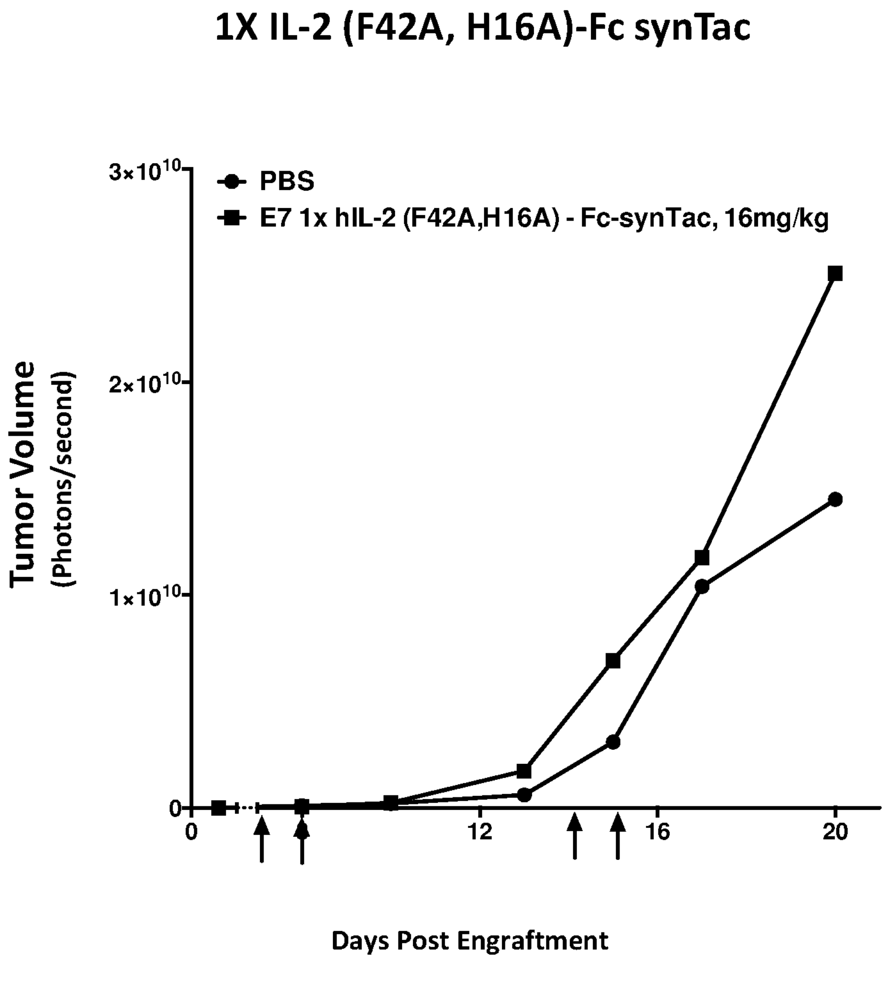
FIG. 17A-17B depict the effect of IL-2 copy number on in vivo efficacy against a tumor.
Figure 17B:
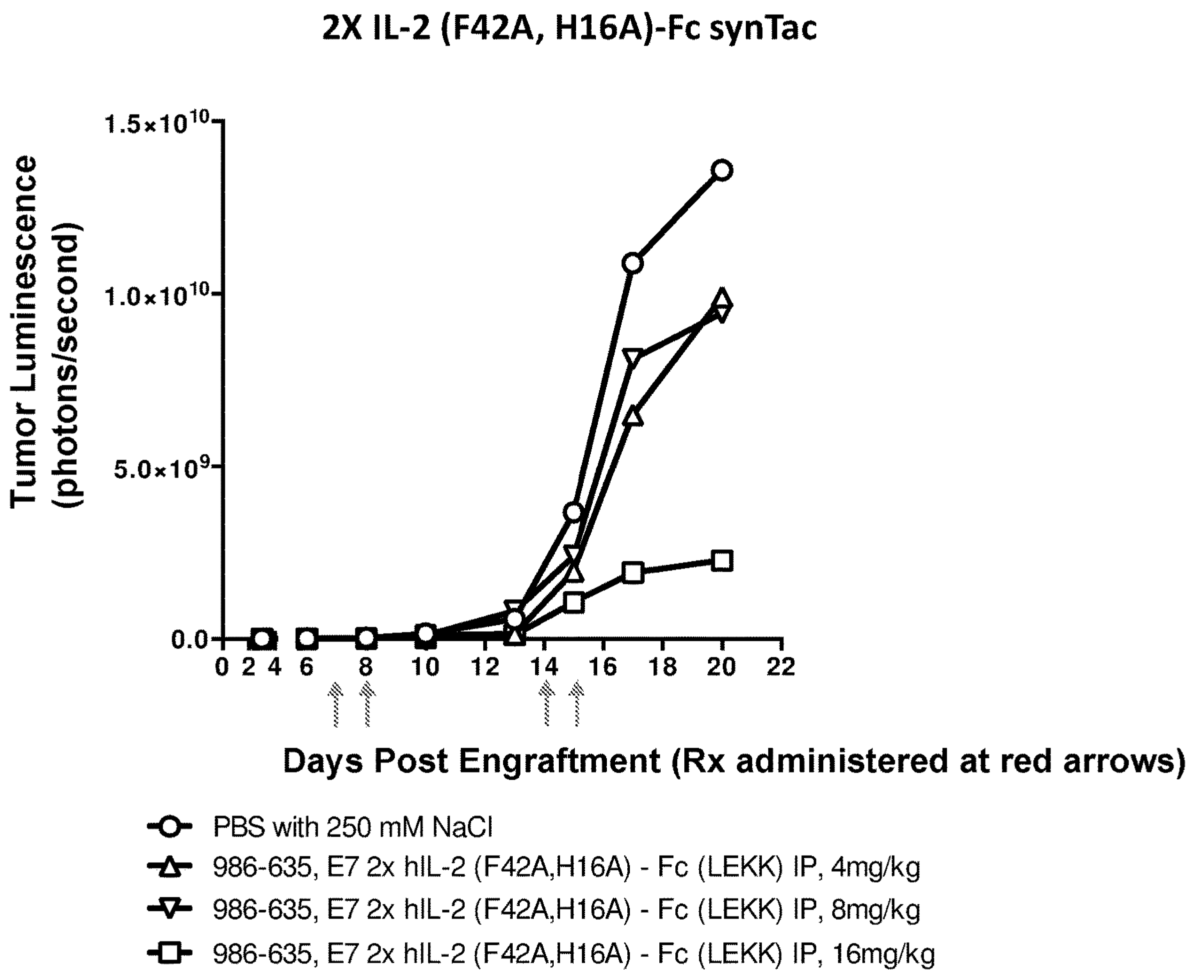

The effect of IL-2 copy number on efficacy was determined. IL-2/synTacs comprising a single copy of IL-2 (F42A, H16A) or two copies of IL-2 (F42A, H16A) were injected into mice with tumors bearing an HPV E7 epitope. The epitope included in the IL-2/synTacs was the HPV E7 epitope. As shown in FIGS. 17A and 17B, an IL-2/synTac comprising two copies of IL-2(F42A, H16A) were more effective at reducing tumor size than an IL-2/synTac comprising only a single copy of IL-2(F42A, H16A).

Example 4: PK/PD and Stability Studies of IL-2/synTac

Figure 18:
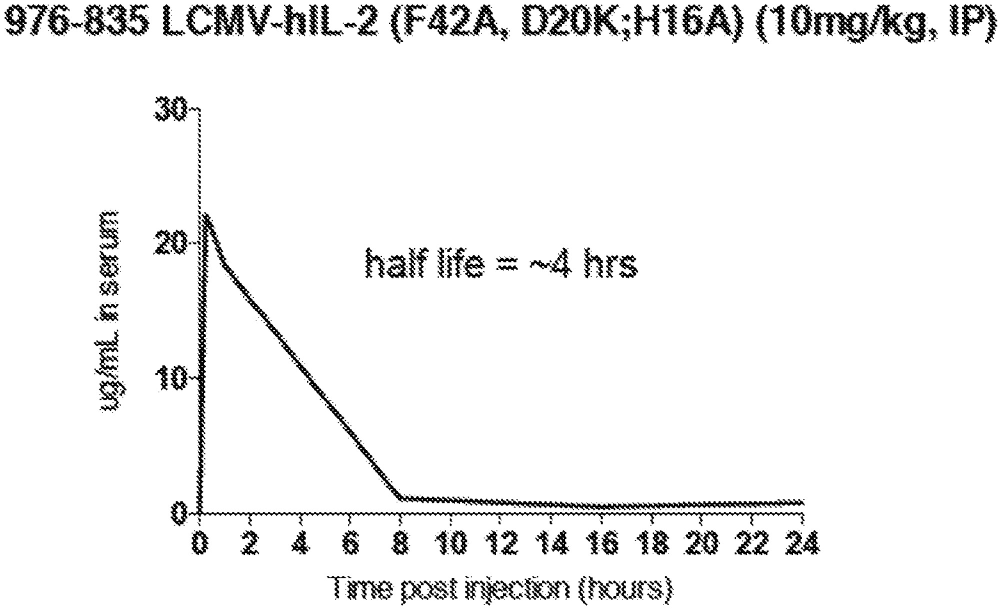
FIG. 18 depicts the serum half-life of an IL-2/synTac of the present disclosure, following intraperitoneal administration of the IL-2/synTac in an amount of 10 mg/kg.

Pharmacokinetic (PK) analysis of IL-2/synTac was carried out. IL-2/synTac (F42A, D20K, H16A) was administered IP at 10 mg/kg. At various time points post-administration, serum samples were obtained and the level of IL-2/synTac was measured in the serum samples. As shown in FIG. 18, the serum half-life of the IL-2/synTac was about 4 hours.

Figure 19:
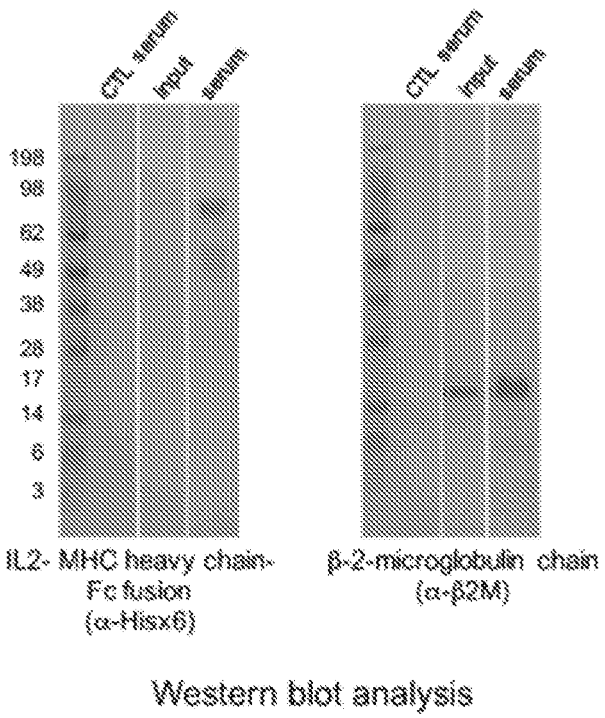
FIG. 19 depicts stability of an IL-2/synTac of the present disclosure 2 hours following intraperitoneal administration of the IL-2/synTac in an amount of 10 mg/kg.

IL-2/synTac was injected IP into a C57BL/6 mouse at 10 mg/kg, and serum was collected two hours after injections. The IL-2/synTac included a $His_6$ tag. 100 ng of the input protein, or the equivalent of 40 μl of serum, was subjected to sodium dodecyl sulfate-polyacrylamide gel electrophoresis (SDS-PAGE), and probed with an anti-$(His)_6$ antibody or an anti-β-2M antibody. The results, depicted in FIG. 19, show that IL-2/synTac remains stable and intact for at least 2 hours in vivo.

Figure 20:
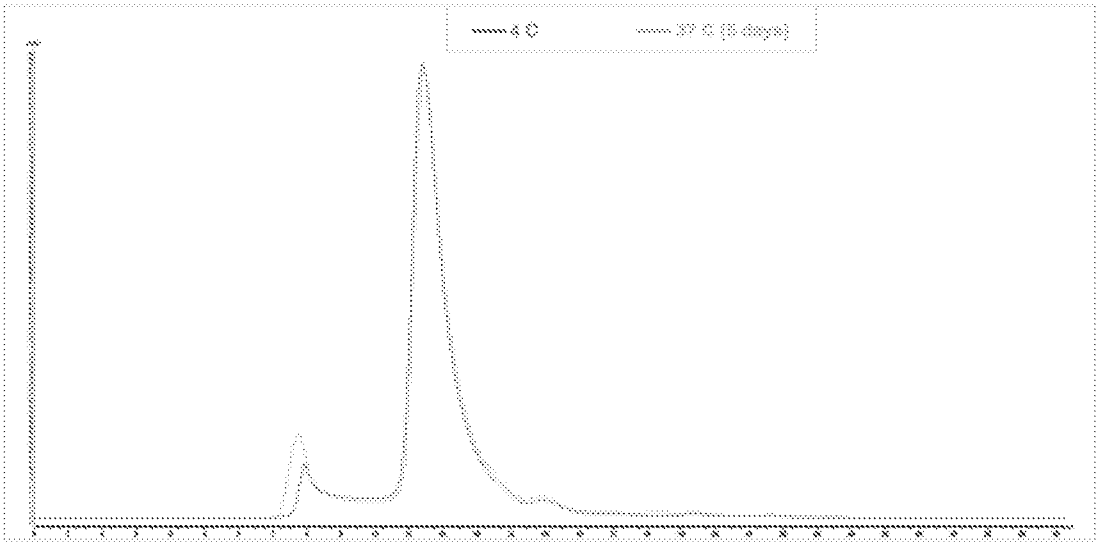
FIG. 20 depicts size exclusion chromatography data on an IL-2/synTac of the present disclosure after keeping the IL-2/synTac at 4° C. or 37° C. for 5 days.

IL-2/synTac was kept at 4° C. or 37° C. for 5 days. 0.5 mg of each sample (at 10 mg/ml) was analyzed by size exclusion chromatography. As shown in FIG. 20, IL-2/synTac is stable and intact for at least 5 days at 4° C. or 37° C.

Example 5: Effect of an IL-2/synTac and an Anti-PD1 Antibody on Tumor Volume

Figure 35:
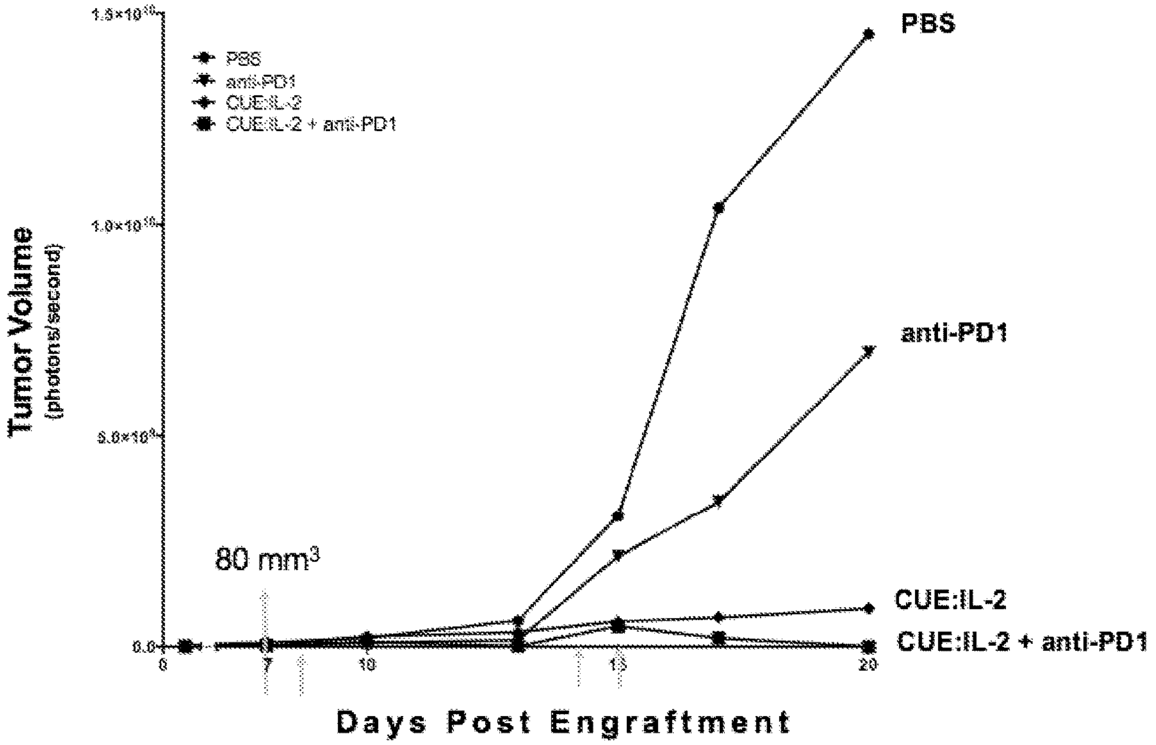
FIG. 35 depicts synergistic effects of an IL-2/synTac and an anti-PD1 antibody on reducing tumor volume.
Figure 38A:
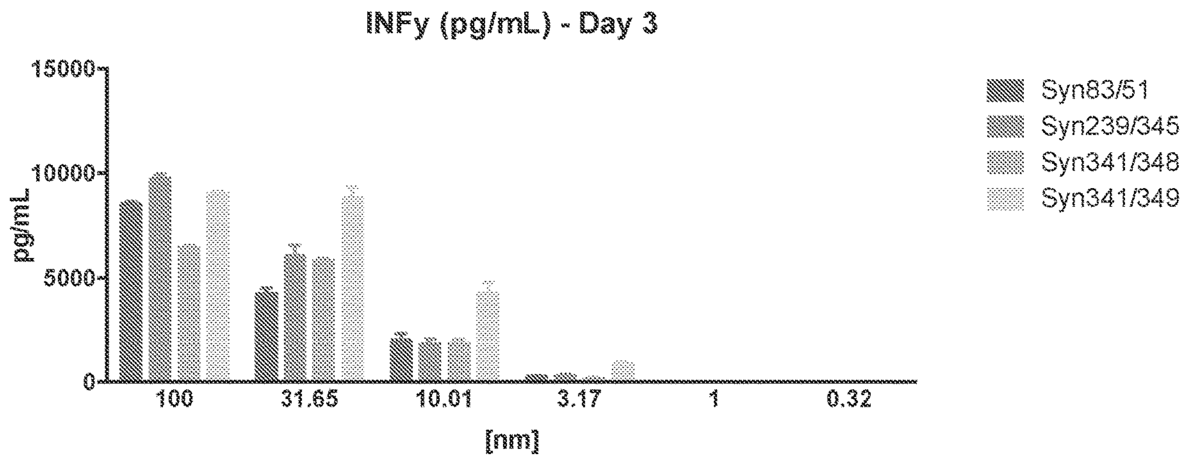
FIG. 38A-38B depicts interferon-gamma (IFN-γ) secretion by target cells contacted with a synTac polypeptide for 3 days (FIG. 38A) or 5 days (FIG. 8B) according to an embodiment of the present disclosure.
Figure 38B:
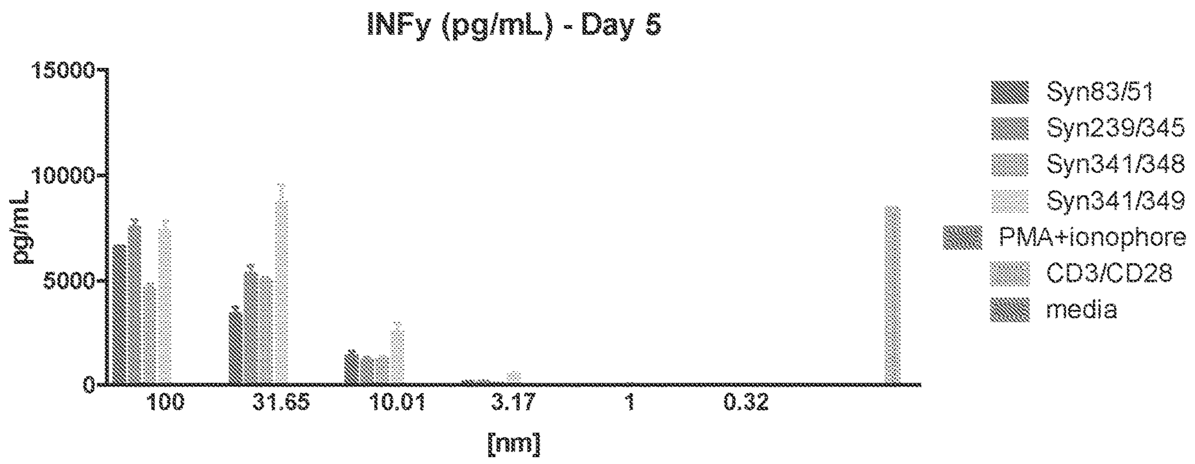
Figure 39A:
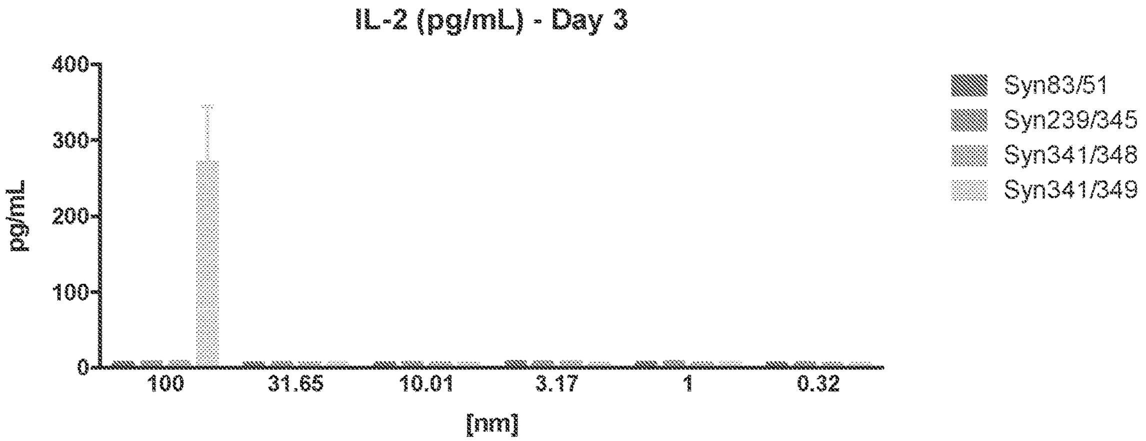
FIG. 39A-39B depicts interleukin-2 (IL-2) secretion by target cells contacted with a synTac polypeptide for 3 days (FIG. 39A) or 5 days (FIG. 9B) according to an embodiment of the present disclosure.
Figure 39B:
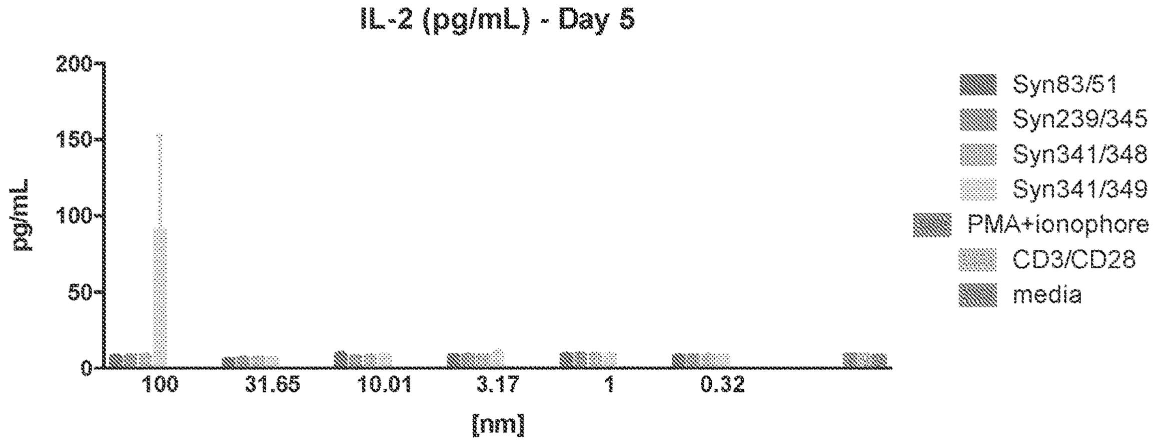
Figure 40A:
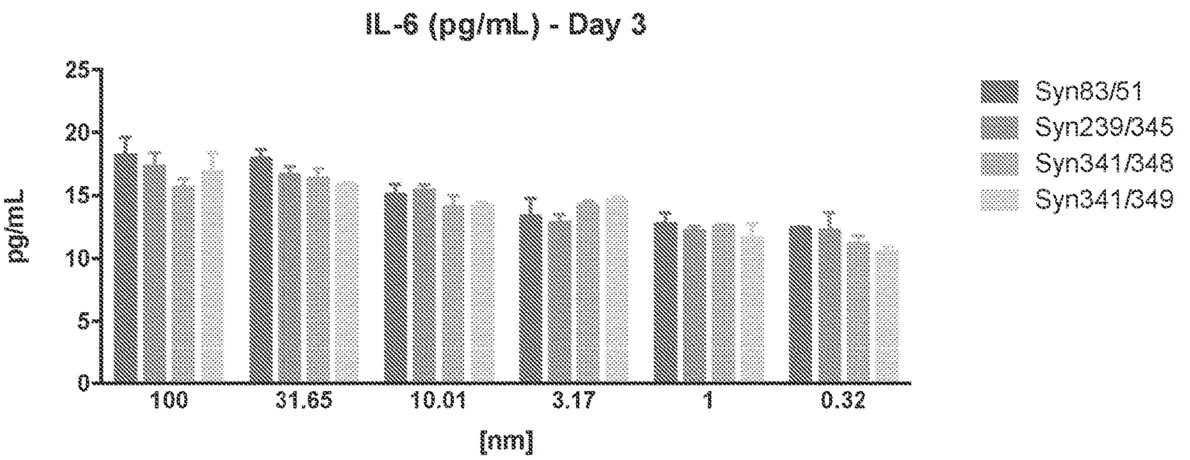
FIG. 40A-40B depicts interleukin-6 (IL-6) secretion by target cells contacted with a synTac polypeptide for 3 days (FIG. 40A) or 5 days (FIG. 40B) according to an embodiment of the present disclosure.
Figure 40B:
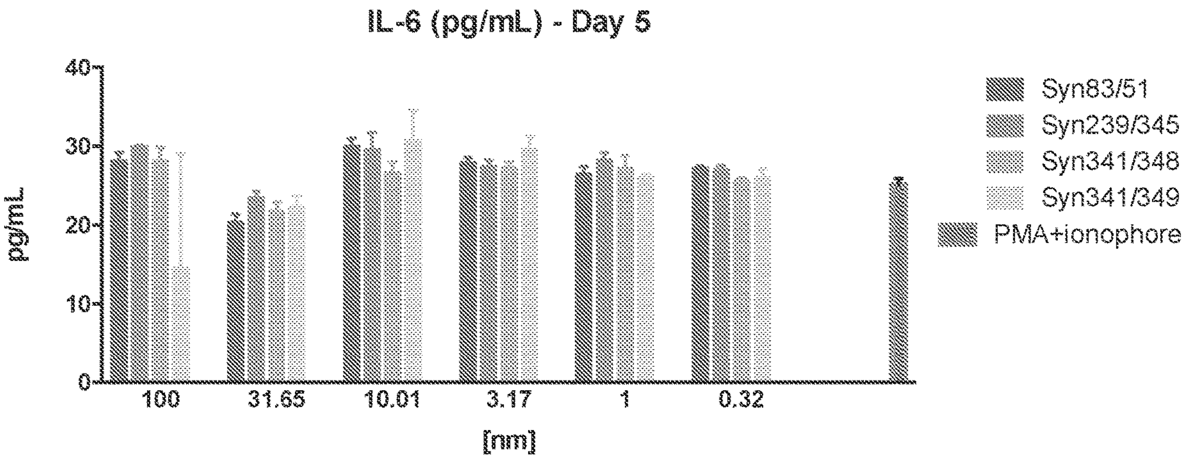
Figure 41A:
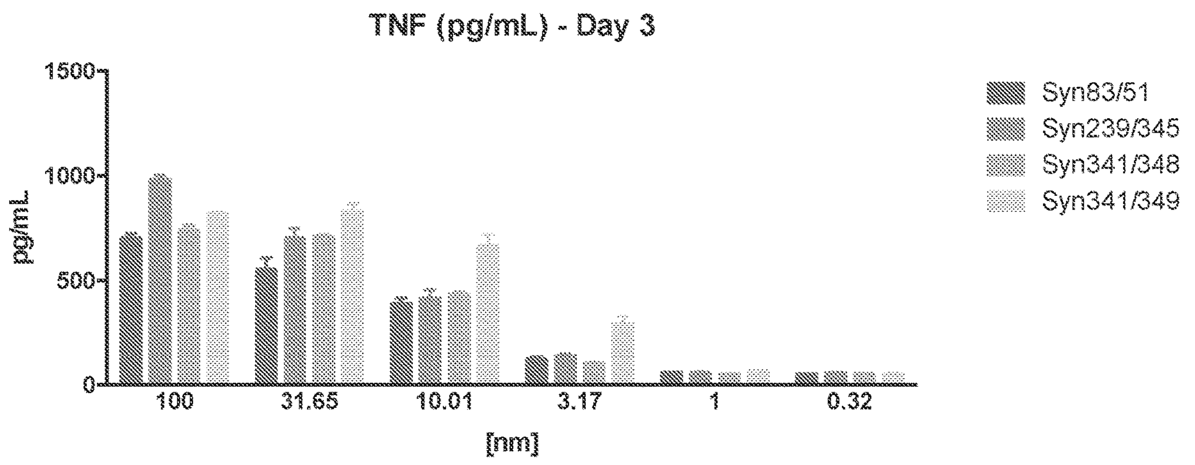
FIG. 41A-41B depicts tumor necrosis factor-alpha (TNFα) secretion by target cells contacted with a synTac polypeptide for 3 days (FIG. 41A) or 5 days (FIG. 41B) according to an embodiment of the present disclosure.
Figure 41B:
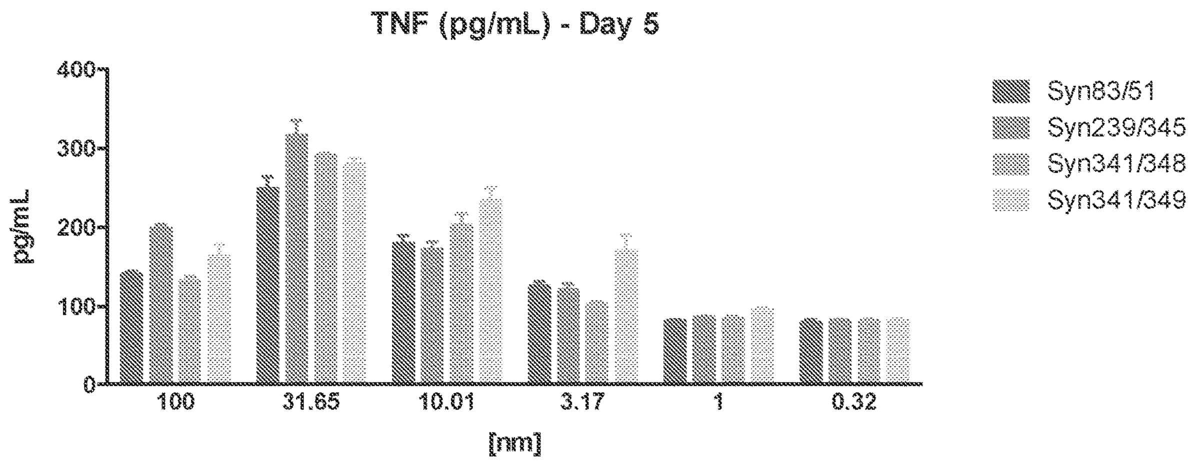
Figure 42A:
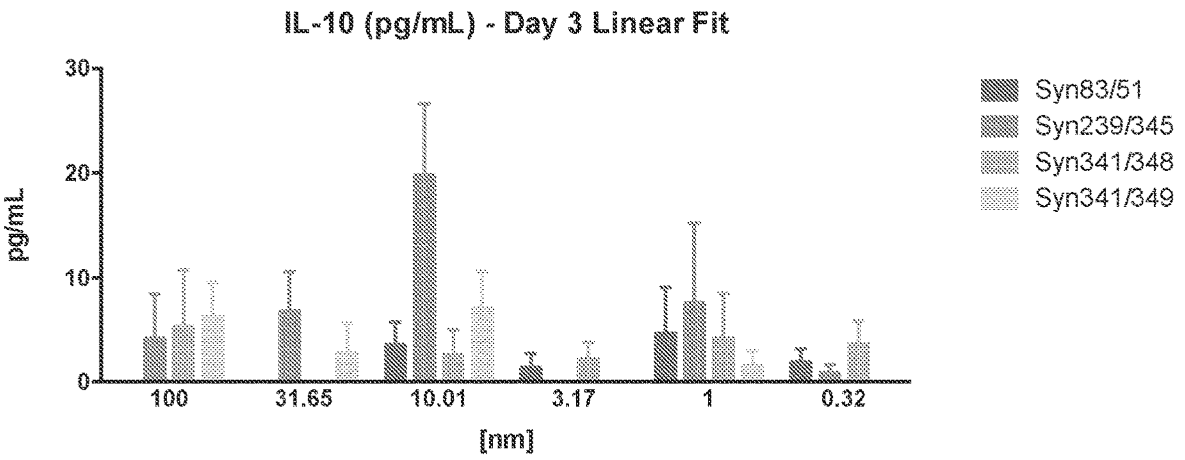
FIG. 42A-42B depicts interleukin-10 (IL-10) secretion by target cells contacted with a synTac polypeptide for 3 days (FIG. 42A) or 5 days (FIG. 42B) according to an embodiment of the present disclosure.
Figure 42B:
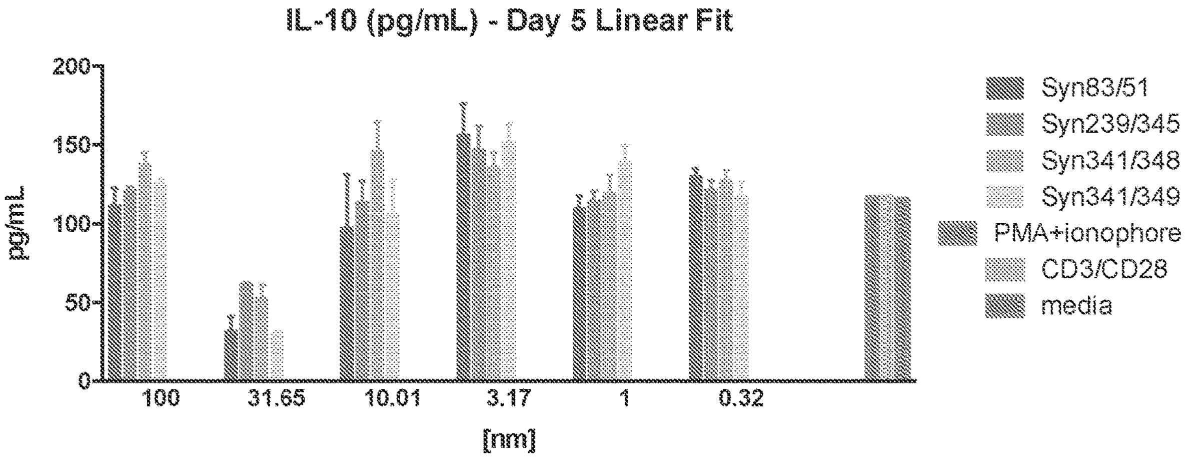
Figure 43A:
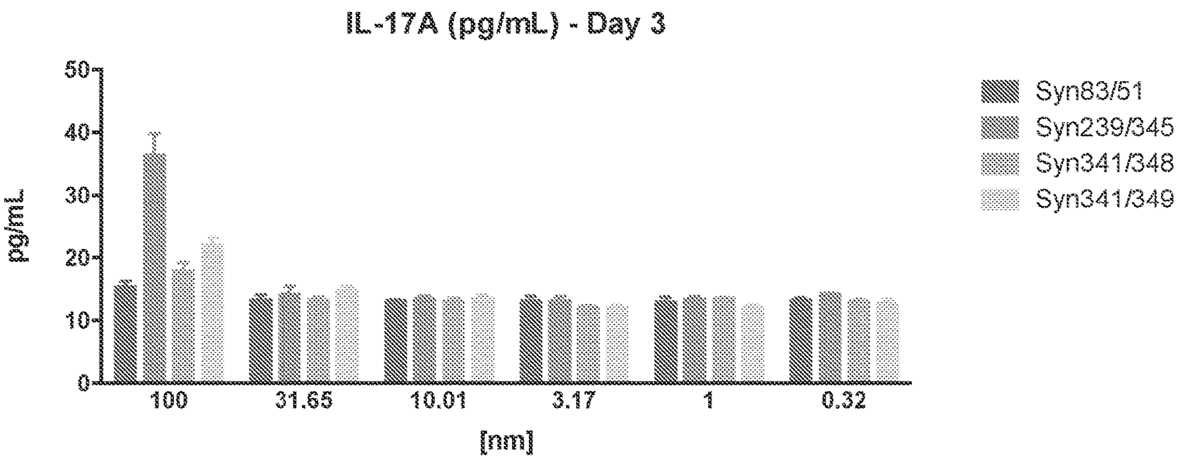
FIG. 43A-43B depicts interleukin-17A (IL-17A) secretion by target cells contacted with a synTac polypeptide for 3 days (FIG. 43A) or 5 days (FIG. 43B) according to an embodiment of the present disclosure.
Figure 43B:
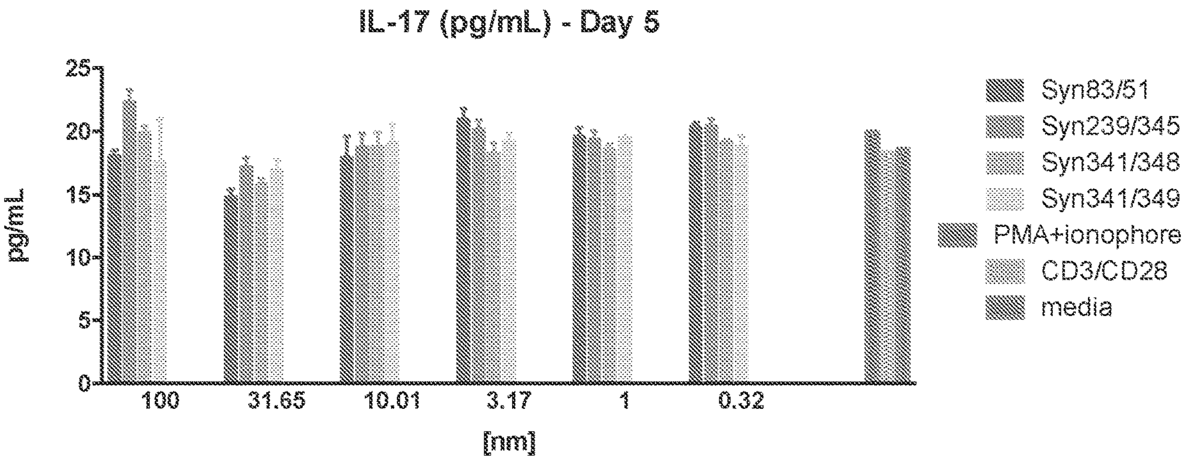
Figure 44A:
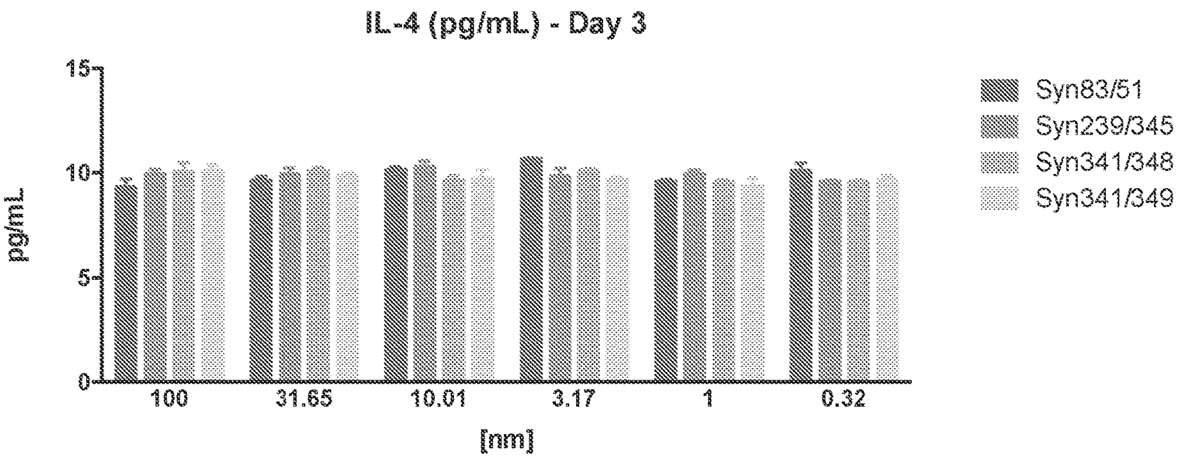
FIG. 44A-44B depicts interleukin-4 (IL-4) secretion by target cells contacted with a synTac polypeptide for 3 days (FIG. 44A) or 5 days (FIG. 44B) according to an embodiment of the present disclosure.
Figure 44B:
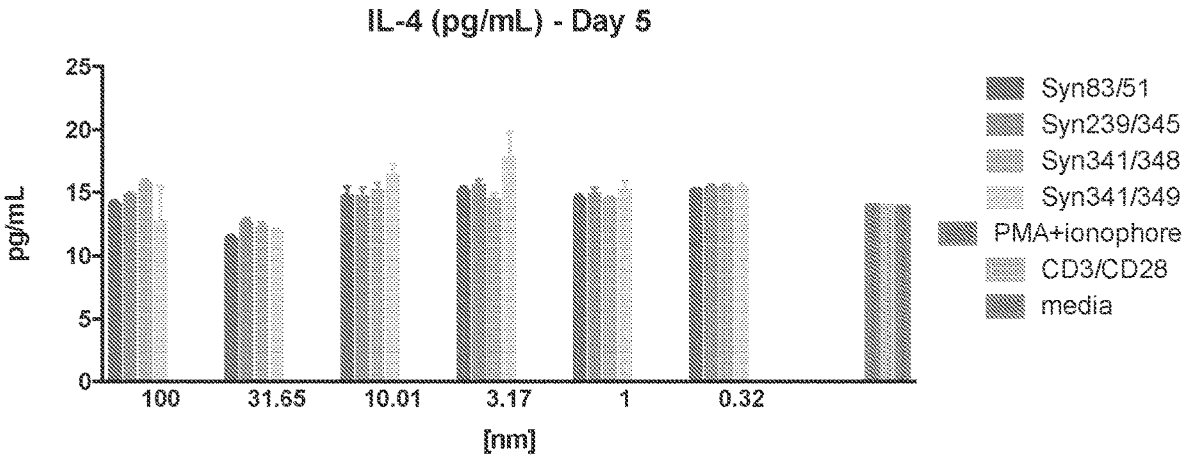
Figure 45:
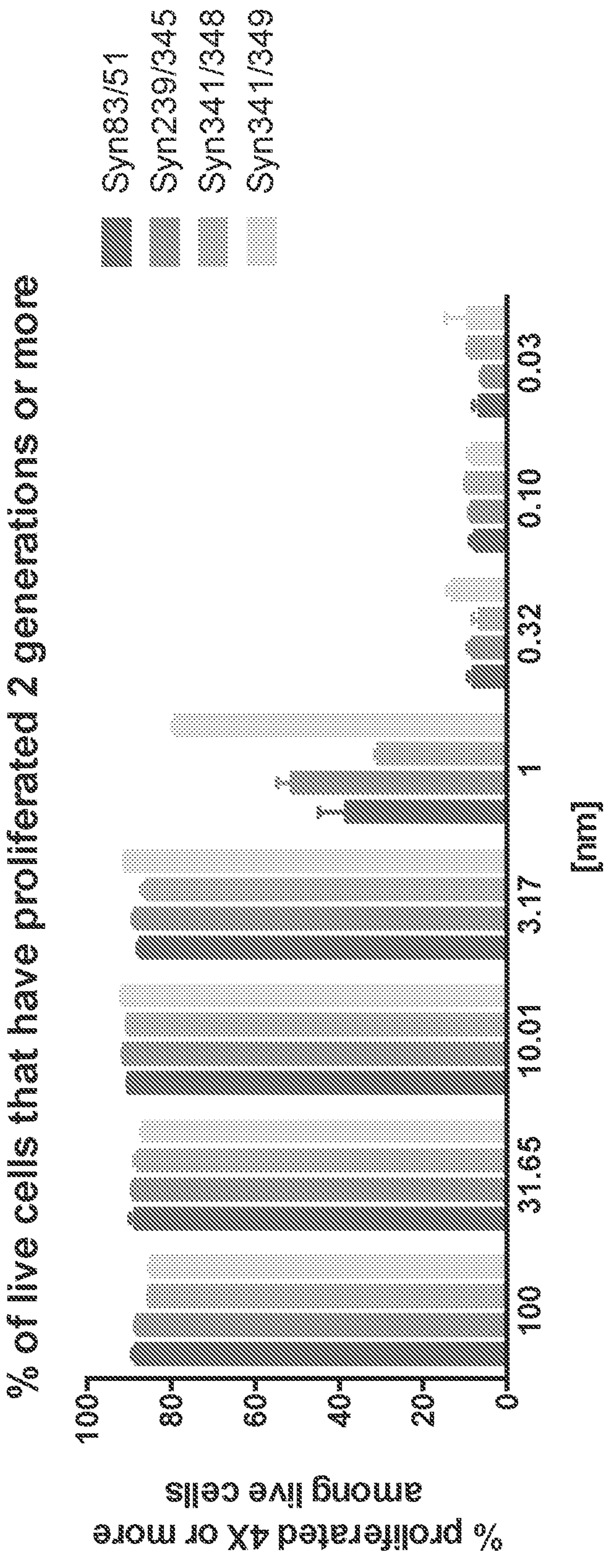
FIG. 45 depicts proliferation of target cells contacted with a synTac polypeptide according to an embodiment of the present disclosure.
Figure 46:
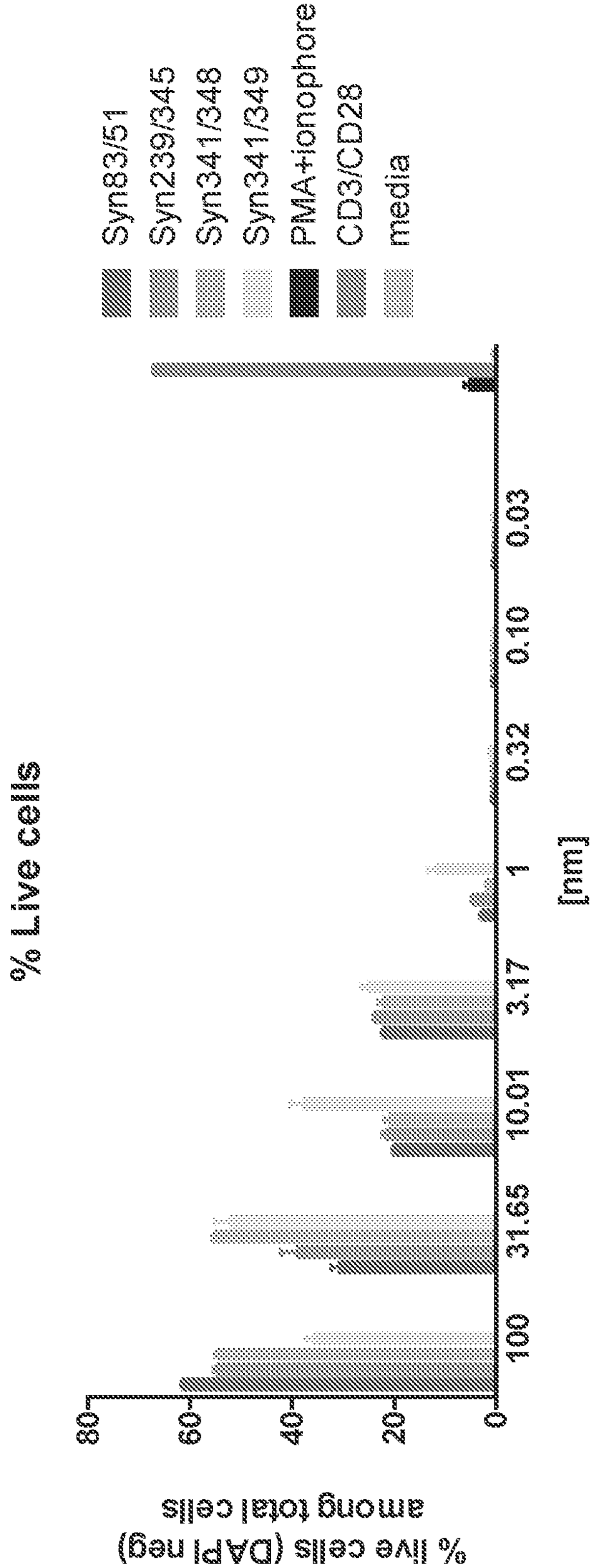
FIG. 46 depicts viability of target cells contacted with a synTac polypeptide according to an embodiment of the present disclosure.

As shown in FIG. 35, administration of an IL-2/synTac and an anti-PD1 antibody to a mouse having a tumor reduced tumor volume.

Example 6: Generation and Characterization of synTac Polypeptides with Variant 4-1BBL synTac polypeptides were synthesized and characterized. The following synTac polypeptides were tested for activity on ovalbumin (OVA)-specific T cells:

1) Syn83/51. The light chain of Syn83/51 comprises: a) an OVA T-cell epitope; b) amino acids 50-254 of a wild-type 4-1BBL polypeptide; and c) β2M; and the heavy chain of Syn83/51 comprises: a) MHC heavy chain; and b) Ig Fc.

2) Syn239/345. The light chain of Syn239/345 comprises: a) an OVA T-cell epitope; b) a trimer of amino acids 80-254 of wild-type 4-1BBL; and c) β2M; and the heavy chain of Syn239/345 comprises: a) MHC heavy chain; and b) IgG2a Fc.

3) Syn341/348. The light chain of Syn341/348 comprises: a) an OVA T-cell epitope; b) a trimer of wild-type 4-1BBL; and c) β2M; and the heavy chain of Syn239/345 comprises: a) MHC heavy chain; and b) IgG2a Fc. In Syn341/348 the first unit of the 4-1BBL trimer comprises amino acids 50-254 of wild-type 4-1BBL; the second and third units of the 4-1BBL trimer comprise amino acids 80 to 254 of wild-type 4-1BBL.

4) Syn341/349. The light chain of Syn341/349 comprises: an OVA T-cell epitope; b) a trimer of amino acids 80-254 of 4-1BBL comprising a K127A substitution in each unit of the trimer, with a linker GlySerSerSerSer between the first and second units and between the second and third units of the trimer; and c) β2M; and the heavy chain of Syn239/345 comprises: a) MHC heavy chain; and b) IgG2a Fc.

The resulting synTac heterodimers were cultured in vitro with ovalbumin-specific T cells for 3 days or 5 days, at concentrations of 0, 1, 3.17, 10.01, 31.65, and 100 nM synTac. Controls included: a) medium alone; b) phorbol 12-myristate 13-acetate (PMA) and the ionophore A23187; and c) an anti-CD3 antibody and an anti-CD28 antibody.

After 3 days, and after 5 days, the concentration of IFN-γ, IL-2, IL-6, TNF, IL-10, IL-17A, and IL-4 in the culture medium was determined. In addition, the viability of the OVA-specific T cells, and the proliferation of the OVA-specific T cells, was determined.

The data are depicted in FIGS. 38-46.

As shown in FIG. 38 through FIG. 46, Syn 341/349 induces production of IL-2 (a cellular fitness cytokine); induces production of cytotoxic cytokines TNFα and IFN-γ; and also induces proliferation and enhances viability of epitope-specific T cells.

Example 7: Production of synTacs in CHO Cells

SynTacs comprising wild-type (wt) 4-1BBL, or comprising 4-1BBL with amino acid substitutions as set out in FIG. 47 were transiently expressed in CHO cells. The amount of synTac produced was determined. The amounts produced are provided in FIG. 47.

Example 8: In Vivo Effect of a 4-1BBL synTac

Figure 48:
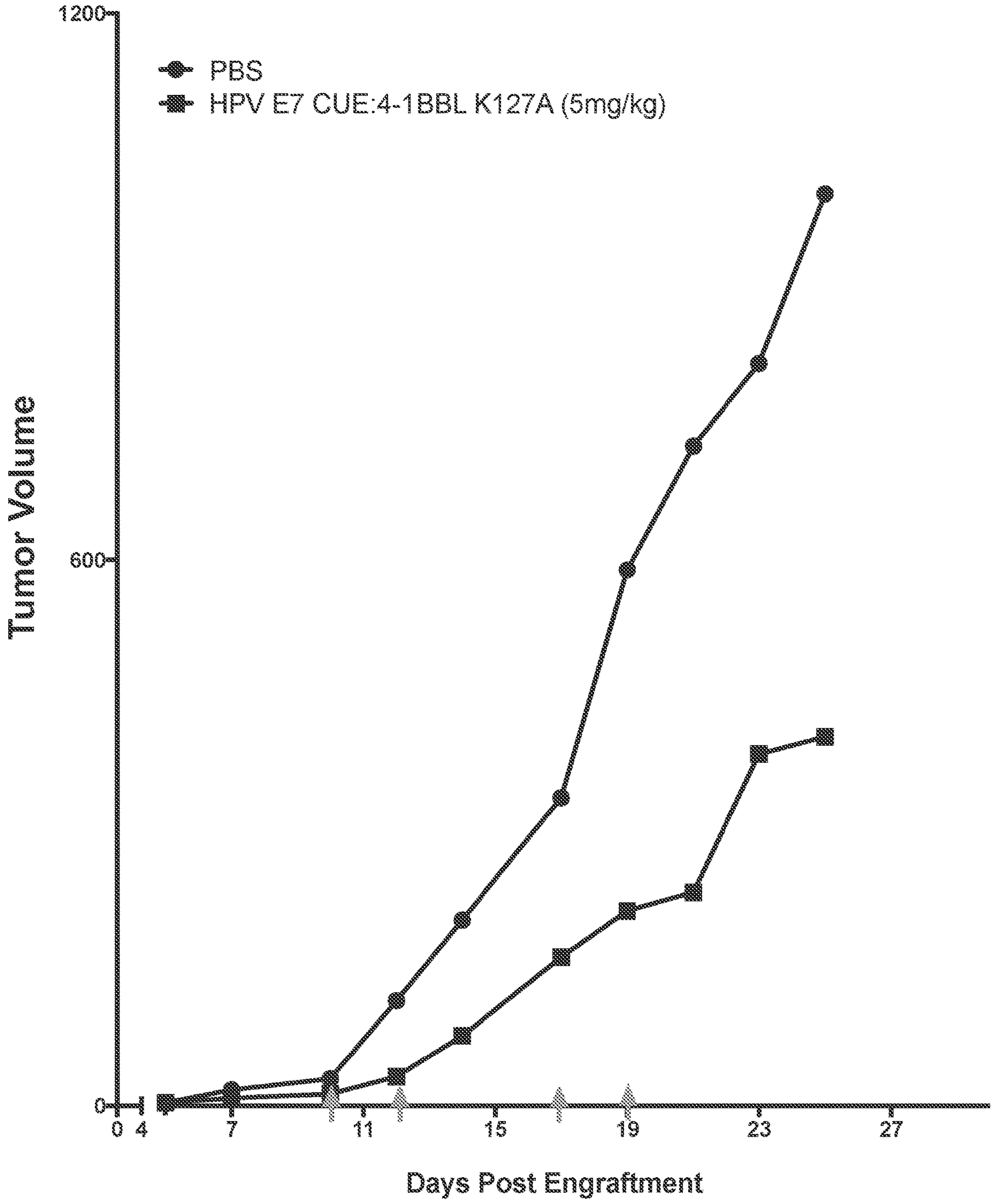
FIG. 48 depicts the in vivo effect of a synTac polypeptide of the present disclosure on tumor volume.

A synTac comprising a human papilloma virus (HPV) E7 antigenic peptide and a 4-1BBL K127A variant of the present disclosure (referred to as "CUE:4-1BBL (K127A)" in FIG. 48) was administered at 5 mg/kg by intraperitoneal (IP) injection into mice bearing flank engrafted $HPV^+$ TC-1 lung carcinoma. As a control, phosphate buffered saline (PBS) was administered to mice bearing the same tumor. As shown in FIG. 48, tumor volume was decreased in mice treated with CUE:4-1BBL (K127A), compared to mice treated with PBS.

Figure 49:
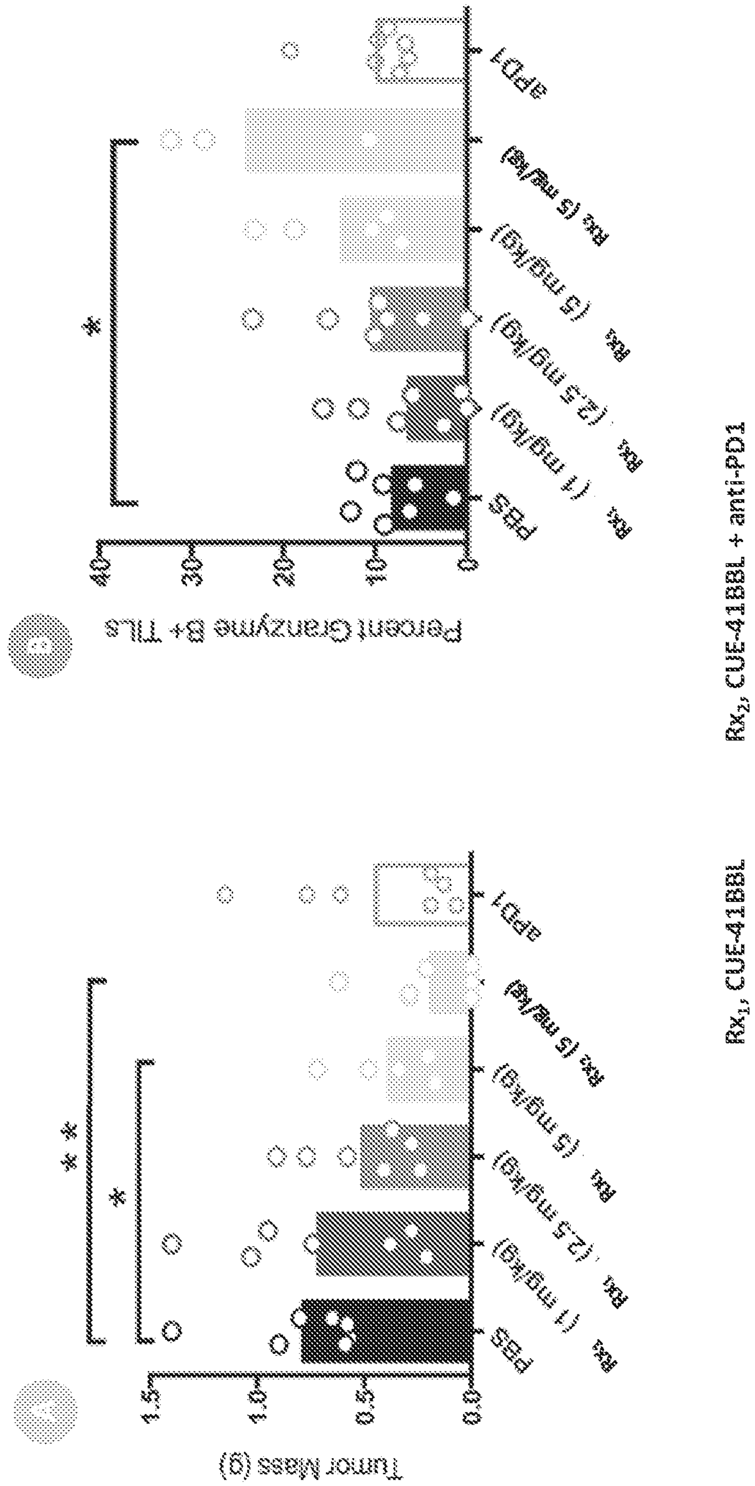
FIG. 49 depicts the effect of co-administration of various doses of a 4-1BBL/synTac and an anti-PD1 antibody on tumor mass and percent granzyme $B^+$ tumor infiltrating lymphocytes (TILs).

Example 9: In Vivo Effects of Co-Administration of a 4-1BBL synTac and an Immune Checkpoint Inhibitor As depicted in FIG. 49, co-administration of a 4-1BBL synTac of the present disclosure and an anti-PD1 antibody reduced tumor volume in a mouse tumor model, and increased the percent of tumor infiltrating lymphocytes (TILs) that were granzyme $B^+$.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of treating an individual having a cancer that expresses an HPV16 E7 antigen, the method comprising administering to the individual a combination of (i) an effective amount of an immune checkpoint inhibitor that targets PD-1, wherein the immune checkpoint inhibitor comprises pembrolizumab, and (ii) an effective amount of a protein that is a homodimer of two multimeric polypeptides, wherein each multimeric polypeptide comprises:

a) a first polypeptide comprising from N-terminus to C-terminus:
   i) an HPV16 E7 epitope comprising amino acid sequence YMLDLQPETT (SEQ ID NO:77);
   ii) a linker comprising amino acid sequence GGGGSGGGGSGGGGS (SEQ ID NO:207); and
   iii) a β2-microglobulin (β2M) polypeptide comprising the amino acid sequence set forth in SEQ ID NO:48; and b) a second polypeptide comprising two variant IL-2 polypeptides, a class I MHC heavy chain polypeptide, and a variant immunoglobulin Fc polypeptide, wherein the second polypeptide comprises the amino acid sequence set forth in SEQ ID NO:36, wherein the first and second polypeptides are covalently linked to one another via a disulfide bond between the Cys residue at amino acid 12 of the β2M polypeptide and the Cys residue at amino acid 236 of the class I MHC heavy chain polypeptide, and wherein the multimeric polypeptides are joined to each other by one or more disulfide bonds that join the variant immunoglobulin Fc polypeptide of one multimeric polypeptide to the variant immunoglobulin Fc polypeptide of the other multimeric polypeptide, and wherein the immune checkpoint inhibitor and the protein are administered at the same time or at different times.

2. A method according to claim 1, wherein the cancer is a head and neck cancer, a cervical cancer, or a genitoanal cancer.

3. A method according to claim 1, wherein the individual has become refractory to a prior treatment for the cancer.

4. A method according to claim 2, wherein the individual has become refractory to a prior treatment for the cancer.

5. A method according to claim 1, wherein the individual has failed to respond to a prior treatment for the cancer.

6. A method according to claim 2, wherein the individual has failed to respond to a prior treatment for the cancer.

7. A method according to claim 1, wherein the protein is administered in an amount of 100 μg to 1 mg per kg of body weight.

8. A method according to claim 1, wherein the protein is administered in an amount of 1-5 mg per kg of body weight.

9. A method according to claim 1, wherein the protein is administered in an amount of 5-10 mg per kg body weight.

10. A method according to claim 1, wherein the protein is administered in an amount of 10-15 mg per kg body weight.

11. A method according to claim 1, wherein the protein is administered in an amount of 15-20 mg per kg body weight.

12. A method according to claim 2, wherein the protein is administered in an amount of 100 μg to 1 mg per kg of body weight.

13. A method according to claim 2, wherein the protein is administered in an amount of 1-5 mg per kg of body weight.

14. A method according to claim 2, wherein the protein is administered in an amount of 5-10 mg per kg body weight.

15. A method according to claim 2, wherein the protein is administered in an amount of 10-15 mg per kg body weight.

16. A method according to claim 2, wherein the protein is administered in an amount of 15-20 mg per kg body weight.

* * * * *